(12) United States Patent
Mizuno et al.

(10) Patent No.: US 11,084,814 B2
(45) Date of Patent: Aug. 10, 2021

(54) PYRIDO[3, 4-D]PYRIMIDINE DERIVATIVE AND PHARMACEUTICALLY ACCEPTABLE SALT THEREOF

(71) Applicant: Teijin Pharma Limited, Tokyo (JP)

(72) Inventors: Tsuyoshi Mizuno, Tokyo (JP); Tomohiro Shimada, Tokyo (JP); Gen Unoki, Tokyo (JP); Akinobu Maruyama, Tokyo (JP); Kosuke Sasaki, Tokyo (JP); Takuya Yokosaka, Tokyo (JP); Hiroshi Takahashi, Tokyo (JP); Kyohei Horie, Tokyo (JP); Yuri Sakai, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 0 days.

(21) Appl. No.: 16/463,458

(22) PCT Filed: Nov. 27, 2017

(86) PCT No.: PCT/JP2017/042443
§ 371 (c)(1),
(2) Date: May 23, 2019

(87) PCT Pub. No.: WO2018/097297
PCT Pub. Date: May 31, 2018

(65) Prior Publication Data
US 2019/0367510 A1   Dec. 5, 2019

(30) Foreign Application Priority Data
Nov. 28, 2016 (JP) .............................. JP2016-229969

(51) Int. Cl.
C07D 471/04 (2006.01)
A61P 35/04 (2006.01)
A61P 19/02 (2006.01)

(52) U.S. Cl.
CPC .................................. *C07D 471/04* (2013.01)

(58) Field of Classification Search
CPC ........................ C07D 471/04; C07D 519/00
See application file for complete search history.

(56) References Cited

U.S. PATENT DOCUMENTS

| | | | |
|---|---|---|---|
| 9,902,721 B2 * | 2/2018 | Woodward | ............ C07D 519/00 |
| 2003/0149001 A1 | 8/2003 | Barvian et al. | |
| 2010/0105653 A1 | 4/2010 | Besong et al. | |
| 2010/0160340 A1 | 6/2010 | Coates et al. | |
| 2011/0224227 A1 | 9/2011 | Sharpless et al. | |
| 2015/0175601 A1 | 6/2015 | Qian et al. | |
| 2015/0239884 A1 | 8/2015 | Hoelder et al. | |
| 2018/0161329 A1 | 6/2018 | Mizuno et al. | |

FOREIGN PATENT DOCUMENTS

| CN | 107614499 A | 1/2018 |
|---|---|---|
| WO | 03062236 A1 | 7/2003 |
| WO | 2010020675 A1 | 2/2010 |
| WO | 2010075074 A1 | 7/2010 |
| WO | 2014037750 A1 | 3/2014 |
| WO | 2015027222 A2 | 2/2015 |
| WO | WO 2015128676 * | 9/2015 |
| WO | 2016/015597 A1 | 2/2016 |

OTHER PUBLICATIONS

Johnson, D.G., et al., "Cyclins and Cell Cycle Checkpoints", Annual Review of Pharmacology and Toxicology, 1999, vol. 39, pp. 295-312.

Ortega, S., et al., "Cyclin D-dependent kinases, INK4 inhibitors and cancer", Biochimica et Biophysica Acta—Reviews on Cancer, 2002, vol. 1602, No. 1, pp. 73-87.

Shapiro, G., "Cyclin-Dependent Kinase Pathways As Targets for Cancer Treatment", Journal of Clinical Oncology, Apr. 10, 2006, vol. 24, No. 11, pp. 1770-1783.

Lundberg, A., et al., "Functional Inactivation of the Retinoblastoma Protein Requires Sequential Modification by at Least Two Distinct Cyclin-cdk Complexes", Molecular and Cellular Biology, Feb. 1998, vol. 18, No. 2, pp. 753-761.

Olaharski, A., et al., "Identification of a Kinase Profile that Predicts Chromosome Damage Induced by Small Molecule Kinase Inhibitors", PLoS Computational Biology, Jul. 2009, vol. 5, Issue 7, e1000446, pp. 1-10.

Kamb, A., et al., "A Cell Cycle Regulator Potentially Involved in Genesis of Many Tumor Types", Science, vol. 264, No. 5157, Apr. 15, 1994, pp. 436-440.

Taniguchi, K., "Induction of the p16$^{INK4a}$ senescence gene as a new therapeutic strategy for the treatment of rheumatoid arthritis", Nature Medicine, vol. 5, No. 7, Jul. 1999, pp. 760-767.

Sekine, C., et al., "Successful Treatment of Animal Models of Rheumatoid Arthritis with Small-Molecule Cyclin-Dependent Kinase Inhibitors", The Journal of Immunology, 2008, vol. 180, pp. 1954-1961.

Hosoya, T., "Cell Cycle regulation therapy combined with cytokine blockade enhances antiarthritic effects without increasing immune suppression", Annual Rheumatic Disease, 2016 (ePub in 2014), vol. 75, pp. 253-259.

(Continued)

*Primary Examiner* — Susanna Moore
(74) *Attorney, Agent, or Firm* — Sughrue Mion, PLLC

(57) ABSTRACT

The purpose of the present invention is to provide a compound that has excellent CDK4/6 inhibitory activity. The present invention is a compound represented by formula (I) or a pharmaceutically acceptable salt of the compound.

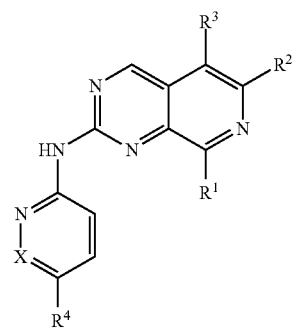

(I)

27 Claims, No Drawings

(56) References Cited

OTHER PUBLICATIONS

Nonomura, Y., et al., "Direct Modulation of Rheumatoid Inflammatory Mediator Expression in Retinoblastoma Protein-Dependent and -Independent Pathways by Cyclin-Dependent Kinase 4/6", Arthritis & Rheumatism2, vol. 54, No. 7, Jul. 2006, pp. 2074-2083.
Chang, M., et al., "Adenovirus-mediated Over-expression of the Cyclin/Cyclin-dependent Kinase Inhibitor, p21 Inhibits Vascular Smooth Muscle Cell Proliferation and Neointima Formation in the Rat Carotid Artery Model of Balloon Angioplasty", Journal of Clinical Investigation, vol. 96, Nov. 1995, pp. 2260-2268.
Yang, Z-Y., "Role of the p21 cyclin-dependent kinase inhibitor in limiting intimal cell proliferation in response to arterial injury", Proceedings of the National Academy of Sciences USA, vol. 93, Jul. 1996, pp. 7905-7910.
Bukanov, N., et al., "Long-lasting arrest of murine polycystic kidney disease with CDK inhibitor roscovitine", Nature, vol. 444, Dec. 14, 2006, pp. 949-952.
Inoshima, I., et al., "Induction of CDK inhibitor p21 gene as a new therapeutic strategy against pulmonary fibrosis", American Journal Physiology: Lung Cellular and Molecular Physiology, 2004, vol. 286, pp. L727-L733.
Osuga, H., et al., "Cyclin-dependent kinases as a therapeutic target for stroke", Proceedings of the National Academy of Sciences USA, Aug. 29, 2000, vol. 97, No. 18, pp. 10254-10259.
Weinberg, R., "Tumor Suppressor Genes", Science, vol. 254, Nov. 22, 1991, pp. 1138-1145.
Khatib, Z., et al., "Coamplification of the CDK4 Gene with MDM2 and GLI in Human Sarcomas", Cancer Research, vol. 53, Nov. 15, 1993, pp. 5535-5541.
Bartek, J., et al., "The retinoblastoma protein pathway and the restriction point", Current Opinion in Cell Biology, 1996, vol. 8, pp. 805-814.
Guha, et al., "Blockbuster dreams for Pfizer's CDK inhibitor", Nature Biotechnology, vol. 31, No. 3, Mar. 2013, p. 187.
Johnson, S., et al., "Mitigation of hematologic radiation toxicity in mice through pharmacological quiescence induced by CDK4/6 inhibition", The Journal of Clinical Investigation, vol. 120, No. 7, Jul. 2010, pp. 2528-2536.
Vanderwel, S., et al., "Pyrido[2,3-d] pyrimidin-7-ones as Specific Inhibitors of Cyclin-Dependent Kinase 4", Journal of Medicinal Chemistry, 2005, vol. 48, No. 7, pp. 2371-2387.
Barvian, M., et al., "Pyrido[2,3-d] pyrimidin-7-one Inhibitors of Cyclin-Dependent Kinases", The Journal of Medicinal Chemistry, 2000, vol. 43, No. 24, pp. 4606-4616.
Toogood, P., et al., "Discovery of a Potent and Selective Inhibitor of Cyclin-Dependent Kinase 4/6", The Journal of Medicinal Chemistry, 2005, vol. 48, No. 7, pp. 2388-2406.
Cho., Y., et al., "4-(Pyrazol-4-yl)-pyrimidines as Selective Inhibitors of Cyclin-Dependent Kinase 4/6", The Journal of Medicinal Chemistry, 2010, vol. 53, No. 22, pp. 7938-7957.
Li., Z., et al., "Discovery of AMG 925, a FLT3 and CDK4 Dual Kinase Inhibitor with Preferential Affinity for the Activated State of FLT3", The Journal of Medicinal Chemistry, 2014, vol. 57, pp. 3430-3449.
Innocenti, P., et al., "Expanding the scope of fused pyrimidines as kinase inhibitor scaffolds: synthesis and modification of pyrido[3,4-d]pyrimidines", Organic & Biomolecular Chemistry, 2015, vol. 13, pp. 893-904.
Innocenti, P., et al., "Rapid Discovery of Pyrido[3,4-d] pyrimidine Inhibitors of Monopolar Spindle Kinase 1 (MPS1) Using a Structure-Based Hybridization Approach", The Journal of Medicinal Chemistry, 2016, vol. 59, pp. 3671-3688.
Parrish, K., et al,, "Efflux Transporters at the Blood-Brain Barrier Limit Delivery and Efficacy of Cyclin-Dependent Kinase 4/6 Inhibitor Palbociclib (PD-0332991) in an Orthotopic Brain Tumor Model", Journal of Pharmacology and Experimental Therapeutics, 2015, vol. 355, pp. 264-271.
Communication, dated Apr. 23, 2021, issued by The State Intellectual Property Office of People's Republic of China in corresponding application No. 201780072637.3.

* cited by examiner

PYRIDO[3, 4-D]PYRIMIDINE DERIVATIVE AND PHARMACEUTICALLY ACCEPTABLE SALT THEREOF

CROSS REFERENCE TO RELATED APPLICATIONS

This application is a National Stage of International Application No. PCT/JP2017/042,443, filed Nov. 27, 2017, claiming priority to Japanese Patent Application No. 2016-229969, filed Nov. 28, 2016.

TECHNICAL FIELD

The present invention relates to a pyrido[3,4-d]pyrimidine derivative and a pharmaceutically acceptable salt thereof. In particular, the present invention relates to a compound that exhibits an inhibitory activity against cyclin-dependent kinase 4 and/or cyclin-dependent kinase 6 (hereinafter referred to as "CDK4/6") and that is useful for the prevention or treatment of rheumatoid arthritis, arteriosclerosis, pulmonary fibrosis, cerebral infarction, or cancer.

BACKGROUND ART

Cell growth, which is a process involving proliferation and division of cells, occurs in response to various stimuli.

Pathological conditions caused by hyperproliferation of cells, such as cancer, are characterized by uncontrollable cell cycle progression and thus excessive progression of the cell cycle, for example, resulting from abnormality in genes or proteins that directly or indirectly regulate the cell cycle progression. Substances that regulate hyperproliferation of cells through control of the cell cycle can be used for the treatment of various pathological conditions characterized by uncontrollable or unwanted cell growth.

Cell cycle progression is a complicated process involving highly regulated transition of phases and multiple checkpoints.

Cyclin-dependent kinases and associated serine/threonine protein kinases are important intracellular enzymes that play essential roles in the regulation of division and proliferation of cells. Catalytic subunits of cyclin-dependent kinases are activated by regulatory subunits known as cyclins, and multiple cyclins have been identified in mammals (NPL1).

The retinoblastoma (Rb) protein is a checkpoint protein for transition from the G1 phase to the S phase in the cell cycle. The Rb protein associates with the E2F transcription factor family and inhibits the activity thereof in the absence of appropriate growth stimulation (NPLs 2 and 3). A cell stimulated by a mitogen enters the S phase through synthesis of cyclin D, which is a CDK4/6 activator. The cyclin D-bound CDK4/6 inactivates the Rb protein through phosphorylation. The phosphorylation of the Rb protein releases E2F in order to indirective the transcription of a gene necessary for the S phase. The complete inactivation of the Rb protein requires phosphorylation of both cyclin D-CDK4/6 and cyclin E-CDK2. The phosphorylation of the Rb protein by CDK4/6 at a specific site is essential in the phosphorylation of cyclin E-CDK2 (NPL4). Thus, cyclin D-CDK4/6 is an important enzyme complex which controls the transition from the G1 phase to the S phase.

CDK2 forms a complex with cyclin E and also forms a complex with cyclin A. CDK2 also acts on steps subsequent to the S phase and is responsible for DNA replication. The inhibition of CDK2 probably leads to the expression of genotoxicity (NPL5).

Cyclin D has a molecular mechanism that positively regulates the activity of CDK4/6. In contrast, p16 encoded by the INK4a gene negatively regulates the activity of CDK4/6 (NPL6).

CDK inhibitors can be used for the treatment of various diseases caused by abnormal cell growth, such as cancer, cardiovascular disorder, renal disease, specific infections, and autoimmune diseases. CDK inhibitors is also expected to be effective for the treatment of diseases including but not limited to rheumatoid arthritis, arteriosclerosis, pulmonary fibrosis, cerebral infarction, and cancer. The inhibition of cell cycle progression and cell growth through CDK inhibition is expected to be effective for such a disease on the basis of the technical findings described below.

Rheumatoid arthritis involves the formation of pannus through hyperproliferation of synovial cells. This hyperproliferation can be reduced by the introduction of p16 into an affected area of a model animal or the administration of a CDK4/6 inhibitor to the animal (NPLs 7 to 9). A CDK4-cyclin D complex regulates the production of MMP3 in synovial cells derived from a patient with rheumatoid arthritis. The negative regulation of the activity of CDK4/6 inhibits not only the proliferation but also production of MMP3 (NPL10).

Thus, CDK4/6 inhibitors are expected to exhibit both an inhibitory effect on proliferation of synovial cells and a cartilage protective effect in rheumatoid arthritis.

A pathway for the regulation of cell growth including genes responsible for the checkpoints in the G1 and S phases of the cell cycle is associated with plaque progression, stenosis, and restenosis after angiogenesis. The overexpression of the CDK inhibitory protein p21 inhibits angiogenesis and subsequent growth of vascular smooth muscle and intimal hyperplasia (NPLs 11 and 12).

Abnormal regulation of the cell cycle is also associated with polycystic kidney disease, which is characterized by growth of cysts filled with fluid in the renal tubule. A small-molecule CDK inhibitor is effective for the treatment of the disease (NPL13).

The induction of expression of the cell cycle inhibitory protein p21 with an adenoviral vector is effective in a murine pulmonary fibrosis model (NPL14).

The level of cyclin D1/CDK4 is known to increase in a rat cerebral infarction model in association with neuronal death caused by local ischemia. The neuronal death is reduced by administering flavopiridol, which is a nonselective CDK inhibitor (NPL15).

The cyclin D-CDK4/6-INK4a-Rb pathway is frequently detected in human cancer caused by abnormality of any factors contributing to growth of cancer cells, such as loss of functional p16INK4a, overexpression of cyclin D1, overexpression of CDK4, or loss of functional Rb (NPLs 16 to 18). Such abnormality promotes the cell cycle progression from the G1 phase to the S phase, and this pathway certainly plays an important role in oncogenic transformation or abnormal growth of cancer cells.

CDK4/6 inhibitors may be effective, particularly for tumors involving abnormality in genes that activate the CDK4/6 kinase activity, such as cancers involving the translocation of cyclin D, cancers involving the amplification of cyclin D, cancers involving the amplification or overexpression of CDK4 or CDK6, and cancers involving the inactivation of p16. CDK4/6 inhibitors may be effective for the treatment of cancers involving genetic abnormality in the upstream regulator of cyclin D, the amount of which increases due to defects in the upstream regulator.

In fact, many compounds that inhibit the CDK4/6 activity have been synthesized and disclosed in the art, and such compounds have been clinically tested for the treatment of cancers, such as breast cancer (NPL19).

Glioblastoma, which is a glioma manifesting a high degree of malignancy, is known to be one of the tumors on which a CDK4/6 inhibitor is expected to exert a therapeutic effect. A CDK4/6 inhibitor has been shown to exhibit an antiproliferative effect on the cell line derived from glioblastoma. In order to expect such an effect on a lesion in the brain, it is necessary to cause migration from the blood via the blood brain barrier into the brain, or to carry out administration without transfer via the blood flow, such as intracerebral administration, intracerebral implant device, or intranasal administration. The permeability of compounds at the blood brain barrier is restricted by efflux transporters, such as P-glycoproteins and BCRP. In fact, it has been reported that palbociclib, CDK4/6 inhibitor, exhibited an antiproliferative effect in the flank but not in the brain according to the experiments of mice xenograft model with glioblastoma implanted in either the flank or intracranially, indicating that the onset of effects on brain tumor by palbociclib was limited due to its low permeability via the blood brain barrier (NPL28).

Most acute and severe radiotherapeutic and chemotherapeutic toxicities are caused by the effects on stem cells and progenitor cells. A CDK4/6 inhibitor causes temporary cell cycle arrest to hematopoietic stem and progenitor cells, and protects them from radiotherapeutic or chemotherapeutic cytotoxicity. After the treatment with the inhibitor, hematopoietic stem and progenitor cells (HSPCs) return from the temporary dormancy and then function normally. Thus, the chemotherapeutic resistance with use of a CDK4/6 inhibitor is expected to provide a significant protection of bone marrow (NPL20).

Hence, CDK4/6 inhibitors are expected to be effective for the treatment of rheumatoid arthritis, arteriosclerosis, pulmonary fibrosis, cerebral infarction, or cancer, and the protection of bone marrow, in particular, for the treatment of rheumatoid arthritis or cancer and the protection of bone marrow.

PTL1 and NPL21 disclose CDK4 inhibitors, PTLs 2 and 3 and NPLs 22 to 24 disclose CDK4/6-containing CDK inhibitors, and NPL25 discloses CDK4/FLT3 inhibitors.

Pyrido[3,4-d]pyrimidine derivatives exhibit an inhibitory effect on Mps1 (also known as TTK) (PTL4). This inhibitory effect is completely different from the CDK4/6 inhibitory effect disclosed in the present invention.

NPL26 and NPL27 disclose that a plurality of pyrido[3,4-d]pyrimidine derivatives exhibit a CDK2 inhibitory activity, which is completely different from the superior CDK4/6 inhibitory effect exhibited by the present invention.

PTL5 describes pyrido[3,4-d]pyrimidine derivatives known to exhibit EGFR inhibitory effects, which are completely different from the CDK4/6 inhibitory effects according to the present invention.

LIST OF CITATIONS

Patent Literature

[PTL1] WO2003/062236A
[PTL2] WO2010/020675A
[PTL3] WO2010/075074A
[PTL4] WO2014/037750A
[PTL5] WO2015/027222A

Non-Patent Literature

[NPL1] Johnson D. G. and Walker C. L., Annual Review of Pharmacology and Toxicology 1999; 39: p. 295-312
[NPL2] Ortega et al., Biochimica et Biophysica Acta-Reviews on Cancer 2002; 1602 (1): p. 73-87
[NPL3] Shapiro, Journal of Clinical Oncology 2006: 24 (11): p. 1770-1783
[NPL4] Lundberg et al., Molecular and Cellular Biology 1998; 18 (2): p. 753-761
[NPL5] Andrew J. Olaharski, PLoS Computational Biology 2009; 5 (7): e1000446
[NPL6] Kamb et al., Science 1994; 264 (5157): p. 436-440
[NPL7] Taniguchi, K et al., Nature Medicine, Vol. 5, p. 760-767 (1999)
[NPL8] Sekine, C et al., Journal of immunology 2008, 180: p. 1954-1961
[NPL9] Hosoya, T et al., Annnl Rheumatic Diseases 2014, Aug. 27 Epub ahead of print
[NPL10] Nonomura Y et al., Arthritis & Rheumatology 2006, July: 54 (7): p. 2074-83
[NPL11] Chang M. W. et al., Journal of Clinical Investigation, 1995, 96: p. 2260
[NPL12] Yang Z. Y. et al., Proceedings of the National Academy of Sciences (USA) 1996, 93: p. 9905
[NPL13] Bukanov N. O. et al., Nature, 2006, 4444: p. 949-952
[NPL14] American Journal Physiology: Lung Cellular and Molecular Physiology, 2004, Vol. 286. p. L727-L733
[NPL15] Proceedings of the National Academy of Sciences of the United States of America, 2000, Vol. 97, p. 10254-10259
[NPL16] Science, Vol. 254, p. 1138-1146 (1991)
[NPL17] Cancer Research, 1993, Vol. 53, p. 5535-5541
[NPL18] Current Opinion in Cell Biology, 1996, Vol. 8, p. 805-814
[NPL19] Guha M, Nature Biotechnology 2013, March; 31 (3): p. 187
[NPL20] Journal of Clinical Investigation 2010; 120 (7): p. 2528-2536 Soren M. Johnson
[NPL21] Journal of Medicinal Chemistry, 2005, 48, p. 2371-2387
[NPL22] Journal of Medicinal Chemistry, 2000, 43, p. 4606-4616
[NPL23] Journal of Medicinal Chemistry, 2005, 48, p. 2388-2406
[NPL24 hours] Journal of Medicinal Chemistry, 2010, 53, p. 7938-7957
[NPL25] Journal of Medicinal Chemistry, 2014, 57. p. 3430-3449
[NPL26] Organic & Biomolecular Chemistry, 2015, 13, p. 893-904
[NPL27] Rapid Discovery of Pyrido[3,4-d]pyrimidine Inhibitors of Monopolar Spindle Kinase 1 (MPS1) Using a Structure-Based Hybridization Approach, Paolo Innocenti et al, J. Med. Chem., Article ASAP, Publication Date (Web): Apr. 7, 2016, DOI: 10.1021/acs.jmedchem.5b01811.
[NPL28] J. Pharm. Exp. Ther., 2015, 355, 264-271

SUMMARY OF INVENTION

Problem to be Solved by the Invention

An object of the present invention is to provide a compound exhibiting a superior CDK4/6 inhibitory activity.

Means to Solve the Problem

The present inventors have conducted extensive studies for solving the problems described above and have found that a novel pyrido[3,4-d]pyrimidine derivative represented by Formula (I) exhibits a CDK4/6 inhibitory activity. The present invention has been accomplished on the basis of this finding.

The present invention includes the following aspects:
Aspect (1) A compound represented by formula (I):

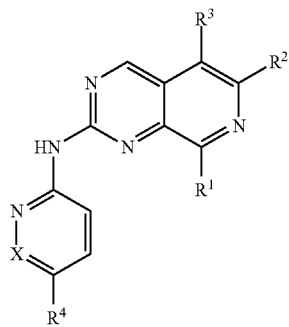

(I)

wherein in the formula, $R^1$ represents $C_{3-12}$ cycloalkyl, $C_{4-12}$ cycloalkenyl, 4- to 12-membered heterocyclyl, $C_{6-10}$ aryl, or 5- to 10-membered heteroaryl, wherein each heteroatom-containing group represented by $R^1$ contains one to four heteroatoms independently selected from oxygen, sulfur, and nitrogen atoms, $R^1$ is optionally substituted with one to six substituents selected from the group consisting of a halogen atom, =O, —OH, —CN, —COOH, —COOR$^6$, —R$^7$, $C_{3-6}$ cycloalkyl substituted with [zero to two —OH groups, zero to two $C_{1-8}$ alkoxy groups, and zero to six fluorine atoms], 3- to 10-membered heterocyclyl substituted with [zero to two —OH groups, zero to two $C_{1-8}$ alkoxy groups, and zero to six fluorine atoms], $C_{1-8}$ acyl substituted with [zero to two —OH groups, zero to two $C_{1-8}$ alkoxy groups, and zero to six fluorine atoms], and $C_{1-8}$ alkoxy substituted with [zero to two —OH groups, zero to two $C_{1-8}$ alkoxy groups, and zero to six fluorine atoms];

$R^6$ and $R^7$ each independently represent $C_{1-6}$ alkyl substituted with [zero to two —OH groups, zero to two $C_{1-8}$ alkoxy groups, and zero to six fluorine atoms]:

$R^2$ represents $C_{1-8}$ alkyl, $C_{3-8}$ cycloalkyl, 4- to 6-membered heterocyclyl, $C_{1-8}$ acyl, —COOR$^8$, or —CONR$^9$R$^{10}$, wherein each of $C_{1-8}$ alkyl represented by $R^2$ is substituted independently with zero to one —OH group, zero to two $C_{1-8}$ alkoxy groups substituted with [zero to one —OH group, zero to one $C_{1-4}$ alkoxy group, and zero to three fluorine atoms], and zero to five fluorine atoms; each of $C_{3-8}$ cycloalkyl represented by $R^2$ is independently substituted with zero to one —OH group, zero to two $C_{1-8}$ alkoxy groups substituted with [zero to one —OH group, zero to one $C_{1-4}$ alkoxy group, and zero to three fluorine atoms], zero to one hydroxymethyl group, and zero to five fluorine atoms; provided that $R^2$ is neither an unsubstituted $C_{1-8}$alkyl, nor an unsubstituted $C_{3-8}$ cycloalkyl, nor trifluoromethyl group:

each of $R^8$, $R^9$, and $R^{10}$ independently represents a hydrogen atom or $C_{1-8}$ alkyl;

each 4- to 6-membered heterocyclyl represented by $R^2$ is optionally substituted with one to four substituents selected from the group consisting of a fluorine atom, —OH group, $C_{1-4}$ alkyl groups, and $C_{1-4}$ alkoxy groups;

each of $C_{1-8}$ acyl group, —COOR$^8$, and —CONR$^9$R$^{10}$ represented by $R^2$ is optionally substituted independently with one to four substituents selected from the group consisting of a fluorine atom, —OH group, and $C_{1-4}$ alkoxy groups;

$R^9$ and $R^{10}$ of —CONR$^9$R$^{10}$ represented by $R^2$ are optionally bonded via a single bond or —O— to form a ring including the nitrogen atom bonded to $R^9$ and $R^{10}$;

each heterocyclyl group represented by $R^2$ contains one oxygen atom as a heteroatom in the case of a 4- or 5-membered ring, and one to two oxygen atoms as heteroatoms in the case of a 6-membered ring;

$R^3$ represents a hydrogen atom, $C_{1-8}$ alkyl, or a halogen atom;

X represents CR$^{11}$ or a nitrogen atom;

$R^{11}$ represents a hydrogen atom, $C_{1-6}$ alkyl, or $C_{3-6}$ cycloalkyl;

$R^4$ is represented by -A$^1$-A$^2$-A$^3$;

A$^1$ represents a single bond or $C_{1-8}$ alkylene;

one to two sp$^3$ carbon atoms at any positions of A$^1$ are optionally replaced independently with one to two structures selected from the group consisting of [—O—, —NR$^{14}$—, —C(=O)—, —C(=O)—O—, —O—C(=O)—, —O—C(=O)—O—, —C(=O)—NR$^{15}$—, —O—C(=O)—NR$^{16}$—, —NR$^{17}$—C(=O)—, —NR$^{18}$—C(=O)—O—, —NR$^{19}$—C(=O)—NR$^{20}$—, —S(=O)$_p$—, —S(=O)$_2$—NR$^{21}$—, —NR$^{22}$—S(=O)$_2$—, and —NR$^{23}$—S(=O)$_2$—NR$^{24}$—], provided that no structure selected from —O—O—, —O—NR$^{14}$—, —NR$^{14}$—O—, —O—CH$_2$—O—, —O—CH$_2$—NR$^{14}$—, and —NR$^{14}$—CH$_2$—O— is formed in the case of replacement of two sp$^3$ carbon atoms;

A$^2$ represents a single bond, $C_{1-7}$ alkylene, $C_{3-12}$ cycloalkylene, $C_{3-12}$ cycloalkylidene, 4- to 12-membered heterocyclylene, 4- to 12-membered heterocyclylidene, $C_{6-10}$ arylene, or 5- to 10-membered heteroarylene:

A$^3$ represents a halogen, —CN, —NO$_2$, —R$^{25}$, —OR$^{26}$, —NR$^{27}$R$^{28}$, —C(=O)R$^{29}$, —C(O)—OR$^{30}$, —O—C(=O)R$^{31}$, —O—C(=O)—NR$^{32}$R$^{33}$, —C(=O)—NR$^{34}$R$^{35}$, —NR$^{36}$—C(=O)R$^{37}$, —NR$^{38}$—C(=O)—OR$^{39}$, —S(=O)$_2$—R$^{40}$, —S(=O)$_2$—NR$^{41}$R$^{42}$, or —NR$^{43}$—S(=O)$_2$R$^{44}$; provided that A$^3$ represents —R$^{25}$ if the terminal of A$^1$ on the side of A$^2$ is a structure selected from the group consisting of [—O—, —NR$^{14}$—, —C(=O)—, —C(=O)—O—, —O—C(=O)—, —O—C(=O)—O—, —C(=O)—NR$^{15}$—, —O—C(=O)—NR$^{16}$—, —NR$^{17}$—C(=O)—, —NR$^{18}$—C(=O)—O—, —NR$^{19}$—C(=O)—NR$^{20}$—, —S(=O)$_p$—, —S(=O)$_2$—NR$^{21}$—, —NR$^{22}$—S(=O)$_2$—, and —NR$^{23}$—S(=O)$_2$—NR$^{24}$—] and A$^2$ is a single bond;

each of $R^{14}$, $R^{32}$, $R^{34}$, $R^{36}$, $R^{38}$, $R^{41}$, and $R^{43}$ independently represents a hydrogen atom, $C_{1-8}$ alkyl, $C_{1-8}$ acyl, $C_{1-8}$ alkylsulfonyl, 4- to 12-membered heterocyclyl, $C_{3-12}$ cycloalkyl, $C_{6-10}$ aryl, 5- to 10-membered heteroaryl, (4- to 12-membered heterocyclyl)$C_{1-3}$ alkyl, ($C_{3-12}$ cycloalkyl)$C_{1-3}$ alkyl, ($C_{6-10}$ aryl)$C_{1-3}$ alkyl, or (5- to 10-membered heteroaryl)$C_{1-3}$ alkyl;

each of $R^{15}$ to $R^{31}$, $R^{33}$, $R^{35}$, $R^{37}$, $R^{39}$, $R^{40}$, $R^{42}$, and $R^{44}$ independently represents a hydrogen atom, $C_{1-8}$ alkyl, 4- to 12-membered heterocyclyl, $C_{3-12}$ cycloalkyl, $C_{6-10}$ aryl, 5- to 10-membered heteroaryl, (4- to 12-membered heterocyclyl)$C_{1-3}$ alkyl, ($C_{3-12}$ cycloalkyl)$C_{1-3}$ alkyl, ($C_{6-10}$ aryl)$C_{1-3}$ alkyl, or (5- to 10-membered heteroaryl)$C_{1-3}$ alkyl:

each of $A^1$, $A^2$, $A^3$, and $R^{14}$ to $R^{44}$ contained in $A^1$, $A^2$, and $A^3$ are optionally substituted independently with one to four substituents selected from the group consisting of —OH, =O, —COOH, —SO$_3$H, —PO$_3$H$_2$, —CN, —NO$_2$, a halogen, $C_{1-8}$ alkyl substituted with [zero to two —OH groups, zero to two —OR$^{45}$ groups, and zero to six fluorine atoms], $C_{3-12}$ cycloalkyl substituted with [zero to two —OH groups, zero to two —OR$^{46}$ groups, and zero to six fluorine atoms], $C_{1-8}$ alkoxy substituted with [zero to two —OH groups, zero to two —OR$^{47}$ groups, and zero to six fluorine atoms], and 4- to 12-membered heterocyclyl substituted with [zero to two —OH groups, zero to two —OR$^{49}$ groups, and zero to six fluorine atoms]:

$R^{14}$ to $R^{44}$ are optionally bonded in $A^1$, in $A^2$, in $A^3$, [between $A^1$ and $A^2$], [between $A^1$ and $A^3$], or [between $A^2$ and $A^3$] via [a single bond, —O—, —NR$^{50}$—, or —S(=O)$_p$-] to form a ring;

$R^{11}$ is optionally bonded with [$A^1$, $A^2$, or $A^3$] via [a single bond, —O—, —NR$^{51}$—, or —S(=O)$_p$-] to form a ring;

$R^{45}$ to $R^{51}$ each represents a hydrogen atom, or $C_{1-4}$ alkyl substituted with [zero to one —OH group and zero to six fluorine atoms]:

p represents an integer of zero to two; and each of the heterocyclyl, heteroaryl, (heterocyclyl)alkyl, and (heteroaryl)alkyl represented by $A^1$ and $A^3$ and the heterocyclylene, heterocyclylidene, and heteroarylene represented by $A^2$ contains one to four heteroatoms independently selected from oxygen, sulfur, and nitrogen atoms, or a pharmaceutically acceptable salt thereof.

Aspect (2) The compound or pharmaceutically acceptable salt thereof according to aspect (1), wherein $R^1$ represents $C_{3-8}$ cycloalkyl, $C_{4-7}$ cycloalkenyl, 4- to 8-membered heterocyclyl, phenyl, or 5- to 10-membered heteroaryl:

each heteroatom-containing group represented by $R^1$ contains one to four heteroatoms independently selected from oxygen, sulfur, and nitrogen atoms;

$R^1$ is optionally substituted with one to six substituents selected from the group consisting of a fluorine atoms, =O, —OH, —COOH, and $C_{1-6}$ alkyl substituted with [zero to two —OH groups, zero to two $C_{1-8}$ alkoxy groups, and zero to six fluorine atoms];

$R^2$ represents $C_{1-8}$ alkyl, 4- to 6-membered heterocyclyl, $C_{1-8}$ acyl, —COOR$^8$, or —CONR$^9$R$^{10}$;

$C_{1-8}$ alkyl represented by $R^2$ is substituted with zero to one —OH, zero to two $C_{1-8}$ alkoxy groups substituted with [zero to one —OH group, zero to one $C_{1-4}$ alkoxy group, and zero to three fluorine atoms], and zero to five fluorine atoms;

provided that $R^2$ is neither an unsubstituted $C_{1-8}$ alkyl nor trifluoromethyl;

each of $R^8$, $R^9$, and $R^{10}$ independently represents a hydrogen atom or $C_{1-8}$ alkyl;

$R^3$ represents a hydrogen atom or $C_{1-8}$ alkyl;

X represents CR$^{11}$ or a nitrogen atom;

$R^{11}$ represents a hydrogen atom or $C_{1-6}$ alkyl;

$R^4$ is represented by -$A^1$-$A^2$-$A^3$; where $A^1$ represents a single bond or $C_{1-4}$ alkylene;

one sp$^3$ carbon atom at any position of $A^1$ is optionally replaced with one structure selected from the group consisting of [—O—, —NR$^{14}$—, —NR$^{17}$—C(=O)—, and —NR$^{22}$—S(=O)$_2$—], $A^2$ represents a single bond, 4- to 12-membered heterocyclylene, $C_{6-10}$ arylene, or 5- to 10-membered heteroarylene;

$A^3$ represents a halogen, —CN, —R$^{25}$, —OR$^{26}$, —NR$^{27}$R$^{28}$, —C(=O)R$^{29}$, —C(=O)—OR$^{30}$, —O—C(=O)R$^{31}$, —O—C(=O)—NR$^{32}$R$^{33}$, —C(=O)—NR$^{34}$R$^{35}$, —NR$^{36}$—C(=O)R$^{37}$, —NR$^{38}$—C(=O)—OR$^{39}$, —S(=O)$_2$—R$^{40}$, —S(=O)$_2$—NR$^{41}$R$^{42}$, or —NR$^{43}$—S(=O)$_2$R$^{44}$; provided that $A^3$ represents —R$^{25}$ if the terminal of $A^1$ on the side of $A^2$ is [—O—, —NR$^{14}$—, —NR$^{17}$—C(=O)—, or —NR$^{22}$—S(=O)$_2$—] and $A^2$ is a single bond:

each of $R^{14}$, $R^{32}$, $R^{34}$, $R^{36}$, $R^{38}$, $R^{41}$, and $R^{43}$ independently represents a hydrogen atom, $C_{1-8}$ alkyl, $C_{1-8}$ acyl, $C_{1-8}$ alkylsulfonyl, 4- to 12-membered heterocyclyl, $C_{3-12}$ cycloalkyl, $C_{6-10}$ aryl, 5- to 10-membered heteroaryl, (4- to 12-membered heterocyclyl)$C_{1-3}$ alkyl, ($C_{3-12}$ cycloalkyl)$C_{1-3}$ alkyl, ($C_{6-10}$ aryl)$C_{1-3}$ alkyl, or (5- to 10-membered heteroaryl)$C_{1-3}$ alkyl;

each of $R^{15}$ to $R^{31}$, $R^{33}$, $R^{35}$, $R^{37}$, $R^{39}$, $R^{40}$, $R^{42}$, and $R^{44}$ independently represents a hydrogen atom, $C_{1-8}$ alkyl, 4- to 12-membered heterocyclyl, $C_{3-12}$ cycloalkyl, $C_{6-10}$ aryl, 5- to 10-membered heteroaryl, (4- to 12-membered heterocyclyl)$C_{1-3}$ alkyl, ($C_{3-12}$ cycloalkyl)$C_{1-3}$ alkyl, ($C_{6-10}$ aryl)$C_{1-3}$ alkyl, or (5- to 10-membered heteroaryl)$C_{1-3}$ alkyl;

each of $A^1$, $A^2$, $A^3$, and $R^{14}$ to $R^{44}$ in $A^1$, $A^2$, and $A^3$ are optionally substituted independently with one to four substituents selected from the group consisting of —OH, =O, halogen, $C_{1-6}$ alkylsulfonyl, and $C_{1-8}$ alkyl substituted with [zero to one —OH group, and zero to six fluorine atoms];

$R^{11}$ and $A^1$ are optionally bonded via a single bond to form a ring.

Aspect (3) The compound or pharmaceutically acceptable salt thereof according to aspect (1), wherein $R^1$ represents $C_{3-12}$ cycloalkyl.

Aspect (4) The compound or pharmaceutically acceptable salt thereof according to aspect (1), wherein $R^1$ represents 4- to 12-membered heterocyclyl.

Aspect (5) The compound or pharmaceutically acceptable salt thereof according to aspect (1), wherein $R^1$ represents $C_{6-10}$ aryl or 5- to 10-membered heteroaryl.

Aspect 6) The compound or pharmaceutically acceptable salt thereof according to any one of aspects (1) to (5), wherein $R^2$ is $C_{1-8}$ alkyl substituted with one to four fluorine atoms.

Aspect (7) The compound or pharmaceutically acceptable salt thereof according to any one of aspects (1) to (5), wherein $R^2$ is $C_{1-8}$ alkyl substituted with zero to one —OH, and zero to two $C_{1-8}$ alkoxy groups substituted with [zero to one —OH group, zero to one $C_{1-4}$ alkoxy group, and zero to three fluorine atoms].

Aspect (8) The compound or pharmaceutically acceptable salt thereof according to any one of aspects (1) and (3) to (5), wherein $R^2$ is 4- to 6-membered heterocyclyl which is optionally substituted with one to four substituents selected from the group consisting of a fluorine atom, —OH, $C_{1-4}$ alkyl, and $C_{1-4}$ alkoxy.

Aspect (9) The compound or pharmaceutically acceptable salt thereof according to any one of aspects (1) and (3) to (5), wherein $R^2$ is a $C_{1-8}$ acyl group, —COOR$^8$, or —CONR$^9$R$^{10}$, each group is optionally substituted with one to four substituents selected from the group consisting of a fluorine atom, —OH, and $C_{1-8}$ alkoxy.

Aspect (10) The compound or pharmaceutically acceptable salt thereof according to any one of aspects (1) to (9), wherein X represents CR$^{11}$.

Aspect (11) The compound or pharmaceutically acceptable salt thereof according to any one of aspects (1) to (9), wherein X represents a nitrogen atom.

Aspect (12) The compound or pharmaceutically acceptable salt thereof according to any one of aspects (1) to (11), wherein $A^1$ is a single bond.

Aspect (13) The compound or pharmaceutically acceptable salt thereof according to any one of aspects (1) to (11), wherein $A^1$ represents a methylene group whose $sp^3$ carbon atom is not replaced with another structure.

Aspect (14) The compound or pharmaceutically acceptable salt thereof according to any one of aspects (1) to (11), wherein $A^1$ is —O—.

Aspect (15) The compound or pharmaceutically acceptable salt thereof according to any one of aspects (1) to (9), wherein X represents $CR^{11}$;
$R^{11}$ represents $C_{1-6}$ alkyl;
$A^1$ represents $C_{1-8}$ alkylene:
one $sp^3$ carbon atom at any position of $A^1$ is replaced with one structure selected from the group consisting of [—$NR^{14}$—, —$NR^{17}$—C(=O)—, and —$NR^{22}$—S(=O)$_2$—]; and
$R^{11}$ and $A^1$ are bonded via a single bond to form a ring.

Aspect (16) The compound or pharmaceutically acceptable salt thereof according to any one of aspects (1) to (15), wherein $A^2$ represents 5- to 9-membered heterocyclylene; wherein $A^2$ is optionally substituted with one to four substituents selected from the group consisting of —OH, =O, —COOH, —SO$_3$H, —PO$_3$H$_2$, —CN, —NO$_2$, halogen, $C_{1-8}$ alkyl substituted with [zero to two —OH groups, zero to two —$OR^{45}$ groups, and zero to six fluorine atoms], $C_{3-12}$ cycloalkyl substituted with [zero to two —OH groups, zero to two —$OR^{46}$ groups, and zero to six fluorine atoms], $C_{1-8}$ alkoxy substituted with [zero to two —OH groups, zero to two —$OR^{47}$ groups, and zero to six fluorine atoms], and 4- to 12-membered heterocyclyl substituted with [zero to two —OH groups, zero to two —$OR^{49}$ groups, and zero to six fluorine atoms].

Aspect (17) The compound or pharmaceutically acceptable salt thereof according to any one of aspects (1) to (16), wherein $A^3$ is a hydrogen atom.

Aspect (18) The compound or pharmaceutically acceptable salt thereof according to any one of aspects (1) to (16), wherein $A^3$ is a halogen, —CN, —$R^{25}$, —$OR^{26}$, —$NR^{27}R^{28}$, —C(=O)$R^{29}$, or —C(=O)—$OR^{30}$, and each of $R^{25}$ to $R^{30}$ independently represents a hydrogen atom, optionally substituted $C_{1-8}$ alkyl, optionally substituted 4- to 12-membered heterocyclyl, optionally substituted $C_{3-12}$ cycloalkyl, optionally substituted (4- to 12-membered heterocyclyl)$C_{1-3}$ alkyl, or optionally substituted ($C_{3-12}$ cycloalkyl)$C_{1-3}$ alkyl.

Aspect (19) The compound or pharmaceutically acceptable salt thereof according to any one of aspects (1) to (18), wherein $R^3$ is a hydrogen atom.

Aspect (20) The compound or pharmaceutically acceptable salt thereof according to any one of aspects (1) and (3) to (19), wherein $R^3$ represents $C_{1-4}$ alkyl, a fluorine atom, or a chlorine atom.

Aspect (21) A compound or pharmaceutically acceptable salt thereof selected from:

[2-[[5-(4-methylpiperazin-1-yl)pyridin-2-yl]amino]-8-morpholin-4-ylpyrido[3,4-d]pyrimidin-6-yl]methanol
[2-[[5-(4-methylpiperazin-1-yl)pyridin-2-yl]amino]-8-piperidin-1-ylpyrido[34-d]pyrimidin-6-yl]methanol
1-[6-(hydroxymethyl)-2-[[5-(4-methylpiperazin-1-yl)pyridin-2-yl]amino]pyrido[3,4-d]pyrimidin-8-yl]piperidin-2-one
6-(difluoromethyl)-N-[5-(4-methylpiperazin-1-yl)pyridin-2-yl]-8-morpholin-4-ylpyrido[3,4-d]pyrimidin-2-amine
[8-cyclohexyl-2-[[5-(4-methylpiperazin-1-yl)pyridin-2-yl]amino]pyrido[3,4-d]pyrimidin-6-yl]methanol
[2-[[5-(4-methylpiperazin-1-yl)pyridin-2-yl]amino]-8-phenylpyrido[3,4-d]pyrimidin-6-yl]methanol
[8-morpholin-4-yl-2-[(5-piperazin-1-ylpyridin-2-yl)amino]pyrido[3,4-d]pyrimidin-6-yl]methanol
6-(difluoromethyl)-8-morpholin-4-yl-N-(5-piperazin-1-ylpyridin-2-yl)pyrido[3,4-d]pyrimidin-2-amine
[2-[(5-piperazin-1-ylpyridin-2-yl)amino]-8-piperidin-1-ylpyrido[3,4-d]pyrimidin-6-yl]methanol
[8-phenyl-2-[(5-piperazin-1-ylpyridin-2-yl)amino]pyrido[3,4-d]pyridin-6-yl]methanol
6-(difluoromethyl)-N-(5-piperazin-1-ylpyridin-2-yl)-8-piperidin-1-ylpyrido[3,4-d]pyrimidin-2-amine
6-(difluoromethyl)-8-phenyl-N-(5-piperazin-1-ylpyridin-2-yl)pyrido[3,4-d]pyrimidin-2-amine
6-(difluoromethyl)-N-[5-(4-methylpiperazin-1-yl)pyridin-2-yl]-8-piperidin-1-ylpyrido[3,4-d]pyrimidin-2-amine
[8-(4-methylphenyl)-2-[(5-piperazin-1-ylpyridin-2-yl)amino]pyrido[3,4-d]pyrimidin-6-yl]methanol
[8-(2-methylphenyl)-2-[(5-piperazin-1-ylpyridin-2-yl)amino]pyrido[3,4-d]pyrimidin-6-yl]methanol
[2-[(5-piperazin-1-ylpyridin-2-yl)amino]-8-thiophen-3-ylpyrido[3,4-d]pyrimidin-6-yl]methanol
[8-(furan-3-yl)-2-[(5-piperazin-1-ylpyridin-2-yl)amino]pyrido[3,4-d]pyrimidin-6-yl]methanol
[8-(4-methylphenyl)-2-[[5-(4-methylpiperazin-1-yl)pyridin-2-yl]amino]pyrido[3,4-d]pyrimidin-6-yl]methanol
[8-(2-methylphenyl)-2-[[5-(4-methylpiperazin-1-yl)pyridin-2-yl]amino]pyrido[3,4-d]pyrimidin-6-yl]methanol
[2-[[5-(4-methylpiperazin-1-yl)pyridin-2-yl]amino]-8-thiophen-3-ylpyrido[3,4-d]pyrimidin-6-yl]methanol
[8-(furan-3-yl)-2-[[5-(4-methylpiperazin-1-yl)pyridin-2-yl]amino]pyrido[3,4-d]pyrimidin-6-yl]methanol
[8-(cyclohexen-1-yl)-2-[[5-(4-methylpiperazin-1-yl)pyridin-2-yl]amino]pyrido[3,4-d]pyrimidin-6-yl]methanol
2-[(5-piperazin-1-ylpyridin-2-yl)amino]-8-piperidin-1-ylpyrido[3,4-d]pyrimidine-6-carboxylic acid
1-[2-[(5-piperazin-1-ylpyridin-2-yl)amino]-8-piperidin-1-ylpyrido[3,4-d]pyrimidin-6-yl]ethanol
methyl 2-[(5-piperazin-1-ylpyridin-2-yl)amino]-8-piperidin-1-ylpyrido[3,4-d]pyrimidine-6-carboxylate
1-[2-[(5-piperazin-1-yl pyridin-2-yl)amino]-8-piperidin-1-ylpyrido[3,4-d]pyrimidin-6-yl]ethanone
N,N-dimethyl-2-[(5-piperazin-1-ylpyridin-2-yl)amino]-8-piperidin-1-ylpyrido[3,4-d]pyrimidine-6-carboxamide
2-[(5-piperazin-1-ylpyridin-2-yl)amino]-8-piperidin-1-ylpyrido[3,4-d]pyrimidine-6-carboxamide
N-methyl-2-[(5-piperazin-1-ylpyridin-2-yl)amino]-8-piperidin-1-ylpyrido[3,4-d]pyrimidine-6-carboxamide
6-(difluoromethyl)-8-(2-methylphenyl)-N-(5-piperazin-1-ylpyridin-2-yl)pyrido[3,4-d]pyrimidin-2-amine
6-(difluoromethyl)-8-(furan-3-yl)-N-(5-piperazin-1-ylpyridin-2-yl)pyrido[3,4-d]pyrimidin-2-amine
6-(methoxymethyl)-8-morpholin-4-yl-N-(5-piperazin-1-ylpyridin-2-yl)pyrido[3,4-d]pyrimidin-2-amine
[5-methyl-8-morpholin-4-yl-2-[(5-piperazin-1-ylpyridin-2-yl)amino]pyrido[3,4-d]pyrimidin-6-yl]methanol
1-[8-morpholin-4-yl-2-[(5-piperazin-1-ylpyridin-2-yl)amino]pyrido[3,4-d]pyrimidin-6-yl]propan-1-ol
2,2,2-trifluoro-1-[8-morpholin-4-yl-2-[(5-piperazin-1-ylpyridin-2-yl)amino]pyrido[3,4-d]pyrimidin-6-yl]ethanol
6-(1,1-difluoroethyl)-8-morpholin-4-yl-N-(5-piperazin-1-ylpyridin-2-yl)pyrido[3,4-d]pyrimidin-2-amine 2-[8-morpholin-4-yl-2-[(5-piperazin-1-ylpyridin-2-yl)
amino]pyrido[3,4-d]pyrimidin-6-yl]propan-2-ol
2-[8-morpholin-4-yl-2-[(5-piperazin-1-ylpyridin-2-yl)
amino]pyrido[3,4-d]pyrimidin-6-yl]ethanol
1-[6-[(1R)-1-hydroxyethyl]-2-[(6-piperazin-1-ylpyridazin-3-yl)amino]pyrido[3,4-d]pyrimidin-8-yl]pyrrolidine-2-carboxylic acid
1-[6-[(1R)-1-hydroxyethyl-2-[(6-piperazin-1-ylpyridazin-3-yl)amino]pyrido[3,4-d]pyrimidin-8-yl]piperidine-3-carboxylic acid
1-[6-[(1R)-1-hydroxyethyl]-2-[(6-piperazin-1-ylpyridazin-3-yl)amino]pyrido[3,4-d]pyrimidin-8-yl]piperidine-2-carboxylic acid
1-[6-[(1R)-1-hydroxyethyl]-2-[[5-(piperazin-1-ylmethyl)pyridin-2-yl]amino]pyrido[3,4-d]pyrimidin-8-yl]pyrrolidine-2-carboxylic acid
6-(1-methoxyethyl)-N-[5-(piperazin-1-ylmethyl)pyridin-2-yl]-8-piperidin-1-ylpyrido[3,4-d]pyrimidin-2-amine
8-(1,2,3,3a,4,5,7,7a-octahydropyrrolo[2,3-c]pyridin-6-yl)-6-(1-methoxyethyl)-N-[5-(piperazin-1-ylmethyl)pyridin-2-ylpyrido 3,4-d]pyrimidin-2-amine
1-[6-(1-methoxyethyl)-2-[[5-(piperazin-1-ylmethyl)pyridin-2-yl]amino]pyrido[3,4-d]pyrimidin-8-yl]piperidin-4-yl]methanol
6-(1-methoxyethyl)-8-[4-(methoxymethyl)piperidin-1-yl]-N-[5-(piperazin-1-ylmethyl)pyridin-2-yl]pyrido[3,4-d]pyrimidin-2-amine
(1R)-1-[8-(azetidin-1-yl)-2-[[5-[[4-(2-hydroxyethyl)piperazin-1-yl]methyl]pyridin-2-yl]amino]pyrido[3,4-d]pyrimidin-6-yl]ethanol
(1R)-1-[2-[[5-[[4-(2-hydroxyethyl)piperazin-1-yl]methyl]pyridin-2-yl]amino]-8-pyrrolidin-1-ylpyrido[3,4-d]pyrimidin-6-yl]ethanol
(1R)-1-[2-[[5-[[4-(2-hydroxyethyl)piperazin-1-yl]methyl]pyridin-2-yl]amino]-8-piperidin-1-ylpyrido[3,4-d]pyrimidin-6-yl]ethanol
1-[6-[[8-(azetidin-1-yl)-6-[(1R)-1-hydroxyethyl]pyrido[3,4-d]pyrimidin-2-yl]amino]pyridin-3-yl]piperazin-2-one
1-[6-[[6-[(1R)-1-hydroxyethyl]-8-pyrrolidin-1-ylpyrido[3,4-d]pyrimidin-2-yl]amino]pyridin-3-yl]piperazin-2-one
1-[6-[[6-[(1R)-1-hydroxyethyl]-8-piperidin-1-ylpyrido[3,4-d]pyrimidin-2-yl]amino]pyridin-3-yl]piperazin-2-one
(1R)-1-[2-[[6-methyl-5-(4-methylpiperazin-1-yl)pyridin-2-yl]amino]-8-pyrrolidin-1-ylpyrido[3,4-d]pyrimidin-6-yl]ethanol
(1R)-1-[2-[[6-methyl-5-(4-methylpiperazin-1-yl)pyridin-2-yl]amino]-8-piperidin-1-ylpyrido[3,4-d]pyrimidin-6-yl]ethanol
(1R)-1-[2-[[5-(4-methylpiperazin-1-yl)methyl]pyridin-2-yl]amino]-8-pyrrolidin-1-ylpyrido[3,4-d]pyrimidin-6-yl]ethanol
(1R)-1-[2-[[5-[(4-methylpiperazin-1-yl)methyl]pyridin-2-yl]amino]-8-piperidin-1-ylpyrido[3,4-d]pyrimidin-6-yl]ethanol
(1R)-1-[8-(2-azaspiro[3.3]heptan-2-yl)-2-[[5-[[4-(2-hydroxyethyl)piperazin-1-yl]methyl]pyridin-2-yl]amino]pyrido[3,4-d]pyrimidin-6-yl]ethanol
(1R)-1-[2-[[5-[[4-(2-hydroxyethyl)piperazin-1-yl]methyl]pyridin-2-yl]amino]-8-morpholin-4-ylpyrido[3,4-d]pyrimidin-6-yl]ethanol
(1R)-1-[8-(azepan-1-yl)-2-[[5-[[4-(2-hydroxyethyl)piperazin-1-yl]methyl]pyridin-2-yl]amino]pyrido[3,4-d]pyrimidin-6-yl]ethanol
(1R)-1-[2-[[6-[2-(dimethylamino)ethyl]-7,8-dihydro-5H-1,6-naphthyridin-2-yl]amino]-8-piperidin-1-ylpyrido[3,4-d]pyrimidin-6-yl]ethanol
(1R)-1-[2-[[6-[2-(dimethylamino)ethyl]-7,8-dihydro-5H-1,6-naphthyridin-2-yl]amino]-8-(4-fluoropiperidin-1-yl)pyrido[3,4-d]pyrimidin-6-yl]ethanol
(1R)-1-[8-piperidin-1-yl-2-(5,6,7,8-tetrahydro-1,6-naphthyridin-2-ylamino)pyrido[3,4-d]pyrimidin-6-yl]ethanol
(1R)-1-[8-(4-fluoropiperidin-1-yl)-2-(5,6,7,8-tetrahydro-1,6-naphthyridin-2-ylamino)pyrido[3,4-d]pyrimidin-6-yl]ethanol
1-[6-[[8-(4,4-difluoropiperidin-1-yl)-6-[(1R)-1-hydroxyethyl]pyrido[3,4-d]pyrimidin-2-yl]amino]pyridin-3-yl]piperazin-2-one
1-[[6-[[6-[(1R)-1-hydroxyethyl]-8-piperidin-1-ylpyrido[3,4-d]pyrimidin-2-yl]amino]pyridin-3-yl]methyl]piperidin-4-ol
1-[[6-[[6-[(1R)-1-hydroxyethyl]-8-pyrrolidin-1-ylpyrido[3,4-d]pyrimidin-2-yl]amino]pyridin-3-yl]methyl]piperidin-4-ol
1-[[6-[[6-[(1R)-1-hydroxyethyl]-8-morpholin-4-ylpyrido[3,4-d]pyrimidin-2-yl]amino]pyridin-3-yl]methyl]piperidin-4-ol
(1R)-1-[2-[[5-[[4-(hydroxymethyl)piperidin-1-yl]methyl]pyridin-2-yl]amino]-8-piperidin-1-ylpyrido[3,4-d]pyrimidin-6-yl]ethanol
(1R)-1-[2-[[[5-[[4-(hydroxymethyl)piperidin-1-yl]methyl]pyridin-2-yl]amino]-8-pyrrolidin-1-ylpyrido[3,4-d]pyrimidin-6-yl]ethanol
(1R)-1-[2-[[5-[[4-(hydroxymethyl)piperidin-1-yl]methyl]pyridin-2-yl]amino]-8-morpholin-4-ylpyrido[3,4-d]pyrimidin-6-yl]ethanol
1-[6-[(1R)-1-hydroxyethyl-2-[[5-[[4-(hydroxymethyl)piperidin-1-yl]methyl]pyridin-2-yl]amino]pyrido[3,4-d]pyrimidin-8-yl]piperidin-4-ol
1-[6-[[6-[(1R)-1-hydroxyethyl]-8-piperidin-1-ylpyrido[3,4-d]pyrimidin-2-yl]amino]pyridin-3-yl]-4-methylpiperazin-2-one
1-[6-[[6-[(1R)-1-hydroxyethyl]-8-pyrrolidin-1-ylpyrido[3,4-d]pyrimidin-2-yl]amino]pyridin-3-yl]-4-methylpiperazin-2-one
1-[6-[[6-[(1R)-1-hydroxyethyl]-8-morpholin-4-ylpyrido[3,4-d]pyrimidin-2-yl]amino]pyridin-3-yl-4-methylpiperazin-2-one
(1R)-1-[8-(2,2-dimethylpyrrolidin-1-yl)-2-[[5-[[4-(2-hydroxyethyl)piperazin-1-yl]methyl]pyridin-2-yl]amino]pyrido[3,4-d]pyrimidin-6-yl]ethanol
1-[6-[(1R)-1-hydroxyethyl]-2-[[5-[[4-(2-hydroxyethyl)piperazin-1-yl]methyl]pyridin-2-yl]amino]pyrido[3,4-d]pyrimidin-8-yl]piperidine-4-carboxylic acid
(1R)-1-[2-[[5-[[4-(2-hydroxyethyl)piperazin-1-yl]methyl]pyridin-2-yl]amino]-8-(4-methylpiperazin-1-yl)pyrido[3,4-d]pyrimidin-6-yl]ethanol
(1R)-1-[8-(4-fluoropiperidin-1-yl)-2-[[5-[[4-(2-hydroxyethyl)piperazin-1-yl]methyl]pyridin-2-yl]amino]pyrido[3,4-d]pyrimidin-6-yl]ethanol
(1R)-1-[8-(4,4-difluoropiperidin-1-yl)-2-[[5-[[4-(2-hydroxyethyl)piperazin-1-yl]methyl]pyridin-2-yl]amino]pyrido[3,4-d]pyrimidin-6-yl]ethanol
(1R)-1-[8-(4,4-difluoropiperidin-1-yl)-2-(5,6,7,8-tetrahydro-1,6-naphthyridin-2-ylamino)pyrido[3,4-d]pyrimidin-6-yl]ethanol
(1R)-1-[8-(4,4-difluoropiperidin-1-yl)-2-[[6-(2-hydroxyethyl)-7,8-dihydro-5H-1,6-naphthyridin-2-yl]amino]pyrido[3,4-d]pyrimidin-6-yl]ethanol
(1R)-1-[8-(4,4-difluoropiperidin-1-yl)-2-[[6-[2-(dimethylamino)ethyl]-7,8-dihydro-5H-1,6-naphthyridin-2-yl]amino]pyrido[3,4-d]pyrimidin-6-yl]ethanol (1R)-1-[2-[[5-[[4-(2-hydroxyethyl)piperazin-1-yl]methyl]pyridin-2-yl]amino]-8-[(2R)-2-methylpyrrolidin-1-yl]pyrido[3,4-d]pyrimidin-6-yl]ethanol (1R)-1-[2-[[5-[[4-(2-hydroxyethyl)piperazin-1-yl]methyl]pyridin-2-yl]amino]-8-[4-(trifluoromethyl)piperidin-1-yl]pyrido[3,4-d]pyrimidin-6-yl]ethanol (1R)-1-[8-(1,1-dioxo-1,4-thiazinan-4-yl)-2-[[5-[[4-(2-hydroxyethyl)piperazin-1-yl]methyl]pyridin-2-yl]amino]pyrido[3,4-d]pyrimidin-6-yl]ethanol (1R)-1-[2-[(6-methyl-5-piperazin-1-ylpyridin-2-yl)amino]-8-pyrrolidin-1-ylpyrido[3,4-d]pyrimidin-6-yl]ethanol (1R)-1-[2-[(6-methyl-5-piperazin-1-ylpyridin-2-yl)amino]-8-piperidin-1-ylpyrido[3,4-d]pyrimidin-6-yl]ethanol (1R)-1-[2-[[5-[4-(2-hydroxyethyl)piperazin-1-yl]-6-methylpyridin-2-yl]amino]-8-piperidin-1-ylpyrido[3,4-d]pyrimidin-6-yl]ethanol 4-[6-[[6-[(1R)-1-hydroxyethyl]-8-piperidin-1-ylpyrido[3,4-d]pyrimidin-2-yl]amino]pyridin-3-yl]-1,4-diazepan-5-one 1-[6-[[8-(4-fluoropiperidin-1-yl)-6-[(1R)-1-hydroxyethyl]pyrido[3,4-d]pyrimidin-2-yl]amino]pyridin-3-yl]piperazin-2-one (1R)-1-[2-[(6-piperazin-1-ylpyridazin-3-yl)amino]-8-piperidin-1-ylpyrido[3,4-d]pyrimidin-6-yl]ethanol 2-[2-[[5-(piperazin-1-ylmethyl)pyridin-2-yl]amino]-8-piperidin-1-ylpyrido[3,4-d]pyrimidin-6-yl]ethanol 1-[6-[[6-(2-hydroxyethyl)-8-piperidin-1-ylpyrido[3,4-d]pyrimidin-2-yl]amino]pyridin-3-yl]piperazin-2-one 2-[2-[(6-piperazin-1-ylpyridazin-3-yl)amino]-8-piperidin-1-ylpyrido[3,4-d]pyrimidin-6-yl]ethanol 2-[8-piperidin-1-yl-2-(5,6,7,8-tetrahydro-1,6-naphthyridin-2-ylamino)pyrido[3,4-d]pyrimidin-6-yl]ethanol 2-[4-[[6-[[6-(hydroxymethyl)-8-piperidin-1-ylpyrido[3,4-d]pyrimidin-2-yl]amino]pyridin-3-yl]methyl]piperazin-1-yl]ethanol 1-[6-[[6-(hydroxymethyl)-8-piperidin-1-ylpyrido[3,4-d]pyrimidin-2-yl]amino]pyridin-3-yl]piperazin-2-one (1R)-1-[2-[[5-[[4-(2-hydroxyethyl)piperazin-1-yl]methyl]pyridin-2-yl]amino]-8-[(2S)-2-methylpyrrolidin-1-yl]pyrido[3,4-d]pyrimidin-6-yl]ethanol (1R)-1-[2-[[5-[[4-(2-hydroxyethyl)piperazin-1-yl]methyl]pyridin-2-yl]amino]-8-[(3S)-3-methylpyrrolidin-1-yl]pyrido[3,4-d]pyrimidin-6-yl]ethanol (1R)-1-[2-[[5-[[4-(2-hydroxyethyl)piperazin-1-yl]methyl]pyridin-2-yl]amino]-8-[(3R)-3-methylpyrrolidin-1-yl]amino]pyrido[3,4-d]pyrimidin-6-yl]ethanol (1R)-1-[8-(2,5-dimethylpyrrolidin-1-yl)-2-[[5-[[4-(2-hydroxyethyl)piperazin-1-yl]methyl]pyridin-2-yl]amino]pyrido[3,4-d]pyrimidin-6-yl]ethanol (1R)-1-[8-(3,3-dimethylpyrrolidin-1-yl)-2-[[5-[[4-(2-hydroxyethyl)piperazin-1-yl]methyl]pyridin-2-yl]amino]pyrido[3,4-d]pyrimidin-6-yl]ethanol (1R)-1-[8-(7-azabicyclo[2.2.1]heptan-7-yl)-2-[[5-[[4-(2-hydroxyethyl)piperazin-1-yl]methyl]pyridin-2-yl]amino]pyrido[3,4-d]pyrimidin-6-yl]ethanol (1R)-1-[8-(3-azabicyclo[3.1.0]hexan-3-yl)-2-[[5-[[4-(2-hydroxyethyl)piperazin-1-yl]methyl]pyridin-2-yl]amino]pyrido[3,4-d]pyrimidin-6-yl]ethanol (1R)-1-[8-(8-azabicyclo[3.2.1]octan-8-yl)-2-[[5-[[4-(2-hydroxyethyl 1)piperazin-1-yl]methyl]pyridin-2-yl]amino]pyrido[3,4-d]pyrimidin-6-yl]ethanol 1-[6-[(1R)-1-hydroxyethyl]-2-[[5-[[4-(2-hydroxyethyl)piperazin-1-yl]methyl]pyridin-2-yl]amino]pyrido[3,4-d]pyrimidin-8-yl]piperidin-4-ol

[2-[(6-piperazin-1-ylpyridazin-3-yl)amino]-8-piperidin-1-ylpyrido[3,4-d]pyrimidin-6-yl]methanol

[2-[[5-(piperazin-1-ylmethyl)pyridin-2-yl]amino]-8-piperidin-1-ylpyrido[3,4-d]pyrimidin-6-yl]methanol 2-[2-[[6-(2-hydroxyethyl)-7,8-dihydro-5H-1,6-naphthyridin-2-yl]amino]-8-piperidin-1-ylpyrido[3,4-d]pyrimidin-6-yl]ethanol 2-[2-[[6-[2-(dimethylamino)ethyl]-7,8-dihydro-5H-1,6-naphthyridin-2-yl]amino]-8-piperidin-1-ylpyrido[3,4-d]pyrimidin-6-yl]ethanol (1R)-1-[2-[[6-(2-hydroxyethyl)-7,8-dihydro-5H-1,6-naphthyridin-2-yl]amino]-8-piperidin-1-ylpyrido[3,4-d]pyrimidin-6-yl]ethanol (1R)-1-[8-(4-fluoropiperidin-1-yl)-2-[[6-(2-hydroxyethyl)-7,8-dihydro-5H-1,6-naphthyridin-2-yl]amino]pyrido[3,4-d]pyrimidin-6-yl]ethanol (1R)-1-[8-(3,4-dimethylpyrrolidin-1-yl)-2-[[5-[[4-(2-hydroxyethyl)piperazin-1-yl]methyl]pyridin-2-yl]amino]pyrido[3,4-d]pyrimidin-6-yl]ethanol (1R)-1-[2-[[6-[4-(2-methylsulfonylethyl)piperazin-1-yl]pyridazin-3-yl]amino]-8-piperidin-1-ylpyrido[3,4-d]pyrimidin-6-yl]ethanol (1R)-1-[8-(4-fluoropiperidin-1-yl)-2-[[5-[(4-methyl)piperazin-1-yl]methyl]pyridin-2-yl]amino]pyrido[3,4-d]pyrimidin-6-yl]ethanol (1R)-1-[8-[(3R)-3-fluoropyrrolidin-1-yl]-2-[[5-[(4-methylpiperazin-1-yl)methyl]pyridin-2-yl]amino]pyrido[3,4-d]pyrimidin-6-yl]ethanol (1R)-1-[8-(3S)-3-fluoropyrrolidin-1-yl-2-[[5-[(4-methylpiperazin-1-yl)methyl]pyridin-2-yl]amino]pyrido[3,4-d]pyrimidin-6-yl]ethanol 6-[(1R)-1-methoxyethyl]-N-(6-piperazin-1-ylpyridazin-3-yl)-8-piperidin-1-ylpyrido[3,4-d]pyrimidin-2-amine 6-[(1R)-1-methoxyethyl]-N-[5-(piperazin-1-ylmethyl)pyridin-2-yl]-8-piperidin-1-ylpyrido[3,4-d]pyrimidin-2-amine 4-[6-[[6-[(1R)-1-hydroxyethyl]-8-pyrrolidin-1-ylpyrido[3,4-d]pyrimidin-2-yl]amino]pyridin-3-yl]-1-methyl-1,4-diazepan-5-one 4-[6-[[6-[(1R)-1-hydroxyethyl]-8-piperidin-1-ylpyrido[3,4-d]pyrimidin-2-yl]amino]pyridin-3-yl]-1-methyl-1,4-diazepan-5-one (1R)-1-[2-[[5-(4-ethylpiperazin-1-yl)methyl]pyridin-2-yl]amino]-8-piperidin-1-ylpyrido[3,4-d]pyrimidin-6-yl]ethanol (1R)-1-[2-[[6-(4-methylpiperazin-1-yl)pyridazin-3-yl]amino]-8-piperidin-1-ylpyrido[3,4-d]pyrimidin-6-yl]ethanol (1R)-1-[8-(4-fluoropiperidin-1-yl)-2-[[6-(4-methylpiperazin-1-yl)pyridazin-3-yl]amino]pyrido[3,4-d]pyrimidin-6-yl]ethanol 8-(4-fluoropiperidin-1-yl)-6-[(1R)-1-methoxyethyl]-N-[6-(4-methylpiperazin-1-yl)pyridazin-3-yl]pyrido[3,4-d]pyrimidin-2-amine 8-(4-fluoropiperidin-1-yl)-6-[(1R)-1-methoxyethyl]-N-(6-piperazin-1-ylpyridazin-3-yl)pyrido[3,4-d]pyrimidin-2-amine 1-[6-[[6-[(1R)-1-hydroxyethyl]-8-piperidin-1-ylpyrido[3,4-d]pyrimidin-2-yl]amino]pyridin-3-yl]-1,4-diazepan-2-one 2-[4-[[6-[[6-(difluoromethyl)-8-piperidin-1-ylpyrido[3,4-d]pyrimidin-2-yl]amino]pyridin-3-yl]methyl]piperazin-1-yl]ethanol 1-[6-(difluoromethyl)-2-[[5-[[4-(2-hydroxyethyl)piperazin-1-yl]methyl]pyridin-2-yl]amino]pyrido[3,4-d]pyrimidin-8-yl]piperidin-4-ol 3-[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]propan-1-ol (1R)-1-[2-[[5-[(3S,4S)-3-fluoro-1-(2-hydroxyethyl)piperidin-4-yl]oxypyridin-2-yl]amino-8-piperidin-1-ylpyrido[3,4-d]pyrimidin-6-yl]ethanol (1R)-1-[2-[[5-[(3S,4R)-3-fluoro-1-(2-hydroxyethyl)piperidin-4-yl]oxypyridin-2-yl]amino]-8-piperidin-1-ylpyrido[3,4-d]pyrimidin-6-yl]ethanol (1R)-1-[8-(3,3-difluoroazetidin-1-yl)-2-[[5-(4-methylpiperazin-1-yl)methyl]pyridin-2-yl]amino]pyrido[3,4-d]pyrimidin-6-yl]ethanol 1-[6-[(1R)-1-hydroxyethyl]-2-[[5-[(4-methylpiperazin-1-yl)methyl]pyridin-2-yl]amino]pyrido[3,4-d]pyrimidin-8-yl]piperidin-4-ol 2-[2-[[6-(hydroxymethyl)-8-piperidin-1-ylpyrido[3,4-d]pyrimidin-2-yl]amino]-7,8-dihydro-5H-1,6-naphthyridin-6-yl]ethanol (1R)-1-[2-[[5-[(4-methylpiperazin-1-yl)methyl]pyridin-2-yl]amino]-8-[(2R)-2-methylpyrrolidin-1-yl]pyrido[3,4-d]pyrimidin-6-yl]ethanol (1R)-1-[2-[[5-(4-methylpiperazin-1-yl)methyl]pyridin-2-yl]amino]-8-[(2S)-2-methylpyrrolidin-1-yl]pyrido[3,4-d]pyrimidin-6-yl]ethanol (1R)-1-[2-[[5-[(4-methylpiperazin-1-yl)methyl]pyridin-2-yl]amino]-8-[(3R)-3-methylpyrrolidin-1-yl]pyrido[3,4-d]pyrimidin-6-yl]ethanol (1R)-1-[2-[[5-[(4-methylpiperazin-1-yl)methyl]pyridin-2-yl]amino]-8-[(3S)-3-methylpyrrolidin-1-yl]pyrido[3,4-d]pyrimidin-6-yl]ethanol (1R)-1-[8-(2,5-dimethylpyrrolidin-1-yl)-2-[[5-[(4-methylpiperazin-1-yl)methyl]pyridin-2-yl]amino]pyrido[3,4-d]pyrimidin-6-yl]ethanol (1R)-1-[8-(3,4-dimethylpyrrolidin-1-yl)-2-[[5-[(4-methylpiperazin-1-yl)methyl]pyridin-2-yl]amino]pyrido[3,4-d]pyrimidin-6-yl]ethanol (1R)-1-[8-(3,3-dimethylpyrrolidin-1-yl)-2-[[5-[(4-methylpiperazin-1-yl)methyl]pyridin-2-yl]amino]pyrido[3,4-d]pyrimidin-6-yl]ethanol (1R)-1-[8-(7-azabicyclo[2.2.1]heptan-7-yl)-2-[[5-(4-methylpiperazin-1-yl)methyl]pyridin-2-yl]amino]pyrido[3,4-d]pyrimidin-6-yl]ethanol (1R)-1-[2-[[5-[(4-methylpiperazin-1-yl)methyl]pyridin-2-yl]amino]-8-[4-(trifluoromethyl)piperidin-1-yl]pyrido[3,4-d]pyrimidin-6-yl]ethanol (1R)-1-[2-[[5-[(4-methylpiperazin-1-yl)methyl]pyridin-2-yl]amino]-8-morpholin-4-ylpyrido[3,4-d]pyrimidin-6-yl]ethanol 1-[2-[[5-[(4-methylpiperazin-1-yl)methyl]pyridin-2-yl]amino]-8-piperidin-1-ylpyrido[3,4-d]pyrimidin-6-yl]propan-1-ol

[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl-piperidin-4-yl]methanone

[1-(2-hydroxyethyl)piperidin-4-yl]-[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]methanone

[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]-(1-methylpiperidin-4-yl)methanone (1R)-1-[8-(4,4-difluoropiperidin-1-yl)-2-[[5-[(4-methylpiperazin-1-yl)methyl]pyridin-2-yl]amino]pyrido[3,4-d]pyrimidin-6-yl]ethanol 1-(2-hydroxyethyl)-4-[6-[[6-[(1R)-1-hydroxyethyl]-8-piperidin-1-ylpyrido[3,4-d]pyrimidin-2-yl]amino]pyridin-3-yl]-1,4-diazepan-5-one (1R)-1-[2-[[5-[[(2R)-2,4-dimethylpiperazin-1-yl]methyl]pyridin-2-yl]amino]-8-piperidin-1-ylpyrido[3,4-d]pyrimidin-6-yl]ethanol (1R)-1-[8-cyclopropyl-2-[[5-[[4-(2-hydroxyethyl)piperazin-1-ylmethyl]pyridin-2-yl]amino]pyrido[3,4-d]pyrimidin-6-yl]ethanol 1-[6-[[8-cyclopropyl-6-[(1R)-1-hydroxyethyl]pyrido[3,4-d]pyrimidin-2-yl]amino]pyridin-3-yl]piperazin-2-one (1R)-1-[2-[[5-(piperazin-1-ylmethyl)pyridin-2-yl]amino]-8-piperidin-1-ylpyrido[3,4-d]pyrimidin-6-yl]ethanol (1R)-1-[8-(cyclohexen-1-yl)-2-[[5-[[4-(2-hydroxyethyl)piperazin-1-yl]methyl]pyridin-2-yl]amino]pyrido[3,4-d]pyrimidin-6-yl]ethanol (1R)-1-[8-(3-azabicyclo[3.1.0]hexan-3-yl)-2-[[5-[(4-methylpiperazin-1-yl)methyl]pyridin-2-yl]amino]pyrido[3,4-d]pyrimidin-6-yl]ethanol (1R)-1-[8-(azepan-1-yl)-2-[[5-[(4-methylpiperazin-1-yl)methyl]pyridin-2-yl]amino]pyrido[3,4-d]pyrimidin-6-yl]ethanol (1R)-1-[2-[[5-[[4-(2-hydroxyethyl)piperazin-1-yl]methyl]pyridin-2-yl]amino]-8-piperidin-1-ylpyrido[3,4-d]pyrimidin-6-yl]propan-1l-ol (1S)-1-[2-[[5-[[4-(2-hydroxyethyl)piperazin-1-ylmethyl]pyridin-2-yl]amino]-8-piperidin-1-ylpyrido[3,4-d]pyrimidin-6-yl]propan-1-ol (1R)-1-[2-[[6-(oxetan-3-yl)-7,8-dihydro-5H-1,6-naphthyridin-2-yl]amino]-8-piperidin-1-yl]pyrido[3,4-d]pyrimidin-6-yl]ethanol (1R)-1-[2-[[6-(2-morpholin-4-ylethyl)-7,8-dihydro-5H-1,6-naphthyridin-2-yl]amino]-8-piperidin-1-ylpyrido[3,4-d]pyrimidin-6-yl]ethanol (1R)-1-[8-piperidin-1-yl-2-[(6-piperidin-4-ylsulfonyl-7,8-dihydro-5H-1,6-naphthyridin-2-yl)amino]pyrido[3,4-d]pyrimidin-6-yl]ethanol (1R)-1-[8-piperidin-1-yl-2-[(5-piperidin-4-yl)oxypyridin-2-yl)amino]pyrido[3,4-d]pyrimidin-6-yl]ethanol (1R)-1-[2-[[5-[1-(2-hydroxyethyl)piperidin-4-yl]oxypyridin-2-yl]amino]-8-piperidin-1-ylpyrido[3,4-d]pyrimidin-6-yl]ethanol (2S)-2-[8-piperidin-1-yl-2-(5,6,7,8-tetrahydro-1,6-naphthyridin-2-ylamino)pyrido[3,4-d]pyrimidin-6-yl]propan-1-ol (2R)-2-[2-[[5-[[4-(2-hydroxyethyl)piperazin-1-yl]methyl]pyridin-2-yl]amino]-8-piperidin-1-ylpyrido[3,4-d]pyrimidin-6-yl]propan-1-ol (2R)-1-[2-[[5-[[4-(2-hydroxyethyl)piperazin-1-yl]methyl]pyridin-2-yl]amino]-8-piperidin-1-ylpyrido[3,4-d]pyrimidin-6-yl]propan-2-ol 1-[6-[[6-[(2R)-2-hydroxypropyl]-8-piperidin-1-yl pyrido[3,4-d]pyrimidin-2-yl]amino]pyridin-3-yl]piperazin-2-one (2R)-1-[2-[[6-(2-hydroxyethyl)-7,8-dihydro-5H-1,6-naphthyridin-2-yl]amino]-8-piperidin-1-ylpyrido[3,4-d]pyrimidin-6-yl]propan-2-ol (2R)-2-[2-[[6-(2-hydroxyethyl)-7,8-dihydro-5H-1,6-naphthyridin-2-yl]amino]-8-piperidin-1-ylpyrido[3,4-d]pyrimidin-6-yl]propan-1-ol (1R)-1-[8-(azetidin-1-yl)-2-[[5-(4-methylpiperazin-1-yl)methyl]pyridin-2-yl]amino]pyrido[3,4-d]pyrimidin-6-yl]ethanol (1R)-1-[8-(2,2-dimethylpyrrolidin-1-yl)-2-[[5-[(4-methylpiperazin-1-yl)methyl]pyridin-2-yl]amino]pyrido[3,4-d]pyrimidin-6-yl]ethanol (1R)-1-[8-(8-azabicyclo[3.2.1]octan-8-yl)-2-[[5-(4-methylpiperazin-1-yl)methyl]pyridin-2-yl]amino]pyrido[3,4-d]pyrimidin-6-yl]ethanol (1R)-1-[2-[[6-(azetidin-3-yl)-7,8-dihydro-5H-1,6-naphthyridin-2-yl]amino]-8-piperidin-1-ylpyrido[3,4-d]pyrimidin-6-yl]ethanol (1R)-1-[2-[[6-[1-(2-hydroxyethyl)azetidin-3-yl]-7,8-dihydro-5H-1,6-naphthyridin-2-yl]amino]-8-piperidin-1-ylpyrido[3,4-d]pyrimidin-6-yl]ethanol (1R)-1-[2-[[5-[(4-methylpiperazin-1-yl)methyl]pyridin-2-yl]amino]-8-(1,4-oxazepan-4-yl)pyrido[3,4-d]pyrimidin-6-yl]ethanol (1R)-1-[2-[[5-[[4-(2-hydroxyethyl)piperazin-1-yl]methyl]pyridin-2-yl]amino]-8-(1,4-oxazepan-4-yl)pyrido[3,4-d]pyrimidin-6-yl]ethanol (1R)-1-[8-[(3S)-3-fluoropiperidin-1-yl]-2-[[5-(4-methylpiperazin-1-yl)methyl]pyridin-2-yl]amino]pyrido[3,4-d]pyrimidin-6-yl]ethanol (1R)-1-[8-[(3S)-3-fluoropiperidin-1-yl-2-[[5-[[4-(2-hydroxyethyl)piperazin-1-yl]methyl]pyridin-2-yl]amino]pyrido[3,4-d]pyrimidin-6-yl]ethanol (1R)-1-[8-[(3S)-3-fluoropyrrolidin-1-yl]-2-[[5-[[4-(2-hydroxyethyl)piperazin-1-yl]methyl]pyridin-2-yl]amino]pyrido[3,4-d]pyrimidin-6-yl]ethanol (1R)-1-[8-[(3R)-3-fluoropyrrolidin-1-yl]-2-[[5-[[4-(2-hydroxyethyl)piperazin-1-yl]methyl]pyridin-2-yl]amino]pyrido[3,4-d]pyrimidin-6-yl]ethanol (2S)-1-[4-[[6-[[6-[(1R)-1-hydroxyethyl]-8-piperidin-1-ylpyrido[3,4-d]pyrimidin-2-yl]amino]pyridin-3-yl]methyl]piperazin-1-yl]propan-2-ol (2R)-1-[4-[[6-[[6-[(1R)-1-hydroxyethyl]-8-piperidin-1-ylpyrido[3,4-d]pyrimidin-2-yl]amino]pyridin-3-ylmethyl]piperazin-1-yl]propan-2-ol (1R)-1-[8-(7-azabicyclo[2.2.1]heptan-7-yl)-2-[[6-methyl-5-(4-methylpiperazin-1-yl)pyridin-2-yl]amino]pyrido[3,4-d]pyrimidin-6-yl]ethanol (1R)-1-[2-[[5-[[(2S)-2,4-dimethylpiperazin-1-yl]methyl]pyridin-2-yl]amino]-8-piperidin-1-ylpyrido[3,4-d]pyrimidin-6-yl]ethanol (1R)-1-[8-(7-azabicyclo[2.2.1]heptan-7-yl)-2-[[5-[[(2S)-2,4-dimethylpiperazin-1-yl]methyl]pyridin-2-yl]amino]pyrido[3,4-d]pyrimidin-6-yl]ethanol (1R)-1-[2-[[5-[[(3S)-3,4-dimethylpiperazin-1-yl]methyl]pyridin-2-yl]amino]-8-piperidin-1-ylpyrido[3,4-d]pyrimidin-6-yl]ethanol (1R)-1-[8-(7-azabicyclo[2.2.1]heptan-7-yl)-2-[[5-[[(3S)-3,4-dimethylpiperazin-1-yl]methyl]pyridin-2-yl]amino]pyrido[3,4-d]pyrimidin-6-yl]ethanol (1R)-1-[2-[[5-[[4-(2-hydroxyethyl)piperazin-1-yl]methyl]pyridin-2-yl]amino]-8-phenylpyrido[3,4-d]pyrimidin-6-yl]ethanol 1-[6-[[6-[(1R)-1-hydroxyethyl]-8-phenylpyrido[3,4-d]pyrimidin-2-yl]amino]pyridin-3-yl]piperazin-2-one 1-[6-[[6-[(2S)-1-hydroxypropan-2-yl]-8-piperidin-1-ylpyrido[3,4-d]pyrimidin-2-yl]amino]pyridin-3-yl]piperazin-2-one (2S)-2-[2-[[6-(2-hydroxyethyl)-7,8-dihydro-5H-1,6-naphthyridin-2-yl]amino]-8-piperidin-1-ylpyrido[3,4-d]pyrimidin-6-yl]propan-1-ol 1-[6-[[6-[(2R)-1-hydroxypropan-2-yl]-8-piperidin-1-ylpyrido[3,4-d]pyrimidin-2-yl]amino]pyridin-3-ylpiperazin-2-one (2S)-2-[2-[[5-[[4-(2-hydroxyethyl)piperazin-1-yl]methyl]pyridin-2-yl]amino]-8-piperidin-1-ylpyrido[3,4-d]pyrimidin-6-yl]propan-1-ol 2-[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]acetonitrile (1R)-1-[2-[[6-(oxetan-3-ylmethyl)-7,8-dihydro-5H-1,6-naphthyridin-2-yl]amino]-8-piperidin-1-ylpyrido[3,4-d]pyrimidin-6-yl]ethanol (1R)-1-[8-[(3R)-3-fluoropiperidin-1-yl]-2-[[5-(4-methylpiperazin-1-yl)methyl]pyridin-2-yl]amino]pyrido[3,4-d]pyrimidin-6-yl]ethanol (1R)-1-[8-[(3R)-3-fluoropiperidin-1-yl]-2-[[5-[[4-(2-hydroxyethyl)piperazin-1-yl]methyl]pyridin-2-yl]amino]pyrido[3,4-d]pyrimidin-6-yl]ethanol (1R)-1-[2-[[6-(1-methylazetidin-3-yl)-7,8-dihydro-5H-1,6-naphthyridin-2-yl]amino]-8-piperidin-1-ylpyrido[3,4-d]pyrimidin-6-yl]ethanol (1R)-1-[2-[[6-(2-hydroxyethyl)-5,7-dihydropyrrolo[3,4-b]pyridin-2-yl]amino]-8-piperidin-1-ylpyrido[3,4-d]pyrimidin-6-yl]ethanol (2S)-1-[2-[[5-[[4-(2-hydroxyethyl)piperazin-1-yl]methyl]pyridin-2-yl]amino]-8-piperidin-1-ylpyrido[3,4-d]pyrimidin-6-yl]propan-2-ol 1-[6-[[6-[(2S)-2-hydroxypropyl]-8-piperidin-1-ylpyrido[3,4-d]pyrimidin-2-yl]amino]pyridin-3-yl]piperazin-2-one (2S)-1-[2-[[6-(2-hydroxyethyl)-7,8-dihydro-5H-1,6-naphthyridin-2-yl]amino]-8-piperidin-1-ylpyrido[3,4-d]pyrimidin-6-yl]propan-2-ol 8-(7-azabicyclo[2.2.1]heptan-7-yl)-6-(oxolan-3-yl)-N-[5-(piperazin-1-ylmethyl)pyridin-2-yl]pyrido[3,4-d]pyrimidin-2-amine 6-(oxolan-3-yl)-N-[5-(piperazin-1-ylmethyl)pyridin-2-yl]-8-piperidin-1-ylpyrido[3,4-d]pyrimidin-2-amine 8-(7-azabicyclo[2.2.1]heptan-7-yl)-6-(oxolan-3-yl)-N-(6-piperazin-1-ylpyridazin-3-yl)pyrido[3,4-d]pyrimidin-2-amine 6-(oxolan-3-yl)-N-(6-piperazin-1-ylpyridazin-3-yl)-8-piperidin-1-ylpyrido[3,4-d]pyrimidin-2-amine

[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]-[(2R)-pyrrolidin-2-yl]methanone

[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]-[(3S)-pyrrolidin-3-yl]methanone

[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]-[(2R)-piperidin-2-yl]methanone

[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]-[(2R,4S)-4-hydroxypyrrolidin-2-yl]methanone

[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]-[(2R,4R)-4-hydroxypyrrolidin-2-yl]methanone

[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl-[(3R)-piperidin-3-yl]methanone

[(2R)-azetidin-2-yl]-[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]methanone

[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl-morpholin-2-yl]methanone (1R)-1-[2-[[6-(2-aminoethyl)-7,8-dihydro-5H-1,6-naphthyridin-2-yl]amino]-8-piperidin-1-ylpyrido[3,4-d]pyrimidin-6-yl]ethanol

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R)-1-methylpyrrolidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S)-1-methylpyrrolidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(3S)-1-methylpyrrolidin-3-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(3R)-1-methylpyrrolidin-3-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R)-1-methyl]piperidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S)-1-methylpiperidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R,4S)-4-hydroxy-1-methylpyrrolidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S,4R)-4-hydroxy-1-methylpyrrolidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R,4R)-4-hydroxy-1-methylpyrrolidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S,4S)-4-hydroxy-1-methylpyrrolidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl-[(3R)-1-methyl]piperidin-3-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(3S)-1-methylpiperidin-3-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R)-1-methylazetidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S)-1-methylazetidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-(4-methylmorpholin-3-yl)methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-(4-methylmorpholin-2-yl)methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-(1-methylazetidin-3-yl)methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R)-1-(2-hydroxyethyl)pyrrolidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S)-1-(2-hydroxyethyl)pyrrolidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(3S)-1-(2-hydroxyethyl)pyrrolidin-3-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl-[(3R)-1-(2-hydroxyethyl)pyrrolidin-3-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R)-1-(2-hydroxyethyl)piperidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S)-1-(2-hydroxyethyl)piperidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R,4S)-4-hydroxy-1-(2-hydroxyethyl)pyrrolidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S,4R)-4-hydroxy-1-(2-hydroxyethyl)pyrrolidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl-j (2R,4R)-4-hydroxy-1-(2-hydroxyethyl)pyrrolidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S,4S)-4-hydroxy-1-(2-hydroxyethyl)pyrrolidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(3R)-1-(2-hydroxyethyl)piperidin-3-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(3S)-1-(2-hydroxyethyl)piperidin-3-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R)-1-(2-hydroxyethyl)azetidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S)-1-(2-hydroxyethyl)azetidin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[4-(2-hydroxyethyl)morpholin-3-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[4-(2-hydroxyethyl)morpholin-2-yl]methanone

[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[1-(2-hydroxyethyl)azetidin-3-yl]methanone 1-[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-2-pyrrolidin-1-ylethanone 1-[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-2-(3-hydroxypyrrolidin-1-yl)ethanone 1-[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-2-(3-fluoropyrrolidin-1-yl)ethanone 1-[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-2-(azetidin-1-yl)ethanone 1-[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-2-(3-hydroxyazetidine-1-yl)ethanone 1-[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-2-(3-fluoroazetidin-1-yl)ethanone 1-[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-2-piperidin-1-yl)ethanone 1-[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-2-(4-hydroxypiperidin-1-yl)ethanone 1-[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-2-(4-fluoropiperidin-1-yl)ethanone 1-[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-2-(3-hydroxypiperidin-1-yl)ethanone 1-[2-[[8-(7-azabicyclo[12.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-2-(3-fluoropiperidin-1-yl)ethanone 2-[4-[[6-[[6-(oxetan-3-yl)-8-piperidin-1-ylpyrido[3,4-d]pyrimidin-2-yl]amino]pyridin-3-yl]methyl]piperazin-1-yl]ethanol 2-[4-[[6-[[8-(7-azabicyclo[2.2.1]heptan-7-yl)-6-(oxetan-3-yl)pyrido[3,4-d]pyrimidin-2-yl]amino]pyridin-3-yl]methyl]piperazin-1-yl]ethanol

[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]-morpholin-3-yl]methanone morpholin-2-yl-[2-[[6-(oxetan-3-yl)-8-piperidin-1-ylpyrido[3,4-d]pyrimidin-2-yl]aminol]-7,8-dihydro-5H-1,6-naphthyridin-6-yl]methanone morpholin-3-yl-[2-[[6-(oxetan-3-yl)-8-piperidin-1-ylpyrido[3,4-d]pyrimidin-2-yl]amino]-7,8-dihydro-5H-1,6-naphthyridin-6-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2R)-1-methylpyrrolidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2S)-1-methylpyrrolidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(3S)-1-methylpyrrolidin-3-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(3R)-1-methylpyrrolidin-3-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2R)-1-methylpiperidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2S)-1-methylpiperidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2R,4S)-4-hydroxy-1-methylpyrrolidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2S,4R)-4-hydroxy-1-methylpyrrolidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2R,4R)-4-hydroxy-1-methylpyrrolidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2S,4S)-4-hydroxy-1-methylpyrrolidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(3R)-1-methylpiperidin-3-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(3S)-1-methylpiperidin-3-yl]methanone

[2-[[8-(7-azabicyclo[2.2.1]heptan-7-yl)-6-(oxetan-3-yl)pyrido[3,4-d]pyrimidin-2-ylamino]-7,8-dihydro-5H-1,6-naphthyridin-6-yl]-[(2R)-1-methylazetidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2S)-1-methylazetidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl-(4-methylmorpholin-3-yl)methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-(4-methylmorpholin-2-yl)methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-(1-methylazetidin-3-yl)methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2R)-1-(2-hydroxyethyl)pyrrolidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2S)-1-(2-hydroxyethyl)pyrrolidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(3S)-1-(2-hydroxyethyl)pyrrolidin-3-yl]methanone

[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-[(3R)-1-(2-hydroxyethyl)pyrrolidin-3-
    yl]methanone

[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-[(2R)-1-(2-hydroxyethyl)piperidin-2-
    yl]methanone

[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-[(2S)-1-(2-hydroxyethyl)piperidin-2-
    yl]methanone

[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-[(2R,4S)-4-hydroxy-1-(2-hydroxy-
    ethyl)pyrrolidin-2-yl]methanone

[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-[(2S,4R)-4-hydroxy-1-(2-hydroxy-
    ethyl)pyrrolidin-2-yl]methanone

[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl-[(2R,4R)-4-hydroxy-1-(2-hydroxy-
    ethyl)pyrrolidin-2-yl]methanone

[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl-[(2S,4S)-4-hydroxy-1-(2-hydroxy-
    ethyl)pyrrolidin-2-yl]methanone

[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-[(3R)-1-(2-hydroxyethyl)piperidin-3-
    yl]methanone

[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-[(3S)-1-(2-hydroxyethyl)piperidin-3-
    yl]methanone

[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl-[(2R)-1-(2-hydroxyethyl)azetidin-2-yl]
    methanone

[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl-[(2S)-1-(2-hydroxyethyl)azetidin-2-yl]
    methanone

[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-[4-(2-hydroxyethyl)morpholin-3-yl]
    methanone

[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-[4-(2-hydroxyethyl)morpholin-2-yl]
    methanone

[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-[1-(2-hydroxyethyl)azetidin-3-yl]
    methanone 1-[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl-2-pyrrolidin-1-ylethanone 1-[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-2-(3-hydroxypyrrolidin-1-yl)ethanone 1-[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-2-(3-fluoropyrrolidin-1-yl)ethanone 1-[2-[[8-(7-azabicyclo[2.2.1]heptan-7-yl)-6-(oxetan-3-yl)
    pyrido[3,4-d]pyrimidin-2-ylamino]-7,8-dihydro-5H-1,6-
    naphthyridin-6-yl]-2-(azetidin-1-yl)ethanone 1-[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl-2-(3-hydroxyazetidin-1-yl)ethanone 1-[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl-2-(3-fluoroazetidin-1-yl)ethanone 1-[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-2-piperidin-1-ylethanone 1-[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-2-(4-hydroxypiperidin-1-yl)ethanone 1-[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-2-(4-fluoropiperidin-1-yl)ethanone 1-[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-2-(3-hydroxypiperidin-1-yl)ethanone 1-[2-[[8-(7-azabicyclo[2.2.1]heptan-7-yl)-6-(oxetan-3-yl)
    pyrido[3,4-d]pyrimidin-2-yl]amino]-7,8-dihydro-5H-1,6-
    naphthyridin-6-yl]-2-(3-fluoropiperidin-1-yl)ethanone 4-(2-hydroxyethyl)-1-[6-[[6-[(1R)-1-hydroxyethyl]-8-pip-
    eridin-1-ylpyrido[3,4-d]pyrimidin-2-yl]amino]pyridin-3-
    yl]piperazin-2-one (1R)-1-[8-(7-azabicyclo[2.2.1]heptan-7-yl)-2-[[5-[4-(2-hy-
    droxyethyl)piperazin-1-yl]-6-methyl]pyridin-2-yl]amino]
    pyrido[3,4-d]pyrimidin-6-yl]ethanol (1R)-1-[2-[[6-[4-(2-hydroxyethyl)piperazin-1-yl]pyridazin-
    3-yl]amino]-8-piperidin-1-ylpyrido[3,4-d]pyrimidin-6-
    yl]ethanol (1R)-1-[8-(7-azabicyclo[2.2.1]heptan-7-yl)-2-[[6-[4-(2-hy-
    droxyethyl)piperazin-1-yl]pyridazin-3-yl]amino]pyrido
    [3,4-d]pyrimidin-6-yl]ethanol 1-[6-[[6-[(1R)-1-hydroxypropyl-8-piperidin-1-ylpyrido[3,
    4-d]pyrimidin-2-yl]amino]pyridin-3-yl]-1,4-diazepan-2-
    one 4-(2-hydroxyethyl)-1-[6-[[6-[(1R)-1-hydroxyethyl]-8-pip-
    eridin-1-ylpyrido[3,4-d]pyrimidin-2-yl]amino]pyridin-3-
    yl]-1,4-diazepan-2-one 1-[6-[[8-(7-azabicyclo[2.2.1]heptan-7-yl)-6-[(1R)-1-hy-
    droxyethyl]pyrido[3,4-d]pyrimidin-2-yl]amino]pyridin-
    3-yl]-4-methylpiperazin-2-one 1-[6-[[8-(8-azabicyclo[3.2.1]octan-8-yl)-6-[(1R)-1-hy-
    droxyethyl]pyrido[3,4-d]pyrimidin-2-yl]amino]pyridin-
    3-yl]-4-methylpiperazin-2-one.

Aspect (22) A pharmaceutical composition comprising a compound or a pharmaceutically acceptable salt thereof according to any one of aspects (1) to (21) and a pharmaceutically acceptable carrier.

Aspect (23) A pharmaceutical composition having CDK4/6 inhibitory activity, comprising a compound or a pharmaceutically acceptable salt thereof according to any one of aspects (1) to (21) as an active ingredient.

Aspect (24 hours) A drug for prevention or treatment of rheumatoid arthritis, arteriosclerosis, pulmonary fibrosis, cerebral infarction, or cancer, comprising a compound or a pharmaceutically acceptable salt thereof according to any one of aspects (1) to (21) as an active ingredient.

Aspect (25) A pyrido[3,4-d]pyrimidine derivative represented by formula (II):

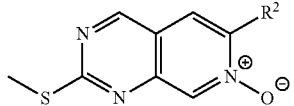

(II)

wherein in formula (II), $R^2$ represents $C_{1-8}$ alkyl, $C_{3-8}$ cycloalkyl, 4- to 6-membered heterocyclyl, $C_{1-8}$ acyl, —COOR$^8$, or —CONR$^9$R$^{10}$;

each $C_{1-8}$ alkyl represented by $R^2$ is substituted independently with zero to one —OH, zero to two $C_{1-8}$ alkoxy groups substituted with [zero to one —OH group, zero to one $C_{1-4}$ alkoxy group, and zero to three fluorine atoms], and zero to five fluorine atoms; each of $C_{3-8}$ cycloalkyl represented by $R^2$ is substituted independently with zero to one —OH, zero to two $C_{1-8}$ alkoxy groups substituted with [zero to one —OH group, zero to one $C_{1-4}$ alkoxy group, and zero to three fluorine atoms], zero to one hydroxymethyl, and zero to five fluorine atoms;

provided that $R^2$ is neither an unsubstituted $C_{1-8}$ alkyl, nor an unsubstituted $C_{3-8}$ cycloalkyl, nor trifluoromethyl;

each of $R^8$, $R^9$, and $R^{10}$ independently represents a hydrogen atom or $C_{1-8}$ alkyl;

each 4- to 6-membered heterocyclyl represented by $R^2$ is optionally substituted with one to four substituents selected from the group consisting of a fluorine atom, —OH, $C_{1-4}$ alkyl, and $C_{1-4}$ alkoxy;

each of $C_{1-8}$ acyl group, —COOR$^8$, and —CONR$^9$R$^{10}$ represented by $R^2$ is optionally substituted with one to four substituents selected from the group consisting of a fluorine atom, —OH, and $C_{1-4}$ alkoxy;

$R^9$ and $R^{10}$ of —CONR$^9$R$^{10}$ represented by $R^2$ are optionally bonded via a single bond or —O— to form a ring including the nitrogen atom to which $R^9$ and $R^{10}$ are bonded;

each heterocyclyl group represented by $R^2$ contains one oxygen atom as a heteroatom in the case of a 4- or 5-membered ring, and one to two oxygen atoms as heteroatoms in the case of a 6-membered ring, and $R^2$ is optionally protected with a suitable protective group, or a salt thereof.

Aspect (26) A pyrido[3,4-d]pyrimidine derivative represented by formula (III):

(III)

wherein in formula (III), $R^2$ represents $C_{1-8}$ alkyl, $C_{3-8}$ cycloalkyl, 4- to 6-membered heterocyclyl. $C_{1-8}$ acyl, —COOR$^8$, or —CONR$^9$R$^{10}$;

each $C_{1-8}$ alkyl represented by $R^2$ is independently substituted with zero to one —OH, zero to two $C_{1-8}$ alkoxy groups substituted with [zero to one —OH, zero to one $C_{1-4}$ alkoxy group, and zero to three fluorine atoms], and zero to five fluorine atoms;

each $C_{3-8}$ cycloalkyl represented by $R^2$ is independently substituted with zero to one —OH, zero to two $C_{1-8}$ alkoxy groups substituted with [zero to one —OH, zero to one $C_{1-4}$ alkoxy group, and zero to three fluorine atoms], zero to one hydroxymethyl, and zero to five fluorine atoms:

provided that $R^2$ is neither an unsubstituted $C_{1-8}$ alkyl, nor an unsubstituted $C_{3-8}$ cycloalkyl, nor trifluoromethyl;

each of $R^8$, $R^9$, and $R^{10}$ independently represents a hydrogen atom or $C_{1-8}$ alkyl;

each 4- to 6-membered heterocyclyl represented by $R^2$ is optionally substituted with one to four substituents selected from the group consisting of a fluorine atom, —OH, $C_{1-4}$ alkyl, and $C_{1-4}$ alkoxy;

each of $C_{1-8}$ acyl group, —COOR$^8$, and —CONR$^9$R$^{10}$ represented by $R^2$ is optionally substituted with one to four substituents selected from the group consisting of a fluorine atom, —OH, and $C_{1-4}$ alkoxy;

$R^9$ and $R^{10}$ of —CONR$^9$R$^{10}$ represented by $R^2$ are optionally bonded via a single bond or —O— to form a ring including the nitrogen atom to which $R^9$ and $R^{10}$ are bonded:

each heterocyclyl group represented by $R^2$ contains one oxygen atom as a heteroatom in the case of a 4- or 5-membered ring, and one to two oxygen atoms as heteroatoms in the case of a 6-membered ring, Z represents a halogen atom, and $R^2$ is optionally protected with a suitable protective group, or a salt thereof.

Aspect (27) A pyrido[3,4-d]pyrimidine derivative represented by formula (IV):

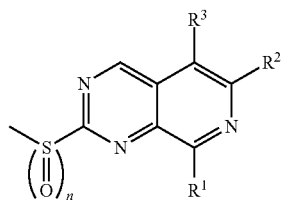

(IV)

wherein in formula (IV), $R^1$ represents $C_{3-12}$ cycloalkyl, $C_{4-12}$ cycloalkenyl, 4- to 12-membered heterocyclyl, $C_{6-10}$ aryl, or 5- to 10-membered heteroaryl; each of the heteroatom-containing group represented by $R^1$ contains one to four heteroatoms independently selected from oxygen, sulfur, and nitrogen atoms;

$R^1$ is optionally substituted with one to six substituents selected from the group consisting of a halogen, =O, —OH, —CN, —COOH, —COOR$^6$, —R$^7$, $C_{3-6}$ cycloalkyl substituted with [zero to two —OH groups, zero to two $C_{1-8}$ alkoxy groups, and zero to six fluorine atoms], 3- to 10-membered heterocyclyl substituted with [zero to two —OH groups, zero to two $C_{1-8}$ alkoxy groups, and zero to six fluorine atoms], $C_{1-8}$ acyl substituted with [zero to two —OH groups, zero to two $C_{1-8}$ alkoxy groups, and zero to six fluorine atoms], and $C_{1-8}$ alkoxy substituted with [zero to two —OH groups, zero to two $C_{1-8}$ alkoxy groups, and zero to six fluorine atoms];

each of $R^6$ and $R^7$ independently represents $C_{1-6}$ alkyl substituted with [zero to two —OH groups, zero to two $C_{1-8}$ alkoxy groups, and zero to six fluorine atoms]:

$R^2$ represents $C_{1-8}$ alkyl, $C_{3-8}$ cycloalkyl, 4- to 6-membered heterocyclyl, $C_{1-8}$ acyl, —COOR$^8$, or —CONR$^9$R$^{10}$;

each $C_{1-8}$ alkyl represented by $R^2$ is independently substituted with zero to one —OH, zero to two $C_{1-8}$ alkoxy groups substituted with [zero to one —OH, zero to one $C_{1-4}$ alkoxy group, and zero to three fluorine atoms], and zero to five fluorine atoms:

each $C_{3-8}$ cycloalkyl represented by $R^2$ is independently substituted with zero to one —OH, zero to two $C_{1-8}$ alkoxy groups substituted with [zero to one —OH, zero to one $C_{1-4}$ alkoxy group, and zero to three fluorine atoms], zero to one hydroxymethyl, and zero to five fluorine atoms;

provided that $R^2$ is neither an unsubstituted $C_{1-8}$ alkyl, nor an unsubstituted $C_{3-8}$ cycloalkyl, nor trifluoromethyl;

each of $R^8$, $R^9$, and $R^{10}$ independently represents a hydrogen atom or $C_{1-8}$ alkyl; each 4- to 6-membered heterocyclyl represented by $R^2$ is optionally substituted with one to four substituents selected from the group consisting of a fluorine atom, —OH, $C_{1-4}$ alkyl, and $C_{1-4}$ alkoxy;

each of $C_{1-8}$ acyl group, —COOR$^8$, and —CONR$^9$R$^{10}$ represented by $R^2$ is optionally substituted with one to four substituents selected from the group consisting of a fluorine atom, —OH, and $C_{1-4}$ alkoxy;

$R^9$ and $R^{10}$ of —CONR$^9$R$^{10}$ represented by $R^2$ are optionally bonded via a single bond or —O— to form a ring including the nitrogen atom to which $R^9$ and $R^{10}$ are bonded;

each heterocyclyl group represented by $R^2$ contains one oxygen atom as a heteroatom in the case of a 4- or 5-membered ring, and one to two oxygen atoms as heteroatoms in the case of a 6-membered ring;

n represents 0, 1, or 2, and each of $R^1$ and $R^2$ is optionally protected with a suitable protective group, or a salt thereof.

Effect of the Invention

The compound of the present invention exhibits a superior CDK4/6 inhibitory activity and is useful as a drug for prevention or treatment of rheumatoid arthritis, arteriosclerosis, pulmonary fibrosis, cerebral infarction, or cancer.

Modes for Carrying Out the Invention

Now will be described the structures (groups) of the compound of the present invention represented by Formula (I). The description of "groups" with parentheses is as follows: For example, the term "(cycloalkyl)-alkyl" refers to a cycloalkyl group bonded to an alkyl group such that the alkyl group is bonded to a structure other than the cycloalkyl group. Similarly, the term "(heterocyclyl)-alkyl" refers to a heterocyclyl group bonded to an alkyl group such that the alkyl group is bonded to a structure other than the heterocyclyl group.

It must be noted that the singular form expression "a", "an", or "the", used herein or in the annexed claims, also refers to two or more unless the context clearly indicates otherwise.

As used herein, "$C_{3-6}$ cycloalkyl group substituted with zero to two —OH groups, zero to two $C_{1-8}$ alkoxy groups, and zero to six fluorine atoms" refers to the case where the $C_{3-6}$ cycloalkyl group is substituted with the following substituents: zero to two —OH groups, zero to two $C_{1-8}$ alkoxy groups, and zero to six fluorine atoms. Examples of the substituted $C_{3-6}$ cycloalkyl group include a $C_{3-6}$ cycloalkyl group substituted with two —OH groups, one $C_{1-8}$ alkoxy group, and three fluorine atoms; a $C_{3-6}$ cycloalkyl group substituted with two $C_{1-8}$ alkoxy groups and four fluorine atoms; and a $C_{3-6}$ cycloalkyl group substituted with one —OH group, and the like. The $C_{3-6}$ cycloalkyl group is not substituted in the case where the number of all the substituents is zero. Moreover, as for the number of substituents, chemically possible numbers are allowed. For example, the statement "$C_1$ alkyl substituted with zero to six fluorine atoms" actually means "$C_1$ alkyl substituted with zero to three fluorine atoms".

As used herein, "$C_{1-8}$" refers to a group having one to eight carbon atoms, and "$C_{1-6}$" refers to a group having one to six carbon atoms. Similarly, "5- to 10-membered" refers to a structure having 5 to 10 carbon atoms, and "5- or 6-membered" refers to a structure having five or six carbon atoms.

Non-limiting examples of the groups described in this specification are as follows:

The term "alkyl" as used herein refers to a monovalent group obtained by removal of one hydrogen atom from an alkane at any carbon atom.

The term "alkylene" as used herein refers to a divalent group obtained by removal of two hydrogen atoms from an alkane at any two different carbon atoms.

The term "alkane" as used herein refers to a saturated aliphatic hydrocarbon.

The term "$C_{1-8}$ alkyl" as used herein refers to a linear or branched hydrocarbon group having one to eight carbon atoms. Examples of the C-s alkyl include methyl, ethyl, n-propyl, isopropyl, n-butyl, isobutyl, sec-butyl, tert-butyl, n-pentyl, neopentyl, isopentyl, 1,2-dimethylpropyl, n-hexyl, isohexyl, 1,1-dimethylbutyl, 2,2-dimethylbutyl, I-ethylbutyl, 2-ethylbutyl, isoheptyl, n-octyl, isooctyl, and the like.

The alkane of "$C_{1-8}$ alkylene" as used herein refers to a linear or branched hydrocarbon having one to eight carbon atoms. Examples of the alkane include methane, ethane, propane, n-butane, 2-methylpropane, n-pentane, 2,2-dimethylpropane, n-hexane, 2-methylpentane, 3-methylpentane, 2,2-dimethylbutane, 2,3-dimethylbutane, n-heptane, 2,2-dimethylhexane, 2,3-dimethylhexane, n-octane, 2-methylheptane, and the like.

The term "cycloalkyl" as used herein refers to a monovalent group obtained by removal of one hydrogen atom from a cycloalkane at any carbon atom.

The term "cycloalkenyl" as used herein refers to a monovalent group obtained by removal of one hydrogen atom from a cycloalkene at any carbon atom.

The term "cycloalkylene" as used herein refers to a divalent group obtained by removal of two hydrogen atoms from a cycloalkane at any two different carbon atoms.

The term "cycloalkylidene" refers to a divalent group obtained by removal of two hydrogen atoms from a cycloalkane at any one carbon atom.

The term "cycloalkane" as used herein refers to an alicyclic hydrocarbon.

The cycloalkane of "$C_{3-12}$ cycloalkyl," "$C_{3-12}$ cycloalkylene," or "$C_{3-12}$ cycloalkylidene" as used herein refers to a monocyclic or polycyclic 3- to 12-membered aliphatic hydrocarbon ring system. Specific examples of the cycloalkane include cyclopropane, cyclobutane, cyclopentane, cyclohexane, cycloheptane, cyclooctane, spiro[3.3]heptane, bicyclo[1.1.1]pentane, bicyclo[2.2.2]octane, adamantane, and the like.

The cycloalkene of "$C_{4-12}$ cycloalkenyl" as used herein refers to a monocyclic or polycyclic 4- to 12-membered aliphatic hydrocarbon ring system. Specific examples of the cycloalkene include cyclobutene, cyclopentene, cyclohexene, cycloheptene, cyclooctene, spiro[3.3]heptene, and bicyclo[2.2.2]octene.

The term "heterocyclyl" as used herein refers to a monovalent group obtained by removal of one hydrogen atom from a heterocycle at any carbon or nitrogen atom.

The term "heterocyclylene" as used herein refers to a divalent group obtained by removal of two hydrogen atoms from a heterocycle at any two different carbon or nitrogen atoms.

The term "heterocyclylidene" as used herein refers to a divalent group obtained by removal of two hydrogen atoms from a heterocycle at any one carbon atom.

The term "heterocycle" as used herein refers to a partially or fully aliphatic ring system which contains one or more heteroatoms selected from sulfur, nitrogen, and oxygen atoms.

The heterocycle of "4- to 12-membered heterocyclyl," "4- to 12-membered heterocyclylene," or "4- to 12-membered heterocyclylidene" as used herein refers to "4- to 12-membered heterocycloalkane," "4- to 12-membered heterocycloalkane" having an unsaturated bond, a 4- to 12-membered ring system composed of a heterocycloalkane and a heteroarene or arene bonded to a portion of the heterocycloalkane, a 4- to 12-membered ring system composed of a cycloalkane and a heteroarene bonded to a portion of the cycloalkane, a 4- to 12-membered ring system containing a heteroatom and having a spiro structure, or a 4- to 12-membered ring system containing a heteroatom and having a cross-linked structure. The term "4- to 12-membered heterocycloalkane" refers to a 4- to 12-membered cyclic heteroalkane; i.e., a monocyclic or polycyclic aliphatic hydrocarbon ring system containing one to four heteroatoms selected from sulfur, nitrogen, and oxygen atoms. Specific examples of the "4- to 12-membered heterocycloalkane" include aziridine, thiirane, azetidine, oxetane, thietane, tetrahydrofuran, tetrahydropyran, 1,4-dioxane, piperidine, piperazine, pyrrolidine, imidazolidine, pyrazolidine, morpholine, thiomorpholine, tetrahydrothiopyran, tetrahydrothiophene, 1,4-diazepane, oxepane, and the like. A compound having a "spiro structure" is composed of two cyclic structures (cycloalkanes or heterocycloalkanes) that are bonded to one common carbon atom. Examples of the compound include 2-azaspiro[3.3]heptane, 1,6-diazaspiro[3.3]heptane, 2,6-diazaspiro[3.3]heptane, 2,6-diazaspiro[3.4]octane, 2,7-diazaspiro[3.5]nonane, 1,7-diazaspiro[4.5]decane, 2,8-diazaspiro[4.5]decane, 4,7-diazaspiro[2.5]octane, and the like. A compound having a "cross-linked structure" is composed of two cyclic structures (cycloalkanes and heterocycloalkanes) that are bonded to two or more common carbon, nitrogen, or oxygen atoms. Examples of the compound include 2,5-diazabicyclo[2.22]octane, 3,8-diazabicyclo[3.2.1]octane, 1,4-diazabicyclo[3.2.2]nonane, octahydropyrrolo[3,4-b]pyrrole, and the like.

The term "aryl" as used herein refers to a monovalent group obtained by removal of one hydrogen atom from an arene at any carbon atom.

The term "arylene" as used herein refers to a divalent group obtained by removal of two hydrogen atoms from an arene at any two different carbon atoms.

The term "arene" as used herein refers to an aromatic hydrocarbon.

The arene of "$C_{6-10}$ aryl" or "$C_{6-10}$ arylene" as used herein refers to an aromatic hydrocarbon ring system having six to ten carbon atoms. Specific examples of the arene include benzene, naphthalene, and the like.

The term "heteroaryl" as used herein refers to a monovalent group obtained by removal of one hydrogen atom from a heteroarene at any carbon or nitrogen atom.

The term "heteroarylene" as used herein refers to a divalent group obtained by removal of two hydrogen atoms from a heteroarene at any two different carbon or nitrogen atoms.

The term "heteroarene" as used herein refers to an aromatic heterocyclic ring system containing a heteroatom selected from sulfur, nitrogen, and oxygen atoms.

The heteroarene of "5- to 10-membered heteroaryl" or "5- to 10-membered heteroarylene" as used herein refers to a 5- to 10-membered aromatic heterocyclic ring system containing one to four heteroatoms selected from sulfur, nitrogen, and oxygen atoms. Specific examples of the heteroarene include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinolone, isoquinolone, benzofuran, benzothiophene, indole, indazole, benzimidazole, and the like.

The term "(4- to 12-membered heterocyclyl)-$C_{1-6}$ alkyl" as used herein refers to a 4- to 12-membered heterocyclyl group bonded to a $C_{1-6}$ alkyl group such that the $C_{1-6}$ alkyl group is bonded to a structure other than the 4- to 12-membered heterocyclyl group. Specific examples of the (4- to 12-membered heterocyclyl)-$C_{1-6}$ alkyl include groups prepared by bonding of any of the above-exemplified 4- to 12-membered heterocyclyl groups to any of the above-exemplified $C_{1-6}$ alkyl groups.

The term "($C_{6-10}$ aryl)-$C_{1-6}$ alkyl" as used herein refers to a $C_{6-10}$ aryl group bonded to a $C_{1-6}$ alkyl group such that the $C_{1-6}$ alkyl group is bonded to a structure other than the $C_{6-10}$ aryl group. Specific examples of the ($C_{6-10}$ aryl)-$C_{1-6}$ alkyl include groups prepared by bonding of any of the above-exemplified $C_{6-10}$ aryl groups to any of the above-exemplified $C_{1-8}$ alkyl groups.

The term "(5- to 10-membered heteroaryl)-$C_{1-6}$ alkyl" as used herein refers to a 5- to 10-membered heteroaryl group bonded to a $C_{1-6}$ alkyl group such that the $C_{1-6}$ alkyl group is bonded to a structure other than the 5- to 10-membered heteroaryl group. Specific examples of the (5- to 10-membered heteroaryl)-$C_{1-8}$ alkyl include groups prepared by bonding of any of the above-exemplified 5- to 10-membered heteroaryl groups to any of the above-exemplified $C_{1-6}$ alkyl groups.

The term "$C_{1-8}$ alkylsulfonyl" as used herein refers to a $C_{1-8}$ alkyl group bonded to a sulfonyl (—S(=O)$_2$—) group such that the sulfonyl group is bonded to a structure other than the $C_{1-8}$ alkyl group.

The term "$C_{1-8}$ acyl" as used herein refers to a $C_{1-7}$ alkyl group bonded to a carbonyl (—CO—) group such that the carbonyl group is bonded to a structure other than the $C_{1-7}$ alkyl group.

The term "halogen" as used herein refers to fluorine, chlorine, bromine, or iodine atom.

The term "$C_{1-8}$ alkoxy" as used herein refers to a linear, branched, or cyclic alkoxy group having one to eight carbon atoms. Specific examples of the $C_{1-8}$ alkoxy include methoxy, ethoxy, n-propoxy, isopropoxy, n-butoxy, isobutoxy, sec-butoxy, tert-butoxy, n-pentyloxy, neopentyloxy, tert-pentyloxy, 2-methylbutoxy, n-hexyloxy, isohexyloxy, cyclopropyloxy, cyclobutyloxy, cyclopentyloxy, cyclohexyloxy, cycloheptyloxy, cyclooctyloxy, spiro[3.3]heptyloxy, bicyclo[2.2.2]octyloxy, and the like.

The "$C_{3-12}$ cycloalkyl" of $R^1$ is preferably cyclopropyl, cyclobutyl, cyclopentyl, cyclohexyl, spiro[3.3]heptyl, bicyclo[1.1.1]pentane, bicyclo[2.2.2]octyl, or adamantyl.

The "$C_{3-12}$ cycloalkenyl" of $R^1$ is preferably cyclopentenyl, cyclohexenyl, or cycloheptenyl.

The heterocycle of "4- to 12-membered heterocyclyl" in $R^1$ is preferably azetidine, oxetane, thietane, tetrahydrofuran, 1,4-dioxane, morpholine, thiomorpholine, tetrahydropyran, tetrahydrothiophene, or oxepane.

The "$C_{6-10}$ aryl" of $R^1$ is preferably phenyl.

The "5- to 10-membered heteroaryl" of $R^1$ is preferably furanyl, pyrazolyl, or thienyl.

The "halogen" in the substituent of $R^1$ is preferably fluorine or chlorine atom.

The "—COOR$^6$" in the substituent of $R^1$ is preferably —COOH or —COOCH$_3$.

The "$R^7$" in the substituent of $R^1$ is preferably methyl, ethyl, n-propyl, isopropyl, n-butyl, isobutyl, sec-butyl, tert-butyl, n-pentyl, neopentyl, isopentyl, 1,1-dimethyl-2-methoxyethyl, 1-methyl-2-methoxyethyl, 1-methyl-2-hydroxyethyl, 2,2,2-trifluoroethyl, hydroxymethyl, or 1-methyl-2,2,2-trifluoroethyl.

The "$C_{3-6}$ cycloalkyl substituted with [zero to two —OH groups, zero to two $C_{1-8}$ alkoxy groups, and zero to six fluorine atoms]" in the substituent of $R^1$ is preferably cyclopentyl, cyclohexyl, 4-methoxycyclohexyl, or 4-isopropoxycyclohexyl.

The 3- to 10-membered heterocyclyl substituted with [zero to two —OH groups, zero to two $C_{1-8}$ alkoxy groups, and zero to six fluorine atoms] in the substituent of $R^1$ is preferably tetrahydrofuranyl, tetrahydropyranyl, or 2,2-dimethyltetrahydropyranyl.

$R^1$ preferably has any of the following structures:

[Chemical formula 5]

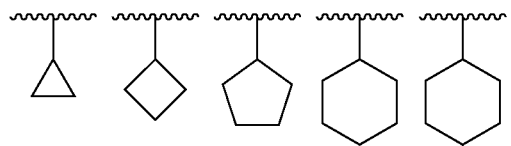
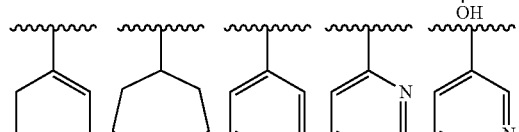
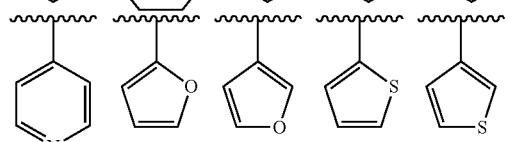
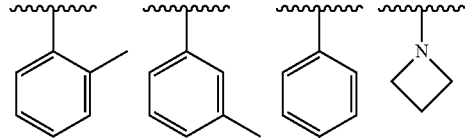
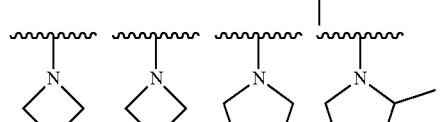
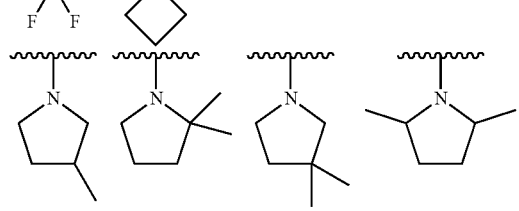
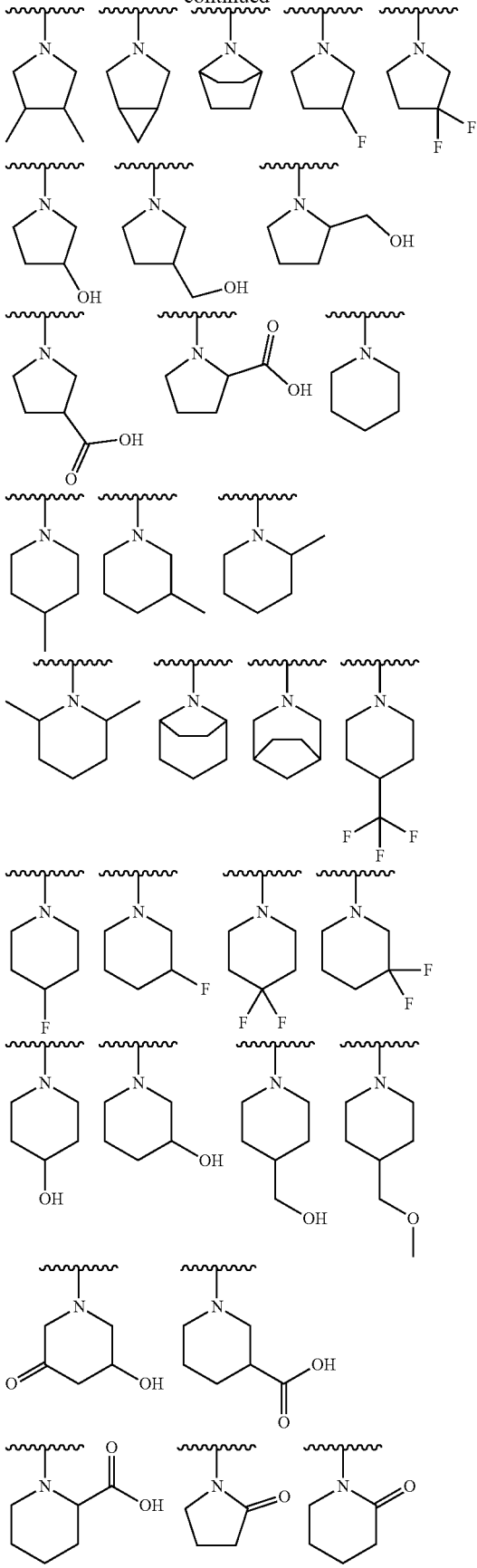

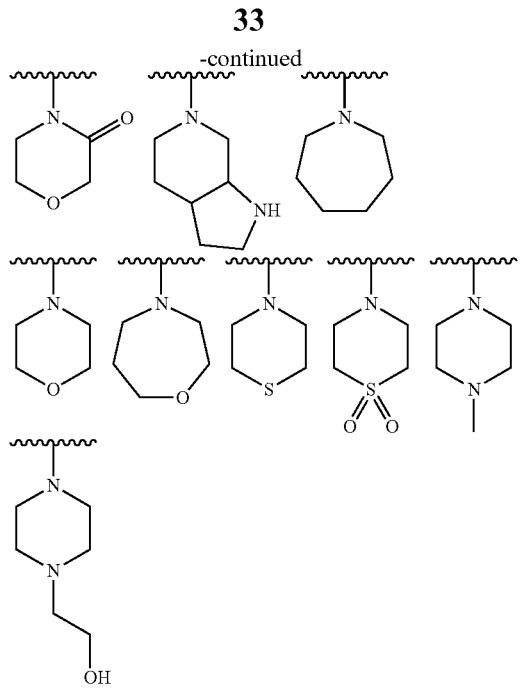

The "$C_{1-8}$ cycloalkyl" of $R^2$ is preferably methyl, ethyl, or n-propyl, and the substituent is preferably hydroxy, methoxy, or ethoxy group or fluorine atom.

The "$C_{3-8}$ cycloalkyl" of $R^2$ is preferably cyclopropyl, and the substituent is preferably hydroxy or hydroxymethyl group or fluorine atom.

The "4- to 6-membered heterocyclyl" of $R^2$ is preferably oxetanyl or tetrahydrofuranyl.

The "$C_{1-8}$ acyl" of $R^2$ is preferably acetyl.

The "—COOR$^8$" of $R^2$ is preferably —COOH or —COOCH$_3$.

The "—CONR$^9$R$^{10}$" of $R^2$ is preferably —CON(CH$_3$)$_2$.

$R^9$ and $R^{10}$ of —CONR$^9$R$^{10}$ of $R^2$ are optionally bonded via single bond or —O— to form a ring including the nitrogen atom bonded to $R^9$ and $R^{10}$. Examples of such a ring include the following structures:

[Chemical formula 6]

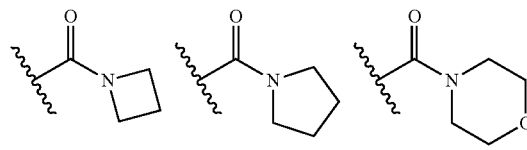

Entire $R^2$ preferably has any of the following structures:

[Chemical formula 7]

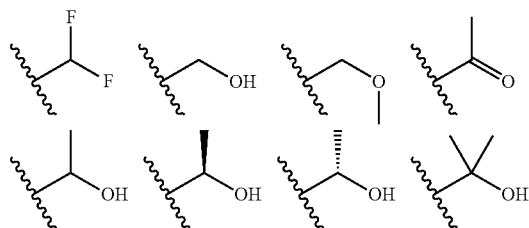

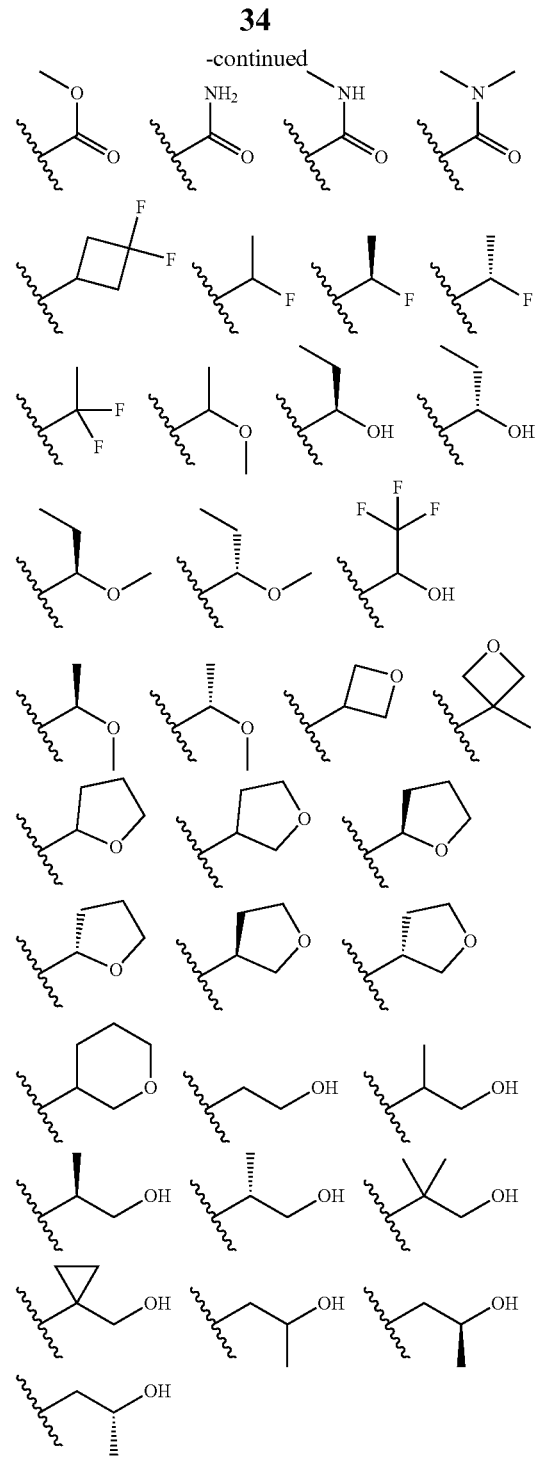

The "$C_{1-8}$ alkyl" of $R^3$ is preferably methyl.

The "halogen" of $R^3$ is preferably fluorine or chlorine atom.

$R^3$ is preferably hydrogen, fluorine, or chlorine atom or methyl group.

$R^{11}$ is preferably hydrogen atom or methyl, ethyl, or cyclopropyl group.

The "$C_{1-8}$ alkylene" of $A^1$ is preferably methylene, ethylene, or n-propylene.

The structure obtained by replacement of one or two sp$^3$ carbon atoms at any positions of $A^1$ is preferably —O—, —OCH$_2$—, —OCH$_2$CH$_2$—, —OCH$_2$CH$_2$CH$_2$—, —CH$_2$O—, —CH$_2$OCH$_2$—, —CH$_2$OCH$_2$CH$_2$—, —CH$_2$CO—, —COCH$_2$—, —CH$_2$CH$_2$CO—, —COCH$_2$CH$_2$—, —CH$_2$COCH$_2$—, —CH$_2$COCH$_2$CH$_2$—, —NR$^{14}$—, —NR$^{14}$CH$_2$—, —CH$_2$NR$^{14}$—, —NR$^{14}$CH$_2$CH$_2$—, —CH$_2$NR$^{14}$CH$_2$—, or —CH$_2$CH$_2$NR$^{14}$—.

When R$^{11}$ is bonded with A$^1$ via a single bond to form a ring, then A$^1$ is preferably a structure derived by replacing one sp$^3$ carbon atom at any position with one structure selected from the group consisting of [—NR$^{14}$— or —C(=O)—NR$^{15}$—], and A$^1$ is preferably —CH$_2$NR$^{14}$—, —C(=O)NR$^{15}$—, —CH$_2$—NR$^{17}$—C(=O)—, or —CH$_2$—NR$^{22}$—S(=O)$_2$—.

The "C$_{1-7}$ alkylene" of A$^2$ is preferably methylene, ethylene, or n-propylene.

The "C$_{3-12}$ cycloalkylene" of A$^2$ is preferably cyclopropylene, cyclobutylene, cyclopentylene, or cyclohexylene.

The "C$_{3-12}$ cycloalkylidene" of A$^2$ is preferably cyclopropylidene, cyclobutylidene, cyclopentylidene, or cyclohexylidene.

The heterocycle of "4- to 12-membered heterocyclylene" of A$^2$ is preferably piperidine, piperazine, pyrrolidine, morpholine, tetrahydrofuran, tetrahydropyran, 1,4-diazepane, oxepane, 2-azaspiro[3.3]heptane, 1,6-diazaspiro[3.3]heptane, 2,6-diazaspiro[3.3]heptane, 2,6-diazaspiro[3.4]octane, 2,5-diazabicyclo[2.2.2]octane, 3,8-diazabicyclo[3.2.1]octane, 2,7-diazaspiro[3.5]nonane, 1,7-diazaspiro[4.5]decane, 2,8-diazaspiro[4.5]decane, 4,7-diazaspiro[2.5]octane, 1,4-diazabicyclo[3.2.2]nonane, or octahydropyrrolo[3,4-b]pyrrole.

The heterocycle of "4- to 12-membered heterocyclylidene" of A$^2$ is preferably oxetane, tetrahydrofuran, tetrahydropyran, pyrrolidine, piperidine, piperazine, morpholine, or oxepane.

The "C$_{6-10}$ arylene" of A$^2$ is preferably phenylene.

The heteroarene of "5- to 10-membered heteroarylene" of A$^2$ is preferably furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinolone, isoquinoline, benzofuran, benzothiophene, indole, indazole, or benzimidazole.

The "halogen" of A$^3$ is preferably a fluorine or chlorine atom.

The "—R$^{25}$" of A$^3$ is a hydrogen atom or a methyl, ethyl, n-propyl, isopropyl, n-butyl, isobutyl, or tert-butyl group. The —R$^{25}$ substituted with a substituent is preferably a hydroxymethyl, 1-hydroxyethyl, 2-hydroxyethyl, 2-hydroxy-2-propyl, 2-hydroxy-1-propyl, 1-hydroxy-2-propyl, 1-hydroxy-2-methyl-2-propyl, 2-hydroxy-2-methyl-1-propyl, trifluoromethyl, 2,2,2-trifluoroethyl, carboxymethyl, 1-carboxyethyl, 2-carboxyethyl, 2-carboxy-2-propyl, or cyanomethyl group.

The "—OR$^{26}$" of A$^3$ is preferably —OH, methoxy, ethoxy, or isopropoxy.

The "—NR$^{17}$R$^{28}$" of A$^3$ is preferably amino, dimethylamino, methylamino, pyrrolidin-1-yl, piperidin-1-yl, piperazin-1-yl, or morpholin-1-yl.

The "—C(=O)R$^{29}$" of A$^3$ is preferably acetyl, tetrahydrofuran-2-carbonyl, tetrahydrofuran-3-carbonyl, pyrrolidine-2-carbonyl, pyrrolidine-3-carbonyl, piperidine-2-carbonyl, piperidine-3-carbonyl, piperidine-4-carbonyl, picolinoyl, nicotinoyl, or isonicotinoyl. When —C(=O)R$^{29}$ is substituted with a substituent, —C(=O)R$^{29}$ is preferably hydroxyacetyl.

The "—C(=O)—OR$^{30}$" of A$^3$ is preferably —COOH, methoxycarbonyl, ethoxycarbonyl, or isopropoxycarbonyl.

The "—O—C(=O)R$^{31}$" of A$^3$ is preferably acetoxy.

The "—O—C(=O)—NR$^{32}$R$^{33}$" of A$^3$ is preferably ((dimethylamino)carbonyl)oxy, ((pyrrolidine-1-yl)carbonyl)oxy, ((piperidine-1-yl)carbonyl)oxy, ((morpholin-1-yl)carbonyl)oxy, or ((piperazin-1-yl)carbonyl)oxy.

The "—C(=O)—NR$^{34}$R$^{35}$" of A$^3$ is preferably aminocarbonyl (or carbamoyl), (methylamino)carbonyl, (dimethylamino)carbonyl, (pyrrolidin-1-yl)carbonyl, (piperidin-1-yl)carbonyl, (morpholin-1-yl)carbonyl, or (piperazin-1-yl)carbonyl.

The "—NR$^{36}$—C(=O)R$^{37}$" of A$^3$ is preferably (acetyl)amino, (hydroxyacetyl)amino, (tetrahydrofuran-2-carbonyl)amino, (tetrahydrofuran-3-carbonyl)amino, 2-oxopyrrolidine-1-yl, or 3-oxomorpholino.

The "—NR$^{38}$—C(=O)—OR$^{39}$" of A$^3$ is preferably (methoxycarbonyl)amino, (methoxycarbonyl)(methyl)amino, or (2-oxo)oxazolidin-3-yl.

The "—S(=O)$_2$—R$^{40}$" of A$^3$ is preferably methanesulfonyl, ethylsulfonyl, (pyrrolidin-3-yl)sulfonyl, (piperidin-3-yl)sulfonyl, or (piperidin-4-yl)sulfonyl.

The "—S(=O)$_2$—NR$^{41}$R$^{42}$" of A$^3$ is preferably (dimethylamino)sulfonyl, (pyrrolidin-1-yl)sulfonyl, (piperidin-1-yl)sulfonyl, (morpholin-1-yl)sulfonyl, or (piperazin-1-yl)sulfonyl.

The "—NR$^{43}$—S(=O)$_2$R$^{44}$" of A$^3$ is preferably methanesulfonylamino, (methanesulfonyl)(methyl)amino, 1,1-dioxidoisothiazolidin-2-yl, 1,1-dioxido-1,2,5-thiadiazinan-2-yl, or 3,3-dioxido-1,3,4-oxathiazinan-4-yl.

R$^{14}$ to R$^{44}$ in A$^1$, A$^2$, and A$^3$ are optionally bonded in A$^1$, A$^2$, or A$^3$ or between A$^1$ and A$^2$, between A$^1$ and A$^3$, or between A$^2$ and A$^3$ via a single bond, —O—, —NR$^{50}$—, or —S(=O)$_p$— to form a ring. Examples of such a ring include the following structures:

[Chemical formula 8]

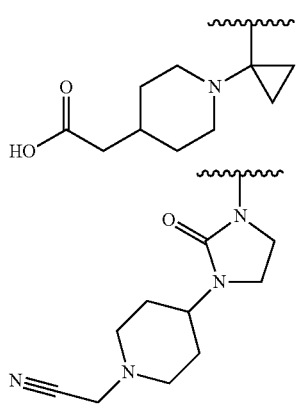

$R^{11}$ is optionally bonded to $A^1$, $A^2$, or $A^3$ via a single bond, —O—, —$NR^{51}$—, or —$S(=O)_p$— to form a ring. Examples of such a ring include the following structures:
[Chemical formula 9]
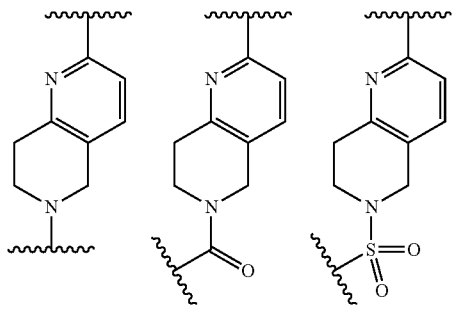
[Chemical formula 10]
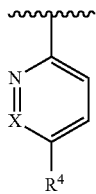
Preferred examples of the aforementioned entire structure are as follows:
[Chemical formula 11]
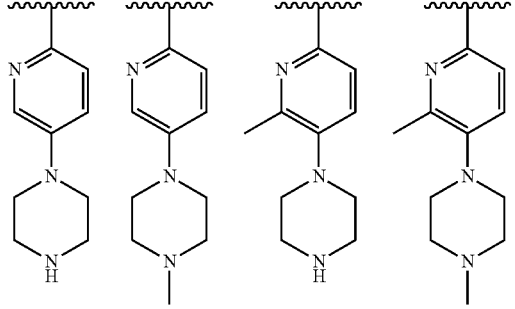
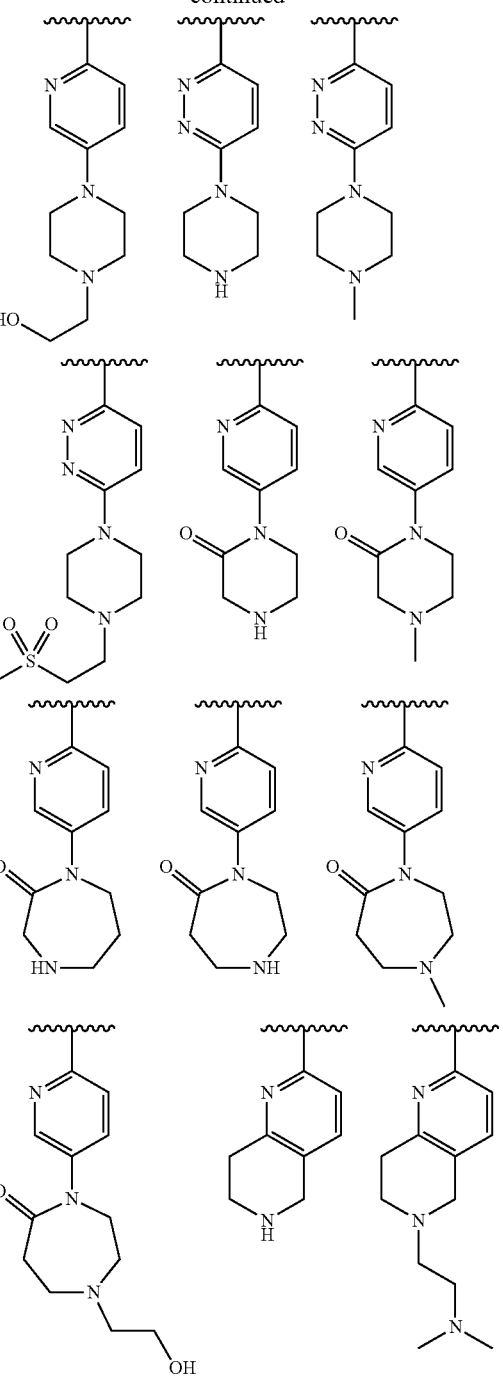
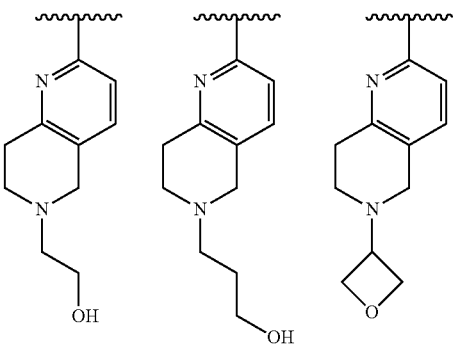

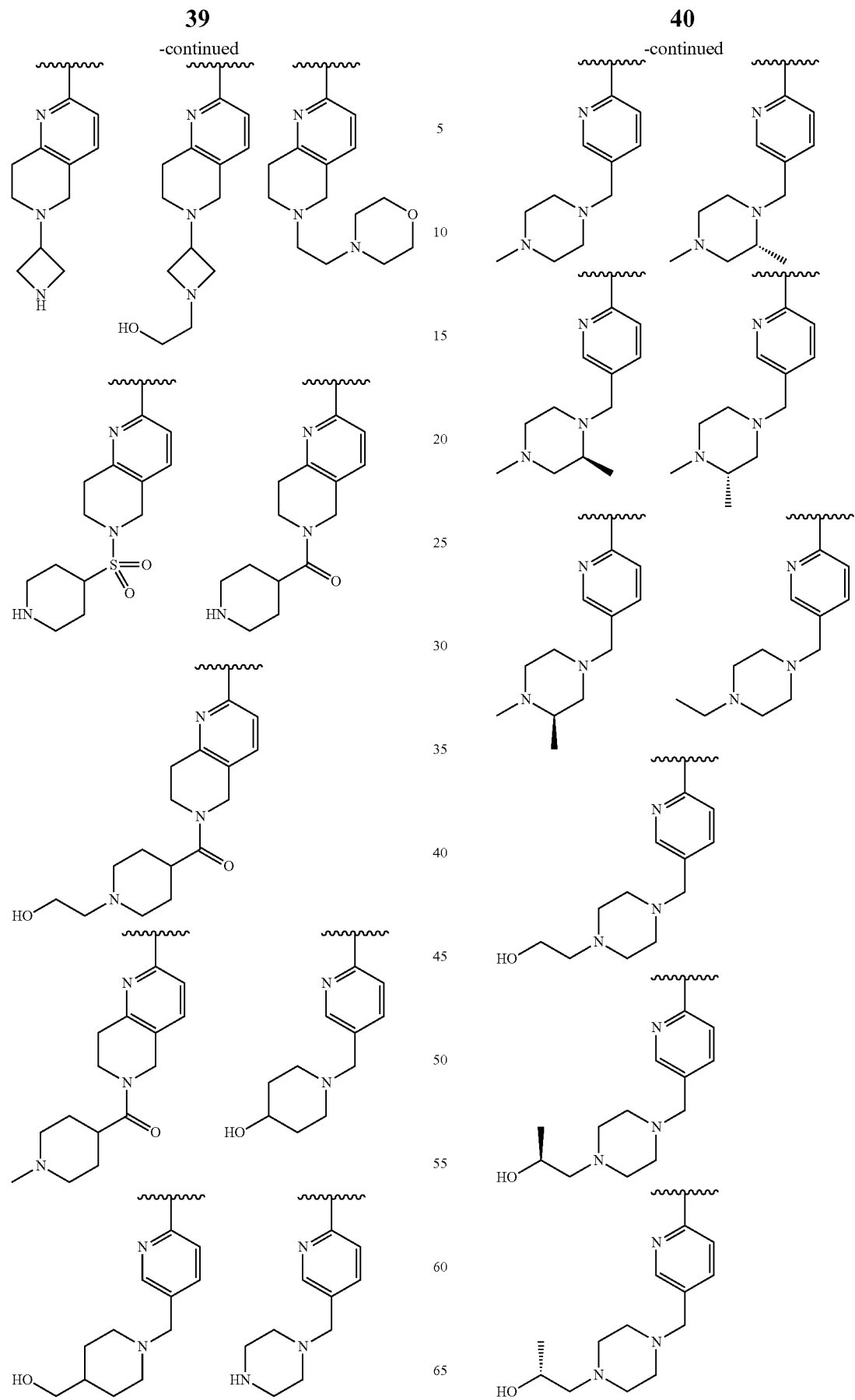

-continued

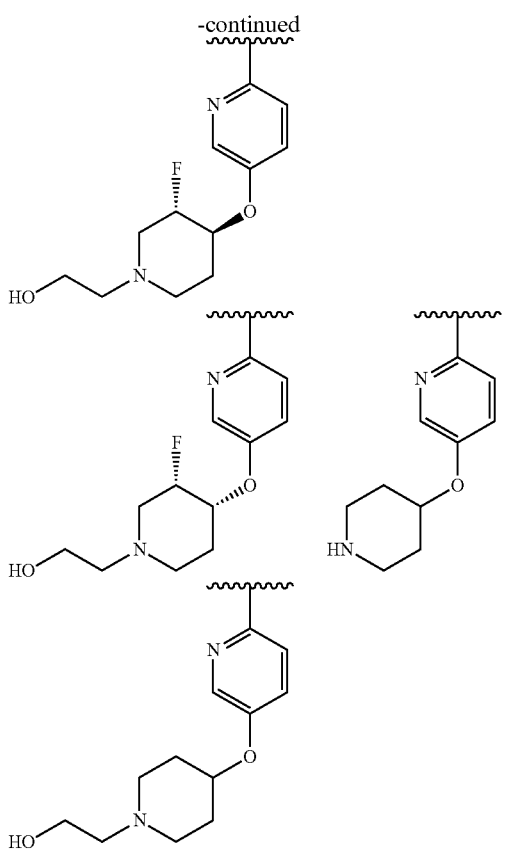

As a compound represented by Formula (I), a compound having one or more preferred group is a preferred compound, and a combination of preferred groups also gives a preferred compound.

Examples of the protective group suitable for protecting —OH of $R^1$, $R^2$, and $R^4$ as used herein include acetyl, benzoyl, tert-butyldimethylsilyl, tert-butyldiphenylsilyl, benzyl, 4-methoxybenzyl, 2,4-dimethoxybenzyl, (methoxy)methyl, or 2-(trimethylsilyl)ethoxymethyl and the like.

Examples of the protective group suitable for protecting NH amino, alkylamino, and nitrogen-containing heteroaryl of $R^1$ and $R^4$ as used herein include tert-butoxycarbonyl, benzyloxycarbonyl, benzyl, 4-methoxybenzyl, 2,4-dimethoxybenzyl, trifluoroacetyl, or 2-(trimethylsilyl)ethoxymethyl and the like.

The compound of the present invention represented by Formula (I) may optionally be formed into a pharmaceutically acceptable salt. Examples of the salt include salts with inorganic acids, such as hydrochloric acid, hydrobromic acid, hydroiodic acid, sulfuric acid, nitric acid, phosphoric acid, carbonic acid, and the like; salts with organic acids, such as formic acid, acetic acid, propionic acid, trifluoroacetic acid, phthalic acid, oxalic acid, malonic acid, succinic acid, fumaric acid, maleic acid, lactic acid, malic acid, tartaric acid, citric acid, benzoic acid, methanesulfonic acid, ethanesulfonic acid, benzenesulfonic acid, p-toluenesulfonic acid, and the like; salts with amino acids, such as lysine, arginine, omithine, glutamic acid, aspartic acid, and the like; salts with alkali metals, such as sodium, potassium, lithium, and the like; salts with alkaline earth metals, such as calcium magnesium, and the like; salts with metals, such as aluminum, zinc, iron, and the like; salts with organic bases, such as methylamine, ethylamine, t-octylamine, diethylamine, trimethylamine, triethylamine, ethylenediamine, piperidine, piperazine, pyridine, picoline, ethanolamine, diethanolamine, triethanolamine, cyclohexylamine, dicyclohexylamine, N-methylglucamine, tris(hydroxymethyl)aminomethane, N,N'-dibenzylethylenediamine, and the like; and ammonium salts and the like.

The present invention also encompasses compounds prepared through replacement of one or more atoms of the compound represented by Formula (I) with stable isotopes or radioisotopes.

The present invention also encompasses stereoisomers, racemates, and all acceptable optical isomers of the compound represented by Formula (I).

Tautomers of the compound of the present invention may be generated depending on the combination of substituents. The present invention also encompasses such tautomers.

Now will be described a typical process for synthesizing the compound of the present invention represented by Formula (I).

The compound of the present invention can be synthesized by the process described below. $R^1$, $R^2$, $R^3$, and $R^4$ shown in the following reaction schemes are as defined in Formula (I). The reagents or solvents and the like shown in the reaction schemes are for illustrative purposes only as described below. Each substituent may optionally be protected with an appropriate protective group or deprotected in an appropriate step (reference: PROTECTIVE GROUPS in ORGANIC SYNTHESIS, 4TH EDITION. John Wiley & Sons, Inc.). The abbreviations of substituents, reagents, and solvents described below and in tables are as follows:

Me: methyl
Et: ethyl
Ph: phenyl
Boc: tert-butoxycarbonyl
Cbz: benzyloxycarbonyl
THF: tetrahydrofuran
DMF: N,N-dimethylformamide
NMP: N-methylpyrrolidone
TFA: trifluoroacetic acid
TBS: tert-butyldimethylsilyl
BINAP: 2,2'-bis(diphenylphosphino)-1,1'-binaphthyl
TBDPS: tert-butyldiphenylsilyl
DIPEA: N,N-Diisopropylethylamine
LAH: Lithium aluminium hydride
DMAP: 4-Dimethylaminopyridine
Ac: acetyl
Ms: mesyl
WSC: water-soluble carbodiimide (1-Ethyl-3-(3-dimethylaminopropyl)carbodiimide)
m-CPBA: m-chloroperoxybenzoic acid
DAST: diethylaminosulfur trifluoride
dba: dibenzylideneacetone
DIBAL-H: diisobutylaluminum hydride
dppf: 1,1'-bis(diphenylphosphino)ferrocene
HATU: O-(7-azabenzotriazol-1-yl)-N,N,N'N'-tetramethyluronium hexafluorophosphate 1) Synthesis of Compound I-e

[Chemical formula 12]

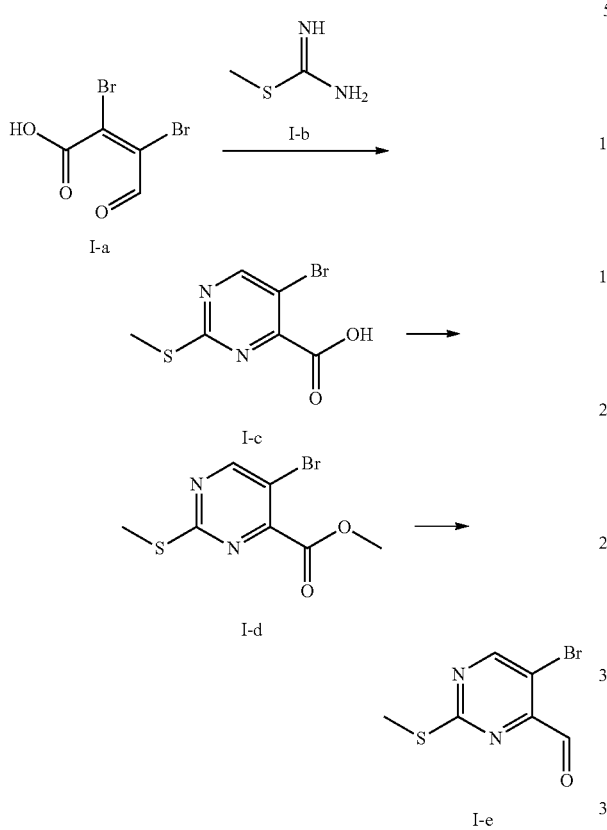

Compound I-e, which is a known compound, can be synthesized by any process known to those skilled in the art: for example, the aforementioned process.

2) Synthesis of Compound I-f from Compound I-e

[Chemical formula 13]

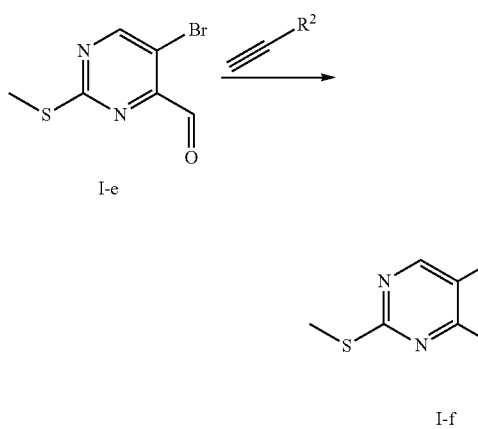

Compound I-e is reacted with a terminal alkyne derivative represented by the formula $R^2$—C≡CH in an appropriate organic solvent (e.g., THF or DMF) in the presence of an appropriate palladium catalyst (e.g., tetrakis(triphenylphosphin)palladium), appropriate copper catalyst (e.g., copper iodide (I)) and appropriate base (e.g., triethylamine) at a temperature of 0° C. to the reflux temperature of the solvent, to yield compound I-f.

3) Synthesis of Compound I-h from Compound I-f

[Chemical formula 14]

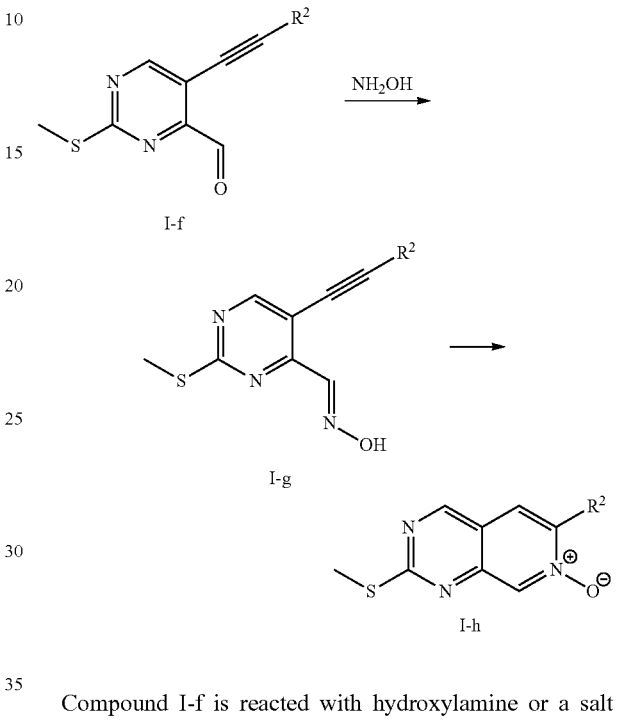

Compound I-f is reacted with hydroxylamine or a salt thereof in an appropriate organic solvent (e.g., ethanol) in the presence or absence of an appropriate base (e.g., sodium acetate) at a temperature of 0° C. to the reflux temperature of the solvent. The resultant hydroxyimine compound is reacted with an appropriate acid or base (e.g., silver triflate or potassium carbonate) to yield compound I-h.

4) Synthesis of Compound I-i from Compound I-h

[Chemical Formula 15]

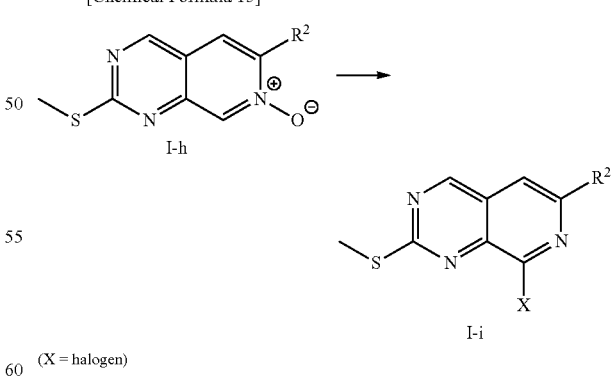

(X = halogen)

Compound I-h is reacted with an appropriate halogenating agent (e.g., thionyl chloride) in an appropriate organic solvent (e.g., dichloromethane) or under solvent-free conditions at a temperature of 0° C. to 140° C., to yield compound I-i.

5) Synthesis of Compound I-j from Compound I-i

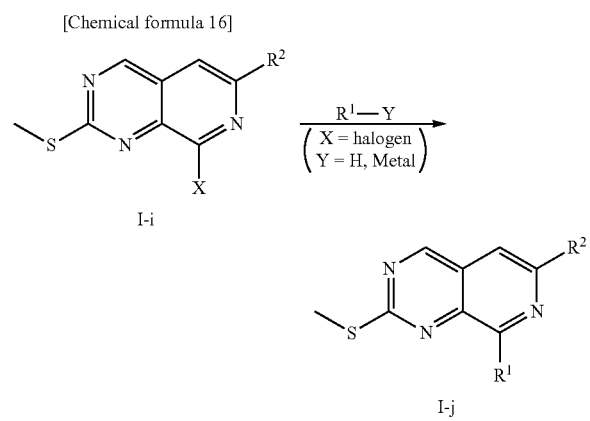

When R¹—Y is a cyclic secondary amine derivative, compound I-i is reacted with a cyclic secondary amine derivative represented by the formula R¹—Y in an appropriate organic solvent (e.g., THF or 1,4-dioxane) or under solvent-free conditions in the presence or absence of an appropriate base (e.g., triethylamine, potassium carbonate, or sodium hydride) at a temperature within the range from 0° C. to the reflux temperature of the solvent, to yield compound I-j.

When R¹—Y is an organometallic reagent such as a boric acid derivative, compound I-i is reacted with an organometallic reagent represented by formula R¹—Y such as a boric acid derivative, in the presence of an appropriate catalyst (e.g., palladium acetate or palladium chloride), in the presence or absence of an appropriate ligand (e.g., triphenylphosphine, BINAP, or dppf), in the presence or absence of an appropriate base (e.g., triethylamine, potassium carbonate, sodium hydride), in an appropriate organic solvent (e.g., THF or 1,4-dioxane), at a temperature within the range from 0° C. to the reflux temperature of the solvent, to yield compound I-j.

Moreover, in this step, R² may be modified by any process known to those skilled in the art in view of the intended structure of the compound.

6) Synthesis of Compound I-k from Compound I-j

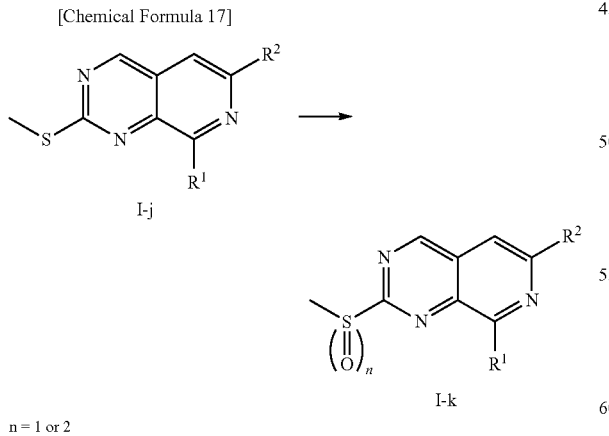

Compound I-j is reacted with an appropriate oxidant (e.g., Oxone (R) or m-chloroperbenzoic acid) in an appropriate organic solvent (e.g., dichloromethane or water) at a temperature of 0° C. to the reflux temperature of the solvent, to yield compound I-k.

7) Synthesis of Compound I-l from Compound I-j or Compound I-k

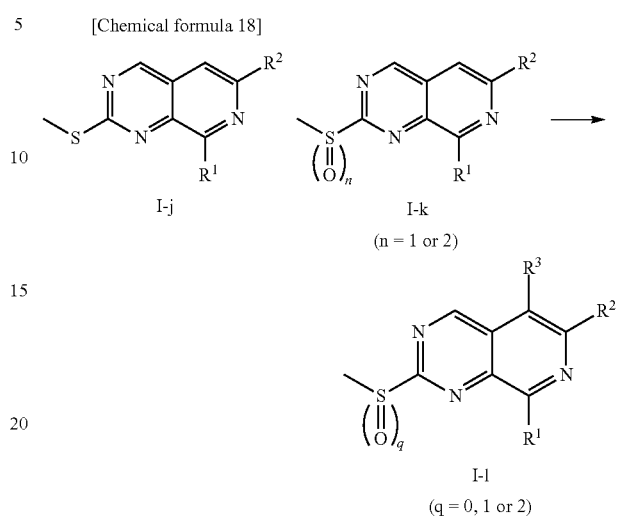

Compound I-j or compound I-k is reacted with an appropriate halogenating agent (e.g., N-chlorosuccinimide) in an appropriate organic solvent (e.g., dichloromethane or 1,2-dichloroethane) at a temperature within the range from 0° C. to the reflux temperature of the solvent, to yield compound I-l. Moreover, in this step, R³ can be converted into a desired structure in accordance with a method known to those skilled in the art.

In the case of compound I-l where q=0, oxidation reaction of a sulfur atom can subsequently be carried out in accordance with the method mentioned in item 6) above.

8) Synthesis of Compound I-m from Compound I-l

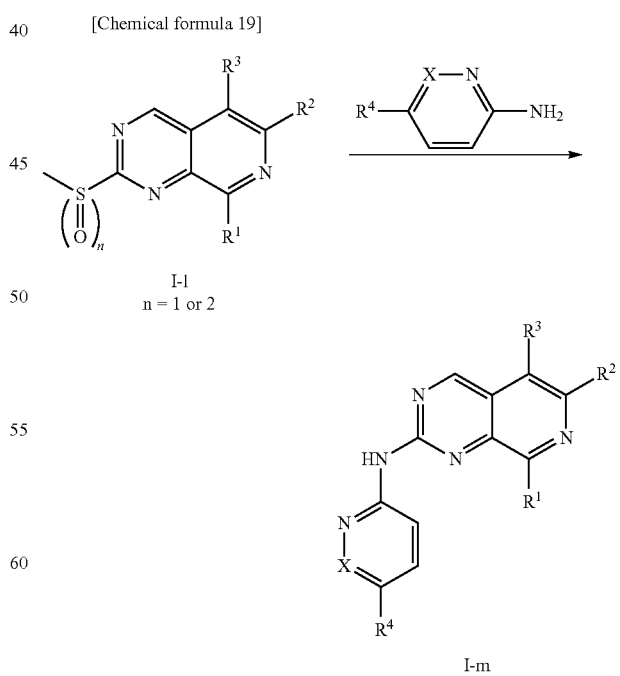

Compound I-l is reacted with an amine derivative represented by the formula R⁴-(nitrogen-containing heteroaryl with X)—NH$_2$ in an appropriate organic solvent (e.g., NMP, THF, or toluene) or under solvent-free conditions in the presence or absence of an appropriate base (e.g., sodium hydride, triethylamine, or N,N-diisopropyl-N-ethylamine) at a temperature of 0° C. to the reflux temperature of the solvent, to yield compound I-m.

If R$^1$, R$^2$, or R$^4$ of compound I-m is protected with an appropriate protective group, deprotection can be performed by any process known to those skilled in the art. For example, deprotection can be performed through reaction of the compound with an appropriate deprotecting reagent (e.g., TFA or hydrogen chloride for a Boc protective group, lithium hydroxide for a benzoyl protective group, or hydrogen in the presence of Pd/C for a Cbz protective group) in an appropriate organic solvent (e.g., dichloromethane, methanol, or THF) or under solvent-free conditions at a temperature of 0° C. to the reflux temperature of the solvent (reference: Green's Protective Groups in Organic Synthesis, 4th edition, John Wiley & Sons Inc.).

If compound I-m is protected with two or more protective groups, deprotection may be performed in an appropriate order depending on the structure of compound I-m.

In each of the reactions 9) to 13) described below, R$^1$, R$^2$, or R$^4$ of compound I-m is appropriately protected depending on the corresponding reaction conditions. After completion of the reaction, deprotection can be performed by an appropriate process.

9) Synthesis of Compound I-n from Compound I-m

[Chemical formula 20]

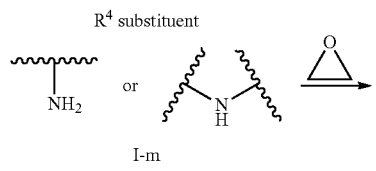

I-m

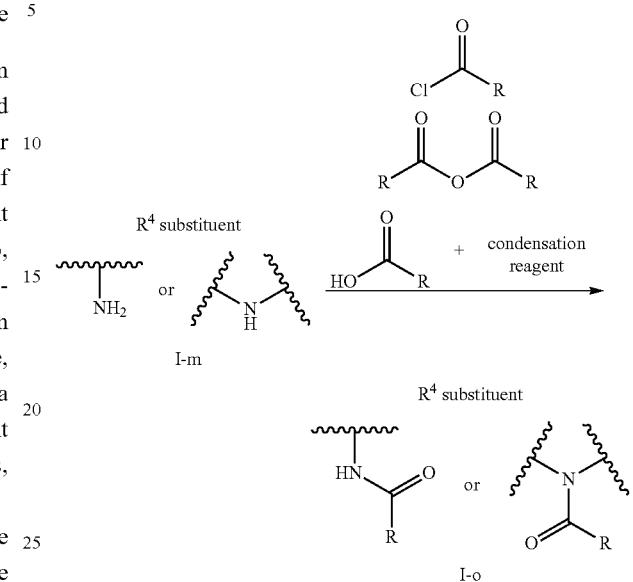

I-n

Compound I-m in which R$^4$ has a primary or secondary amine structure is reacted with an optionally substituted epoxide in an appropriate organic solvent (e.g., dichloromethane, NMP, or THF) in the presence or absence of an appropriate acid (e.g., boron trifluoride-diethyl ether complex) or an appropriate base (e.g., potassium carbonate or triethylamine) at a temperature of 0° C. to the reflux temperature of the solvent, to yield compound I-n.

10) Synthesis of Compound I-o from Compound I-m

[Chemical formula 21]

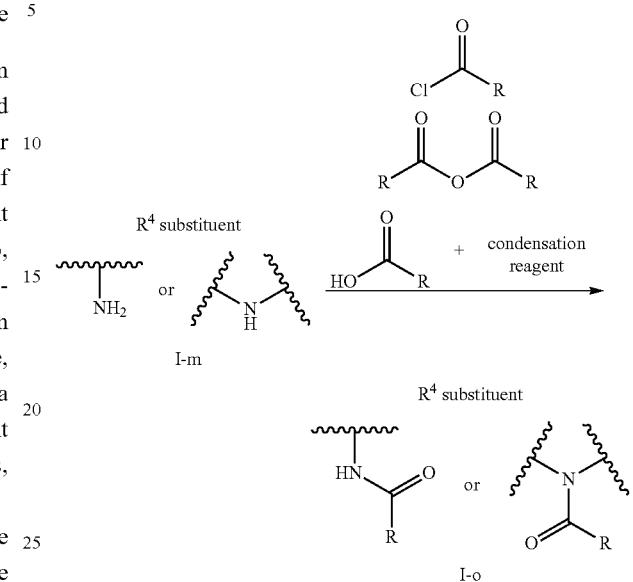

I-m

I-o

Compound I-m in which R$^4$ has a primary or secondary amine structure is reacted with a carboxylic acid chloride, a carboxylic anhydride, or a carboxylic acid and a condensation reagent in an appropriate organic solvent (e.g., NMP, THF, or pyridine) in the presence or absence of an appropriate base (e.g., triethylamine or N,N-diisopropyl-N-ethylamine) at a temperature of 0° C. to the reflux temperature of the solvent, to yield compound I-o. In this formula. R represents a hydrogen atom, C$_{1-8}$ alkyl, 4- to 12-membered heterocyclyl, C$_{3-12}$ cycloalkyl, C$_{6-10}$ aryl, 5- to 10-membered heteroaryl, (4- to 12-membered heterocyclyl, C$_{3-12}$ alkyl, (C$_{3-12}$ cycloalkyl)C$_{1-3}$ alkyl, (C$_{6-10}$ aryl)C$_{1-3}$ alkyl, or (5- to 10-membered heteroaryl)C$_{1-3}$ alkyl.

11) Synthesis of Compound I-p from Compound I-m

[Chemical formula 22]

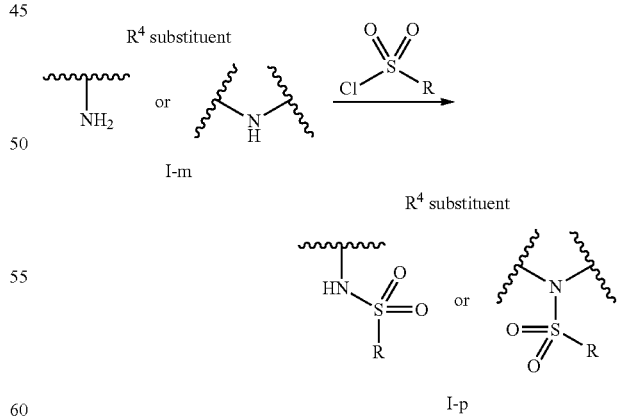

I-m

I-p

Compound I-m in which R$^4$ has a primary or secondary amine structure is reacted with sulfonic acid chloride in an appropriate organic solvent (e.g., NMP, THF, or pyridine) in the presence or absence of an appropriate base (e.g., triethylamine or N,N-diisopropyl-N-ethylamine) at a temperature of 0° C. to the reflux temperature of the solvent, to yield compound I-p. In this formula. R represents $C_{1-8}$ alkyl, 4- to 12-membered heterocyclyl, $C_{3-12}$ cycloalkyl, $C_{6-10}$ aryl, 5- to 10-membered heteroaryl, (4- to 12-membered heterocyclyl)$C_{1-3}$ alkyl, ($C_{3-12}$ cycloalkyl)$C_{1-3}$ alkyl, ($C_{6-10}$ aryl)$C_{1-3}$ alkyl, or (5- to 10-membered heteroaryl)$C_{1-3}$ alkyl.

12) Synthesis of Compound I-q from Compound I-m

[Chemical formula 23]

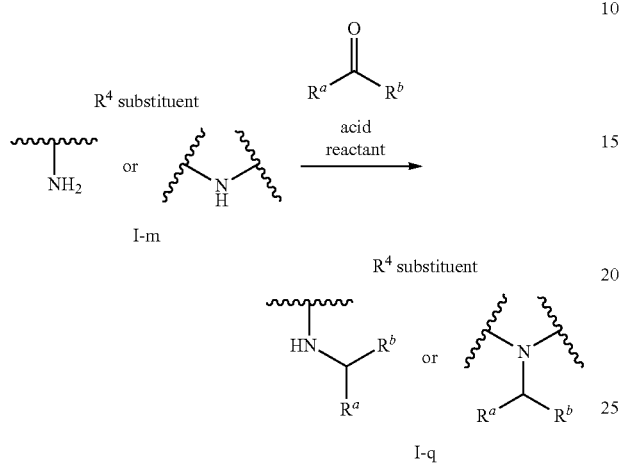

Compound I-m in which $R^4$ has a primary or secondary amine structure is reacted with an optionally substituted ketone or aldehyde and an appropriate reductant (e.g., sodium triacetoxyborohydride or sodium cyanoborohydride) in an appropriate organic solvent (e.g., NMP or methanol) in the presence of an appropriate acid (e.g., acetic acid) at a temperature of room temperature to the reflux temperature of the solvent, to yield compound I-q. In this formula. $R^a$ and $R^b$ form —CHR$^a$R$^b$ along with —CH to which $R^a$ and $R^b$ are bonded. Entire —CHR$^a$R$^b$ represents $C_{1-8}$ alkyl, 4- to 12-membered heterocyclyl, $C_{3-12}$ Cycloalkyl, (4- to 12-membered heterocyclyl)$C_{1-3}$ alkyl, ($C_{3-12}$ cycloalkyl)$C_{1-3}$ alkyl, ($C_{6-10}$ aryl)$C_{1-3}$ alkyl, or (5- to 10-membered heteroaryl)$C_{1-3}$ alkyl.

13) Synthesis of Compound I-r from Compound I-m

[Chemical formula 24]

Compound I-m in which $R^4$ has a primary or secondary amine structure is reacted with a compound having a leaving group (e.g., a halogen atom or a sulfonyloxy group) in an appropriate organic solvent (e.g., NMP, THF, or pyridine) in the presence or absence of an appropriate base (e.g., triethylamine or N,N-diisopropyl-N-ethylamine) at a temperature of 0° C. to the reflux temperature of the solvent, to yield compound I-r. In this formula. R represents $C_{1-8}$ alkyl, 4- to 12-membered heterocyclyl, $C_{3-12}$ cycloalkyl, (4- to 12-membered heterocyclyl)$C_{1-3}$ alkyl, ($C_{3-12}$ cycloalkyl)$C_{1-3}$ alkyl, ($C_{6-10}$ aryl)$C_{1-3}$ alkyl, or (5- to 10-membered heteroaryl)$C_{1-3}$ alkyl.

14) Synthesis of Compound I-s from Compound I-m

[Chemical formula 25]

Compound I-m in which $R^4$ has a primary or secondary amine structure is reacted with a compound having a structure of Michael acceptor in an appropriate organic solvent (e.g., methanol, THF) at a temperature of 0° C. to the reflux temperature of the solvent to yield compound I-s. In this formula, $R^a$, $R^b$, and $R^c$ form —CR$^a$R$^b$—CHR$^c$— along with —C—CH-structure to which $R^a$, $R^b$, and $R^c$ are bonded. Entire —CR$^a$R$^b$—CHR$^c$ represents $C_{1-8}$ alkyl, 4- to 12-membered heterocyclyl, $C_{3-12}$ cycloalkyl, (4- to 12-membered heterocyclyl)$C_{1-3}$ alkyl, ($C_{3-12}$ cycloalkyl)$C_{1-3}$ alkyl, ($C_{6-10}$ aryl)$C_{1-3}$ alkyl, or (5- to 10-membered heteroaryl)$C_{1-3}$ alkyl.

The compound of the present invention exhibits a CDK4/6 inhibitory activity and thus is useful for the prevention or treatment of a disease associated with CDK4/6. Specifically, the compound is useful for the treatment of rheumatoid arthritis, arteriosclerosis, pulmonary fibrosis, cerebral infarction, or cancer and the protection of bone marrow. In particular, the compound is effective for the treatment of rheumatoid arthritis or cancer and the protection of bone marrow.

The compound of the present invention preferably exhibits selectivity for the CDK4/6 inhibitory activity compared to the inhibitory activity against another cyclin-dependent kinase, such as CDK2 inhibitory activity. Such selectivity of the compound is expected to reduce the expression of genotoxicity because the inhibition of CDK2 is also involved in DNA replication. Preferably, the compound of the present invention selectively inhibits CDK4 rather than CDK2.

The active ingredient of the present invention may be provided in any preparation form, such as a solid, semisolid, or liquid form, and the like. The active ingredient may be provided in any dosage form, such as an oral form or a parenteral form (e.g., an injection, a transdermal agent, an eye drop, a suppository, a nasal agent, or an inhalant, and the like).

A drug containing the active ingredient of the present invention is prepared with a common additive used for drug preparation. Examples of the additive for solid drugs include excipients, such as lactose, sucrose, glucose, cornstarch, potato starch, crystalline cellulose, light silicic anhydride, synthetic aluminum silicate, magnesium aluminometasilicate, calcium hydrogen phosphate, and the like; binders, such as crystalline cellulose, carboxymethyl cellulose, hydroxypropyl cellulose, sodium carboxymethyl cellulose, poly(vinylpyrrolidone), and the like; disintegrants, such as starch, sodium carboxymethyl cellulose, calcium carboxymethyl cellulose, croscarmellose sodium, sodium carboxymethyl starch, and the like; lubricants, such as talc stearic acid, and the like; coating agents, such as hydroxymethyl propyl cellulose, hydroxypropyl methyl cellulose phthalate, ethyl cellulose, and the like; and colorants. Examples of the additive for semisolid drugs include bases, such as white vaseline, and the like. Examples of the additive for liquid drugs include solvents, such as ethanol, and the like; solubilizers, such as ethanol, and the like; preservatives, such as paraoxybenzoic acid esters, and the like; isotonic agents, such as glucose, and the like; buffers, such as citric acid, and the like; antioxidants, such as L-ascorbic acid, and the like; chelators, such as EDTA, and the like; suspending agents and emulsifiers, such as polysorbate 80, and the like; and the like.

The dose of the active ingredient of the present invention is typically about 1 to 1,000 mg/day. The active ingredient is typically administered once to three times a day.

EXAMPLES

The present invention will now be described by way of specific Examples. These Examples, however, should not be construed to limit the present invention.

The structure of the isolated novel compound was identified by $^1$H-NMR and/or mass spectrometry using single quadrupole instrumentation equipped with electron spray source and other appropriate analytical methods.

For the $^1$H-NMR spectrum (400 MHz, DMSO-$d_6$, $CD_3OD$, or $CDCl_3$), the chemical shift (δ: ppm) and the coupling constant (J: Hz) are shown. The abbreviations each represent as follows: s=singlet, d=doublet, t=triplet, q=quartet, brs=broad singlet, and m=multiplet. For the results of mass spectrometry, the observed values. $(M+H)^+$, corresponding to the molecular mass (M) of the compounds with a proton $(H^+)$ are shown.

Referential Example 11

Synthesis of 5-bromo-2-(methylthio)pyrimidine-4-carboxylic acid

[Formula 26]

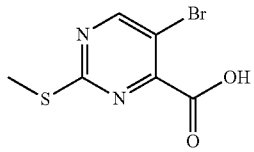

Mucobromic acid (300 g, 1.16 mol) was added to an aqueous solution (2.5 L) of 2-methyl-2-pseudothiourea sulfate (324 g, 1.16 mol) at room temperature. The suspension was cooled to 0° C. with stirring. Triethylamine (486 mL, 3.49 mol) was added dropwise to the solution over four hours. The reaction solution was stirred overnight, and the completion of the reaction was monitored by silica gel TLC. The solution was then acidized with concentrated hydrochloric acid (about 250 mL). The resulting yellow solid was collected by filtration, and washed with water (500 mL) twice and then with diethyl ether (500 mL) twice. The obtained solid was dried under reduced pressure to give the title compound (160 g, yield: 55%).

Referential Example 2

Synthesis of methyl 5-bromo-2-methylthiopyrimidine-4-carboxylate

[Formula 27]

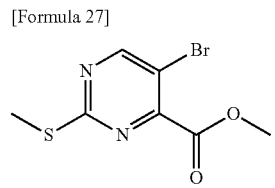

A solution of 5-bromo-2-(methylthio)pyrimidine-4-carboxylic acid (110 g, 0.44 mol) in methanol (1.1 L) was cooled to 0° C. with stirring. Thionyl chloride (50 mL, 0.66 mol) was added dropwise to the solution. The solution was slowly heated and the reaction was conducted under reflux with heating for four hours. The completion of the reaction was monitored by LC/MS and TLC and the solution was cooled to room temperature. The volatiles were distilled away under reduced pressure, and the residue was dissolved in ethyl acetate (1 L). The solution was washed with aqueous 10% sodium carbonate solution (200 mL) three times and with saturated brine (200 mL) twice. The resulting organic phase was dried over anhydrous magnesium sulfate. The solid was filtered out, and the filtrate was concentrated under reduced pressure. The crude product was purified by silica gel column chromatography to give the title compound (88 g, yield: 75%).

Referential Example 3

Synthesis of mixture of 5-bromo-2-methylthiopyrimidine-4-carbaldehyde and (5-bromo-2-methylthiopyrimidin-4-yl)methoxymethanol

[Formula 28]

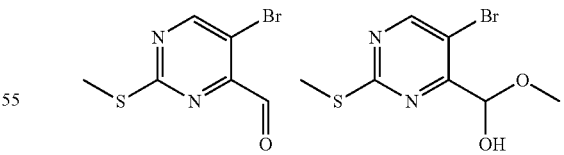

A solution of methyl 5-bromo-2-methylsulfanylpyrimidine-4-carboxylate (25 g, 95 mmol) in THF (375 mL) was cooled to −78° C. with stirring under a nitrogen atmosphere. DIBAL-H (84 mL, 143 mmol, 1.7 M in toluene) was added dropwise to the solution. The reaction mixture was stirred at −78° C. for four hours. The completion of the reaction was monitored by TLC and the reaction was quenched by dropwise addition of methanol at −78° C. The solution was allowed to warm slowly to 0° C. The solution was diluted with ethyl acetate and filtered under reduced pressure through a Celite pad. The filtrate was washed with saturated brine (200 mL) twice. The resulting organic phase was dried over anhydrous magnesium sulfate, and the solid was filtered out. The filtrate was concentrated to give a mixture (25 g, crude product) of the title compounds. The crude product was used in the subsequent reaction without further purification.

Referential Example 4

Synthesis of tert-butyl 4-(6-nitropyridin-3-yl)piperazine-1-carboxylate

[Formula 29]

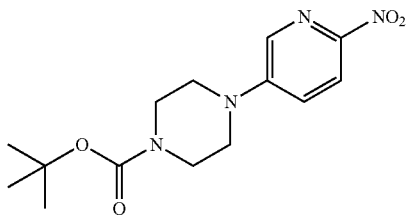

A mixture of 5-Bromo-2-nitropyridine (203 g, 1.37 mol), piperazine (153 g, 1.77 mol), tetrabutylammonium iodide (25.2 g, 0.068 mol) and potassium carbonate (207 g, 1.50 mol) in dimethyl sulfoxide (2.6 L) was stirred at 80° C. overnight. The reaction mixture was cooled to room temperature and poured into water (7 L). The resultant solid was collected by filtration. The solid was washed with dichloromethane (1 L, twice), and dried. The filtrate was extracted with chloroform (2 L, seven times). The extracted organic phase was washed with water (2 L) and then with saturated brine (2 L), followed by concentration under reduced pressure to give solid. The solid products were combined and used in the subsequent reaction without further purification.

The solid (490 g) was dissolved in THF (2 L) and water (500 mL). Sodium hydrogen carbonate (119 g, 1.42 mol) was added to the solution. Di-tert-butyl dicarboxylate (262 g, 1.2 mol) was added to the suspension and the reaction mixture was stirred at room temperature for three hours. The solution was concentrated under reduced pressure. The residue was diluted with water (1 L), and the aqueous phase was extracted with dichloromethane (1 L, three times). The extracted organic phases were combined and washed with water (1 L). The aqueous phase was extracted with dichloromethane (300 mL). The extracted organic phases were combined and dried over anhydrous magnesium sulfate. The solid was filtered out, and the filtrate was concentrated under reduced pressure. The resulting solid was suspended in ethyl acetate (2 L), heated to 60° C. and collected by filtration at 60° C. The solid thus obtained was dried under reduced pressure to give the title compound (191 g, yield: 62%).

APCI-MS (M+H)$^+$ 309.1, $C_{14}H_{20}N_4O_4$=308.15

$^1$H-NMR δ (400 MHz, CDCl$_3$): 8.16 (d, J=−9 Hz, 1H), 8.11 (d, J=3 Hz, 1H), 7.19 (dd, J=9.3 Hz 1H), 3.64-3.61 (m, 4H), 3.45-3.42 (m, 4H), 1.47 (s, 9H).

Referential Example 5

Synthesis of tert-butyl 4-(6-aminopyridin-3-yl)piperazine-1-carboxylate

[Formula 30]

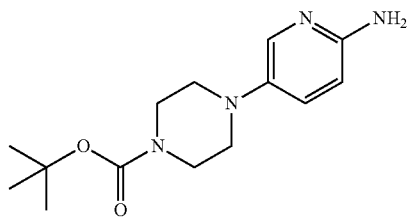

tert-Butyl 4-(6-nitropyridin-3-yl)piperazine-1-carboxylate (83 g, 269 mmol) prepared in Referential Example 4 was dissolved in methanol (1.3 L) in a Parr Shaker and Raney nickel (15 g, 50% aqueous suspension) was added to the solution. The reaction mixture was stirred under a hydrogen atmosphere (50 psi) for five hours. The reaction mixture was passed through Celite pad to filter out a solid. The filtrate was concentrated under reduced pressure. The resulting solid was suspended in diethyl ether (120 mL), and the suspension was stirred for four hours. Heptane was added, and the suspension was cooled at 0° C. for 45 minutes. The solid was collected by filtration, and dried under reduced pressure to give the title compound (62.5 g, yield: 83%).

ESI-MS (M+H)$^+$ 279, $C_{14}H_{22}N_4O_2$=278.17

Intermediates A-1 to A-5 shown below were synthesized in accordance with the processes described in Referential Examples 4 and 5 using the corresponding halopyridine derivatives and amine derivatives with appropriate protection and deprotection when necessary.

[Formula 31]

A-1

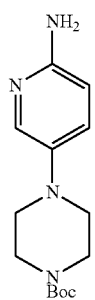

A-2

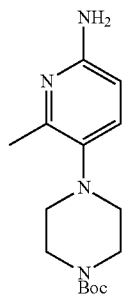

-continued

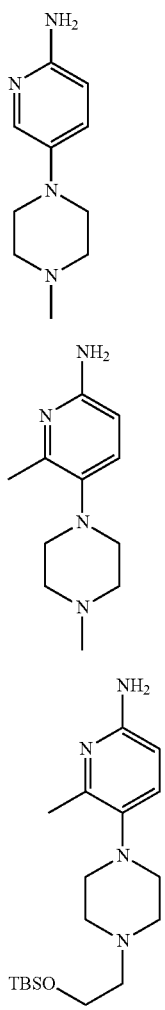

A-3

A-4

A-5

Referential Example 6

Synthesis of 6-aminopyridine-3-carbaldehyde

[Formula 32]

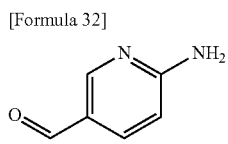

6-Aminopyridine-3-carbonitrile (1.9 g, 16 mmol) was dissolved in THF (160 mL). The solution was cooled to −78° C. with stirring. Diisobutylaluminum hydride (106.5 mL, 1.5 M toluene solution) was slowly added dropwise to the solution at −78° C. The solution was allowed to warm to 20° C. with stirring and further stirred for two hours. The reaction was quenched by addition of iced water (100 mL). The solution was extracted with dichloromethane (50 mL) three times. The extracted organic phases were combined, washed with brine (100 mL) once, and dried over anhydrous sodium sulfate. The solid was filtered out, and the filtrate was concentrated under reduced pressure. The residue was purified by silica gel column chromatography to give a crude product (1.7 g) of the title compound. The crude product was used in the subsequent reaction without further purification.

Referential Example 7

Synthesis of tert-butyl 4-[(6-aminopyridin-3-yl)methyl]piperazine-1-carboxylate

[Formula 33]

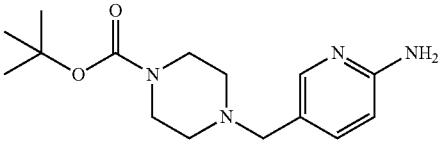

The crude product (1.7 g, 13.9 mmol) of 6-aminopyridine-3-carbaldehyde synthesized in Referential Example 6 and tert-butylpiperazine-1-carboxylate (3.2 g, 17.2 mmol) were dissolved in dichloromethane (50 mL). The solution was stirred at room temperature for eight hours. Sodium triacetoxyborohydride (8.84 g, 40.9 mmol) was added to the reaction solution, and the reaction mixture was stirred at room temperature for two hours. The progress of the reaction was monitored by LC/MS. After the completion of the reaction, the reaction was quenched by addition of saturated aqueous sodium carbonate solution (50 mL). The solution was extracted with ethyl acetate (50 mL) three times. The extracted organic phases were combined, washed with brine (100 mL) once, and dried over anhydrous sodium sulfate. The solid was filtered out, and the filtrate was concentrated under reduced pressure. The residue was purified by silica gel column chromatography to give the crude title compound (3.3 g, yield: 81%).

Referential Example 8

Synthesis of 1-(2-((tert-butyldiphenylsilyl)oxy)ethyl)-4-((6-chloropyridin-3-yl)methylpiperazine

[Formula 34]

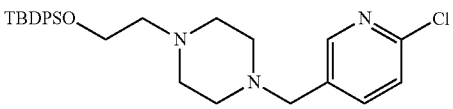

DMF (33.3 mL) was added to a mixture of 2-chloro-5-(chloromethyl)pyridine (1.62 g, 10 mmol), 1-(2-((tert-butyldiphenylsilyl)oxy)ethyl)piperazine (3.87 g, 10.5 mmol), potassium carbonate (4.15 g, 30 mmol) and sodium iodide (150 mg, 1.0 mmol). The solution was stirred at 60° C. for two hours. Water was added to the solution. The solution was extracted with ethyl acetate (80 mL) twice. The extracted organic phases were dried over anhydrous sodium sulfate. The solid was filtered out, and the filtrate was concentrated. The residue was purified by silica gel column chromatography to give the title compound (3.26 g, yield: 66%).

Referential Example 9

Synthesis of 5-((4-(2-((tert-butyldiphenylsilyl)oxy)ethyl)piperazin-1-yl)methyl)pyridine-2-amine

[Formula 35]

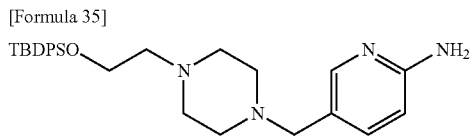

Toluene (33 mL) was added to a mixture of 1-(2-((tert-butyldiphenylsilyl)oxy)ethyl)-4-((6-chloropyridin-3-yl)methylpiperazine (3.26 g, 6.6 mmol) synthesized in Referential Example 8, benzophenoneimine (1.33 mL, 7.92 mmol), tris(dibenzylideneacetone)dipalladium(0) (302 mg, 0.33 mmol), BINAP (411 mg, 0.66 mmol) and sodium tert-butoxide (1.27 g, 13.2 mmol). The reaction mixture was stirred under a nitrogen atmosphere at 120° C. overnight. The reaction mixture was cooled to room temperature and filtered through a Celite pad. The Celite pad was washed with ethyl acetate (80 mL). The filtrate was washed with water and further with saturated brine. The organic phase was dried over anhydrous sodium sulfate. The solid was filtered out, and the filtrate was concentrated. The residue was dissolved in THF (66 mL), and aqueous citric acid solution (16 mL, 2.0 mol/L) was added to the solution. The solution was stirred at room temperature overnight. The solution was passed through a column filled with a strong cation exchange (SCX) resin to adsorb the target product. The resin was washed with methanol. Ammonia (2.0 mol/L, methanol solution) was passed through the column to elute the target product. The eluate was concentrated to give the title compound (1.17 g, yield: 37%).

Intermediates B-1 to B-12 shown below were synthesized in accordance with one or a combination of the processes in Referential Examples 6 and 7 or those in Referential Examples 8 and 9 using the corresponding aldehyde derivatives, alkyl halide derivatives, and amine derivatives with appropriate protection and deprotection when necessary.

[Formula 36]

B-1

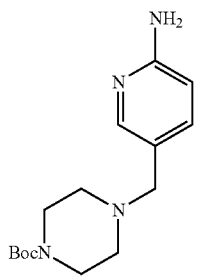

B-2

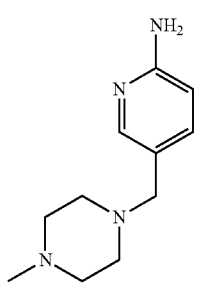

B-3

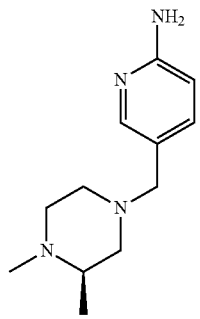

B-4

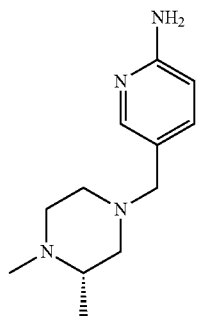

B-5

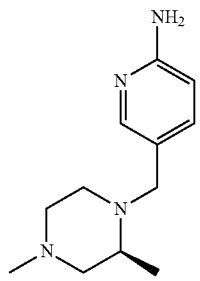

B-6

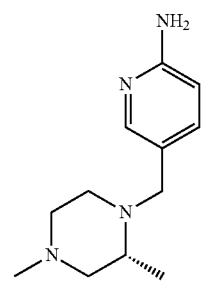

B-8

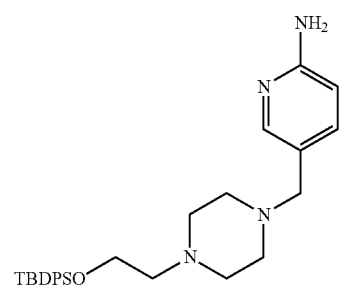

B-9 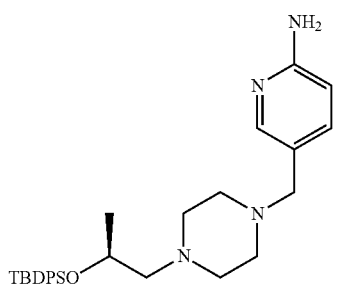

B-10 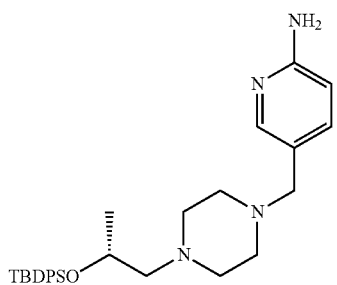

B-11 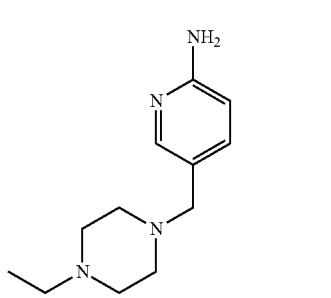

B-12 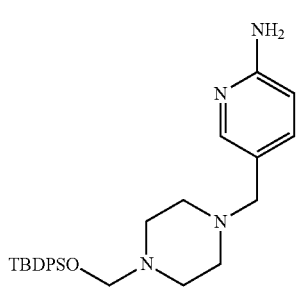

Referential Example 10

Synthesis of tert-butyl 4-(6-nitropyridin-3-yl)-3-yl)-3-oxopiperazine-1-carboxylate

[Formula 37]

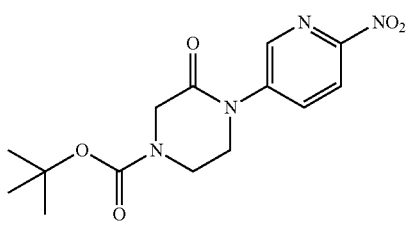

With reference to the process described in WO2012/031004, 2-nitro-5-bromopyridine (1.01 g, 5.0 mmol), tert-butyl 2-oxo-4-piperazinecarboxylate (1.00 g, 5.0 mmol) and cesium carbonate (3.26 g, 10.0 mmol) were suspended in 1,4-dioxane. Nitrogen gas was bubbled into the suspension for 30 minutes. Xantphos (246 mg, 0.43 mmol) and tris(dibenzylideneacetone)dipalladium (229 mg, 0.25 mmol) were added to the suspension and the reaction mixture was stirred under reflux with heating for two hours. The reaction mixture was cooled to room temperature. Water and ethyl acetate were added to the mixture. The solution was filtered through a Celite pad. The organic phase was separated from the filtrate. The aqueous phase was extracted with ethyl acetate. The extracted organic phases were combined and dried over anhydrous sodium sulfate. The solid was filtered out, and the filtrate was concentrated under reduced pressure. The residue was purified by silica gel column chromatography to give the title compound (1.08 g, yield: 67%).

$^1$H-NMR (CDCl$_3$) δ: 8.67 (1H, d, J=2.4 Hz), 8.32 (1H, d, J=8.8 Hz), 8.15 (1H, dd, J=8.8, 2.4 Hz), 4.33 (2H, s), 3.93-3.83 (4H, m), 1.51 (9H, s).

Referential Example 11

Synthesis of tert-butyl 4-(6-aminopyridin-3-yl)-3-oxopiperazine-1-carboxylate

[Formula 38]

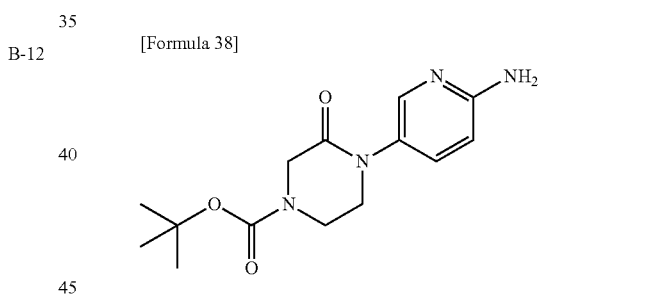

The compound (1.08 g, 3.34 mmol) prepared in Referential Example 10 was dissolved in ethanol (45 mL) and THF (22 mL). Palladium on carbon (108 mg) was added to the solution. The reaction mixture was stirred under a hydrogen atmosphere for 24 hours. The reaction mixture was filtered through a Celite pad. The filtrate was concentrated under reduced pressure. The residue was purified by silica gel column chromatography to give the title compound (0.928 g, yield: 95%). $^1$H-NMR (CDCl$_3$) δ: 7.99 (1H, d, J=2.4 Hz), 7.38 (1H, dd, J=8.8, 2.4 Hz), 6.53 (1H, d, J=8.8 Hz), 4.50 (2H, brs), 4.24 (2H, s), 3.78 (2H, t, J=5.1 Hz), 3.67 (2H, t, J=5.4 Hz), 1.50 (9H, s).

Intermediates C-1 to C-6 shown below were synthesized in accordance with the processes in Referential Examples 13 and 14 using the corresponding halopyridine derivatives and amide derivatives with appropriate protection and deprotection when necessary.

[Formula 39]

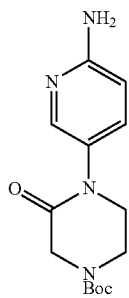
C-1

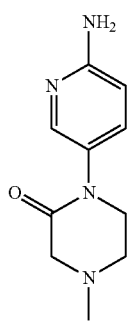
C-2

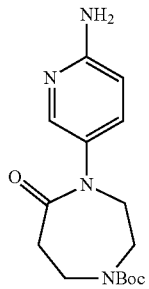
C-3

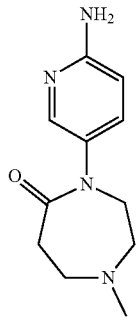
C-4

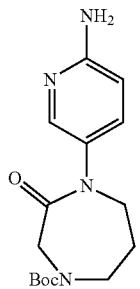
C-5

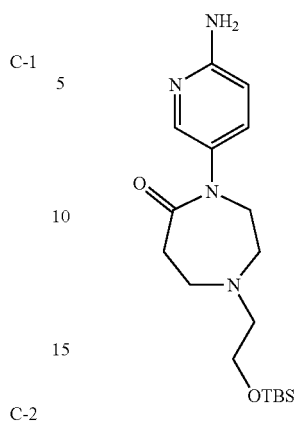
C-6

Referential Example 12

Synthesis of tert-butyl trans-3-fluoro-4-((6-nitropyridin-3-yl)oxy)piperidine-1-carboxylate

[Formula 40]

Sodium hydride (48 mg, 1.2 mmol) was suspended in THF (2 mL). A solution of tert-butyl trans-3-fluoro-4-hydroxypiperidine-1-carboxylate (263 mg, 1.2 mmol) in THF (2 mL) was added and the reaction mixture was stirred at room temperature for one hour. A solution of 5-fluoro-2-nitropyridine (142 mg, 1.0 mmol) in THF (1 mL) was added to the suspension at room temperature and the reaction mixture was stirred at room temperature overnight. The reaction was monitored by LC/MS. After the completion of the reaction, the reaction was quenched by addition of water (10 mL). The solution was extracted with ethyl acetate (10 mL) three times. The extracted organic phases were combined, washed with saturated brine, and dried over anhydrous sodium sulfate. The solid was filtered out, and the filtrate was concentrated under reduced pressure. The residue was purified by silica gel column chromatography to give the title compound (310 mg, yield: 91%).

Referential Example 13

Synthesis of tert-butyl trans-4-((6-aminopyridin-3-yl)oxy)-3-fluoropiperidine-1-carboxylate

[Formula 41]

tert-Butyl trans-3-fluoro-4-((6-nitropyridin-3-yl)oxy)piperidine-1-carboxylate (310 mg, 0.908 mmol) prepared in Referential Example 12 was dissolved in THF (9 mL) and methanol (9 mL). Ammonium chloride (486 mg, 9.08 mmol)

and zinc powder (594 mg, 9.08 mmol) were added to the solution and the reaction mixture was stirred at room temperature for one hour. The reaction mixture was filtered through a Celite pad. The filtrate was concentrated under reduced pressure. A saturated aqueous sodium hydrogen carbonate solution (30 mL) was added to the residue. The aqueous phase was extracted with dichloromethane (30 mL) twice. The extracted organic phases were combined and dried over anhydrous sodium sulfate. The solid was filtered out, and the filtrate was concentrated under reduced pressure to give a crude product of the title compound. The crude product was used in the subsequent reaction without further purification.

Intermediates D-1 to D-3 shown below were synthesized in accordance with the processes described in Referential Examples 15 and 16 using the corresponding halopyridine derivatives and alcohol derivatives with appropriate protection and deprotection when necessary.

[Formula 42]

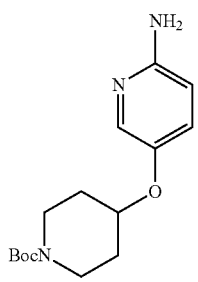
D-1

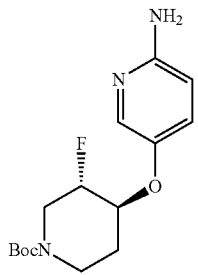
D-2

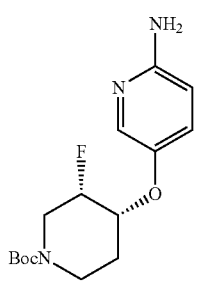
D-3

Referential Example 14

Synthesis of tert-butyl 4-(6-chloropyridazin-3-yl)piperazine-1-carboxylate

[Formula 43]

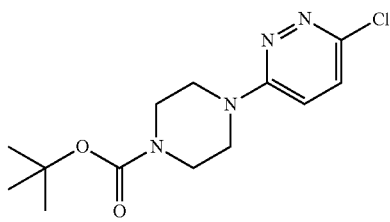

3,6-Dichloropyridazine (5.01 g, 33.6 mmol) and tert-butyl piperazine-1-carboxylate (6.88 g, 37.0 mmol) were dissolved in DMF (50 mL). Triethylamine (11.7 mL, 50.4 mmol) was added to the solution. The resulting mixture was stirred at 80° C. overnight. The reaction mixture was cooled to room temperature and water was added. The solution was extracted with a 95:5 mixed solvent (50 mL) of dichloromethane and methanol three times. The combined organic phase was dried over anhydrous magnesium sulfate. The solid was filtered out, and the filtrate was concentrated under reduced pressure. The crude product was washed with diethyl ether to give the title compound (7.0 g, yield: 70%).

Referential Example 15

Synthesis of tert-butyl 4-(6-((diphenylmethylene)amino)pyridazin-3-yl)piperazine-1-carboxylate

[Formula 44]

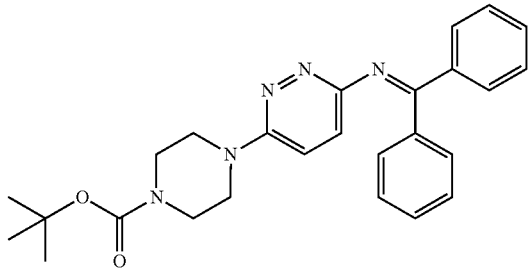

The tert-butyl 4-(6-chloropyridazin-3-yl)piperazine-1-carboxylate (59.8 mg, 0.20 mmol) prepared in Referential Example 14, benzophenone imine (43.5 mg, 0.24 mmol), tris(dibenzylideneacetone)dipalladium (9.2 mg, 0.010 mmol), BINAP (12.5 mg, 0.020 mmol) and cesium carbonate (130.3 mg, 0.40 mmol) were suspended in toluene (1.0 mL). The reaction mixture was stirred at 100° C. overnight. The reaction mixture was cooled to room temperature and filtered through a Celite pad. The Celite pad was washed with ethyl acetate. The filtrate was washed with saturated brine, and dried over anhydrous magnesium sulfate. The solid was filtered out, and the filtrate was concentrated under reduced pressure. The residue was purified by silica gel column chromatography to give the title compound (67 mg, yield: 76%).

Referential Example 16

Synthesis of tert-butyl 4-(6-aminopyridazin-3-yl)piperazine-1-carboxylate

[Formula 45]

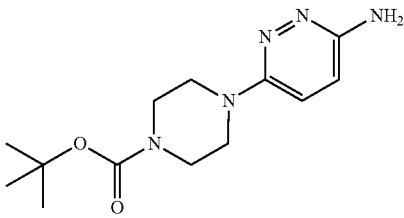

tert-Butyl 4-(6-((diphenylmethylene)amino)pyridazin-3-yl)piperazine-1-carboxylate (67 mg, 0.151 mmol) prepared in Referential Example 15 was dissolved in THF (0.76 mL). Aqueous citric acid solution (0.378 mL, 0.755 mmol, 2 mol/L) was added to the solution. The resulting solution was stirred at room temperature overnight. The solution was neutralized with a saturated aqueous sodium hydrogen carbonate solution (5 mL), and the aqueous phase was extracted with ethyl acetate (5 mL) twice. The extracted organic phases were combined and dried over anhydrous magnesium sulfate. The solid was filtered out, and the filtrate was concentrated under reduced pressure. The crude product was washed with tert-butyl methyl ether (5 mL) to give the title compound (30 mg, yield: 71%).

Intermediates E-1 and E-2 shown below were synthesized in accordance with one or a combination of the processes described in Referential Examples 17 to 19 using the corresponding haloheteroaryl derivatives and amine derivatives with appropriate protection and deprotection when necessary.

[Formula 46]

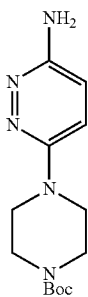

E-1

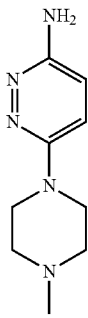

E-2

Referential Example 17

Intermediate F-1 was synthesized in accordance with the process described in Referential Example 9 by reaction of tert-butyl 2-chloro-7,8-dihydro-1,6-naphthyridine-6(5H)-carboxylate with benzophenone imine and tert-butoxy sodium in the presence of a Pd catalyst, followed by deprotection.

[Formula 47]

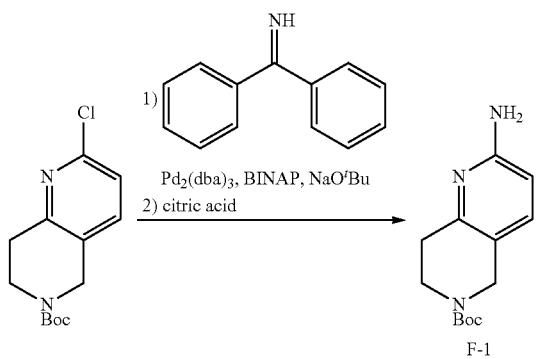

Example 1

Synthesis of 3-(4-formyl-2-methylthiopyrimidin-5-yl)-2-propynyl benzoate

[Formula 48]

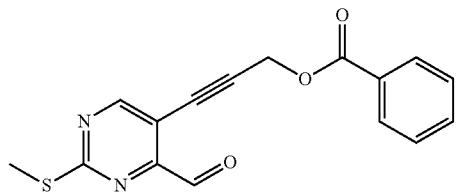

A mixture of Pd(PhCN)$_2$Cl$_2$ (2.4 g, 6.4 mmol), copper iodide (0.82 g, 4.3 mmol) and [(t-Bu)$_3$P]HBF$_4$ (4 g, 13.9 mmol) in 1,4-dioxane (55 mL) was degassed and purged with argon. Diisopropylamine (18.5 mL, 128.8 mmol) was added to the mixture at room temperature. The reaction mixture was stirred at room temperature for five minutes. A solution of the mixture (25 g, crude product) of 5-bromo-2-methylsulfanylpyrimidine-4-carbaldehyde and (5-bromo-2-methylsulfanylpyrimidin-4-yl)methoxymethanol described in Referential Example 3 and propargyl benzoate (20 g, 128.8 mmol) in 1,4-dioxane (55 mL) was slowly added dropwise. The reaction mixture was stirred at room temperature for five hours. The progress of the reaction was monitored by LC/MS. After the completion of the reaction, the reaction mixture was diluted with ethyl acetate (1 L) and filtered under reduced pressure through a Celite pad. The Celite pad was washed with ethyl acetate. The filtrate was concentrated under reduced pressure. The crude product was directly used in the subsequent reaction.

Example 2

Synthesis of 6-((benzoyloxy)methyl)-2-(methylthio)pyrido[3,4-d]pyrimidine 7-oxide (Int-1)

[Formula 49]

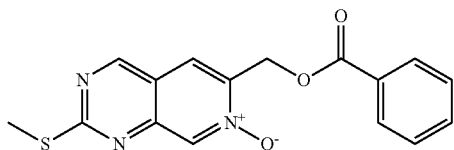

The crude product of 3-(4-formyl-2-methylthiopyrimidin-5-yl)-2-propynyl benzoate synthesized in Example 1 was dissolved in ethanol (500 mL). Hydroxylamine hydrochloride (8.3 g, 120 mmol) and sodium acetate (10 g, 120 mmol) were added to the solution at room temperature. The reaction mixture was stirred at room temperature for six hours. The mixture was diluted with ethanol (1 L). Potassium carbonate (27.8 g, 200 mmol) was added to the mixture. The resulting mixture was stirred at 50° C. for three hours. The progress of the reaction was monitored by LC/MS. After the completion of the reaction, the reaction mixture was filtered under reduced pressure through a Celite pad. The Celite pad was washed with ethyl acetate. The filtrate was dried over anhydrous sodium sulfate. The solid was filtered out, and the filtrate was concentrated under reduced pressure. The crude product was purified by silica gel column chromatography to give the title compound (5.0 g, yield: 16%).

$^1$H-NMR (DMSO-d6) δ: 9.46 (1H, s), 8.93 (1H, s), 8.31 (1H, s), 8.13 (2H, d, J=7.6 Hz), 7.73 (1H, t, J=7.3 Hz), 7.60 (2H, t, J=7.7 Hz), 5.54 (2H, s), 2.62 (3H, s).

LC/MS: (M+H)$^+$=328.2, $C_{16}H_{13}N_3O_3S$=327.07

Compounds Int-2 to Int-9 shown below were synthesized in accordance with the processes described in Examples 1 and 2.

TABLE 1

| Compound No. | Structure | NMR | (M+H)$^+$ | Exact Mass |
|---|---|---|---|---|
| Int-2 | 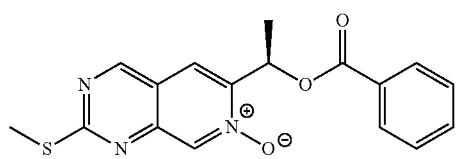 [SMILES: CSc1ncc2cc([C@@H](C)OC(=O)c3ccccc3)[n+]([O-])cc2n1] | 1H-NMR (CDCl3) δ: 9.04 (1H, s), 8.79 (1H, s), 8.14 (2H, d, J = 7.5 Hz), 7.77-7.40 (4H, m), 6.66 (1H, q, J = 6.3 Hz), 2.65 (3H, s), 1.79 (3H, d, J = 6.6 Hz). | 342.0 | 341.08 |
| Int-3 | 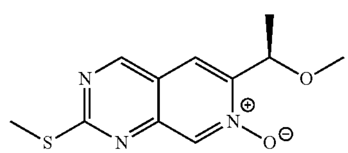 | 1H-NMR (DMSO-d6) δ: 9.44 (1H, d, J = 0.4 Hz), 8.85 (1H, s), 8.09 (1H, s), 4.87 (1H, q, J = 6.4 Hz), 3.32 (3H, s), 2.61 (3H, s), 1.41 (3H, d, J = 6.4 Hz). | 252.1 | 251.07 |
| Int-4 | 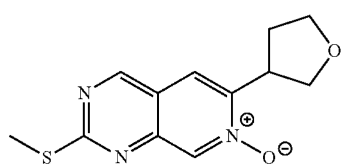 [SMILES: CSc1ncc2cc(C3CCOC3)[n+]([O-])cc2n1] | 1H-NMR (CDCl3) δ: 9.04 (1H, s), 8.79 (1H, s), 7.65 (1H, s), 4.25-3.90 (5H, m), 2.65 (3H, s), 2.62-2.46 (1H, m), 2.13-2.03 (1H, m). | 264.1 | 263.07 |
| Int-5 | 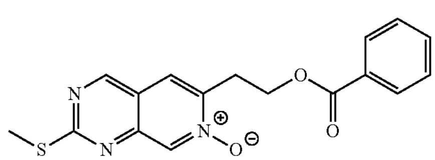 [SMILES: CSc1ncc2cc(CCOC(=O)c3ccccc3)[n+]([O-])cc2n1] | 1H-NMR (CDCl3) δ: 8.99 (1H, s), 8.81 (1H, s), 7.98-7.93 (2H, m), 7.70-7.38 (4H m), 4.78 (2H, t, J = 6.2 Hz), 3.48 (2H, t, J = 6.0 Hz), 2.65 (3H, s). | 342.1 | 341.08 |
| Int-6 | 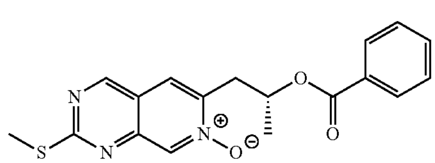 [SMILES: CSc1ncc2cc(C[C@@H](C)OC(=O)c3ccccc3)[n+]([O-])cc2n1] | 1H-NMR (CDCl3) δ: 8.89 (1H, s), 8.78 (1H, s), 7.96-7.91 (2H, m), 7.58-7.50 (2H, m), 7.45-7.36 (2H,m), 5.75-5.62 (1H, m), 3.55-3.45 (1H, m), 3.34-3.22 (1H, m), 2.63 (3H, s), 1.53 (3H, d, J = 6.4 Hz). | 356.1 | 355.1 |

TABLE 2

| Compound No. | Structure | NMR | (M+H)+ | Exact Mass |
|---|---|---|---|---|
| Int-7 | 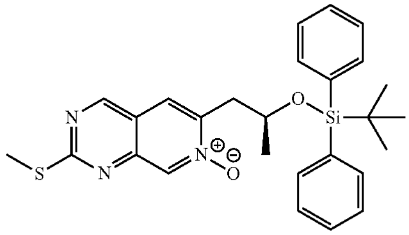 [SMILES: CSc1ncc2cc(C[C@H](C)O[Si](c3ccccc3)(c3ccccc3)C(C)(C)C)[n+]([O-])cc2n1] | 1H-NMR (CDCl3) δ: 8.72 (1H, s), 8.49 (1H, s), 7.52-7.20 (11H, m), 4.58-4.50 (1H, m), 3.28-3.20 (1H, m), 2.98-2.89 (1H, m), 2.65 (3H, s), 1.30 (3H, d, J = 6.4 Hz), 0.96 (9H, s). | 490.2 | 489.19 |
| Int-8 | 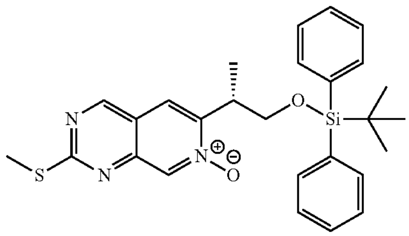 [SMILES: CSc1ncc2cc([C@H](C)CO[Si](c3ccccc3)(c3ccccc3)C(C)(C)C)[n+]([O-])cc2n1] | 1H-NMR (CDCl3) δ: 8.91 (1H, s), 8.65 (1H, s), 7.56-7.24 (11H, m), 4.05-3.92 (3H, m), 2.66 (3H, s), 1.42 (3H, d, J = 1.2 Hz), 0.99 (9H, s). | 490.2 | 489.19 |
| Int-9 | 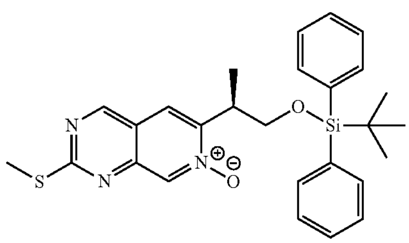 [SMILES: CSc1ncc2cc([C@@H](C)CO[Si](c3ccccc3)(c3ccccc3)C(C)(C)C)[n+]([O-])cc2n1] | | 490.30 | 489.19 |

Example 3

Synthesis of 8-chloro-2-methylthiopyrido[3,4-d]pyrimidin-6-yl benzoate (Int-10)

[Formula 50]

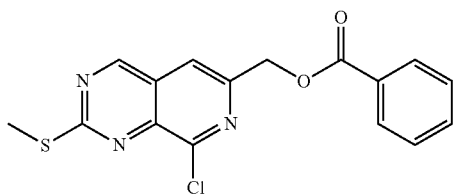

6-((Benzoyloxy)methyl)-2-(methylthio)pyrido[3,4-d]pyrimidine 7-oxide (5.0 g, 15.3 mmol) synthesized in Example 2 was dissolved in dichloromethane (60 mL). The resulting solution was cooled to 0° C. Thionyl chloride (25 mL, 343 mmol) was added dropwise to the solution at 0° C. and the reaction mixture was stirred at room temperature for 16 hours. The progress of the reaction was monitored by TLC. After the completion of the reaction the solution was concentrated under reduced pressure and thionyl chloride was removed by azeotropic distillation with toluene (20 mL) twice. The residue was purified by neutral alumina column chromatography to give the crude title compound (2.75 g, yield: 52%).

$^1$H-NMR (DMSO-d6) δ: 9.64 (1H, s), 8.14 (1H, s), 8.13-8.06 (2H, m), 7.75-7.68 (1H, m), 7.59 (2H, t, J=7.7 Hz), 5.56 (2H, s), 2.69 (3H, s).

LC/MS: (M+H)+=346.0, $C_{16}H_{12}ClN_3O_2S$=345.03

Compounds Int-11 to Int-19 shown below were synthesized in accordance with the process described in Example 3.

TABLE 3

| Compound No. | Structure | NMR | (M+H)+ | Exact Mass |
|---|---|---|---|---|
| Int-11 | 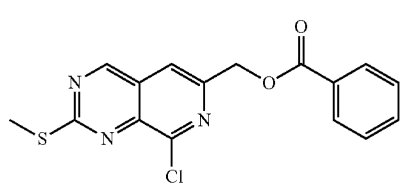 [SMILES: CSc1ncc2cc(COC(=O)c3ccccc3)nc(Cl)c2n1] | 1H-NMR (DMSO-d6) δ: 9.64 (1H, s), 8.14 (1H, s), 8.13-8.06 (2H, m), 7.75-7.68 (1H, m), 7.59 (2H, t, J = 7.7 Hz), 5.56 (2H, s), 2.69 (3H, s). | 346.0 | 345.03 |

TABLE 3-continued

| Compound No. | Structure | NMR | (M+H)+ | Exact Mass |
|---|---|---|---|---|
| Int-12 | 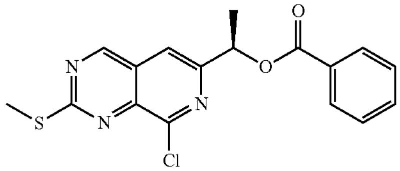 [SMILES: CSc1ncc2cc([C@@H](C)OC(=O)c3ccccc3)nc(Cl)c2n1] | 1H-NMR (CDCl3) δ: 9.19 (1H, s), 8.16-8.12 (2H, m), 7.68 (1H, s), 7.64-7.58 (1H, m), 7.53-7.46 (2H, m). 6.27 (1H, q, J = 6.8 Hz), 2.74 (3H, s), 1.81 (3H, d, J = 6.4 Hz). | 360.15 | 359.05 |
| Int-13 | 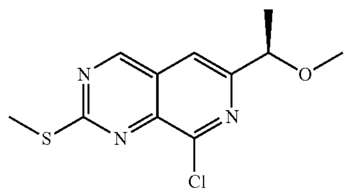 | 1H-NMR (DMSO-d6) δ: 9.62 (1H, s), 8.00 (1H, s), 4.52 (2H, q, J = 6.3 Hz), 3.30 (3H, s), 2.68 (3H, s), 1.38 (3H, d, J = 6.3 Hz). | 269.9 | 269.04 |
| Int-14 | 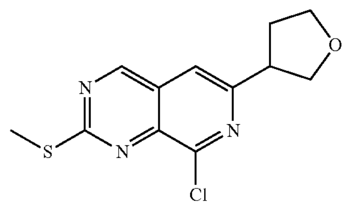 [SMILES: CSc1ncc2cc(C3CCOC3)nc(Cl)c2n1] | 1H-NMR (CDCl3) δ: 9.17 (1H, s), 7.48 (1H, s), 4.25-3.90 (4H, m), 3.76-3.66 (1H, m), 2.74 (3H, s), 2.48-2.22 (2H, m). | 282.1 | 281.04 |
| Int-15 | 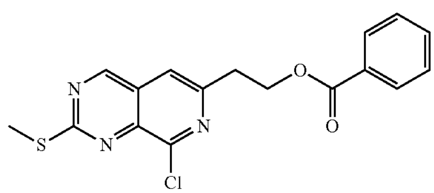 [SMILES: CSc1ncc2cc(CCOC(=O)c3ccccc3)nc(Cl)c2n1] | 1H-NMR (CDCl3) δ: 9.15 (1H, s), 7.98-7.93 (2H, m), 7.58-7.37 (4H, m), 4.78 (2H, t, J = 6.4 Hz), 3.38 (2H, t, J = 6.4 Hz), 2.74 (3H, s). | 360.1 | 359.05 |
| Int-16 | 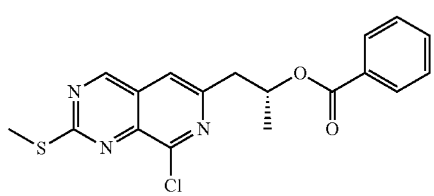 [SMILES: CSc1ncc2cc(C[C@@H](C)OC(=O)c3ccccc3)nc(Cl)c2n1] | 1H-NMR (CDCl3) δ: 9.10 (1H, s), 8.00-7.93 (2H, m), 7.58-7.50 (1H, m), 7.48 (1H, s), 7.47-7.36 (2H, m), 5.66-5.54 (1H, m), 3.39-3.20 (2H, m), 2.72 (3H, s), 1.48 (3H, d. J = 6.4 Hz). | | |

TABLE 4

| Compound No. | Structure | NMR | (M + H)+ | Exact Mass |
|---|---|---|---|---|
| Int-17 | 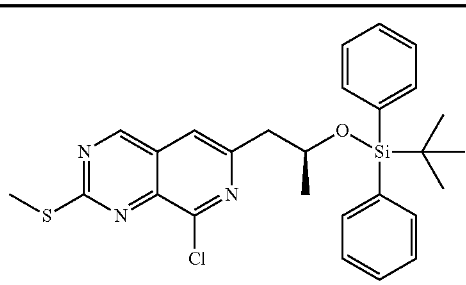 | 1H-NMR (CDCl3) δ: 8.93 (1H, s), 7.52-7.17 (11H, m), 4.49-4.37 (1H, m), 2.99 (2H, d, J = 6.4 Hz), 2.74 (3H, s), 1.25 (3H, d, J = 6.0 Hz), 0.91 (9H, s). | 508.2 | 507.16 |

TABLE 4-continued

| Compound No. | Structure | NMR | (M + H)+ | Exact Mass |
|---|---|---|---|---|
| Int-18 | 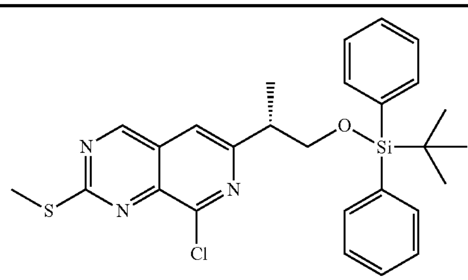 | 1H-NMR (CDCl3) δ: 9.09 (1H, s), 7.52-7.26 (11H, m), 4.00-3.92 (2H, m), 3.29-3.22 (1H, m), 2.75 (3H, s), 1.36 (3H, d, J = 7.6 Hz), 0.93 (9H, s). | 508.2 | 507.16 |
| Int-19 | 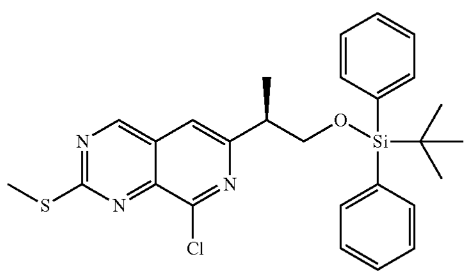 [SMILES: CSc1ncc2cc([C@@H](C)CO[Si](c3ccccc3)(c3ccccc3)C(C)(C)C)nc(Cl)c2n1] | 1H-NMR (CDCl3) δ: 9.09 (1H, s), 7.52-7.44 (4H, m), 7.42-7.34 (3H, m), 7.33-7.26 (4H, m), 4.00-3.92 (2H, m), 3.29-3.22 (1H, m), 2.75 (3H, s), 1.36 (3H, d, J = 7.2 Hz), 0.93 (9H, s). | 508.20 | 507.16 |

Example 4

Synthesis of (R)-1-(2-(methylthio)-8-(piperidin-1-yl)pyrido[3,4-d]pyrimidin-6-yl)ethyl benzoate (Int-20)

[Formula 51]

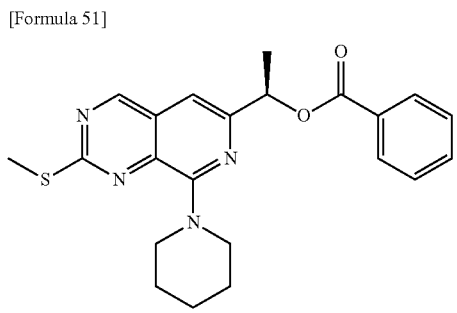

A mixture of (R)-1-(8-chloro-2-(methylthio)pyrido[3,4-d]pyrimidin-6-yl)ethyl benzoate (Int-2, 720 mg, 2.0 mmol) synthesized in accordance with the processes described in Examples 1 to 3 and piperidine (2.0 mL) in 1,4-dioxane (6.0 mL) were stirred at 100° C. overnight. The progress of the reaction was monitored by TLC. After completion of the reaction, the solution was cooled to room temperature. A saturated aqueous sodium hydrogen carbonate solution (40 mL) was added to the reaction mixture. The solution was extracted with ethyl acetate (40 mL) three times. The extracted organic phases were washed with brine, and dried over anhydrous sodium sulfate. The solid was filtered out, and the filtrate was concentrated under reduced pressure. The residue was purified by silica gel column chromatography to give the title compound (808 mg, yield: 99%).

LC/MS: (M+H)+=409.2, $C_{22}H_{24}N_4O_2S$=408.16

Example 5

Synthesis of (R)-1-(2-(methylthio)-8-phenylpyrido[3,4-d]pyrimidin-6-yl)ethyl benzoate (Int-21)

[Formula 52]

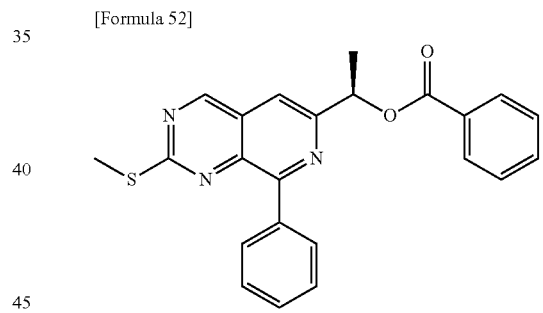

To a mixture of (R)-1-(8-chloro-2-(methylthio)pyrido[3,4-d]pyrimidin-6-yl)ethyl benzoate (Int-2, 290 mg, 0.80 mmol) synthesized in accordance with the processes described in Examples 1 to 3, phenylboric acid (150 mg, 1.2 mmol) and tetrakis(triphenylphosphine)palladium(0) (55 mg, 0.048 mmol) were added 1,4-dioxane (2.7 mL) and a saturated aqueous sodium carbonate solution (1.67 mL). The reaction mixture was stirred under a nitrogen atmosphere at 90° C. overnight. The progress of the reaction was monitored by LC/MS. After the completion of the reaction, the solution was cooled to room temperature. The solution was diluted with water, and the aqueous phase was extracted with ethyl acetate. The extracted organic phase was washed with brine, and dried over anhydrous sodium sulfate. The solid was filtered out, and the filtrate was concentrated under reduced pressure. The residue was purified by silica gel column chromatography and the resultant crude product was used in the subsequent reaction.

Example 6

Synthesis of (2-(methylthio)-8-(piperidin-1-yl)pyrido[3,4-d]pyrimidin-6-yl)methanol

[Formula 53]

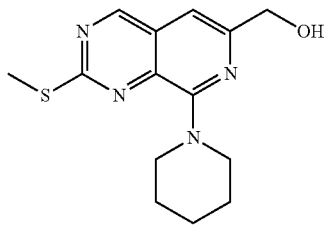

(2-(Methylthio)-8-(piperidin-1-yl)pyrido[3,4-d]pyrimidin-6-yl)methyl benzoate (1.3 g) synthesized in accordance with the processes described in Examples 1 to 4 was dissolved in methanol (30 mL). THF (30 mL) and water (20 mL). Aqueous sodium hydroxide solution (8.2 mL, 2 mol/L) was added dropwise to the solution on an ice bath. The reaction solution was stirred at room temperature for 15 hours. The progress of the reaction was monitored by LC/MS. After the completion of the reaction, the reaction solution was concentrated and iced water was added to the residue. Hydrochloric acid (1 mol/L) was added dropwise to adjust the pH to 5 to 6. The solution was extracted with ethyl acetate three times. The extracted organic phases were combined, washed with saturated brine, and dried over anhydrous sodium sulfate. The solid was filtered out, and the filtrate was dried under reduced pressure. The residue was purified by silica gel column chromatography to give the title compound (0.96 g).

LC/MS: (M+H)$^+$=291.0, $C_{14}H_{18}N_4OS$=290.12

$^1$H-NMR (CDCl$_3$) δ: 9.32 (s, 1H), 7.19 (s, 1H), 5.40 (brs, 1H), 4.50 (s, 2H), 3.89 (brs, 4H), 2.58 (s, 3H), 1.67 (brs, 6H).

Example 7

Synthesis of 2-(methylthio)-8-(piperidin-1-yl)pyrido[3,4-d]pyrimidine-6-carbaldehyde

[Formula 54]

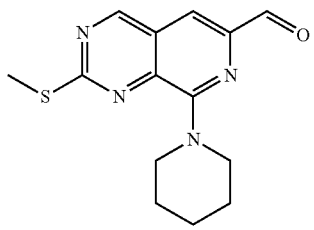

(2-(Methylthio)-8-(piperidin-1-yl)pyrido[3,4-d]pyrimidin-6-yl)methanol (0.20 g, 0.689 mmol) synthesized in Example 6 was dissolved in dichloromethane (3.0 mL) and the solution was stirred at 0° C. Dess-Martin periodinane (1.02 g, 2.0 mmol) was added to the solution under an argon atmosphere at 0° C. and the reaction mixture was stirred at room temperature for 15 hours. The reaction was monitored by TLC and LC/MS. After the completion of the reaction, the solution was diluted with water. An aqueous sodium hydrogen carbonate solution (1 mol/L) was added to adjust the pH to 7 to 8. The solution was extracted with dichloromethane twice. The extracted organic phases were combined, washed with brine, and dried over anhydrous sodium sulfate. The solid was filtered out, and the filtrate was concentrated under reduced pressure to give the title compound (0.19 g).

LC/MS: (M+H)$^+$=289.2, $C_{14}H_{16}N_4OS$=288.10

$^1$H-NMR (CDCl$_3$) δ: 9.89 (s, 1H), 9.49 (s, 1H), 7.80 (s, 1H), 4.02 (brs, 4H), 2.62 (s, 3H), 1.71 (brs, 6H).

Example 8

Synthesis of 6-(di fluoromethyl)-2-(methylthio)-8-(piperidin-1-yl)pyrido[3,4-d]pyrimidine (Int-22)

[Formula 55]

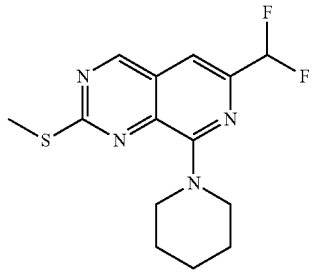

2-(Methylthio)-8-(piperidin-1-yl)pyrido[3,4-d]pyrimidine-6-carbaldehyde (0.19 g, 0.66 mmol) synthesized in Example 7 was dissolved in dichloromethane (5.0 mL) and the solution was stirred at 0° C. DAST (0.85 mL, 3.92 mmol) was added to the solution under argon atmosphere at 0° C. The reaction mixture was stirred at room temperature for 12 hours. The reaction was monitored by TLC and LC/MS. The solution was diluted with water and extracted with dichloromethane twice. The extracted organic phases were combined, washed with saturated brine, and dried over anhydrous sodium sulfate. The solid was filtered out, and the filtrate was concentrated under reduced pressure. The residue was purified by silica gel column chromatography to give the title compound (65 mg, yield: 32% in 3 steps).

LC/MS: (M+H)$^+$=311.4, $C_{14}H_{16}F_2N_4S$=310.11

$^1$H-NMR (CDCl$_3$) δ: 9.40 (s, 1H), 7.43 (s, 1H), 6.85 (t, J=55 Hz, 1H), 3.99 (brs, 4H), 2.60 (s, 3H), 1.70 (brs, 6H).

Example 9

Synthesis of 2-(methylthio)-8-(piperidin-1-yl)pyrido[3,4-d]pyrimidin-6-ylcarboxylic acid

[Formula 56]

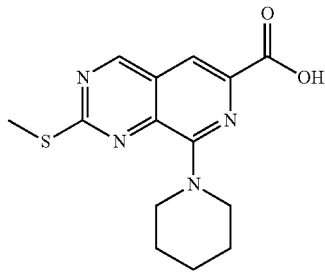

2-(Methylthio)-8-(piperidin-1-yl)pyrido[3,4-d]pyrimidine-6-carbaldehyde (50 mg, 0.173 mmol) synthesized in Example 7 was dissolved in tert-butanol (7.5 mL), and then 2-methyl-2-butene (0.3 mL, 3.47 mmol) was added to the solution. Aqueous solution (2.5 mL) of NaClO$_2$ (157 mg, 1.74 mmol) and sodium dihydrogen phosphate (162 mg, 1.04 mmol) was added to the solution at room temperature. The reaction solution was stirred at room temperature for 16

Example 10

Synthesis of methyl 2-(methylthio)-8-(piperidin-1-yl)pyrido[3,4-d]pyrimidin-6-ylcarboxylate (Int-23)

[Formula 57]

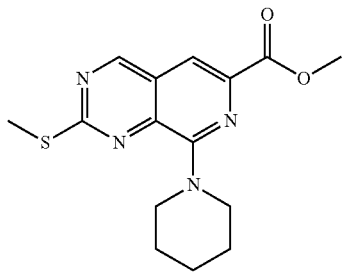

The crude product (100 mg) of 2-(methylthio)-8-(piperidin-1-yl)pyrido[3,4-d]pyrimidin-6-yl-carboxylic acid synthesized by repeating the process in Example 9 twice was dissolved in methanol (1.5 mL). Thionyl chloride (0.8 mL) was added to the solution at 0° C. The reaction solution was stirred at room temperature for 16 hours. The reaction was monitored by TLC. After the completion of the reaction, the solution was concentrated under reduced pressure. The residue was diluted with water. Saturated aqueous sodium hydrogen carbonate solution was added at 0° C. to adjust the pH to 8. The aqueous phase was extracted with ethyl acetate. The extracted organic phase was washed with water and further with saturated brine. The organic phase was dried over anhydrous sodium sulfate. The solid was filtered out, and the filtrate was concentrated under reduced pressure. The residue was purified by silica gel column chromatography to give the title compound (50 mg, yield: 48%).

LC/MS: (M+H)+=319.2, $C_{15}H_{18}N_4O_2S=318.12$

Example 11

Synthesis of (5-bromo-2-(methylthio)-8-morpholinopyrido[3,4-d]pyrimidin-6-yl)methyl benzoate

[Formula 58]

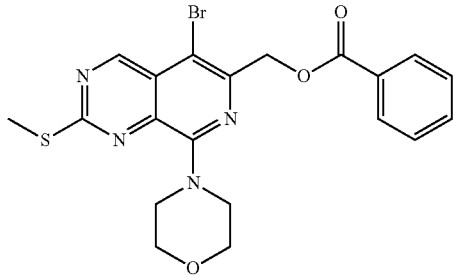

(2-(Methylthio)-8-morpholinopyrido[3,4-d]pyrimidin-6-yl)methyl benzoate (2.0 g, 5.05 mmol) synthesized in accordance with the processes described in Examples 1 to 4 was dissolved in acetonitrile (40 mL). N-bromosuccinimide (0.989 g, 5.56 mmol) was added to the solution at 0° C. and the reaction solution was stirred at 0° C. for one hour. The reaction was monitored by LC/MS and TLC. After the completion of the reaction, the solution was diluted with dichloromethane and washed with water, and then with saturated brine. The organic phase was dried over anhydrous sodium sulfate. The solid was filtered out, and the filtrate was concentrated under reduced pressure. The residue was purified by silica gel column chromatography to give the title compound (2.0 g, yield: 83%).

LC/MS: (M+H)$^+$=474.8 & 477.0, $C_{20}H_{19}BrN_4O_3S=$ 474.04&476.03

Example 11

Synthesis of (5-methyl-2-(methylthio)-8-morpholinopyrido[3,4-d]pyrimidin-6-yl)methyl benzoate (Int-24 hours)

[Formula 59]

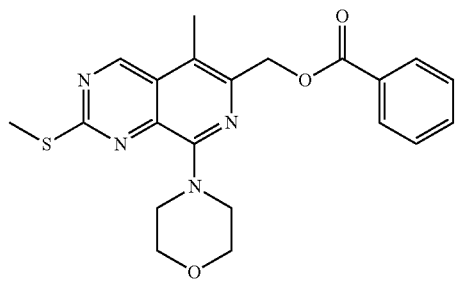

(5-Bromo-2-(methylthio)-8-morpholinopyrido[3,4-d]pyrimidin-6-yl)methyl benzoate (2.0 g, 4.21 mmol) synthesized in Example 10 was dissolved in 1,4-dioxane (50 mL). To the solution were added potassium carbonate (1.16 g, 8.42 mmol), 2,4,6-trimethylboroxine (2.64 g, 21.05 mmol) and tetrakis(triphenylphosphine)palladium (0.438 g, 0.379 mmol) at room temperature. The reaction mixture was stirred at 110° C. for 16 hours. The reaction was monitored by LC/MS and TLC. After the completion of the reaction, the solution was cooled to room temperature and concentrated under reduced pressure. The residue was diluted with ethyl acetate and washed with water, and then with saturated brine. The organic phase was dried over anhydrous sodium sulfate. The solid was filtered out, and the filtrate was concentrated under reduced pressure. The residue was purified by silica gel column chromatography to give the title compound (1.0 g, yield: 58%).

LC/MS: (M+H)$^+$=411.2, $C_{21}H_{22}N_4O_3S=410.14$

Compounds Int-25 to Int-43 shown below were synthesized in accordance with the process described in Example 4 to 11.

TABLE 5

| Compound No. | Structure | NMR | (M + H)+ | exact mass |
|---|---|---|---|---|
| Int-25 | 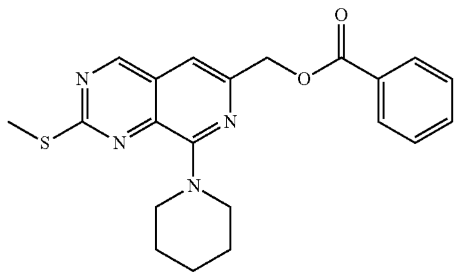 [SMILES: CSc1ncc2cc(COC(=O)c3ccccc3)nc(N3CCCCC3)c2n1] | 1H-NMR (DMSO-d6) δ: 9.33 (1H, s), 8.09 (2H, d, J = 7.3 Hz), 7.71 (1H, t, J = 7.4 Hz), 7.58 (2H, t, J = 7.7 Hz), 7.22 (1H, s), 5.37 (2H, s), 4.00-3.85 (4H, m), 2.67 (3H, s), 1.75-1.50 (6H, m). | 395.2 | 394.15 |
| Int-26 | 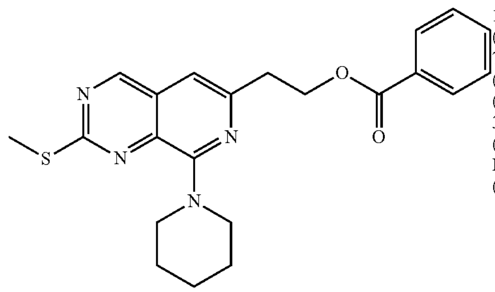 | 1H-NMR (CDCl3) δ: 8.97 (1H, s), 8.00-7.94 (2H, m), 7.57-7.48 (1H, m), 7.44-7.35 (2H, m), 6.85 (1H, s), 4.75 (2H, t, J = 6.4 Hz), 4.00-3.91 (4H, m), 3.19 (2H, t, J = 6.8 Hz), 2.63 (3H, s), 1.79-1.70 (6H, m). | 409.2 | 408.16 |
| Int-27 | 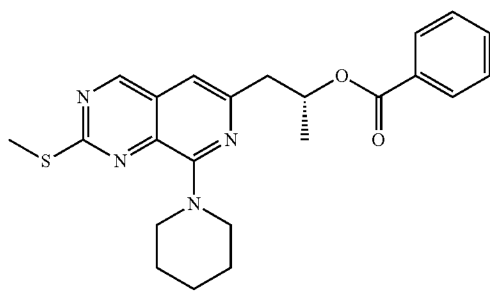 [SMILES: CSc1ncc2cc(C[C@@H](C)OC(=O)c3ccccc3)nc(N3CCCCC3)c2n1] | 1H-NMR (CDCl3) δ: 8.94 (1H, s), 8.00-7.93 (2H, m), 7.57-7.48 (1H, m), 7.44-7.34 (2H, m), 6.83 (1H, s), 5.70-5.58 (1H, m), 4.00-3.85 (4H, m), 3.24-3.14 (1H, m), 3.09-2.99 (1H, m), 2.62 (3H, s), 1.79-1.68 (6H, m), 1.43 (3H, d, J = 6.4 Hz). | 423.2 | 422.18 |
| Int-28 | 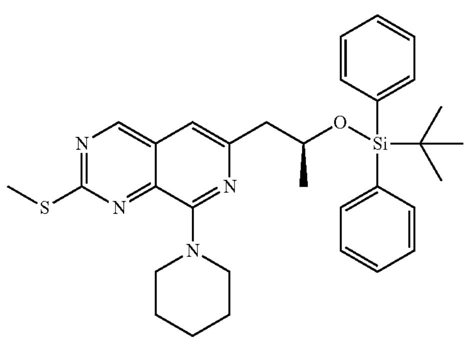 [SMILES: CSc1ncc2cc(C[C@H](C)O[Si](c3ccccc3)(c3ccccc3)C(C)(C)C)nc(N3CCCCC3)c2n1] | | 557.3 | 556.27 |
| Int-29 | 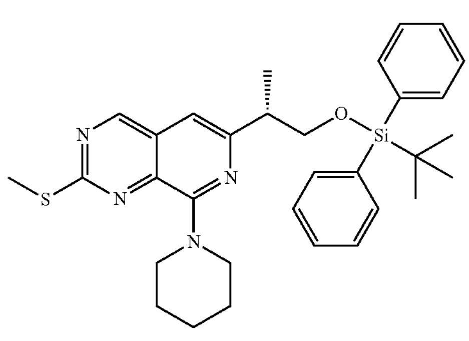 [SMILES: CSc1ncc2cc([C@H](C)CO[Si](c3ccccc3)(c3ccccc3)C(C)(C)C)nc(N3CCCCC3)c2n1] | 1H-NMR (CDCl3) δ: 8.95 (1H, s), 7.58-7.49 (4H, m), 7.42-7.27 (6H, m), 6.79 (1H, s), 4.00-3.75 (6H, m), 3.13-3.04 (1H, m) 2.63 (3H, s), 1.79-1.69 (6H, m), 1.32 (3H, d, J = 6.8 Hz), 0.96 (9H, s). | 557.30 | 556.27 |

TABLE 6

| Compound No. | Structure | NMR | (M + H)⁺ | exact mass |
|---|---|---|---|---|
| Int-30 | 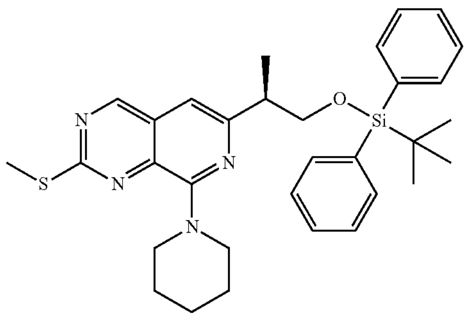 [SMILES: CSc1ncc2cc([C@@H](C)CO[Si](c3ccccc3)(c3ccccc3)C(C)(C)C)nc(N3CCCCC3)c2n1] | 1H-NMR (CDCl3) δ: 8.95 (1H, s), 7.58-7.49 (4H, m), 7.42-7.27 (6H, m), 6.79 (1H, s), 4.00-3.75 (6H, m), 3.13-3.04 (1H, m), 2.63 (3H, s), 1.79-1.69 (6H, m), 1.32 (3H, d, J = 6.8 Hz), 0.96 (9H, s). | 557.30 | 556.27 |
| Int-31 | 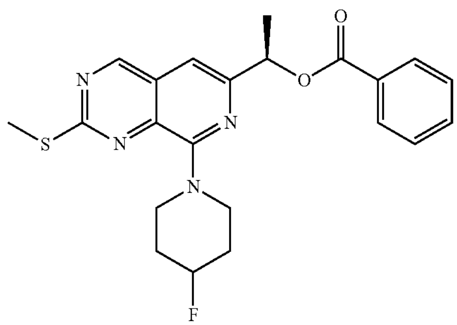 [SMILES: CSc1ncc2cc([C@@H](C)OC(=O)c3ccccc3)nc(N3CCC(F)CC3)c2n1] | 1H-NMR (CDCl3) δ: 9.03 (1H, s), 8.18-8.13 (2H, m), 7.64-7.56 (1H, m), 7.53-7.44 (2H, m), 7.05 (1H, d, J = 0.8 Hz), 6.18-6.09 (1H, m), 5.00-4.83 (1H, m), 4.25-4.06 (4H, m), 2.62 (3H, s), 2.23-1.95 (4H, m), 1.73 (3H, d, J = 6.8 Hz). | 427.2 | 426.15 |
| Int-32 | 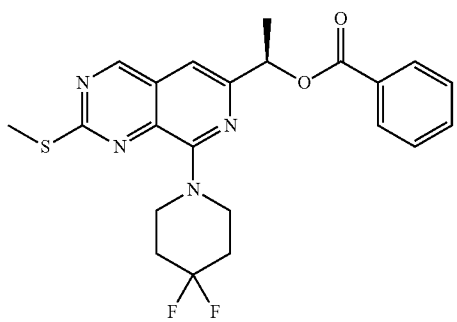 [SMILES: CSc1ncc2cc([C@@H](C)OC(=O)c3ccccc3)nc(N3CCC(F)(F)CC3)c2n1] | 1H-NMR (CDCl3) δ: 9.05 (1H, s), 8.18-8.11 (2H, m), 7.65-7.56 (1H, m), 7.53-7.44 (2H, m), 7.10 (1H, s), 6.19-6.09 (1H, m), 4.25-4.15 (4H, m), 2.61 (3H, s), 2.23-2.06 (4H, m), 1.73 (3H, d, J = 6.4 Hz). | 445.2 | 444.14 |
| Int-33 | 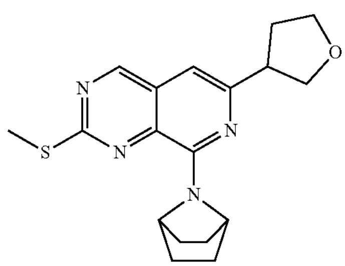 [SMILES: CSc1ncc2cc(C3CCOC3)nc(N3C4CCC3CC4)c2n1] | 1H-NMR (CDCl3) δ: 8.97 (1H, s), 6.83 (1H, s), 5.34 (2H, brs), 4.25-3.85 (4H, m), 3.58-3.44 (1H, m), 2.67 (3H, s), 2.25-2.21 (2H, m), 1.95-1.82 (4H, m), 1.60-1.48 (4H, m). | 343.2 | 342.15 |
| Int-34 | 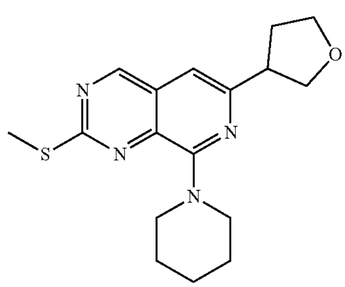 [SMILES: CSc1ncc2cc(C3CCOC3)nc(N3CCCCC3)c2n1] | 1H-NMR (CDCl3) δ: 8.97 (1H, s), 6.81 (1H, s), 4.25-3.85 (8H, m), 3.58-3.44 (1H, m), 2.62 (3H, s), 2.35-2.21 (2H, m), 1.85-1.70 (6H, m). | 331.2 | 330.15 |

TABLE 6-continued

| Compound No. | Structure | NMR | (M + H)+ | exact mass |
|---|---|---|---|---|
| Int-35 | 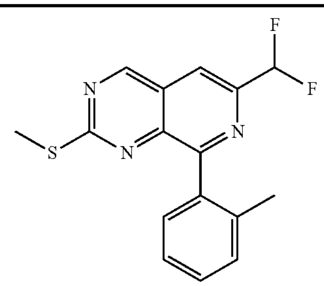 | | 318.0 | 317.08 |

TABLE 7

| Compound No. | Structure | NMR | (M + H)+ | exact mass |
|---|---|---|---|---|
| Int-36 | 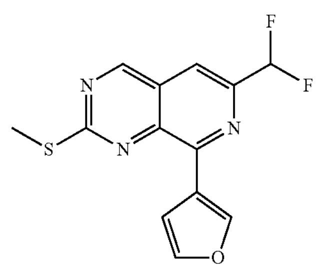 [SMILES: CSc1ncc2cc(C(F)F)nc(-c3ccoc3)c2n1] | | 294.2 | 293.04 |
| Int-37 | 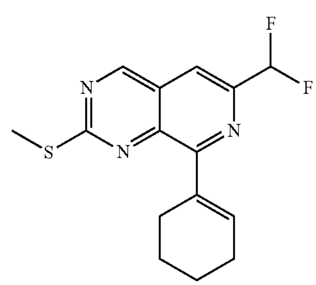 [SMILES: CSc1ncc2cc(C(F)F)nc(C3=CCCCC3)c2n1] | | 308.2 | 307.10 |
| Int-38 | 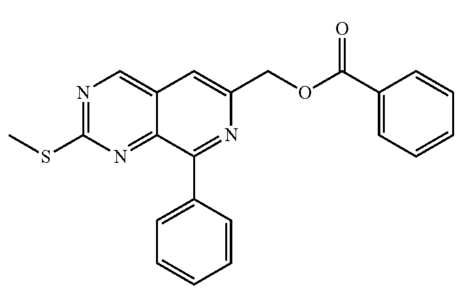 [SMILES: CSc1ncc2cc(COC(=O)c3ccccc3)nc(-c3ccccc3)c2n1] | | 389.2 | 388.10 |

TABLE 7-continued

| Compound No. | Structure | NMR | (M + H)+ | exact mass |
|---|---|---|---|---|
| Int-39 | 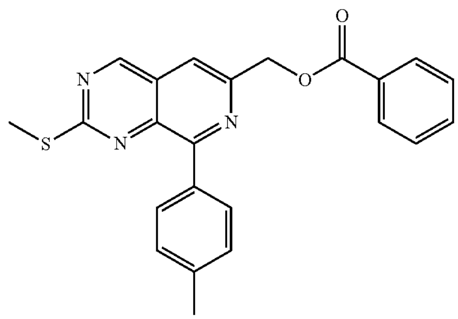 [SMILES: CSc1ncc2cc(COC(=O)c3ccccc3)nc(-c3ccc(C)cc3)c2n1] | | 402.0 | 401.12 |
| Int-40 | 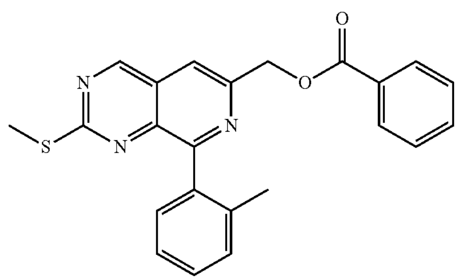 [SMILES: CSc1ncc2cc(COC(=O)c3ccccc3)nc(-c3ccccc3C)c2n1] | | 402.0 | 401.12 |
| Int-41 | 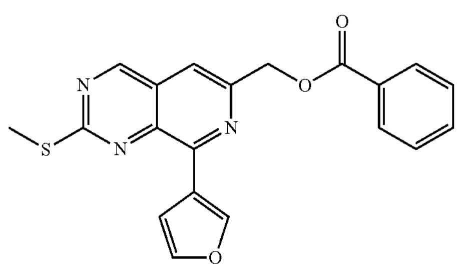 [SMILES: CSc1ncc2cc(COC(=O)c3ccccc3)nc(-c3ccoc3)c2n1] | | 378.0 | 377.08 |
| Int-42 | 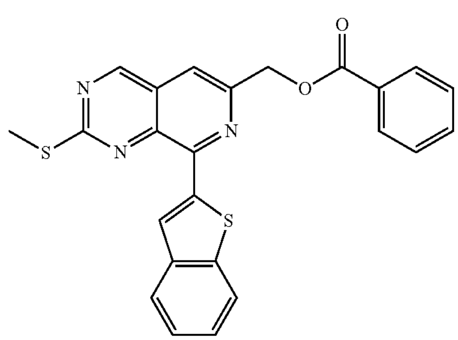 [SMILES: CSc1ncc2cc(COC(=O)c3ccccc3)nc(-c3cc4ccccc4s3)c2n1] | | 444.0 | 443.08 |
| Int-43 | 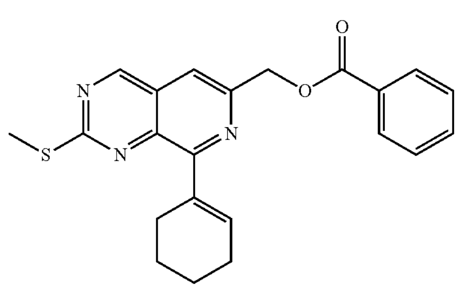 [SMILES: CSc1ncc2cc(COC(=O)c3ccccc3)nc(C3=CCCCC3)c2n1] | | 392.0 | 391.14 |

Example 12

Synthesis of (R)-1-(2-(methylsulfinyl)-8-(piperidin-1-yl)pyrido[3,4-d]pyrimidin-6-yl)ethyl benzoate (Int-44)

[Formula 60]

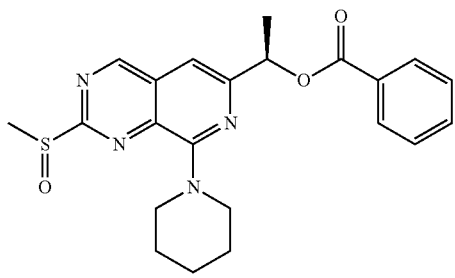

(R)-1-(2-(methylthio)-8-(piperidin-1-yl)pyrido[3,4-d]pyrimidin-6-yl)ethyl benzoate (Int-20, 808 mg, 1.98 mmol) synthesized in Example 4 was dissolved in dichloromethane (20 mL). The solution was cooled to 0° C. m-Chloroperbenzoic acid (488 mg, 1.98 mmol) was added to the solution at 0° C. and the reaction mixture was stirred at room temperature for one hour. The progress of the reaction was monitored by LC/MS. After the completion of the reaction, the solution was diluted with a saturated aqueous sodium hydrogen carbonate solution (30 mL) and extracted with dichloromethane (30 mL) three times. The extracted organic phases were combined and dried over anhydrous sodium sulfate. The solid was filtered out, and the filtrate was concentrated under reduced pressure to give a crude product of the title compound. The crude product was used in the subsequent reaction without purification.

LC/MS: (M+H)$^+$=441.2. $C_{22}H_{24}N_4O_4S$=440.52

Example 13

Synthesis of (1R)-1-(2-(methylsulfinyl)-8-phenylpyrido[3,4-d]pyrimidin-6-yl)ethyl benzoate (Int-45)

[Formula 61]

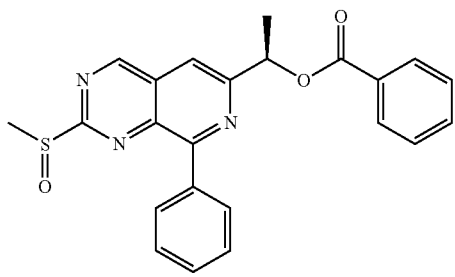

The crude product of (R)-1-(2-(methylthio)-8-phenylpyrido[3,4-d]pyrimidin-6-yl)ethyl benzoate (Int-21) synthesized in Example 5 was dissolved in dichloromethane (7.1 mL). The solution was cooled to 0° C. m-Chloroperbenzoic acid (184 mg, 0.745 mmol) was added to the solution. The reaction mixture was stirred at 0° C. for 20 minutes. The progress of the reaction was monitored by LC/MS. After the completion of the reaction, the reaction solution was filtered through a Celite pad. The Celite pad was washed with a large excess volume of ethyl acetate. The filtrate was washed with saturated aqueous sodium hydrogen carbonate solution, and dried over anhydrous sodium sulfate. The solid was filtered out, and the filtrate was concentrated under reduced pressure. The residue was purified by silica gel column chromatography to give a crude product of the title compound (172 mg, yield: 58% in 2 steps).

LC/MS: (M+H)$^+$=418.2, $C_{23}H_9N_3O_3S$=417.11

Example 14

Synthesis of 6-(difluoromethyl)-2-(methylsulfonyl)-8-(piperidin-1-yl)pyrido[3,4-d]pyrimidine (Int-46)

[Formula 62]

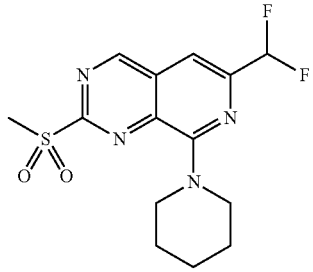

6-(Difluoromethyl)-2-(methylthio)-8-(piperidin-1-yl)pyrido[3,4-d]pyrimidine (Int-22, 195 mg, 0.63 mmol) synthesized in Example 8 was dissolved in THF (10 mL) and water (3 mL). Oxone (R) (967 mg, 1.572 mmol) was added to the solution at 0° C. The reaction solution was stirred at room temperature for five hours. The progress of the reaction was monitored by TLC. After the completion of the reaction, the solution was diluted with water and the aqueous phase was extracted with ethyl acetate twice. The extracted organic phases were combined, washed with saturated brine, and dried over anhydrous sodium sulfate. The solid was filtered out, and the filtrate was concentrated under reduced pressure to give a crude product of the title compound (120 mg). The crude product was used in the subsequent reaction without further purification.

LC/MS: (M+H)$^+$=343.2, $C_{14}H_{16}F_2N_4O_2S$=342.10

Compounds Int-45 to Int-71 shown below were synthesized in accordance with the processes described in Examples 12 to 14.

TABLE 8

| Compound No. | Structure | (M + H)+ | exact mass |
|---|---|---|---|
| Int-47 | 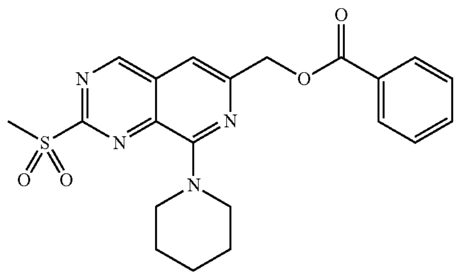 [SMILES: CS(=O)(=O)c1ncc2cc(COC(=O)c3ccccc3)nc(N3CCCCC3)c2n1] | 427.1 | 426.14 |
| Int-48 | 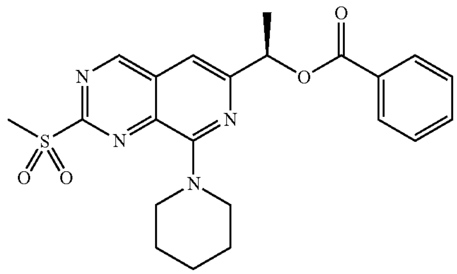 [SMILES: C[C@@H](OC(=O)c1ccccc1)c1cc2cnc(S(C)(=O)=O)nc2c(N2CCCCC2)n1] | 441.2 | 440.52 |
| Int-49 | 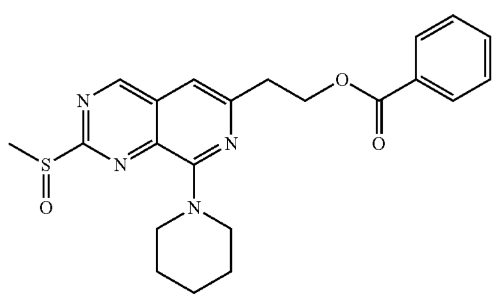 [SMILES: CS(=O)c1ncc2cc(CCOC(=O)c3ccccc3)nc(N3CCCCC3)c2n1] | 425.2 | 424.16 |
| Int-50 | 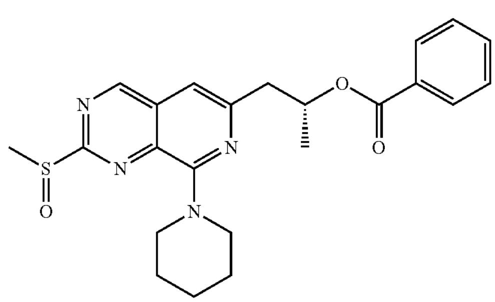 [SMILES: C[C@H](Cc1cc2cnc(S(C)=O)nc2c(N2CCCCC2)n1)OC(=O)c1ccccc1] | 439.2 | 438.17 |

TABLE 9

| Compound No. | Structure | (M + H)+ | exact mass |
| --- | --- | --- | --- |
| Int-51 | 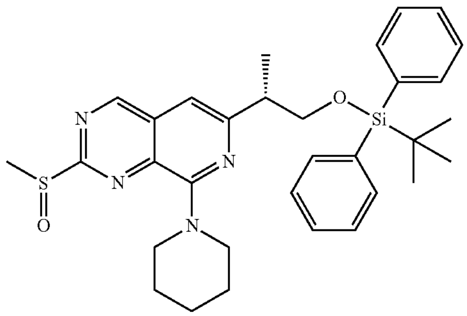 [SMILES: C[C@H](CO[Si](c1ccccc1)(c1ccccc1)C(C)(C)C)c1cc2cnc(S(C)=O)nc2c(N2CCCCC2)n1] | 573.3 | 572.26 |
| Int-52 | 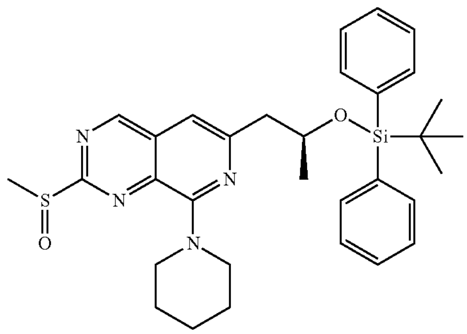 [SMILES: C[C@@H](Cc1cc2cnc(S(C)=O)nc2c(N2CCCCC2)n1)O[Si](c1ccccc1)(c1ccccc1)C(C)(C)C] | 573.3 | 572.26 |
| Int-53 | 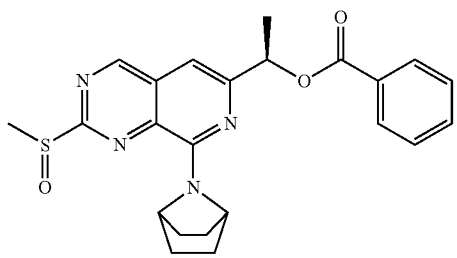 [SMILES: C[C@@H](OC(=O)c1ccccc1)c1cc2cnc(S(C)=O)nc2c(N2C3CCC2CC3)n1] | 437.2 | 436.16 |
| Int-54 | 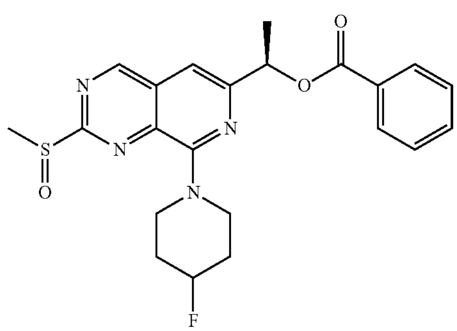 [SMILES: C[C@@H](OC(=O)c1ccccc1)c1cc2cnc(S(C)=O)nc2c(N2CCC(F)CC2)n1] | 443.2 | 442.15 |
| Int-55 | 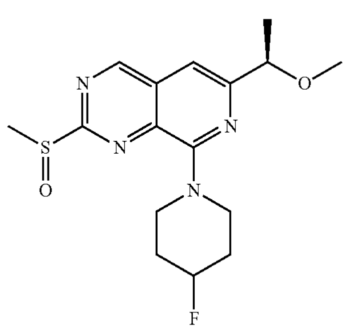 | 353.2 | 352.14 |

TABLE 9-continued
| Compound No. | Structure | (M + H)+ | exact mass |
|---|---|---|---|
| Int-56 | 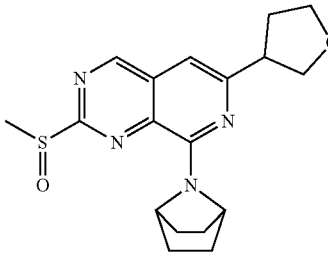 | 359.2 | 358.15 |
| Int-57 | 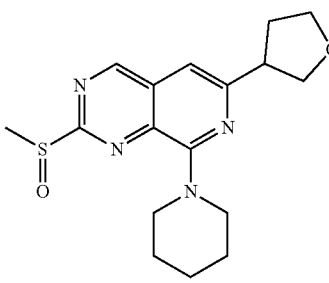 | 347.2 | 346.15 |
| Int-58 | 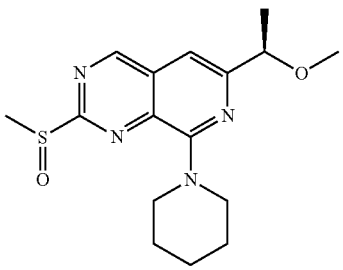 | 335.2 | 334.15 |
TABLE 10
| Compound No. | Structure | (M + H)+ | exact mass |
|---|---|---|---|
| Int-59 | 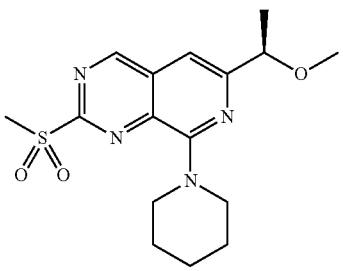 | 351.9 | 350.14 |
| Int-60 | 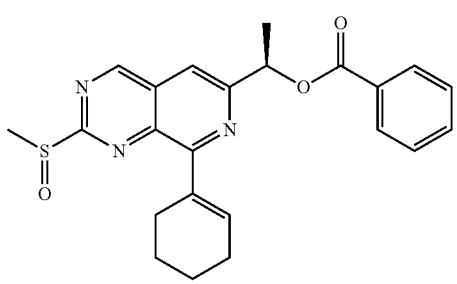 [SMILES: C[C@@H](OC(=O)c1ccccc1)c1cc2cnc(S(C)=O)nc2c(C2=CCCCC2)n1] | 422.2 | 421.15 |

TABLE 10-continued

| Compound No. | Structure | (M + H)+ | exact mass |
|---|---|---|---|
| Int-61 | 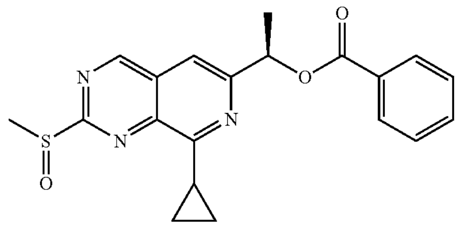 [SMILES: C[C@@H](OC(=O)c1ccccc1)c1cc2cnc(S(C)=O)nc2c(C2CC2)n1] | 382.1 | 381.11 |
| Int-62 | 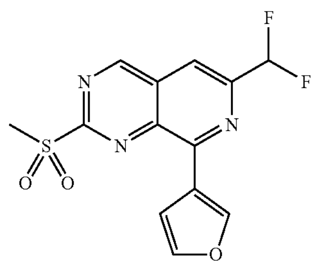 [SMILES: CS(=O)(=O)c1ncc2cc(C(F)F)nc(-c3ccoc3)c2n1] | 326.2 | 325.03 |
| Int-63 | 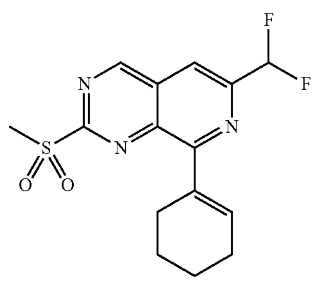 [SMILES: CS(=O)(=O)c1ncc2cc(C(F)F)nc(C3=CCCCC3)c2n1] | 340.2 | 339.09 |
| Int-64 | 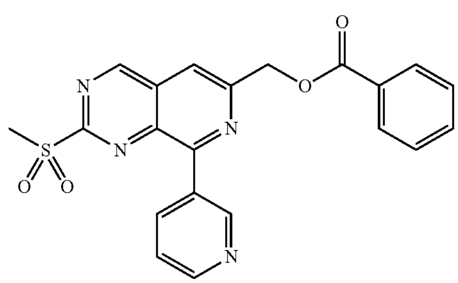 [SMILES: CS(=O)(=O)c1ncc2cc(COC(=O)c3ccccc3)nc(-c3cccnc3)c2n1] | 421.0 | 420.09 |
| Int-65 | 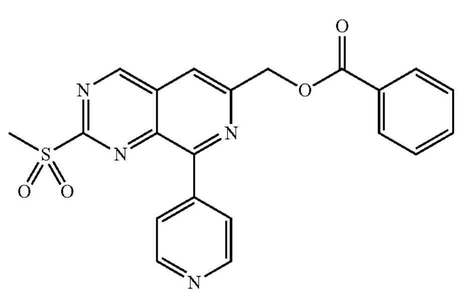 [SMILES: CS(=O)(=O)c1ncc2cc(COC(=O)c3ccccc3)nc(-c3ccncc3)c2n1] | 421.2 | 420.09 |

TABLE 10-continued

| Compound No. | Structure | (M + H)+ | exact mass |
|---|---|---|---|
| Int-66 | 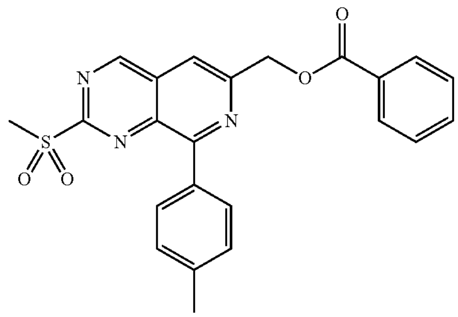 [SMILES: Cc1ccc(-c2nc(COC(=O)c3ccccc3)cc3cnc(S(C)(=O)=O)nc23)cc1] | 433.8 | 433.11 |

TABLE 11

| Compound No. | Structure | (M + H)+ | exact mass |
|---|---|---|---|
| Int-67 | 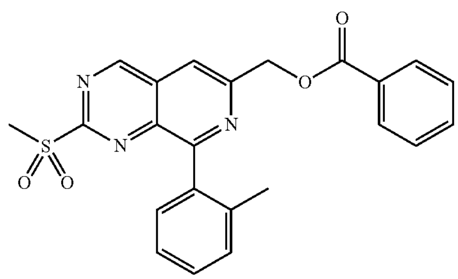 [SMILES: Cc1ccccc1-c1nc(COC(=O)c2ccccc2)cc2cnc(S(C)(=O)=O)nc12] | 433.8 | 433.11 |
| Int-68 | 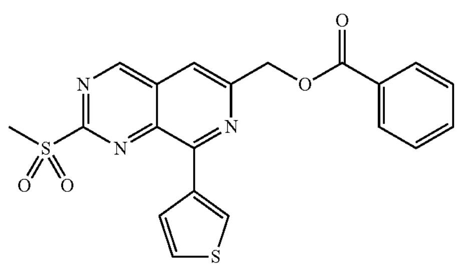 [SMILES: CS(=O)(=O)c1ncc2cc(COC(=O)c3ccccc3)nc(-c3ccsc3)c2n1] | 425.8 | 425.05 |
| Int-69 | 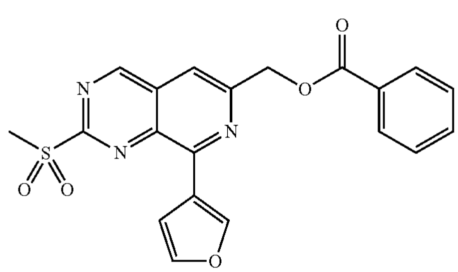 [SMILES: CS(=O)(=O)c1ncc2cc(COC(=O)c3ccccc3)nc(-c3ccoc3)c2n1] | 410.2 | 409.07 |

TABLE 11-continued

| Compound No. | Structure | (M + H)+ | exact mass |
|---|---|---|---|
| Int-70 | 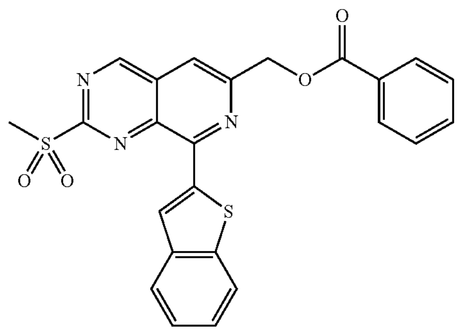 [SMILES: CS(=O)(=O)c1ncc2cc(COC(=O)c3ccccc3)nc(-c3cc4ccccc4s3)c2n1] | 476.0 | 475.07 |
| Int-71 | 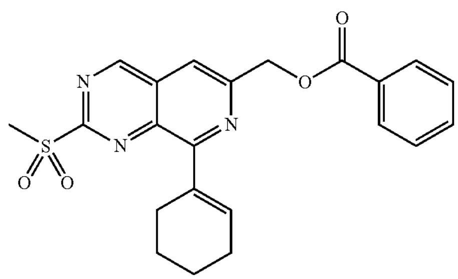 [SMILES: CS(=O)(=O)c1ncc2cc(COC(=O)c3ccccc3)nc(C3=CCCCC3)c2n1] | 424.0 | 423.13 |
| Int-72 | 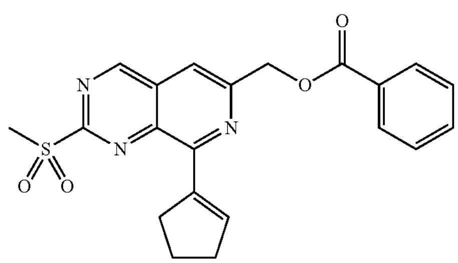 [SMILES: CS(=O)(=O)c1ncc2cc(COC(=O)c3ccccc3)nc(C3=CCCC3)c2n1] | 410.0 | 409.11 |
| Int-73 | 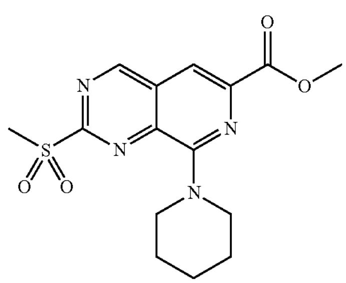 | 351.0 | 350.10 |
| Int-74 | 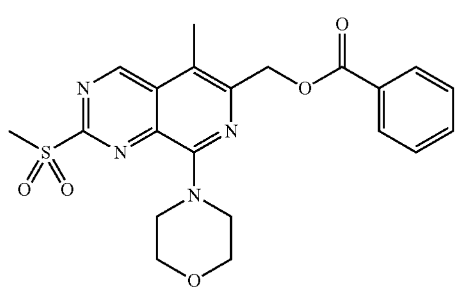 [SMILES: Cc1c(COC(=O)c2ccccc2)nc(N2CCOCC2)c2nc(S(C)(=O)=O)ncc12] | 443.0 | 442.13 |

Example 15

Synthesis of (R)-tert-butyl 4-(6-((6-(1-(benzoyloxy)ethyl)-8-(piperidin-1-yl)pyrido[3,4-d]pyrimidin-2-yl)amino)pyridin-3-yl)-5-oxo-1,4-diazepane-1-carboxylate

[Formula 63]

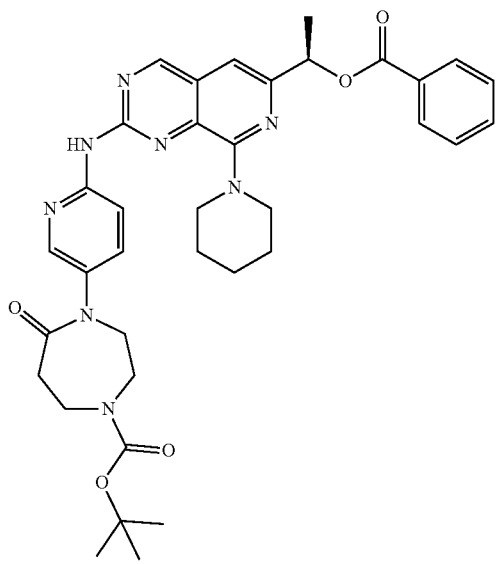

Toluene (0.63 mL) was added to the mixture of (R)-1-(2-(methylsulfonyl)-8-(piperidin-1-yl)pyrido[3,4-d]pyrimidin-6-yl)ethyl benzoate (Int-48, 110.9 mg, 0.252 mmol) synthesized by the process described in Example 14 and tert-butyl 4-(6-aminopyridin-3-yl)-5-oxo-1,4-diazepane-1-carboxylate (C-3, 154.3 mg, 0.504 mmol) synthesized in accordance with the processes described in Referential Examples 10 and 11. The reaction mixture was stirred at 120° C. for four days. The progress of the reaction was monitored by LC/MS. The mixture was cooled to room temperature. The reaction mixture was purified by silica gel column chromatography to give the title compound (19.3 mg, yield: 11.5%).

LC/MS: (M+H)+=667.4, $C_{36}H_{42}N_8O_5$=666.77

Example 16

Synthesis of (R)-1-(2-((5-(7-oxo-1,4-diazepan-1-yl)pyridine-2-yl)amino)-8-(piperidin-1-yl)pyrido[3,4-d]pyrimidin-6-yl)ethyl benzoate

[Formula 64]

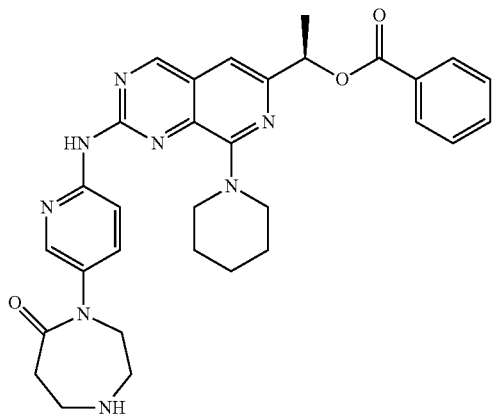

(R)-tert-butyl 4-(6-((6-(1-(benzoyloxy)ethyl)-8-(piperidin-1-yl)pyrido[3,4-d]pyrimidin-2-yl)amino)pyridin-3-yl)-5-oxo-1,4-diazepane-1-carboxylate (19.3 mg) prepared in Example 15 was dissolved in dichloromethane (1.0 mL) and TFA (1.0 mL). The reaction solution was stirred at room temperature for two hours. The progress of the reaction was monitored by LC/MS. After the completion of the reaction, the solution was concentrated under reduced pressure. The crude product was used in the subsequent reaction without purification.

Example 17

Synthesis of (R)-4-(6-((6-(1-(hydroxyethyl)-8-(piperidin-1-yl)pyrido[3,4-d]pyrimidin-2-yl)amino)pyridin-3-yl)-1,4-diazepan-5-one (Compound 89)

[Formula 65]

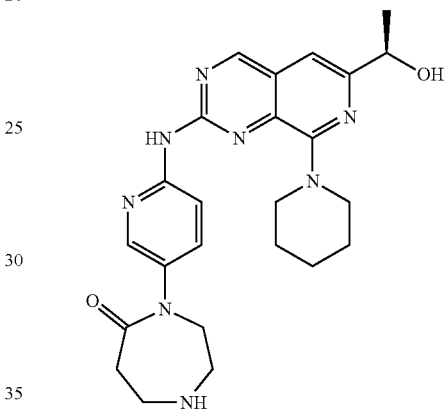

The crude product of (R)-1-(2-((5-(7-oxo-1,4-diazepan-1-yl)pyridin-2-yl)amino)-8-(piperidin-1-yl)pyrido[3,4-d]pyrimidin-6-yl)ethyl benzoate prepared in Example 16 was dissolved in methanol (1.0 mL) and THF (1.0 mL). Potassium carbonate (12.3 mg, 0.089 mmol) was added to the solution. The reaction mixture was stirred at room temperature. The progress of the reaction was monitored by LC/MS. After the completion of the reaction, the solution was filtered, and the filtrate was concentrated under reduced pressure. The crude product was purified by preparative HPLC (acetonitrile/water/TFA system). The fractions containing the target product were passed through a column containing a strong cation exchange (SCX) resin to adsorb the target product onto the resin. The SCX column was washed with dichloromethane. Ammonia (2 mol/L, methanol solution) was further passed through the SCX column to elute the target product. The eluate was concentrated under reduced pressure to give the title compound (13.6 mg).

LC/MS: (M+H)+=463.3, $C_{24}H_{30}N_8O_2$=462.55

Example 18

Synthesis of (R)-1-(2-((6-(4-methylpiperazin-1-yl)pyridazin-3-yl)amino)-8-(piperidin-1-yl)pyrido[3,4-d]pyrimidin-6-yl)ethanol (Compound 123)

[Formula 66]

-continued

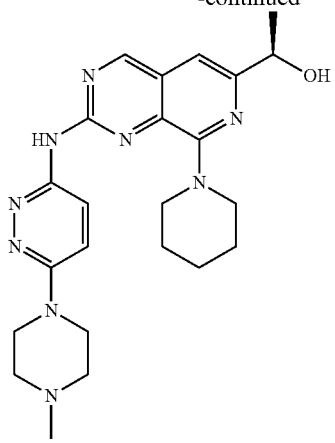

Toluene (0.25 mL) was added to (R)-1-(2-(methylsulfonyl)-8-(piperidin-1-yl)pyrido[3,4-d]pyrimidin-6-yl)ethyl benzoate (Int-48, 44 mg, 0.10 mmol) synthesized in accordance with the process described in Example 14 and 6-(4-methylpiperazin-1-yl)pyridazin-3-amine (E-2, 38.7 mg, 0.20 mmol) synthesized in accordance with the processes described in Referential Examples 15 to 17. The reaction mixture was stirred at 120° C. overnight. The progress of the reaction was monitored by LC/MS. After the completion of the reaction, the mixture was cooled to room temperature. The reaction mixture was purified by silica gel column chromatography to give a crude product. The crude product was used in the subsequent reaction without purification.

The crude product thus obtained was dissolved in methanol (1.0 mL) and THF (1.0 mL). To the solution was added dropwise aqueous lithium hydroxide solution (0.075 mL, 3.0 mmol, 4 mol/L). The reaction mixture was stirred at room temperature overnight. The progress of the reaction was monitored by LC/MS. After the completion of the reaction, the solution was concentrated under reduced pressure. The crude product was purified by preparative HPLC (acetonitrile/water/TFA system). The fractions containing the target product were passed through a column containing a strong cation exchange (SCX) resin to adsorb the target product onto the resin. The SCX column was washed with methanol. Ammonia (2 mol/L, methanol solution) was further passed through the SCX column to elute the target product. The eluate was concentrated under reduced pressure to give the title compound (20.7 mg).

LC/MS: (M+H)$^+$=450.3, $C_{23}H_{31}N_9O$=449.55

Example 19

Synthesis of (R)-1-(2-((6-(4-(2-(methylsulfonyl)ethyl)piperazin-1-yl)pyridazin-3-yl)amino)-8-(piperidin-1-yl)pyrido[3,4-d]pyrimidin-6-yl)ethanol (Compound 114)

[Formula 67]

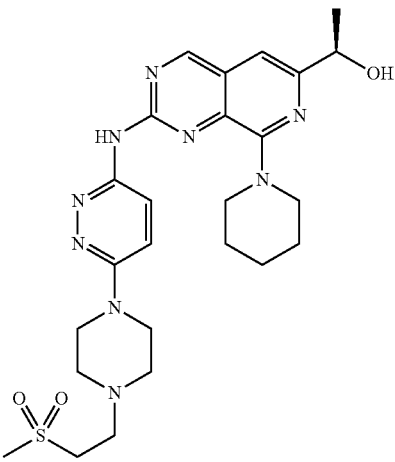

(R)-1-(2-((6-(piperazin-1-yl)pyridazin-3-yl)amino)-8-(piperidin-1-yl)pyrido[3,4-d]pyrimidin-6-yl)ethanol (13.6 mg, 0.0312 mmol) synthesized in accordance with the processes described in Examples 15 to 17 was dissolved in chloroform (0.31 mL). To the solution were added 2-(Methylsulfonyl)ethyl 4-methylbenzenesulfonate (9.6 mg, 0.0344 mmol) and N-ethyldiisopropylamine (6.1 μL, 0.0344 mmol). The reaction solution was stirred at 80° C. overnight. The progress of the reaction was monitored by LC/MS. After the completion of the reaction, the reaction solution was cooled to room temperature, and concentrated under reduced pressure. The residue was purified by preparative HPLC. The fractions containing the target product were passed through a column containing a strong cation exchange (SCX) resin to adsorb the target product onto the resin. The SCX column was washed with methanol, and the target product was eluted with ammonia (2 mol/L, methanol solution). The eluate was concentrated under reduced pressure to give the title compound (8.6 mg, yield: 51%).

LC/MS: (M+H)$^+$=542.3, $C_{25}H_{35}N_9O_3S$=541.26

$^1$H-NMR (CDCl$_3$) δ: 9.08 (1H, s), 8.60 (1H, d, J=9.6 Hz), 8.42 (1H, brs), 7.06 (1H, d, J=9.6 Hz), 6.93 (1H, s), 4.83 (1H, m), 3.98 (1H, m), 3.82 (4H, m), 3.61 (4H, m), 3.20 (2H, t, J=6.4 Hz), 3.05 (3H, s), 2.95 (2H, t, J=6.4 Hz), 2.68 (4H, m), 1.85-1.52 (6H, m), 1.51 (3H, d, J=6.4 Hz).

Example 20

Synthesis of (R)-1-(8-(piperidin-1-yl)-2-((6-(piperidin-4-ylsulfonyl)-5,6,7,8-tetrahydro-1,6-naphthyridin-2-yl)amino)pyrido[3,4-d]pyrimidin-6-yl)ethanol (Compound 163)

[Formula 68]

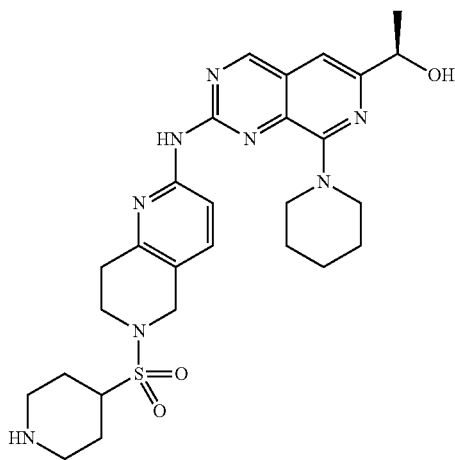

(R)-1-(8-(piperidin-1-yl)-2-((5,6,7,8-tetrahydro-1,6-naphthyridin-2-yl)amino)pyrido[3,4-d]pyrimidin-6-yl)ethyl benzoate (51 mg, 0.10 mmol) synthesized in accordance with the processes described in Examples 15 and 16 was dissolved in dichloromethane (1 mL) and triethylamine (21 µL, 0.012 mmol). tert-Butyl 4-(chlorosulfonyl)piperidine-1-carboxylate (34.1 mg, 0.12 mmol) was added to the solution at 0° C. The reaction mixture was stirred at room temperature overnight. The progress of the reaction was monitored by LC/MS. After the completion of the reaction, the reaction was quenched by addition of a saturated aqueous sodium hydrogen carbonate solution (10 mL). The solution was extracted with dichloromethane (10 mL) three times. The extracted organic phases were combined and dried over anhydrous sodium sulfate. The solid was filtered out, and the filtrate was concentrated. The residue was roughly purified amine-modified silica gel column chromatography. The crude product was used in the subsequent reaction without further purification.

The crude product thus obtained was dissolved in dichloromethane (3 mL) and TFA (1 mL). The solution was stirred at room temperature for two hours. The progress of the reaction was monitored by LC/MS. After the completion of the reaction, the reaction was quenched by addition of a saturated aqueous sodium hydrogen carbonate solution (10 mL). The solution was extracted with dichloromethane (10 mL) three times. The extracted organic phases were combined and dried over anhydrous sodium sulfate. The solid was filtered out, and the filtrate was concentrated. The residue was roughly purified amine-modified silica gel column chromatography. The crude product was used in the subsequent reaction without further purification.

The crude product thus obtained was dissolved in methanol (2.0 mL) and THF (2.0 mL). Potassium carbonate (138 mg, 1.0 mmol) was added to the solution. The mixture was stirred at room temperature for five hours. The progress of the reaction was monitored by LC/MS. After the completion of the reaction, water (10 mL) was added. The solution was extracted with dichloromethane (10 mL) three times. The extracted organic phases were combined and dried over anhydrous sodium sulfate. The solid was filtered out, and the filtrate was concentrated under reduced pressure. The residue was purified by preparative HPLC. The fractions containing the target product were passed through a column containing a strong cation exchange (SCX) resin to adsorb the target product onto the resin. The SCX column was washed with methanol, and the target product was eluted with ammonia (2 mol/L, methanol solution). The eluate was concentrated under reduced pressure to give the title compound (38.4 mg, yield: 70%).

LC/MS: $(M+H)^+=553.3$, $C_{27}H_{36}N_8O_3S=552.26$ $^1$H-NMR (DMSO-d6) δ: 10.12 (1H, s), 9.31 (1H, s), 8.27 (1H, d, J=8.2 Hz), 7.63 (1H, d, J=8.7 Hz), 7.25 (1H, s), 5.27 (1H, d, J=4.1 Hz), 4.70-4.60 (1H, m), 4.46 (2H, s), 3.84-3.68 (4H, m), 3.64 (2H, t, J=5.9 Hz), 2.99 (2H, d, J=11.9 Hz), 2.87 (2H, t, J=5.5 Hz), 2.50-2.39 (2H, m), 1.91-1.81 (2H, m), 1.77-1.60 (6H, m), 1.56-1.42 (2H, m), 1.38 (3H, d, J=6.9 Hz).

Example 21

Synthesis of (S)-1-(4-((6-((6-((R)-1-hydroxyethyl)-8-(piperidin-1-yl)pyrido[3,4-d]pyrimidin-2-yl)amino)pyridin-3-yl)methyl)piperazin-1-yl)propan-2-ol (Compound 183)

[Formula 69]

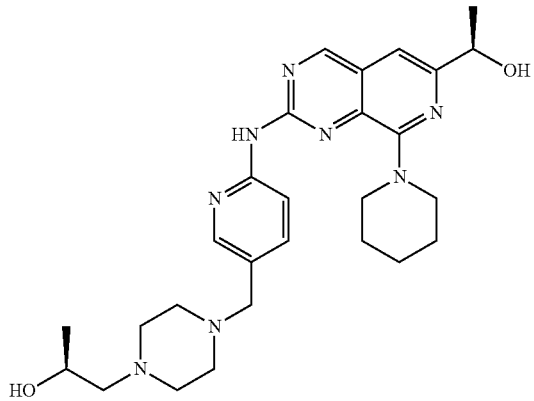

(R)-1-(2-((5-(piperazin-1-ylmethyl)pyridin-2-yl)amino)-8-(piperazin-1-yl)pyrido[3,4-d]pyrimidin-6-yl)ethyl benzoate (72 mg, 0.13 mmol) synthesized in accordance with the processes described in Examples 15 and 16 was dissolved in methanol (1 mL). (S)-propylene oxide (7.6 mg, 0.13 mmol) was added to the solution. The reaction solution was stirred at 55° C. overnight. The progress of the reaction was monitored by LC/MS. After the completion of the reaction, the solution was concentrated under reduced pressure. The crude product was roughly purified by silica gel column chromatography. The crude product was used in the subsequent reaction without further purification.

The crude product thus obtained was dissolved in methanol (1.0 mL) and THF (1.0 mL). Aqueous lithium hydroxide solution (0.2 mL, 0.80 mmol, 4 mol/L) was added to the solution. The reaction solution was stirred at room temperature. The progress of the reaction was monitored by LC/MS. After the completion of the reaction, the solid was filtered out, and the filtrate was concentrated under reduced pressure. The residue was purified by preparative HPLC. The fractions containing the target product were passed through

Example 22

Synthesis of 2-((5-(piperazin-1-yl)pyridin-2-yl)amino-8-(piperidin-1-yl)pyrido[3,4-d]pyrimidine-6-carboxylic acid (Compound 23)

[Formula 70]

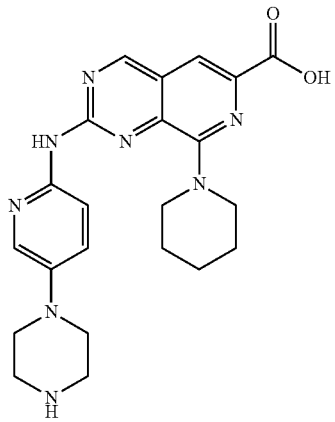

Methyl 2-((5-(4-(tert-butoxycarbonyl)piperazin-1-yl)pyridin-2-yl)amino)-8-(piperidin-1-yl)pyrido[3,4-d]pyrimidine-6-carboxylate (100 mg, 0.182 mmol) synthesized in accordance with the process described in Example 15 was dissolved in methanol (5 mL), THF (4 mL) and water (1 mL). Lithium hydroxide monohydrate (23 mg, 0.546 mmol) was added to the solution at 0° C. The reaction solution was stirred at room temperature for 16 hours. The progress of the reaction was monitored by LC/MS. After the completion of the reaction, the solution was concentrated under reduced pressure. The residue was dissolved in dichloromethane, and washed with water, and further with saturated brine. The organic phase was dried over anhydrous sodium sulfate. The solid was filtered out, and the filtrate was concentrated under reduced pressure to give a crude product (100 mg). The crude product was used in the subsequent reaction without purification.

A part of the crude product (15 mg, 0.028 mmol) was dissolved in dichloromethane (3 mL). A solution of HCl in 1,4-dioxane (0.5 mL, 4 mol/L) was added to the solution at 0° C. The reaction solution was stirred at 0° C. for one hour. The progress of the reaction was monitored by LC/MS. After the completion of the reaction, the solution was concentrated under reduced pressure to give HCl salt (10 mg) of the title compound.

LC/MS: (M+H)$^+$=435.3, $C_{22}H_{26}N_8O_2$=434.22 a column containing a strong cation exchange (SCX) resin to adsorb the target product onto the resin. The SCX column was washed with methanol, and the target product was eluted with ammonia (2 mol/L, methanol solution). The eluate was concentrated under reduced pressure to give the title compound (30.6 mg, yield: 62%).

LC/MS: (M+H)$^+$=507.4, $C_{27}H_{38}N_8O_2$=506.31

Example 23

Synthesis of N,N-dimethyl-2-((5-(piperazin-1-yl)pyridin-2-yl)amino-8-(piperidin-1-yl)pyrido[3,4-d]pyrimidine-6-carboxamide (Compound 27)

[Formula 71]

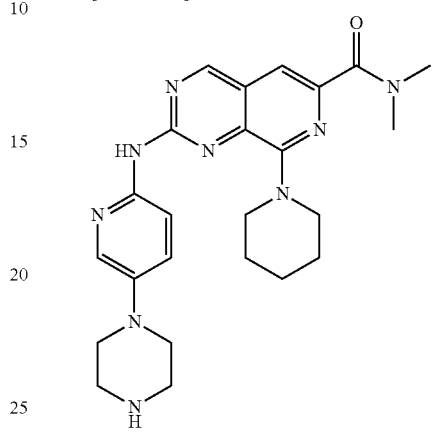

A part of the crude product (50 mg, 0.0936 mmol), which was prepared by reaction of methyl 2-((5-(4-(tert-butoxycarbonyl)piperazin-1-yl)pyridin-2-yl)amino)-8-(piperidin-1-yl)pyrido[3,4-d]pyrimidine-6-carboxylate (100 mg, 0.182 mmol) and lithium hydroxide monohydrate (23 mg, 0.546 mmol) in accordance with the process described in Example 22, was dissolved in THF (2 mL). To the solution were added diisopropylethylamine (0.05 mL, 0.280 mmol) and HATU (53 mg, 0.140 mmol) at 0° C. The reaction solution was stirred at 0° C. for 15 minutes, and a solution (0.25 mL, 2 mol/L) of dimethylamine in THF was added to the reaction solution. The reaction solution was stirred at room temperature for 16 hours. The progress of the reaction was monitored by LC/MS. The solution was concentrated under reduced pressure, and the residue was dissolved in ethyl acetate. The organic phase was washed with water and further with saturated brine. The organic phase was dried over anhydrous sodium sulfate. The solid was filtered out, and the filtrate was concentrated under reduced pressure to give a crude product (50 mg). The crude product was used in the subsequent reaction without purification.

The crude product thus obtained was dissolved in dichloromethane (3 mL). A solution of HCl in 1,4-dioxane (0.5 mL, 4 mol/L) was added to the solution at 0° C. The reaction solution was stirred at 0° C. for one hour. The progress of the reaction was monitored by LC/MS. After the completion of the reaction, the solution was concentrated under reduced pressure. The residue was purified by preparative HPLC to give the title compound (2.0 mg).

LC/MS: (M+H)$^+$=462.41, $C_{24}H_{31}N_9O$=461.27

Example 24

Synthesis of tert-butyl 4-(6-(((6-formyl-8-morpholinopyrido[3,4-d]pyrimidin-2-yl)amino)pyridin-3-yl)piperazine-1-carboxylate

[Formula 72]

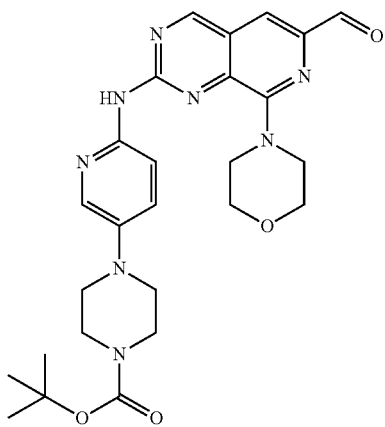

tert-Butyl 4-(6-(((6-(((benzoyloxy)methyl)-8-morpholinopyrido[3,4-d]pyrimidin-2-yl)amino)pyridin-3-yl)piperazine-1-carboxylate (300 mg, 0.256 mmol) synthesized in accordance with the process described in Example 15 was dissolved in THF (2 mL). Magnesium methoxide (25 mL, 7 to 8% methanol solution) was added to the solution. The reaction mixture was stirred at room temperature for 16 hours. The progress of the reaction was monitored by TLC. After the completion of the reaction, the solution was concentrated. The residue was diluted with water (20 mL), and the aqueous phase was extracted with a mixed solvent of methanol and dichloromethane (1:9, 75 mL) three times. The extracted organic phases were dried over anhydrous sodium sulfate. The solid was filtered out, and the filtrate was concentrated under reduced pressure to give a crude product (270 mg). The crude product was used in the subsequent reaction without purification.

The crude product (270 mg) was dissolved in ethyl acetate (30 mL), 2-Iodoxybenzoic acid (162 mg, 0.576 mmol) was added to the solution at room temperature. The reaction solution was stirred at 60° C. for 16 hours. The progress of the reaction was monitored by TLC. After the completion of the reaction, the solution was filtered. The filtrate was washed with water, and further with saturated brine. The organic phase was dried over anhydrous sodium sulfate. The solid was filtered out, and the filtrate was concentrated under reduced pressure. The residue was purified by silica gel column chromatography to give a crude product of the title compound (130 mg, yield: 48%).

LC/MS: (M+H)$^+$=521.0, $C_{26}H_{32}N_8O_4$=520.25

Example 25

Synthesis of 2,2,2-trifluoro-1-(8-morpholino-2-((5-(piperazin-1-yl)pyridin-2-yl)amino)pyrido[3,4-d]pyrimidin-6-yl)ethanol (Compound 35)

[Formula 73]

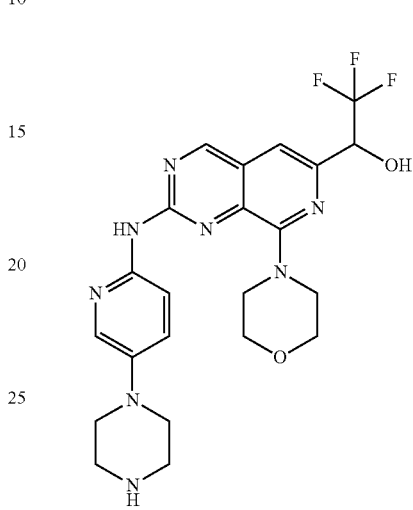

The crude product (25 mg, 0.048 mmol) of tert-butyl 4-(6-(((6-formyl-8-morpholinopyrido[3,4-d]pyrimidin-2-yl)amino)pyridin-3-yl)piperazine-1-carboxylate synthesized in Example 24 was dissolved in THF (0.5 mL). The solution was cooled to 0° C. To the solution was added (trifluoromethyl)trimethylsilane (23 μL, 0.143 mmol) at 0° C., followed by addition of a catalytic amount (1 drop) of tetrabutylammonium fluoride at 0° C. The reaction solution was stirred at 0° C. for two hours. The progress of the reaction was monitored by LC/MS. The solution was concentrated under reduced pressure. The residue was used in the subsequent reaction without purification.

The residue was dissolved in dichloromethane (1 mL). A solution of HCl in 1,4-dioxane (0.2 mL, 4 mol/L) was added to the solution at 0° C. The reaction solution was stirred at 0° C. for 30 minutes. The progress of the reaction was monitored by LC/MS. After the completion of the reaction, the solution was concentrated under reduced pressure. The residue was purified by preparative HPLC. The obtained fraction was basified with saturated aqueous sodium hydrogen carbonate solution, and the aqueous phase was extracted with ethyl acetate (75 mL) twice. The extracted organic phases were combined and concentrated under reduced pressure to give the title compound (6.0 mg, yield: 25%).

LC/MS: (M+H)$^+$=491.39, $C_{22}H_{25}F_3N_8O_2$=490.21

Example 26
Compounds 1 to 337 shown below were synthesized in accordance with the processes described in Examples 15 to 25 with appropriate deprotection when necessary.
TABLE 12
| Compound No. | R1 | R2 | R3 | 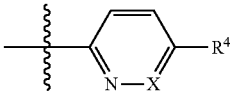 |
|---|---|---|---|---|
| 1 | 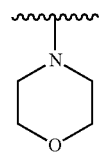 | 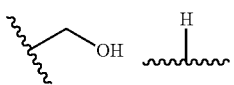 | 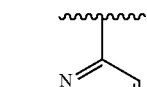 | 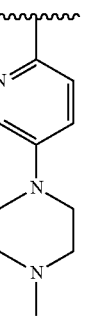 |
| 2 | 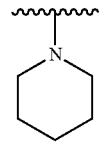 | 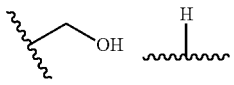 | 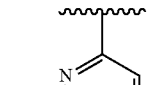 | 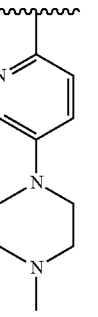 |
| 3 | 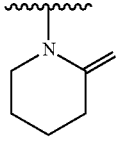 | 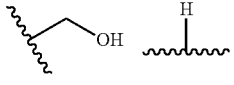 | 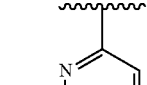 | 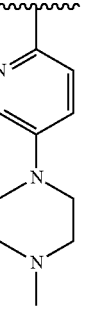 |
| 4 | 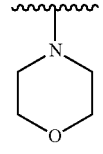 | 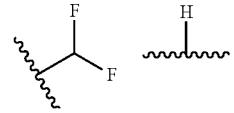 | 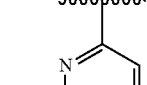 | 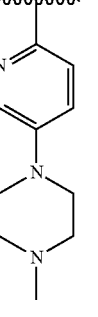 |

TABLE 12-continued
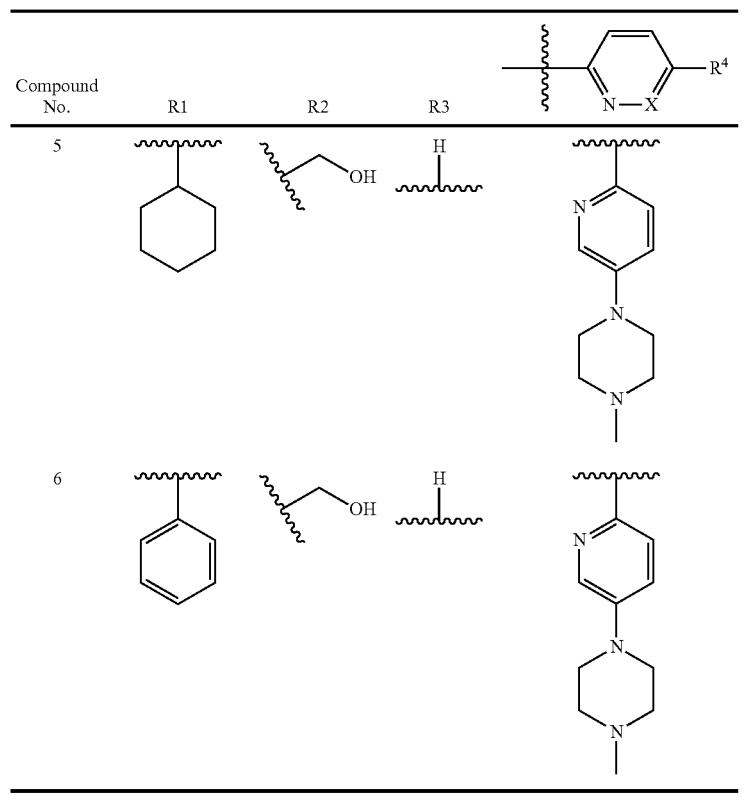
TABLE 13
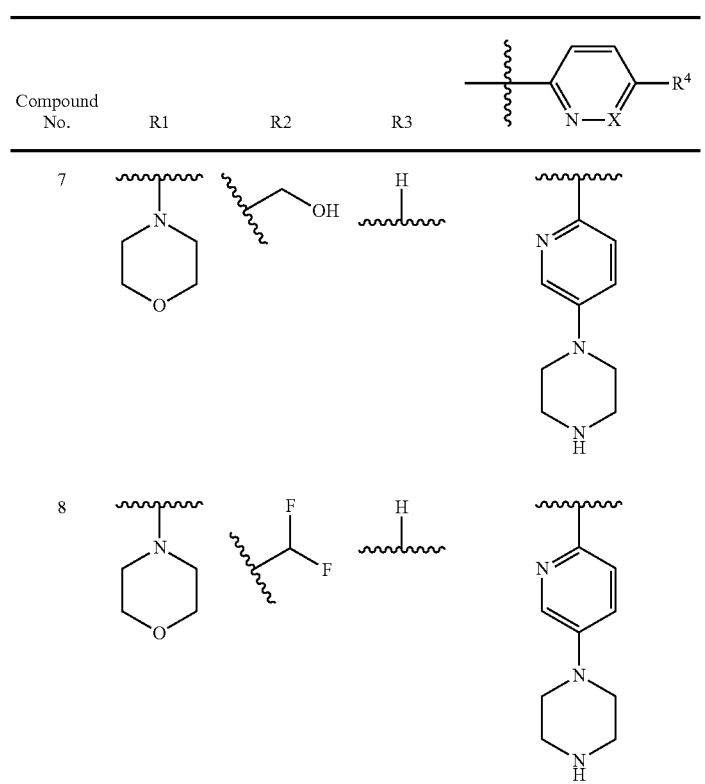

TABLE 13-continued

| Compound No. | R1 | R2 | R3 | ![structure](pyridazine with R4) |
|---|---|---|---|---|
| 9 | piperidin-1-yl | CH2OH | H | 5-(piperazin-1-yl)pyridin-2-yl |
| 10 | phenyl | CH2OH | H | 5-(piperazin-1-yl)pyridin-2-yl |
| 11 | piperidin-1-yl | CHF2 | H | 5-(piperazin-1-yl)pyridin-2-yl |
| 12 | phenyl | CHF2 | H | 5-(piperazin-1-yl)pyridin-2-yl |

TABLE 14

| Compound No. | R1 | R2 | R3 | ![structure with R4, N-X, pyridazine] |
|---|---|---|---|---|
| 13 | piperidin-1-yl | CHF₂ | H | 5-(4-methylpiperazin-1-yl)pyridin-2-yl |
| 14 | 4-methylphenyl | CH₂OH | H | 5-(piperazin-1-yl)pyridin-2-yl |
| 15 | 2-methylphenyl | CH₂OH | H | 5-(piperazin-1-yl)pyridin-2-yl |
| 16 | thiophen-3-yl | CH₂OH | H | 5-(piperazin-1-yl)pyridin-2-yl |
| 17 | furan-3-yl | CH₂OH | H | 5-(piperazin-1-yl)pyridin-2-yl |

TABLE 14-continued
| Compound No. | R1 | R2 | R3 | 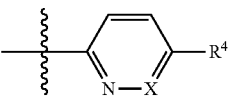 |
|---|---|---|---|---|
| 18 | 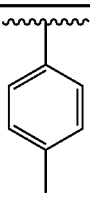 |  |  | 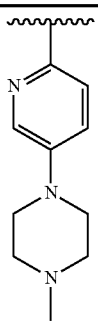 |
20
TABLE 15
| Compound No. | R1 | R2 | R3 | 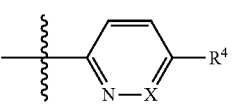 |
|---|---|---|---|---|
| 19 | 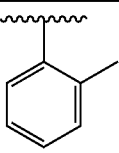 |  |  | 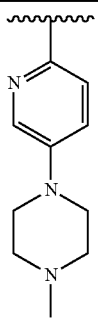 |
| 20 | 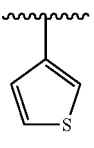 |  |  | 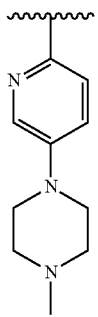 [SMILES: *c1ccc(N2CCN(C)CC2)cn1] |
| 21 | 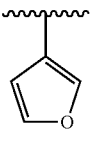 |  |  | 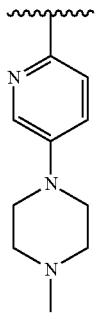 [SMILES: *c1ccc(N2CCN(C)CC2)cn1] |

TABLE 15-continued

| Compound No. | R1 | R2 | R3 | ![](N-X with R4) |
|---|---|---|---|---|
| 22 | cyclohexenyl | CH(OH)- | H | pyridine-piperazine(N-Me) |
| 23 | piperidinyl | -C(=O)OH | H | pyridine-piperazine(NH) |
| 24 | piperidinyl | -CH(OH)CH3 | H | pyridine-piperazine(NH) |

TABLE 16

| Compound No. | R1 | R2 | R3 | pyridazine with R4 |
|---|---|---|---|---|
| 25 | piperidinyl | -C(=O)OCH3 | H | pyridine-piperazine(NH) |

TABLE 16-continued
| Compound No. | R1 | R2 | R3 | 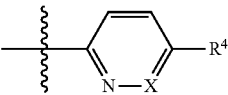 |
|---|---|---|---|---|
| 26 | 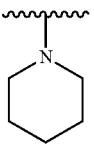 |  | H |  |
| 27 | 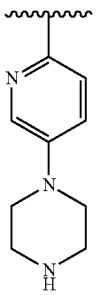 [SMILES: *c1ccc(N2CCNCC2)cn1] | 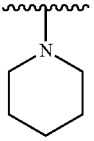 | H |  |
| 28 |  | 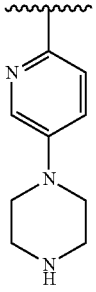 [SMILES: *c1ccc(N2CCNCC2)cn1] | H | 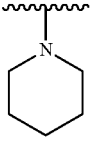 |
| 29 |  |  | H | 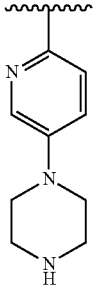 |
| 30 | 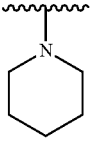 |  | H |  |

TABLE 17

| Compound No. | R1 | R2 | R3 | (structure with R4) |
|---|---|---|---|---|
| 31 | furan-3-yl | CHF₂ | H | 5-(piperazin-1-yl)pyridin-2-yl |
| 32 | morpholin-4-yl | CH₂OCH₃ | H | 5-(piperazin-1-yl)pyridin-2-yl |
| 33 | morpholin-4-yl | CH₂OH | CH₃ | 5-(piperazin-1-yl)pyridin-2-yl |
| 34 | morpholin-4-yl | CH(OH)CH₂CH₃ | H | 5-(piperazin-1-yl)pyridin-2-yl |
| 35 | morpholin-4-yl | CH(OH)CF₃ | H | 5-(piperazin-1-yl)pyridin-2-yl |

TABLE 17-continued
| Compound No. | R1 | R2 | R3 | 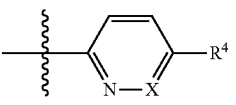 |
|---|---|---|---|---|
| 36 | 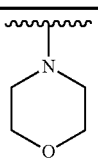 | 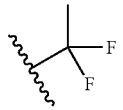 | H |  |
TABLE 18
| Compound No. | R1 | R2 | R3 | 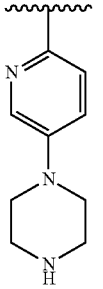 |
|---|---|---|---|---|
| 37 | 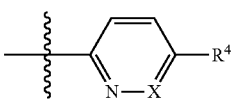 | 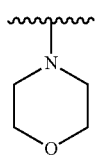 | H | 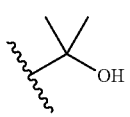 |
| 38 |  | 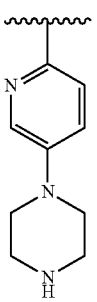 [SMILES: *c1ccc(N2CCNCC2)cn1] | H | 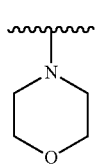 |
| 39 | 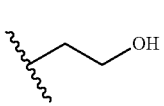 |  | H | 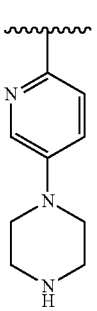 [SMILES: *c1ccc(N2CCNCC2)cn1] |

TABLE 18-continued
| Compound No. | R1 | R2 | R3 | ![](N-X with R4) |
|---|---|---|---|---|
| 40 | 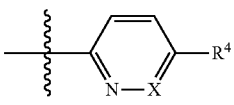 | 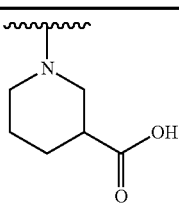 | 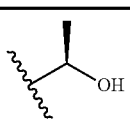 | 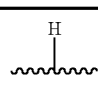 |
| 41 | 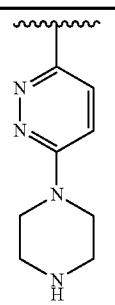 | 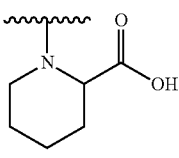 | 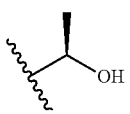 [SMILES: *[C@@H](C)O] | 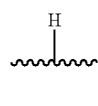 |
| 42 | 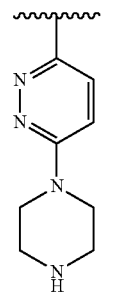 | 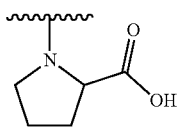 [SMILES: *N1CCCC1C(=O)O] | 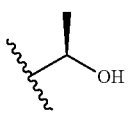 [SMILES: *[C@@H](C)O] | 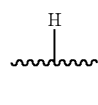 |
TABLE 19
| Compound No. | R1 | R2 | R3 | ![](N-X with R4) |
|---|---|---|---|---|
| 43 | 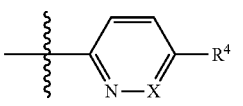 | 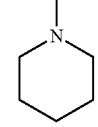 | 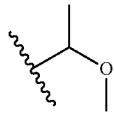 | 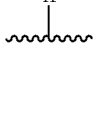 |

TABLE 19-continued

| Compound No. | R1 | R2 | R3 | ![R4 pyridazine] |
|---|---|---|---|---|
| 44 | octahydropyrrolo[3,4-c]pyridin-5-yl | CH(CH₃)OCH₃ | H | 5-(piperazin-1-ylmethyl)pyridin-2-yl |
| 45 | 4-(hydroxymethyl)piperidin-1-yl | CH(CH₃)OCH₃ | H | 5-(piperazin-1-ylmethyl)pyridin-2-yl |
| 46 | 4-(methoxymethyl)piperidin-1-yl | CH(CH₃)OCH₃ | H | 5-(piperazin-1-ylmethyl)pyridin-2-yl |
| 47 | azetidin-1-yl | CH(CH₃)OH | H | 5-{[4-(2-hydroxyethyl)piperazin-1-yl]methyl}pyridin-2-yl |
| 48 | pyrrolidin-1-yl | CH(CH₃)OH | H | 5-{[4-(2-hydroxyethyl)piperazin-1-yl]methyl}pyridin-2-yl |

TABLE 20
| Compound No. | R1 | R2 | R3 | ![structure](R4 header: pyridazine with R4, X) |
|---|---|---|---|---|
| 49 | 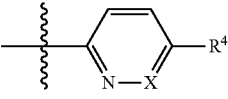 | 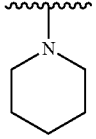 | 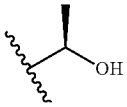 |  |
| 50 | 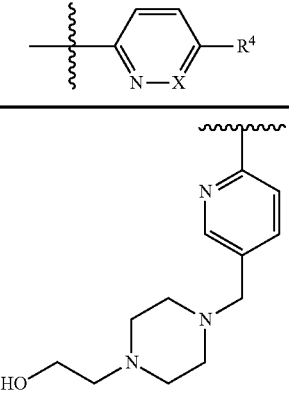 | 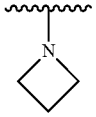 | 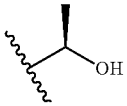 |  |
| 51 | 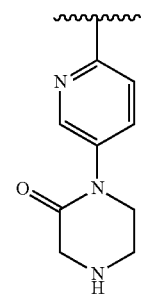 [SMILES: *c1ccc(N2CCNCC2=O)cn1] | 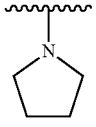 [SMILES: *N1CCCC1] | 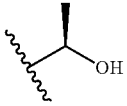 |  |
| 52 | 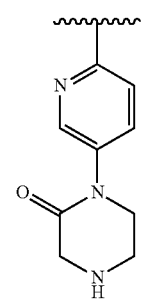 [SMILES: *c1ccc(N2CCNCC2=O)cn1] | 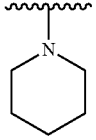 | 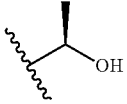 [SMILES: *[C@@H](C)O] |  |
| 53 | 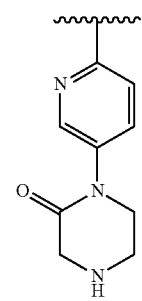 [SMILES: *c1ccc(N2CCNCC2=O)cn1] | 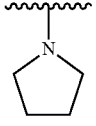 | 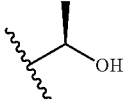 |  |

TABLE 20-continued
| Compound No. | R1 | R2 | R3 | ![structure](N-X with R4) |
|---|---|---|---|---|
| 54 | 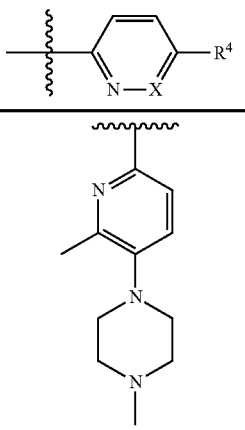 | 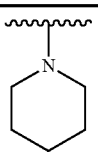 | 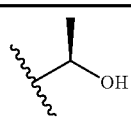 | 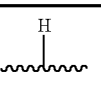 |
TABLE 21
| Compound No. | R1 | R2 | R3 | ![structure](N-X with R4) |
|---|---|---|---|---|
| 55 | 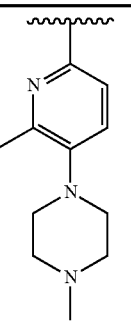 | 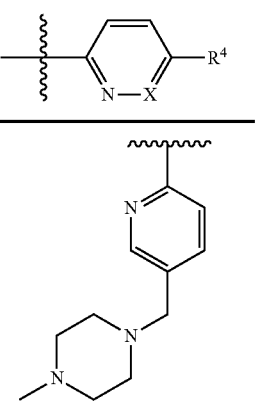 | 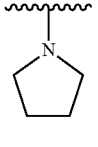 | 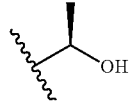 |
| 56 | 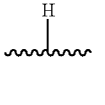 | 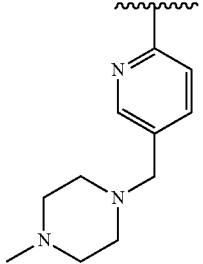 [SMILES: *c1ccc(CN2CCN(C)CC2)cn1] | 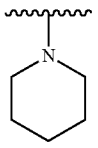 | 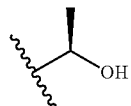 |
| 57 | 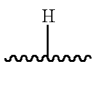 | 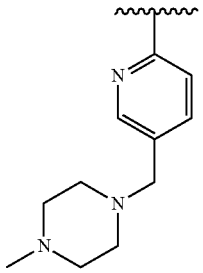 [SMILES: *c1ccc(CN2CCN(C)CC2)cn1] | 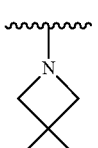 | 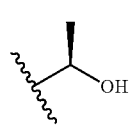 [SMILES: *[C@@H](C)O] |

TABLE 21-continued
| Compound No. | R1 | R2 | R3 | ![structure](N-X, R4) |
|---|---|---|---|---|
| 58 | 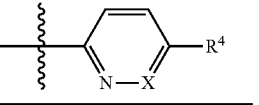 | 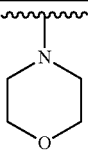 | H | 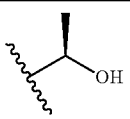 |
| 59 |  | 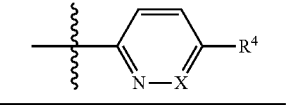 | H | 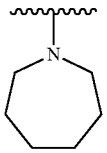 |
| 60 | 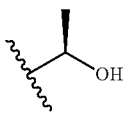 [SMILES: *[C@@H](C)O] |  | H |  |
TABLE 22
| Compound No. | R1 | R2 | R3 | ![structure](N-X, R4) |
|---|---|---|---|---|
| 61 | 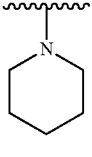 | 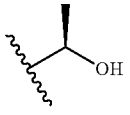 [SMILES: *[C@@H](C)O] | H |  |

TABLE 22-continued
| Compound No. | R1 | R2 | R3 | 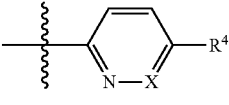 |
|---|---|---|---|---|
| 62 | 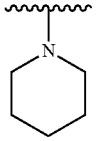 | 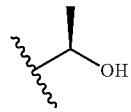 [SMILES: *[C@@H](C)O] | 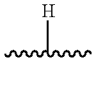 | 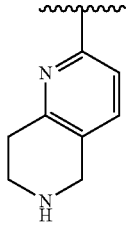 [SMILES: *c1ccc2c(n1)CCNC2] |
| 63 | 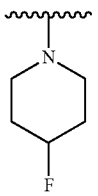 | 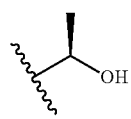 [SMILES: *[C@@H](C)O] | 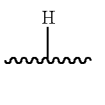 | 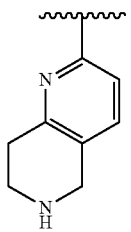 [SMILES: *c1ccc2c(n1)CCNC2] |
| 64 | 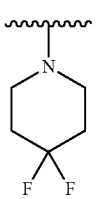 | 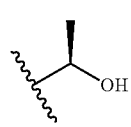 [SMILES: *[C@@H](C)O] | 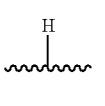 | 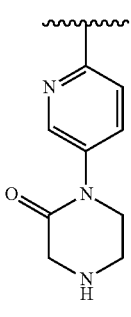 [SMILES: *c1ccc(N2CCNCC2=O)cn1] |
| 65 | 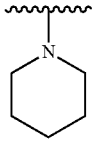 | 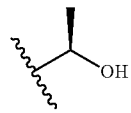 [SMILES: *[C@@H](C)O] | 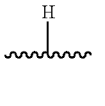 | 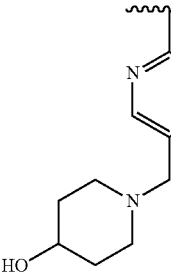 |
| 66 | 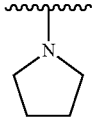 | 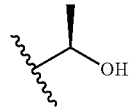 [SMILES: *[C@@H](C)O] | 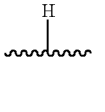 | 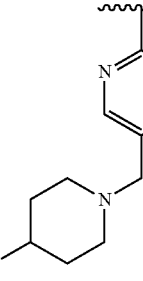 |

TABLE 23

| Compound No. | R1 | R2 | R3 | (pyridazine with R4) |
|---|---|---|---|---|
| 67 | morpholin-4-yl | CH(OH)CH₃ | H | 6-{[4-hydroxypiperidin-1-yl]methyl}pyridin-3-yl |
| 68 | piperidin-1-yl | CH(OH)CH₃ | H | 6-{[4-(hydroxymethyl)piperidin-1-yl]methyl}pyridin-3-yl |
| 69 | pyrrolidin-1-yl | CH(OH)CH₃ | H | 6-{[4-(hydroxymethyl)piperidin-1-yl]methyl}pyridin-3-yl |
| 70 | morpholin-4-yl | CH(OH)CH₃ | H | 6-{[4-(hydroxymethyl)piperidin-1-yl]methyl}pyridin-3-yl |
| 71 | 4-hydroxypiperidin-1-yl | CH(OH)CH₃ | H | 6-{[4-(hydroxymethyl)piperidin-1-yl]methyl}pyridin-3-yl |

TABLE 23-continued

| Compound No. | R1 | R2 | R3 | ![structure](pyridazine with R4) |
|---|---|---|---|---|
| 72 | piperidin-1-yl | CH(CH₃)OH | H | 5-(4-methyl-2-oxopiperazin-1-yl)pyridin-2-yl |

TABLE 24

| Compound No. | R1 | R2 | R3 | pyridazine-R4 |
|---|---|---|---|---|
| 73 | pyrrolidin-1-yl | CH(CH₃)OH | H | 5-(4-methyl-2-oxopiperazin-1-yl)pyridin-2-yl |
| 74 | morpholin-4-yl | CH(CH₃)OH | H | 5-(4-methyl-2-oxopiperazin-1-yl)pyridin-2-yl |
| 75 | 2,2-dimethylpyrrolidin-1-yl | CH(CH₃)OH | H | 5-{[4-(2-hydroxyethyl)piperazin-1-yl]methyl}pyridin-2-yl |

TABLE 24-continued

| Compound No. | R1 | R2 | R3 | ![structure](pyridazine with R4) |
|---|---|---|---|---|
| 76 | piperidine-4-carboxylic acid (N-linked) | CH(OH)CH3 | H | pyridine-CH2-piperazine-CH2CH2OH |
| 77 | 4-methylpiperazine (N-linked) | CH(OH)CH3 | H | pyridine-CH2-piperazine-CH2CH2OH |
| 78 | 4-fluoropiperidine (N-linked) | CH(OH)CH3 | H | pyridine-CH2-piperazine-CH2CH2OH |

TABLE 25

| Compound No. | R1 | R2 | R3 | ![structure](pyridazine with R4) |
|---|---|---|---|---|
| 79 | 4,4-difluoropiperidine (N-linked) | CH(OH)CH3 | H | pyridine-CH2-piperazine-CH2CH2OH |

TABLE 25-continued
| Compound No. | R1 | R2 | R3 | 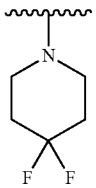 |
|---|---|---|---|---|
| 80 | 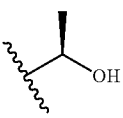 [SMILES: *[C@@H](C)O] |  | 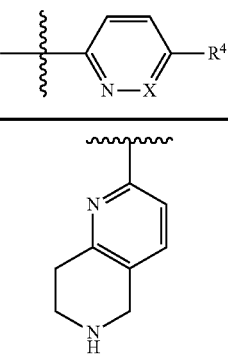 | 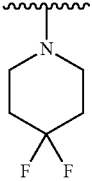 |
| 81 | 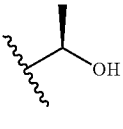 [SMILES: *[C@@H](C)O] |  | 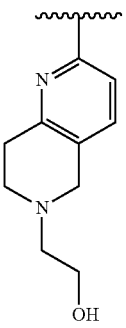 | 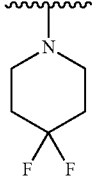 |
| 82 | 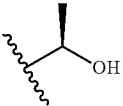 [SMILES: *[C@@H](C)O] |  | 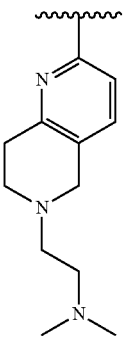 | 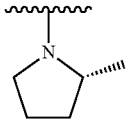 [SMILES: *N1CCC[C@H]1C] |
| 83 | 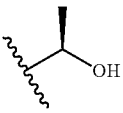 [SMILES: *[C@@H](C)O] |  | 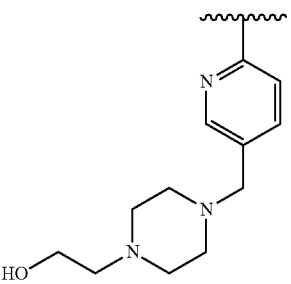 | 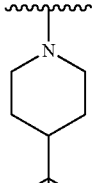 |
| 84 | 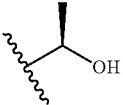 |  | 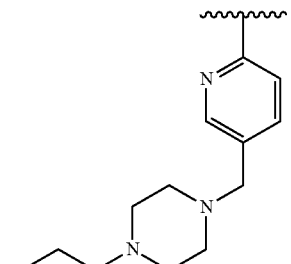 | |

TABLE 26
| Compound No. | R1 | R2 | R3 | 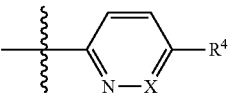 |
|---|---|---|---|---|
| 85 | 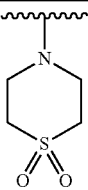 | 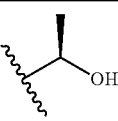 |  | 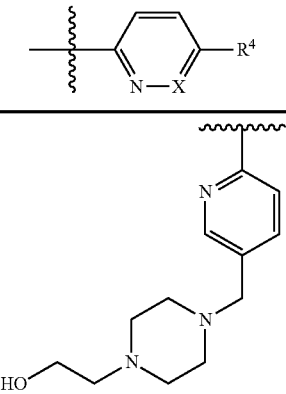 |
| 86 | 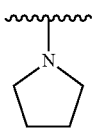 | 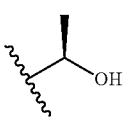 [SMILES: *[C@@H](C)O] |  | 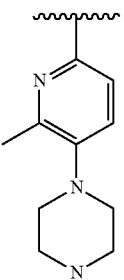 |
| 87 | 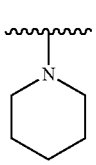 | 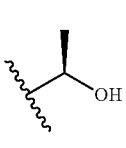 [SMILES: *[C@@H](C)O] |  | 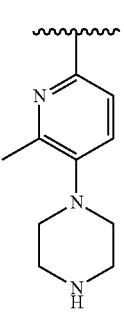 |
| 88 | 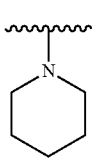 | 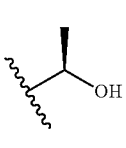 [SMILES: *[C@@H](C)O] |  | 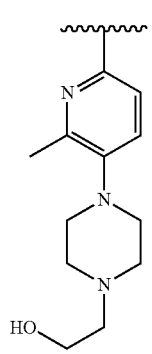 [SMILES: *c1ccc(N2CCN(CCO)CC2)c(C)n1] |
| 89 | 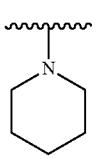 | 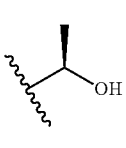 [SMILES: *[C@@H](C)O] |  | 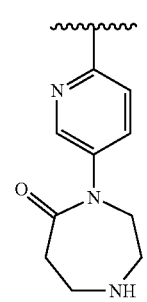 [SMILES: *c1ccc(N2CCNCCC2=O)cn1] |

TABLE 26-continued
| Compound No. | R1 | R2 | R3 | 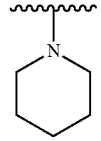 |
|---|---|---|---|---|
| 90 | 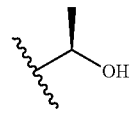 [SMILES: *[C@@H](C)O] | 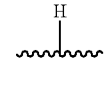 | H | 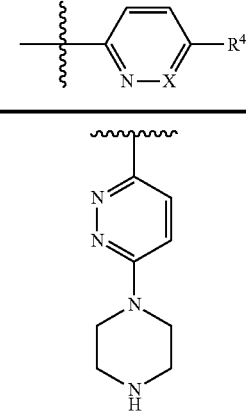 |
TABLE 27
| Compound No. | R1 | R2 | R3 | 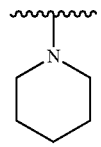 |
|---|---|---|---|---|
| 91 | 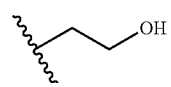 |  | H | 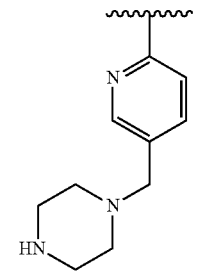 |
| 92 | 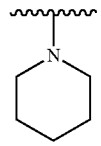 | 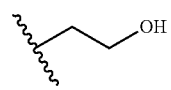 [SMILES: *CCO] | H |  |
| 93 | 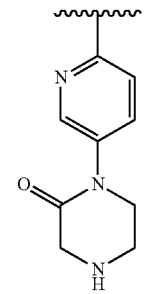 [SMILES: *c1ccc(N2CCNCC2=O)cn1] | 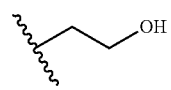 [SMILES: *CCO] | H | 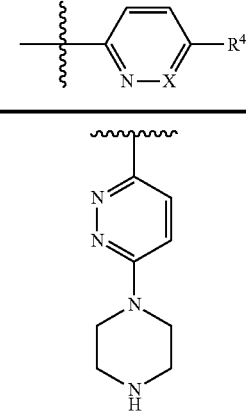 |

TABLE 27-continued

| Compound No. | R1 | R2 | R3 | |
|---|---|---|---|---|
| 94 | piperidin-1-yl | CH(CH₃)CH₂OH | H | 6-(piperazin-1-yl)pyridazin-3-yl |
| 95 | piperidin-1-yl | CH(CH₃)CH₂OH | H | 5,6,7,8-tetrahydro-1,6-naphthyridin-2-yl |
| 96 | piperidin-1-yl | CH₂OH | H | 6-((4-(2-hydroxyethyl)piperazin-1-yl)methyl)pyridin-3-yl |

TABLE 28

| Compound No. | R1 | R2 | R3 | |
|---|---|---|---|---|
| 97 | piperidin-1-yl | CH₂OH | H | 6-(3-oxopiperazin-1-yl)pyridin-3-yl |

TABLE 28-continued

| Compound No. | R1 | R2 | R3 | (R4-pyridazine structure) |
|---|---|---|---|---|
| 98 | (S)-2-methylpyrrolidin-1-yl | CH(CH₃)OH | H | 6-{[4-(2-hydroxyethyl)piperazin-1-yl]methyl}pyridin-3-yl |
| 99 | (S)-3-methylpyrrolidin-1-yl | CH(CH₃)OH | H | 6-{[4-(2-hydroxyethyl)piperazin-1-yl]methyl}pyridin-3-yl |
| 100 | (R)-3-methylpyrrolidin-1-yl | CH(CH₃)OH | H | 6-{[4-(2-hydroxyethyl)piperazin-1-yl]methyl}pyridin-3-yl |
| 101 | 2,5-dimethylpyrrolidin-1-yl | CH(CH₃)OH | H | 6-{[4-(2-hydroxyethyl)piperazin-1-yl]methyl}pyridin-3-yl |
| 102 | 3,3-dimethylpyrrolidin-1-yl | CH(CH₃)OH | H | 6-{[4-(2-hydroxyethyl)piperazin-1-yl]methyl}pyridin-3-yl |

TABLE 29

| Compound No. | R1 | R2 | R3 | (R4-pyridazine group) |
|---|---|---|---|---|
| 103 | N-azabicyclic | CH(OH)CH₃ | H | pyridine-CH₂-piperazine-CH₂CH₂OH |
| 104 | N-azabicyclic (cyclopropane fused) | CH(OH)CH₃ | H | pyridine-CH₂-piperazine-CH₂CH₂OH |
| 105 | N-azabicyclic | CH(OH)CH₃ | H | pyridine-CH₂-piperazine-CH₂CH₂OH |
| 106 | 4-hydroxypiperidin-1-yl | CH(OH)CH₃ | H | pyridine-CH₂-piperazine-CH₂CH₂OH |
| 107 | piperidin-1-yl | CH₂OH | H | pyridazine-piperazine |

TABLE 29-continued
| Compound No. | R1 | R2 | R3 | ![structure](pyridazine with R4) |
|---|---|---|---|---|
| 108 | 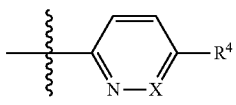 | 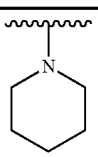 |  |  |
TABLE 30
| Compound No. | R1 | R2 | R3 | ![structure](pyridazine with R4) |
|---|---|---|---|---|
| 109 | 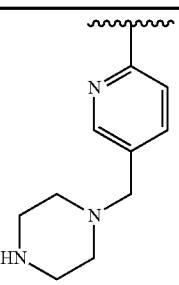 | 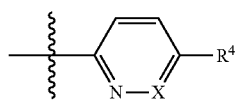 | 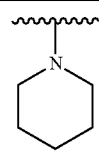 | 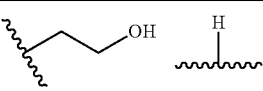 |
| 110 |  | 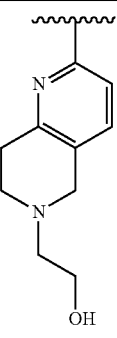 | 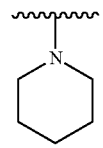 | 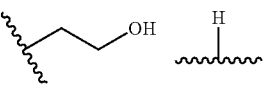 |
| 111 |  | 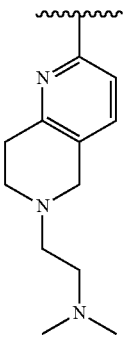 [SMILES: *c1ccc2c(n1)CCN(CCN(C)C)C2] | 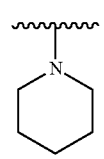 [SMILES: *N1CCCCC1] | 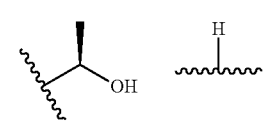 |

TABLE 30-continued
| Compound No. | R1 | R2 | R3 | |
|---|---|---|---|---|
| 112 | 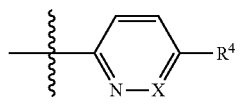 4-fluoropiperidine | 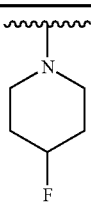 -CH(OH)- | 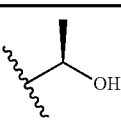 H | 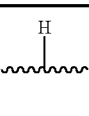 6-(2-hydroxyethyl)-5,6,7,8-tetrahydro-1,6-naphthyridine |
| 113 | 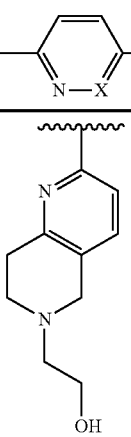 3,4-dimethylpyrrolidine | 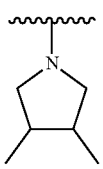 -CH(OH)- | 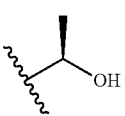 [SMILES: *[C@@H](C)O] H | 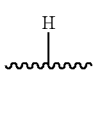 5-((4-(2-hydroxyethyl)piperazin-1-yl)methyl)pyridine |
| 114 | 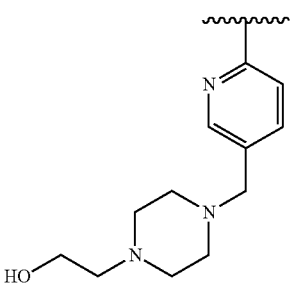 piperidine | 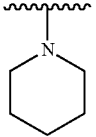 -CH(OH)- | 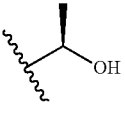 [SMILES: *[C@@H](C)O] H | 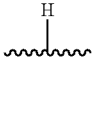 6-(4-(2-(methylsulfonyl)ethyl)piperazin-1-yl)pyridazine |
TABLE 31
| Compound No. | R1 | R2 | R3 | |
|---|---|---|---|---|
| 115 | 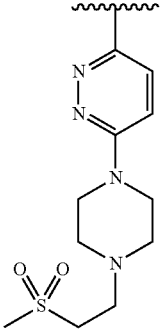 [SMILES: *c1ccc(N2CCN(CCS(C)(=O)=O)CC2)nn1] 4-fluoropiperidine | 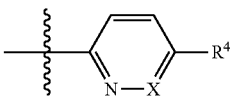 -CH(OH)- | 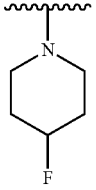 H | 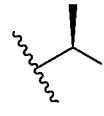 5-((4-methylpiperazin-1-yl)methyl)pyridine |

TABLE 31-continued

| Compound No. | R1 | R2 | R3 | ![pyridazine with R4] |
|---|---|---|---|---|
| 116 | (3-fluoropyrrolidin-1-yl) | CH(OH)CH₃ | H | 6-((4-methylpiperazin-1-yl)methyl)pyridin-3-yl |
| 117 | (3-fluoropyrrolidin-1-yl, other stereo) | CH(OH)CH₃ | H | 6-((4-methylpiperazin-1-yl)methyl)pyridin-3-yl |
| 118 | piperidin-1-yl | CH(OCH₃)CH₃ | H | 6-(piperazin-1-yl)pyridazin-3-yl |
| 119 | piperidin-1-yl | CH(OCH₃)CH₃ | H | 6-(piperazin-1-ylmethyl)pyridin-3-yl |
| 120 | pyrrolidin-1-yl | CH(OH)CH₃ | H | 6-(4-methyl-7-oxo-1,4-diazepan-1-yl)pyridin-3-yl |

TABLE 32

| Compound No. | R1 | R2 | R3 | ⟨ring with N—X and R⁴⟩ |
|---|---|---|---|---|
| 121 | piperidin-1-yl | CH(CH₃)OH | H | 5-(4-methyl-1,4-diazepan-2-on-1-yl)pyridin-2-yl |
| 122 | piperidin-1-yl | CH(CH₃)OH | H | 5-((4-ethylpiperazin-1-yl)methyl)pyridin-2-yl |
| 123 | piperidin-1-yl | CH(CH₃)OH | H | 6-(4-methylpiperazin-1-yl)pyridazin-3-yl |
| 124 | 4-fluoropiperidin-1-yl | CH(CH₃)OH | H | 6-(4-methylpiperazin-1-yl)pyridazin-3-yl |

TABLE 32-continued
| Compound No. | R1 | R2 | R3 | (pyridazine with R4) |
|---|---|---|---|---|
| 125 | 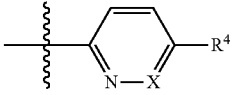 | 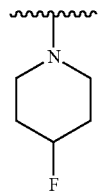 | H | 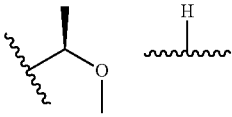 |
| 126 | 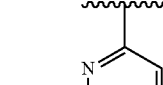 | 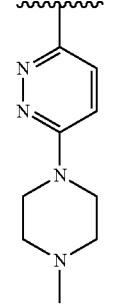 [SMILES: *c1ccc(N2CCN(C)CC2)nn1] | H | 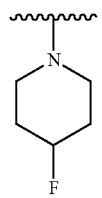 |
TABLE 33
| Compound No. | R1 | R2 | R3 | (pyridazine with R4) |
|---|---|---|---|---|
| 127 | 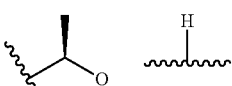 | 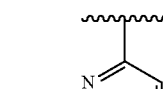 | H | 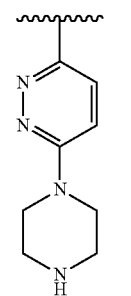 |
| 128 | 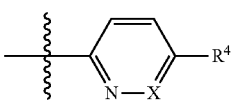 | 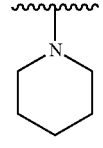 | H | 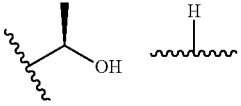 |

TABLE 33-continued

| Compound No. | R1 | R2 | R3 | ![structure](pyridazine with R4) |
|---|---|---|---|---|
| 129 | 4-hydroxypiperidin-1-yl | CHF2 | H | 6-((4-(2-hydroxyethyl)piperazin-1-yl)methyl)pyridin-3-yl |
| 130 | piperidin-1-yl | CH(OH)CH3 | H | 6-(3-hydroxypropyl)-5,6,7,8-tetrahydro-1,6-naphthyridin-2-yl |
| 131 | piperidin-1-yl | CH(OH)CH3 | H | 6-(((3S,4R)-3-fluoro-1-(2-hydroxyethyl)piperidin-4-yl)oxy)pyridin-3-yl |
| 132 | piperidin-1-yl | CH(OH)CH3 | H | 6-(((3R,4S)-3-fluoro-1-(2-hydroxyethyl)piperidin-4-yl)oxy)pyridin-3-yl |

TABLE 34
| Compound No. | R1 | R2 | R3 | 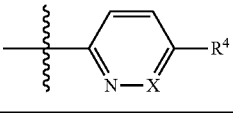 |
|---|---|---|---|---|
| 133 | 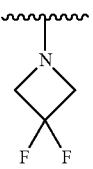 | 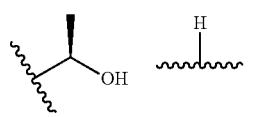 |  | 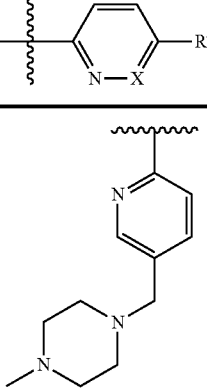 |
| 134 | 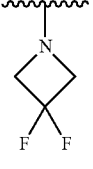 | 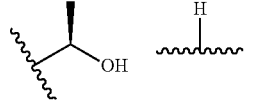 |  | 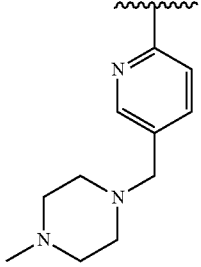 |
| 135 | 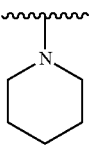 | 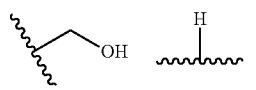 |  | 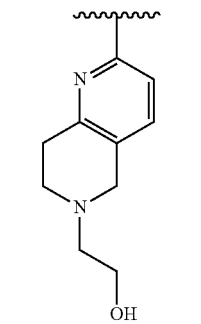 [SMILES: *c1ccc2c(n1)CCN(CCO)C2] |
| 136 | 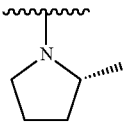 [SMILES: *N1CCC[C@H]1C] | 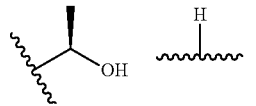 |  | 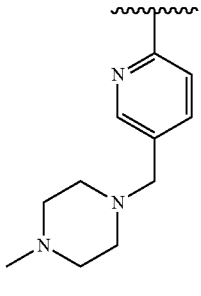 [SMILES: *c1ccc(CN2CCN(C)CC2)cn1] |
| 137 | 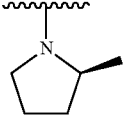 [SMILES: *N1CCC[C@@H]1C] | 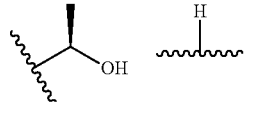 |  | 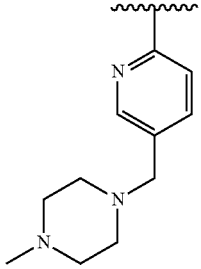 [SMILES: *c1ccc(CN2CCN(C)CC2)cn1] |

TABLE 34-continued
| Compound No. | R1 | R2 | R3 | ![](pyridazine with R4) |
|---|---|---|---|---|
| 138 | 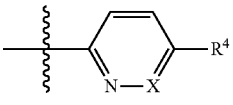 | 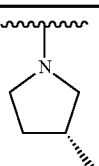 | 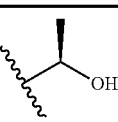 |  |
TABLE 35
| Compound No. | R1 | R2 | R3 | ![](pyridazine with R4) |
|---|---|---|---|---|
| 139 | 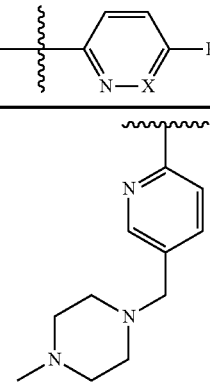 | 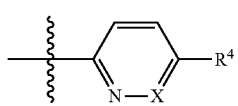 | 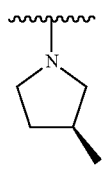 [SMILES: *N1CC[C@H](C)C1] | 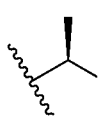 |
| 140 |  | 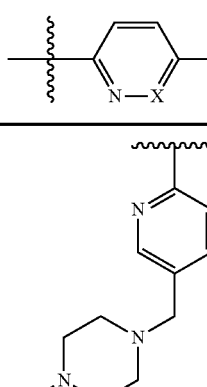 | 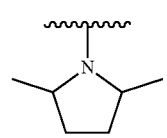 | 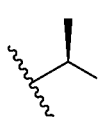 |
| 141 |  | 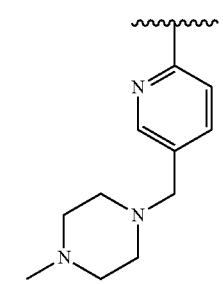 [SMILES: *c1ccc(CN2CCN(C)CC2)cn1] | 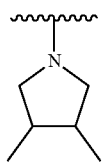 | 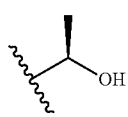 [SMILES: *[C@@H](C)O] |

TABLE 35-continued

| Compound No. | R1 | R2 | R3 | ![structure](pyridazine with R4, N-X) |
|---|---|---|---|---|
| 142 | 3,3-dimethylpyrrolidin-1-yl | CH(OH)CH3 | H | 6-((4-methylpiperazin-1-yl)methyl)pyridin-3-yl |
| 143 | 2-azabicyclo[2.2.1]heptan-2-yl | CH(OH)CH3 | H | 6-((4-methylpiperazin-1-yl)methyl)pyridin-3-yl |
| 144 | 4-(trifluoromethyl)piperidin-1-yl | CH(OH)CH3 | H | 6-((4-methylpiperazin-1-yl)methyl)pyridin-3-yl |

TABLE 36

| Compound No. | R1 | R2 | R3 | pyridazine with R4, N-X |
|---|---|---|---|---|
| 145 | morpholin-4-yl | CH(OH)CH3 | H | 6-((4-methylpiperazin-1-yl)methyl)pyridin-3-yl |

TABLE 36-continued

| Compound No. | R1 | R2 | R3 | ![R4 pyridazine] |
|---|---|---|---|---|
| 146 | piperidin-1-yl | CH(OH)CH2CH3 | H | 6-((4-methylpiperazin-1-yl)methyl)pyridin-3-yl |
| 147 | piperidin-1-yl | CH(OH)CH3 | H | 6-(piperidine-4-carbonyl)-5,6,7,8-tetrahydro-1,6-naphthyridin-2-yl |
| 148 | piperidin-1-yl | CH(OH)CH3 | H | 6-(1-(2-hydroxyethyl)piperidine-4-carbonyl)-5,6,7,8-tetrahydro-1,6-naphthyridin-2-yl |
| 149 | piperidin-1-yl | CH(OH)CH3 | H | 6-(1-methylpiperidine-4-carbonyl)-5,6,7,8-tetrahydro-1,6-naphthyridin-2-yl |

TABLE 36-continued
| Compound No. | R1 | R2 | R3 | |
|---|---|---|---|---|
| 150 |  |  |  | 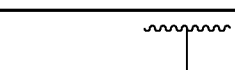 |
TABLE 37
| Compound No. | R1 | R2 | R3 | |
|---|---|---|---|---|
| 151 | 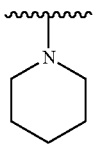 | 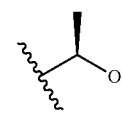 |  | 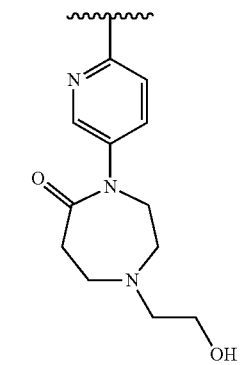 |
| 152 | 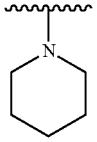 | 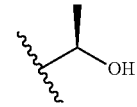 [SMILES: *[C@@H](C)O] |  | 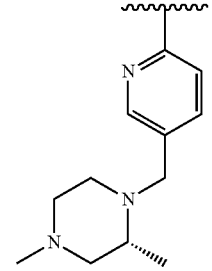 [SMILES: *c1ccc(CN2CCN(C)C[C@H]2C)cn1] |
| 153 |  | 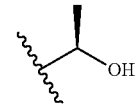 |  | 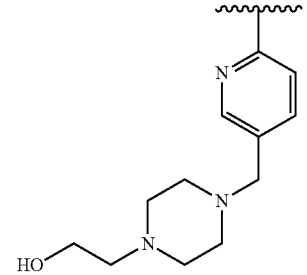 |

TABLE 37-continued
| Compound No. | R1 | R2 | R3 | ![structure](N-X with R4) |
|---|---|---|---|---|
| 154 | 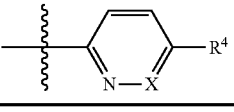 |  | H | 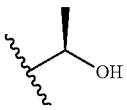 |
| 155 |  | 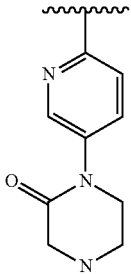 | H | 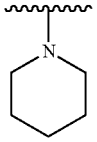 |
| 156 | 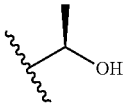 | 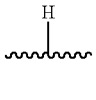 | H | 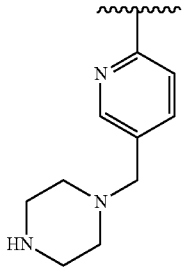 |
TABLE 38
| Compound No. | R1 | R2 | R3 | ![structure](N-X with R4) |
|---|---|---|---|---|
| 157 | 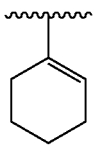 | 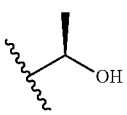 | H |  |

TABLE 38-continued
| Compound No. | R1 | R2 | R3 | ![R4 pyridazine](N-X with R4) |
|---|---|---|---|---|
| 158 | 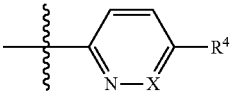 | 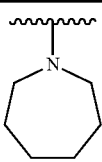 |  |  |
| 159 | 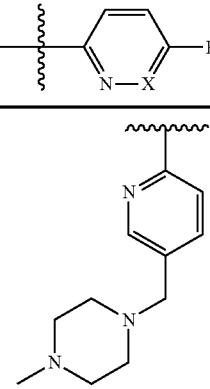 | 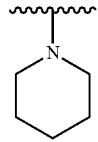 |  |  |
| 160 | 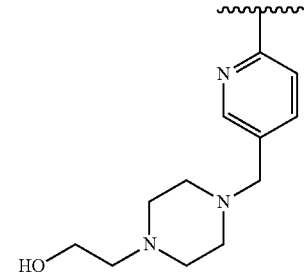 | 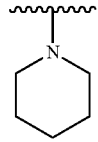 | 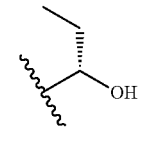 [SMILES: *[C@@H](O)CC] |  |
| 161 | 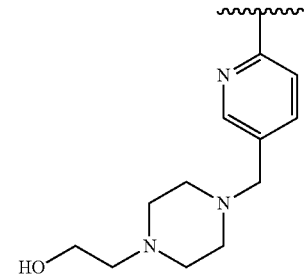 [SMILES: *c1ccc(CN2CCN(CCO)CC2)cn1] | 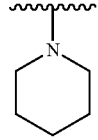 |  |  |
| 162 | 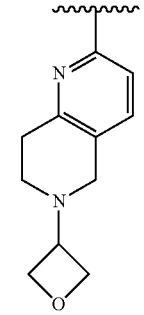 [SMILES: *c1ccc2c(n1)CCN(C1COC1)C2] | 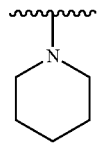 |  |  |

TABLE 39

| Compound No. | R1 | R2 | R3 | ![R4 structure] |
|---|---|---|---|---|
| 163 | piperidin-1-yl | (R)-CH(OH)CH₃ | H | 6-(piperidin-4-ylsulfonyl)-5,6,7,8-tetrahydro-1,6-naphthyridin-2-yl |
| 164 | piperidin-1-yl | (R)-CH(OH)CH₃ | H | 6-(piperidin-4-yloxy)pyridin-3-yl |
| 165 | piperidin-1-yl | (R)-CH(OH)CH₃ | H | 6-((1-(2-hydroxyethyl)piperidin-4-yl)oxy)pyridin-3-yl |
| 166 | piperidin-1-yl | (S)-2-methyl-3-hydroxypropyl | H | 5,6,7,8-tetrahydro-1,6-naphthyridin-3-yl |
| 167 | piperidin-1-yl | (S)-2-methyl-3-hydroxypropyl | H | 6-((4-(2-hydroxyethyl)piperazin-1-yl)methyl)pyridin-3-yl |

TABLE 39-continued

| Compound No. | R1 | R2 | R3 | ![pyridazine with R4] |
|---|---|---|---|---|
| 168 | piperidin-1-yl | (R)-CH(CH3)CH2OH | H | 6-{[4-(2-hydroxyethyl)piperazin-1-yl]methyl}pyridin-3-yl |

TABLE 40

| Compound No. | R1 | R2 | R3 | ![pyridazine with R4] |
|---|---|---|---|---|
| 169 | piperidin-1-yl | (R)-CH(CH3)CH2OH | H | 6-(3-oxopiperazin-1-yl)pyridin-3-yl |
| 170 | piperidin-1-yl | (R)-CH(CH3)CH2OH | H | 7-(2-hydroxyethyl)-5,6,7,8-tetrahydro-1,7-naphthyridin-2-yl |
| 171 | piperidin-1-yl | (S)-CH(CH3)CH2OH | H | 7-(2-hydroxyethyl)-5,6,7,8-tetrahydro-1,7-naphthyridin-2-yl |

TABLE 40-continued
| Compound No. | R1 | R2 | R3 | ![](pyridazine with R4) |
|---|---|---|---|---|
| 172 | 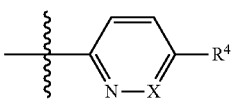 | 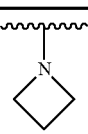 | H | 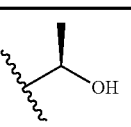 |
| 173 | 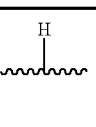 | 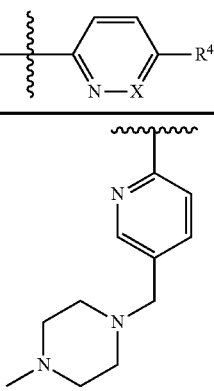 | H | 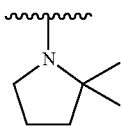 [SMILES: *N1CCCC1(C)C] |
| 174 | 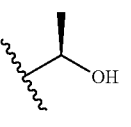 | 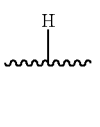 | H | 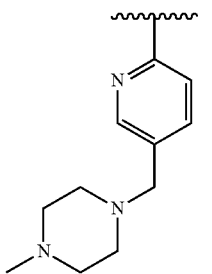 [SMILES: *c1ccc(CN2CCN(C)CC2)cn1] |
TABLE 41
| Compound No. | R1 | R2 | R3 | |
|---|---|---|---|---|
| 175 | 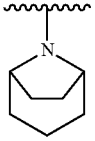 | 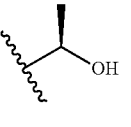 [SMILES: *[C@@H](C)O] | H |  |

TABLE 41-continued
| Compound No. | R1 | R2 | R3 | ![](pyridazine with R4) |
|---|---|---|---|---|
| 176 | 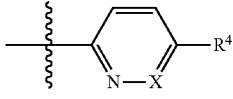 | 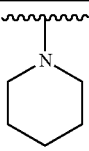 | 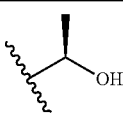 |  |
| 177 | 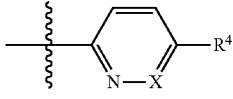 | 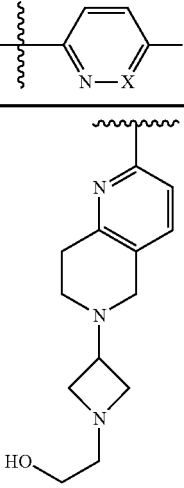 | 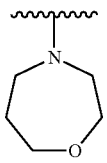 [SMILES: *N1CCCOCC1] | 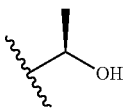 [SMILES: *[C@@H](C)O] |
| 178 |  | 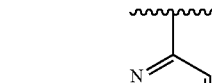 | 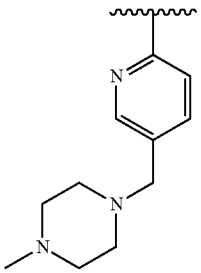 [SMILES: *c1ccc(CN2CCN(C)CC2)cn1] | 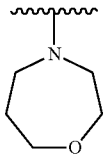 [SMILES: *N1CCCOCC1] |
| 179 | 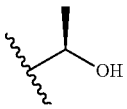 |  |  | 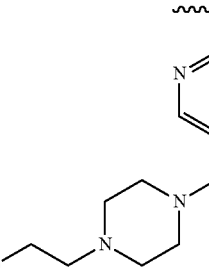 |
| 180 | 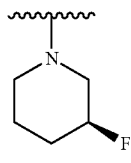 [SMILES: *N1CCC[C@H](F)C1] | 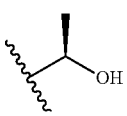 [SMILES: *[C@@H](C)O] |  | 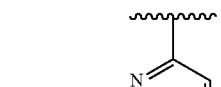 |

TABLE 42

| Compound No. | R1 | R2 | R3 | ![](pyridazine with R4) |
|---|---|---|---|---|
| 181 | (S)-3-fluoropyrrolidin-1-yl | -CH(OH)- | H | 6-{[4-(2-hydroxyethyl)piperazin-1-yl]methyl}pyridin-3-yl |
| 182 | (R)-3-fluoropyrrolidin-1-yl | -CH(OH)- | H | 6-{[4-(2-hydroxyethyl)piperazin-1-yl]methyl}pyridin-3-yl |
| 183 | piperidin-1-yl | -CH(OH)- | H | 6-{[4-(2-hydroxypropyl)piperazin-1-yl]methyl}pyridin-3-yl |
| 184 | piperidin-1-yl | -CH(OH)- | H | 6-{[4-((R)-2-hydroxypropyl)piperazin-1-yl]methyl}pyridin-3-yl |
| 185 | 2-azabicyclo[2.2.1]heptan-2-yl | -CH(OH)- | H | 2-methyl-3-(4-methylpiperazin-1-yl)pyridin-6-yl |

TABLE 42-continued
| Compound No. | R1 | R2 | R3 | |
|---|---|---|---|---|
| 186 | 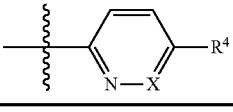 | 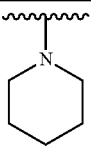 |  | 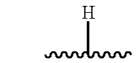 |
TABLE 43
| Compound No. | R1 | R2 | R3 | |
|---|---|---|---|---|
| 187 | 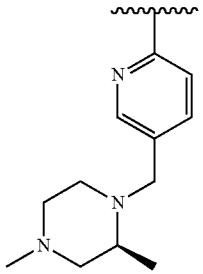 [SMILES: *c1ccc(CN2CCN(C)C[C@@H]2C)cn1] | 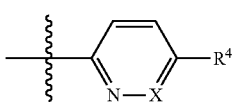 | 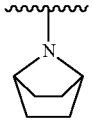 | 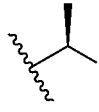 |
| 188 |  | 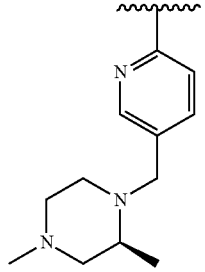 | 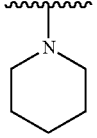 | 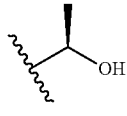 [SMILES: *[C@@H](C)O] |
| 189 |  | 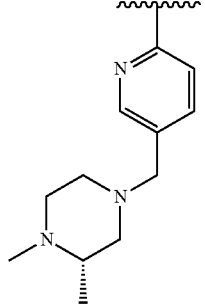 [SMILES: *c1ccc(CN2CCN(C)[C@@H](C)C2)cn1] | 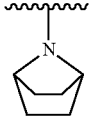 | 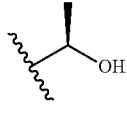 [SMILES: *[C@@H](C)O] |

TABLE 43-continued
| Compound No. | R1 | R2 | R3 | 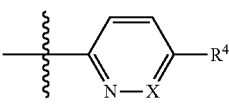 |
|---|---|---|---|---|
| 190 | 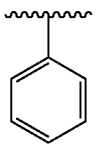 |  | H |  |
| 191 | 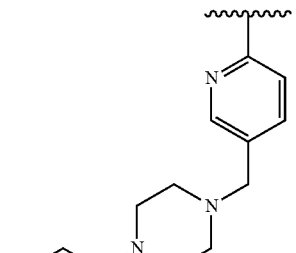 | 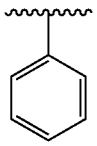 | H |  |
| 192 |  | 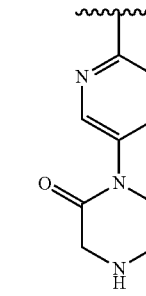 | H | 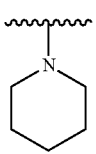 |
TABLE 44
| Compound No. | R1 | R2 | R3 |  |
|---|---|---|---|---|
| 193 |  | 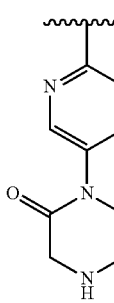 | H | 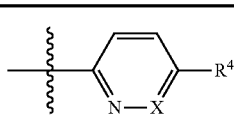 |

TABLE 44-continued
| Compound No. | R1 | R2 | R3 | 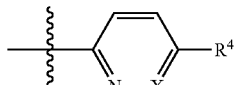 |
|---|---|---|---|---|
| 194 | 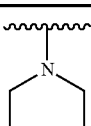 | 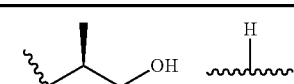 | H |  |
| 195 | 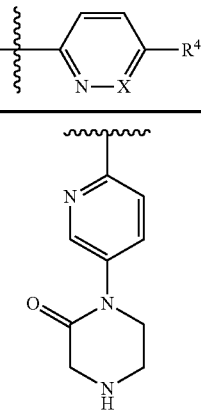 | 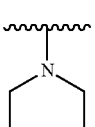 | H | 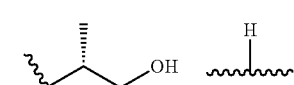 |
| 196 |  | 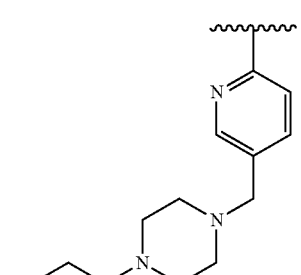 | H | 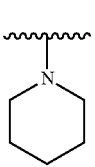 |
| 197 |  |  | H | 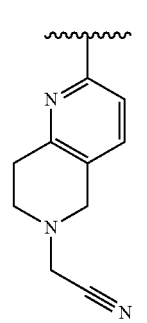 [SMILES: *c1ccc2c(n1)CCN(CC#N)C2] |
| 198 | 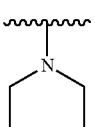 | 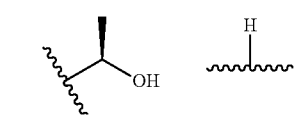 | H |  |

TABLE 45
| Compound No. | R1 | R2 | R3 | 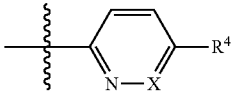 |
|---|---|---|---|---|
| 199 | 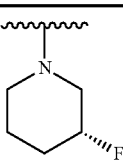 | 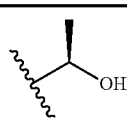 | H |  |
| 200 | 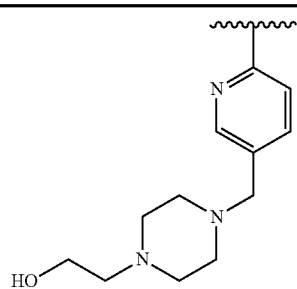 | 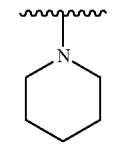 | H | 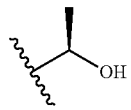 [SMILES: *[C@@H](C)O] |
| 201 |  | 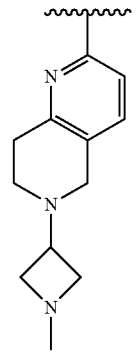 [SMILES: *c1ccc2c(n1)CCN(C1CN(C)C1)C2] | H | 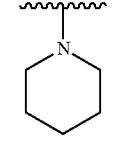 |
| 202 | 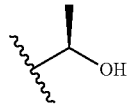 [SMILES: *[C@@H](C)O] |  | H | 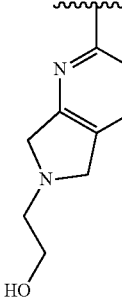 |
| 203 | 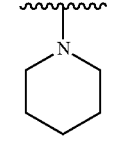 | 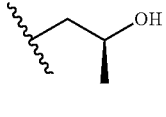 [SMILES: *C[C@H](C)O] | H |  |

TABLE 45-continued
| Compound No. | R1 | R2 | R3 | 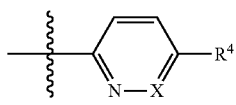 |
|---|---|---|---|---|
| 204 | 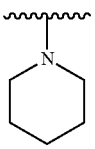 |  |  | 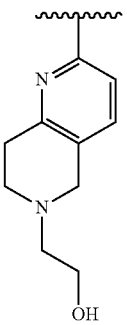 [SMILES: *c1ccc2c(n1)CCN(CCO)C2] |
TABLE 46
| Compound No. | R1 | R2 | R3 | 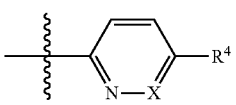 |
|---|---|---|---|---|
| 205 | 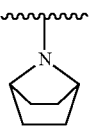 | 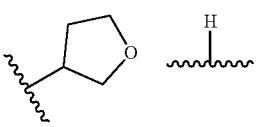 |  | 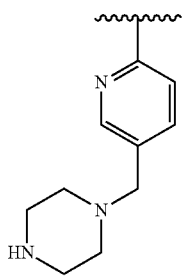 |
| 206 | 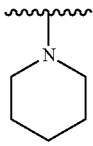 | 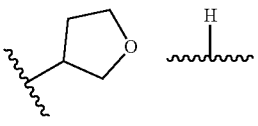 |  | 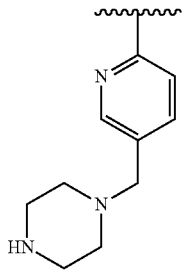 |
| 207 | 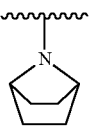 | 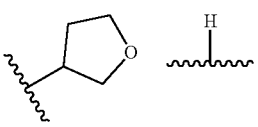 |  | 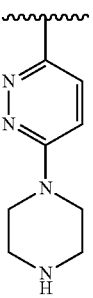 |

TABLE 46-continued
| Compound No. | R1 | R2 | R3 | ![structure](pyridazine with R4) |
|---|---|---|---|---|
| 208 | 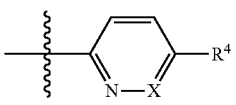 | 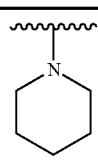 | 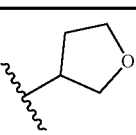 | 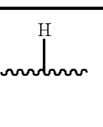 |
| 209 | 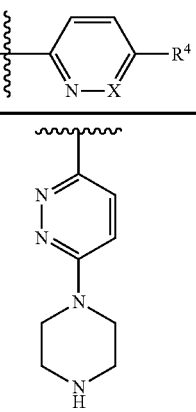 | 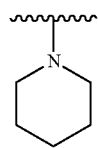 | 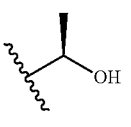 | 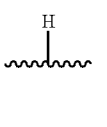 |
| 210 | 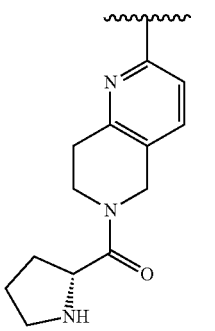 [SMILES: *c1ccc2c(n1)CCN(C(=O)[C@H]1CCCN1)C2] | 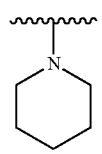 | 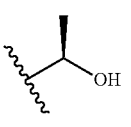 [SMILES: *[C@@H](C)O] | 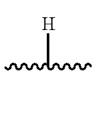 |
TABLE 47
| Compound No. | R1 | R2 | R3 | ![structure](pyridazine with R4) |
|---|---|---|---|---|
| 211 | 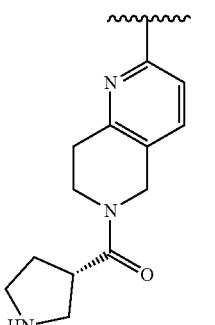 | 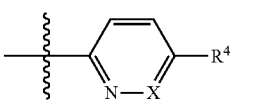 | 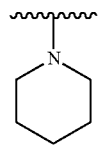 [SMILES: *N1CCCCC1] | 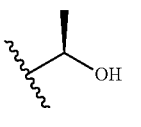 [SMILES: *[C@@H](C)O] |

TABLE 47-continued

| Compound No. | R1 | R2 | R3 | |
|---|---|---|---|---|
| 212 | piperidin-1-yl | CH(CH₃)OH | H | 2-(5,6,7,8-tetrahydro-1,6-naphthyridin-6-yl)- with (2S,4R)-4-hydroxypyrrolidine-2-carbonyl |
| 213 | piperidin-1-yl | CH(CH₃)OH | H | 2-(5,6,7,8-tetrahydro-1,6-naphthyridin-6-yl)- with (2S,4S)-4-hydroxypyrrolidine-2-carbonyl |
| 214 | piperidin-1-yl | CH(CH₃)OH | H | 2-(5,6,7,8-tetrahydro-1,6-naphthyridin-6-yl)- with piperidine-3-carbonyl |
| 215 | piperidin-1-yl | CH(CH₃)OH | H | 2-(5,6,7,8-tetrahydro-2,7-naphthyridin-7-yl)- with azetidine-2-carbonyl |

TABLE 47-continued

| Compound No. | R1 | R2 | R3 | ![pyridazine with R4] |
|---|---|---|---|---|
| 216 | piperidine-N | CH(OH)- | H | 2,3,4,5,6,7-hexahydro-1,6-naphthyridine substituted at N6 with morpholine-2-carbonyl |

TABLE 48

| Compound No. | R1 | R2 | R3 | ![pyridazine with R4] |
|---|---|---|---|---|
| 217 | piperidine-N | CH(OH)- | H | 5,6,7,8-tetrahydro-1,6-naphthyridine with N-CH2CH2NH2 |
| 218 | azabicyclic-N | CH(OH)- | H | pyridine-5-yl-O-piperidine-N-CH2CH2OH |
| 219 | (3-fluoropyrrolidin-1-yl) | CH(OH)- | H | pyridine-5-yl-O-piperidine-N-CH2CH2OH |

TABLE 48-continued
| Compound No. | R1 | R2 | R3 | ![](pyridazine with R4) |
|---|---|---|---|---|
| 220 | 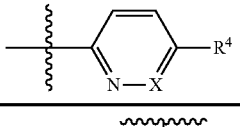 | 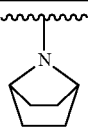 | H | 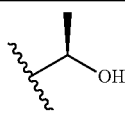 |
| 221 |  | 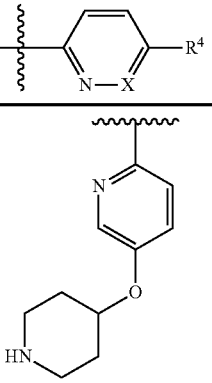 | H | 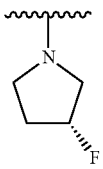 |
| 222 | 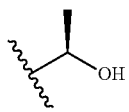 [SMILES: *[C@@H](C)O] |  | H | 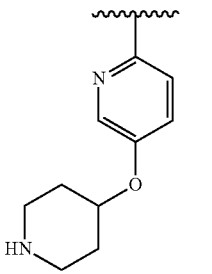 [SMILES: *c1ccc(OC2CCNCC2)cn1] |
TABLE 49
| Compound No. | R1 | R2 | R3 | ![](pyridazine with R4) |
|---|---|---|---|---|
| 223 | 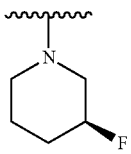 | 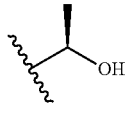 [SMILES: *[C@@H](C)O] | H |  |

US 11,084,814 B2
213 214
TABLE 49-continued
| Compound No. | R1 | R2 | R3 | ![](N-X with R4) |
|---|---|---|---|---|
| 224 | 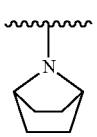 | 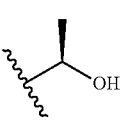 [SMILES: *[C@@H](C)O] | H |  |
| 225 | 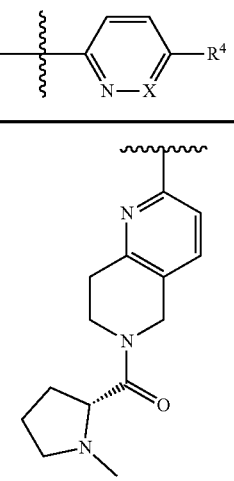 | 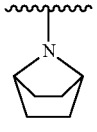 | H | 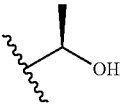 [SMILES: *[C@@H](C)O] |
| 226 |  | 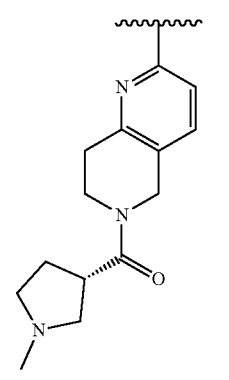 [SMILES: *c1ccc2c(n1)CCN(C(=O)[C@H]1CCN(C)C1)C2] | H | 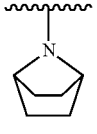 |
| 227 | 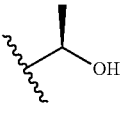 [SMILES: *[C@@H](C)O] |  | H | 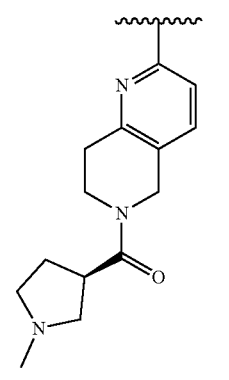 [SMILES: *c1ccc2c(n1)CCN(C(=O)[C@@H]1CCN(C)C1)C2] |

TABLE 49-continued
| Compound No. | R1 | R2 | R3 | ![structure](pyridazine with R4) |
|---|---|---|---|---|
| 228 |  | 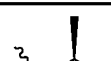 | H |  |
TABLE 50
| Compound No. | R1 | R2 | R3 | ![structure](pyridazine with R4) |
|---|---|---|---|---|
| 229 | pyrrolidinyl | CH(OH)CH3 | H | tetrahydronaphthyridine-N-C(O)CH2-N-azetidinyl-OH |
| 230 | pyrrolidinyl | CH(OH)CH3 | H | tetrahydronaphthyridine-N-C(O)CH2-N-azetidinyl |
| 231 | pyrrolidinyl | CH(OH)CH3 | H | tetrahydronaphthyridine-N-C(O)CH2-N-(3S)-fluoropyrrolidinyl |

TABLE 50-continued
| Compound No. | R1 | R2 | R3 | 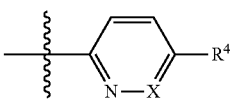 |
|---|---|---|---|---|
| 232 | 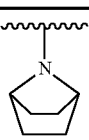 | 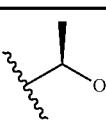 | H | 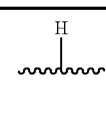 |
| 233 | 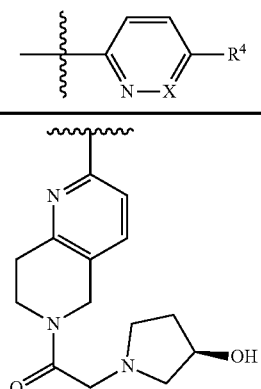 | 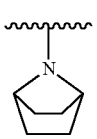 | H | 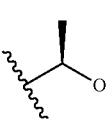 |
| 234 | 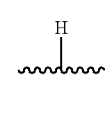 | 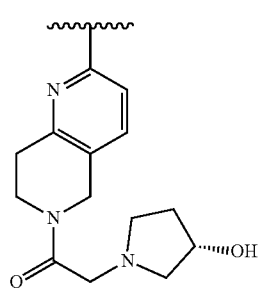 [SMILES: *c1ccc2c(n1)CCN(C(=O)CN1CC[C@H](O)C1)C2] | H | 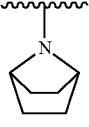 |
TABLE 51
| Compound No. | R1 | R2 | R3 | 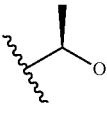 |
|---|---|---|---|---|
| 235 | 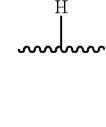 | 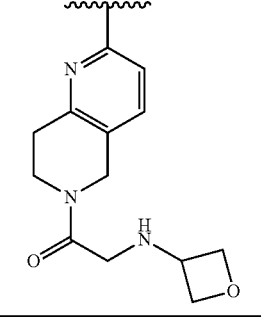 | H | 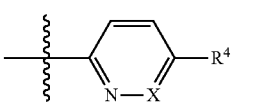 |

TABLE 51-continued

| Compound No. | R1 | R2 | R3 | ![pyridazine with R4] |
|---|---|---|---|---|
| 236 | [N-bridged bicyclic] | [CH(CH3)OH] | H | [tetrahydronaphthyridine-CH2-C(O)-N-oxa-azaspiro] |
| 237 | [N-bridged bicyclic] | [CH(CH3)OH] | H | [tetrahydronaphthyridine-C(O)-N-methylpiperidine] |
| 238 | [N-bridged bicyclic] | [CH(CH3)OH] | H | [tetrahydronaphthyridine-C(O)-N-methylpiperidine] |
| 239 | [N-bridged bicyclic] | [CH(CH3)OH] | H | [tetrahydronaphthyridine-C(O)-N-methylazetidine] |

TABLE 51-continued

| Compound No. | R1 | R2 | R3 | ![structure](pyridazine with R4) |
|---|---|---|---|---|
| 240 | N-azabicycloheptyl | CH(CH₃)OH | H | 5,6,7,8-tetrahydro-1,6-naphthyridine substituted with N-methylazetidin-3-yl |

TABLE 52

| Compound No. | R1 | R2 | R3 | ![structure](pyridazine with R4) |
|---|---|---|---|---|
| 241 | piperidin-1-yl | CH(CH₃)OH | H | pyridine with (piperidin-3-yl)oxy |
| 242 | N-azabicycloheptyl | CH(CH₃)OH | H | pyridine with (piperidin-3-yl)oxy |
| 243 | 3-fluoropiperidin-1-yl | CH(CH₃)OH | H | pyridine with (piperidin-4-yl)oxy |

TABLE 52-continued

| Compound No. | R1 | R2 | R3 | ![structure](pyridazine with R4) |
|---|---|---|---|---|
| 244 | piperidin-1-yl | CH(OH)CH2– | H | pyridine linked to 1,4-diazepan-2-one |
| 245 | (2S)-2-methylpyrrolidin-1-yl | CH(OH)CH2CH3 | H | pyridine linked to piperazin-2-one |
| 246 | (2S)-2-methylpyrrolidin-1-yl | CH(OH)CH2CH3 | H | pyridine linked to piperazin-2-one |

TABLE 53

| Compound No. | R1 | R2 | R3 | ![structure](pyridazine with R4) |
|---|---|---|---|---|
| 247 | (2S)-2-methylpyrrolidin-1-yl | CH(OH)CH2CH3 | H | pyridine-CH2-piperazine-N-CH2CH2OH |

TABLE 53-continued

| Compound No. | R1 | R2 | R3 | ![structure](pyridazine with R4) |
|---|---|---|---|---|
| 248 | (S)-2-methylpyrrolidin-1-yl | (S)-CH(OH)CH₂CH₃ | H | 6-{[4-(2-hydroxyethyl)piperazin-1-yl]methyl}pyridin-3-yl |
| 249 | piperidin-1-yl | CH(OH)CH₃ | H | 6-{[4-(2-hydroxyethyl)-3-oxopiperazin-1-yl]methyl}pyridin-3-yl |
| 250 | (S)-3-fluoropyrrolidin-1-yl | CH(OH)CH₃ | H | 6-(piperidin-3-yloxy)pyridin-3-yl |
| 251 | (S)-3-fluoropiperidin-1-yl | CH(OH)CH₃ | H | 6-(piperidin-3-yloxy)pyridin-3-yl |
| 252 | piperidin-1-yl | CH(OH)CH₃ | H | 6-{[1-(2-hydroxyethyl)piperidin-3-yl]oxy}pyridin-3-yl |

TABLE 54
| Compound No. | R1 | R2 | R3 | |
|---|---|---|---|---|
| 253 |  | 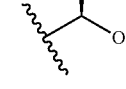 |  | 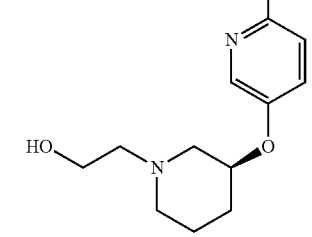 |
| 254 | 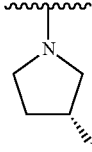 | 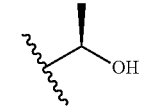 [SMILES: *[C@@H](C)O] |  | 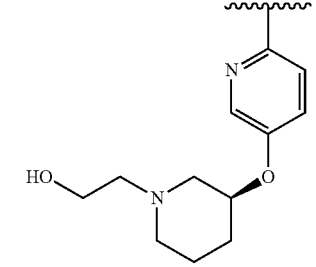 [SMILES: *c1ccc(O[C@H]2CCCN(CCO)C2)cn1] |
| 255 | 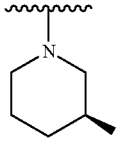 | 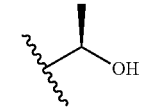 [SMILES: *[C@@H](C)O] |  | 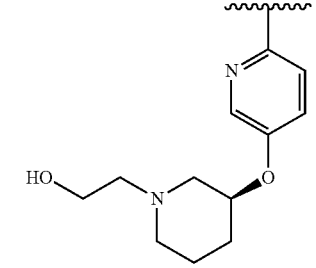 [SMILES: *c1ccc(O[C@H]2CCCN(CCO)C2)cn1] |
| 256 |  | 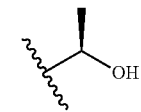 [SMILES: *[C@@H](C)O] |  | 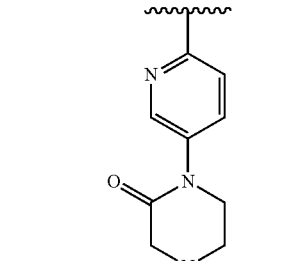 |
| 257 | 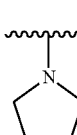 | 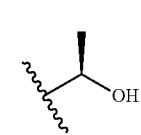 [SMILES: *[C@@H](C)O] |  | 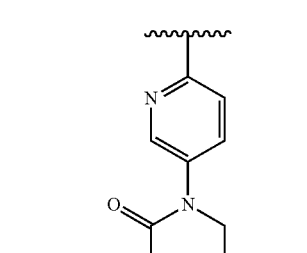 |

TABLE 54-continued

| Compound No. | R1 | R2 | R3 | ![structure](pyridazine with R4) |
|---|---|---|---|---|
| 258 | (S)-3-methylpyrrolidin-1-yl | CH(CH₃)OH | H | 5-(3-oxo-1,4-diazepan-4-yl)pyridin-2-yl |

TABLE 55

| Compound No. | R1 | R2 | R3 | ![structure](pyridazine with R4) |
|---|---|---|---|---|
| 259 | piperidin-1-yl | CH(CH₃)OH | H | 5-[4-(2-methanesulfonylethyl)-7-oxo-1,4-diazepan-1-yl]pyridin-2-yl |
| 260 | piperidin-1-yl | CH(CH₃)OH | H | 2-methyl-5-(3-oxopiperazin-1-yl)pyridin-6-yl |
| 261 | (S)-3-methylpyrrolidin-1-yl | CH(CH₃)OH | H | 2-methyl-5-(3-oxopiperazin-1-yl)pyridin-6-yl |

US 11,084,814 B2
TABLE 55-continued
| Compound No. | R1 | R2 | R3 | ![pyridazine with R4, N-X] |
|---|---|---|---|---|
| 262 | 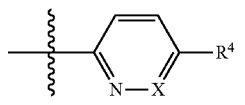 | 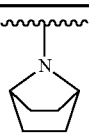 | H | 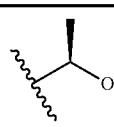 |
| 263 | 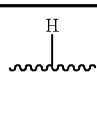 | 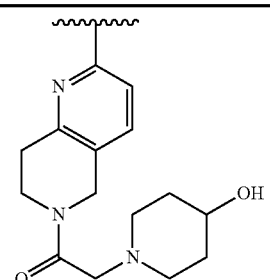 | H | 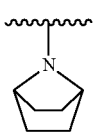 |
| 264 | 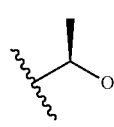 | 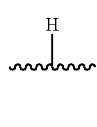 | H | 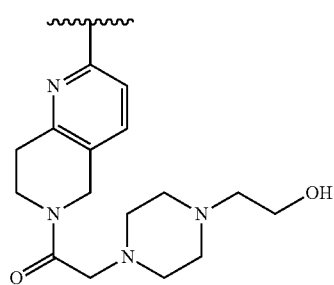 [SMILES: *c1ccc2c(n1)CCN(C(=O)CN1CCN(CCO)CC1)C2] |
TABLE 56
| Compound No. | R1 | R2 | R3 | ![pyridazine with R4, N-X] |
|---|---|---|---|---|
| 265 | 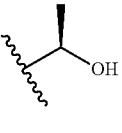 [SMILES: *[C@@H](C)O] | 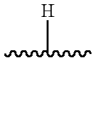 | H | 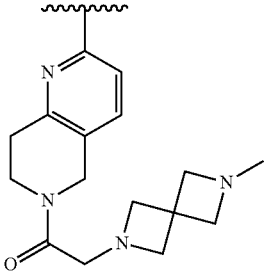 [SMILES: *c1ccc2c(n1)CCN(C(=O)CN1CC3(CN(C)C3)C1)C2] |

TABLE 56-continued

| Compound No. | R1 | R2 | R3 | ![structure](N—X with R⁴) |
|---|---|---|---|---|
| 266 | piperidine (N-linked) | CH(OH) | H | 2-substituted-5,6,7,8-tetrahydro-1,6-naphthyridine with N-acetyl-2-oxa-6-azaspiro[3.3]heptane |
| 267 | 2-azabicyclo[2.2.1]heptane (N-linked) | CH(OH) | H | 5,6,7,8-tetrahydro-1,6-naphthyridine with N-acetyl-6-hydroxy-2-azaspiro[3.3]heptane |
| 268 | piperidine (N-linked) | CH(OH) | H | 5,6,7,8-tetrahydro-1,6-naphthyridine with N-acetyl-6-hydroxy-2-azaspiro[3.3]heptane |
| 269 | piperidine (N-linked) | CH(OH) | H | 5,6,7,8-tetrahydro-1,6-naphthyridine with N-acetyl-3-fluoroazetidine |
| 270 | piperidine (N-linked) | CH(OH) | H | 5,6,7,8-tetrahydro-1,6-naphthyridine with N-acetyl-azetidine |

TABLE 57

TABLE 57-continued

| Compound No. | R1 | R2 | R3 | ![pyridazine-R4] |
|---|---|---|---|---|
| 276 | piperidine (N-linked) | oxetan-3-yl | H | pyridine linked to 1,4-diazepan-2-one |

TABLE 58

| Compound No. | R1 | R2 | R3 | ![pyridazine-R4] |
|---|---|---|---|---|
| 277 | piperidine (N-linked) | oxetan-3-yl | H | pyridazine substituted with piperazine |
| 278 | 4-cyanopiperidine (N-linked) | CH(OH)CH₃ | H | 5,6,7,8-tetrahydro-1,6-naphthyridine N-substituted with 2-hydroxyethyl |
| 279 | 4-cyanopiperidine (N-linked) | CH(OH)CH₃ | H | 5,6,7,8-tetrahydro-1,6-naphthyridine N-substituted with 1-methylazetidin-3-yl |

TABLE 58-continued
| Compound No. | R1 | R2 | R3 | |
|---|---|---|---|---|
| 280 | 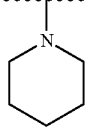 | 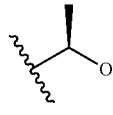 |  | 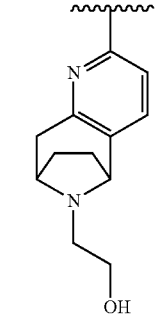 |
| 281 | 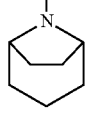 | 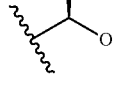 | 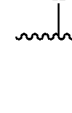 | 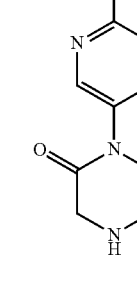 |
| 282 | 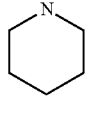 | 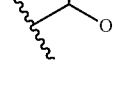 | 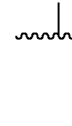 | 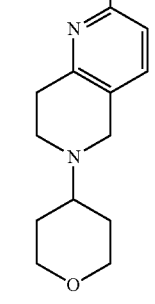 |

TABLE 59

| Compound No. | R1 | R2 | R3 | ![](R4 structure header: pyridazine with R4) |
|---|---|---|---|---|
| 283 | piperidin-1-yl | CH(CH₃)OH | H | 2-yl-5,6,7,8-tetrahydro-1,6-naphthyridin-6-yl linked to trans-4-hydroxycyclohexyl |
| 284 | piperidin-1-yl | CH(CH₃)OH | H | 2-yl-5,6,7,8-tetrahydro-1,6-naphthyridin-6-yl linked to cis-4-hydroxycyclohexyl |
| 285 | piperidin-1-yl | CH(CH₃)OH | H | 2-yl-5,6,7,8-tetrahydro-1,6-naphthyridin-6-yl with 2-(pyridin-4-yl)acetyl |
| 286 | piperidin-1-yl | CH(CH₃)OH | H | 2-yl-5,6,7,8-tetrahydro-1,6-naphthyridin-6-yl with 2-(imidazol-1-yl)acetyl |

TABLE 59-continued

| Compound No. | R1 | R2 | R3 | ![pyridazine with R4] |
|---|---|---|---|---|
| 287 | piperidine (N-linked) | CH(CH₃)OH | H | 2-(7-methyl-5,6,7,8-tetrahydro-1,6-naphthyridinyl) |
| 288 | 3-methylmorpholine (N-linked) | CH(CH₃)OH | H | 5-(piperazin-1-yl)pyridin-2-yl |

TABLE 60

| Compound No. | R1 | R2 | R3 | ![pyridazine with R4] |
|---|---|---|---|---|
| 289 | (3R)-3-methylmorpholine (N-linked) | CH(CH₃)OH | H | 5-(piperazin-1-yl)pyridin-2-yl |
| 290 | 3-methylmorpholine (N-linked) | CH(CH₃)OH | H | 5-((4-methylpiperazin-1-yl)methyl)pyridin-2-yl |

TABLE 60-continued
| Compound No. | R1 | R2 | R3 | 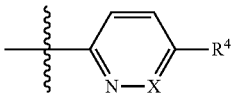 |
|---|---|---|---|---|
| 291 | 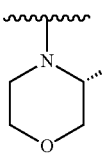 | 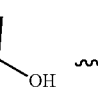 | H |  |
| 292 | 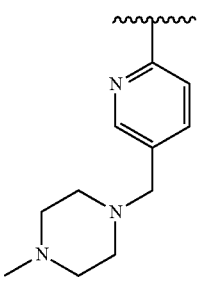 [SMILES: *c1ccc(CN2CCN(C)CC2)cn1] | 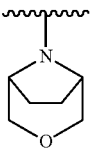 | H | 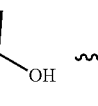 |
| 293 |  | 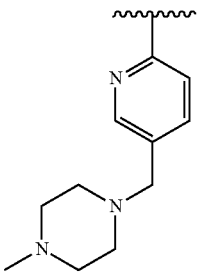 [SMILES: *c1ccc(CN2CCN(C)CC2)cn1] | H | 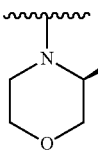 |
| 294 | 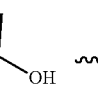 | 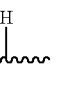 | H | 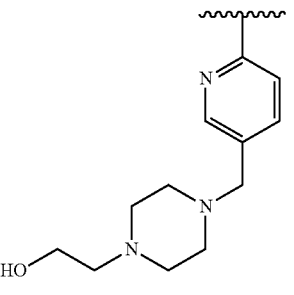 [SMILES: *c1ccc(CN2CCN(CCO)CC2)cn1] |

TABLE 61
| Compound No. | R1 | R2 | R3 | |
|---|---|---|---|---|
| 295 | 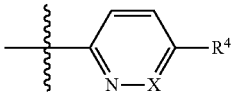 | 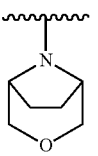 | H | 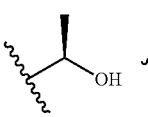 |
| 296 |  | 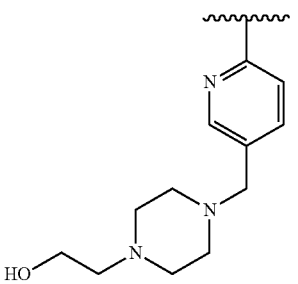 [SMILES: *c1ccc(CN2CCN(CCO)CC2)cn1] | H | 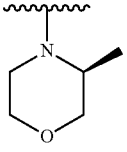 |
| 297 | 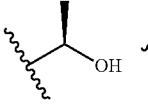 |  | H | 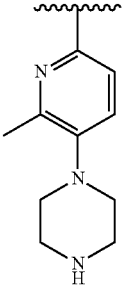 [SMILES: *c1ccc(N2CCNCC2)c(C)n1] |
| 298 | 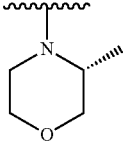 | 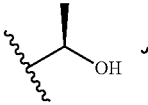 | H |  |
| 299 | 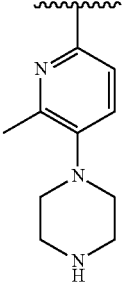 | 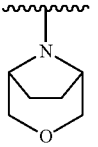 | H | 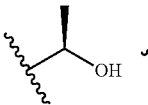 |

TABLE 61-continued
| Compound No. | R1 | R2 | R3 | ![structure](pyridazine with R4) |
|---|---|---|---|---|
| 300 | 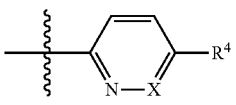 | 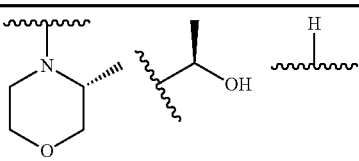 | 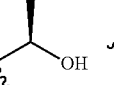 |  |
TABLE 62
| Compound No. | R1 | R2 | R3 | ![structure](pyridazine with R4) |
|---|---|---|---|---|
| 301 | 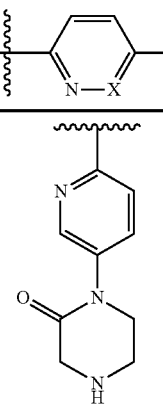 | 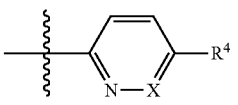 | 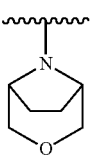 | 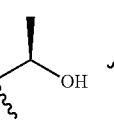 |
| 302 |  | 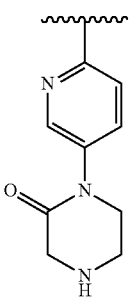 [SMILES: *c1ccc(N2CCNCC2=O)cn1] | 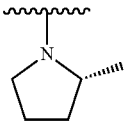 [SMILES: *N1CCC[C@H]1C] | 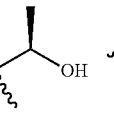 |
| 303 |  | 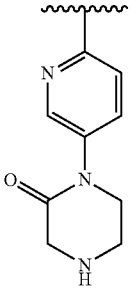 [SMILES: *c1ccc(N2CCNCC2=O)cn1] | 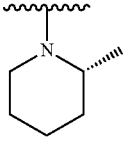 [SMILES: *N1CCCC[C@H]1C] | 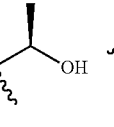 |

TABLE 62-continued
| Compound No. | R1 | R2 | R3 | 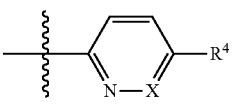 |
|---|---|---|---|---|
| 304 | 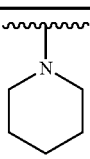 | 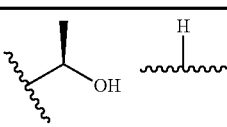 | H |  |
| 305 | 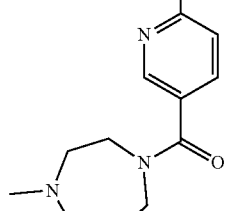 | 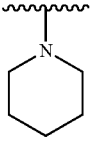 | H | 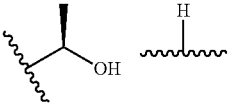 |
| 306 |  | 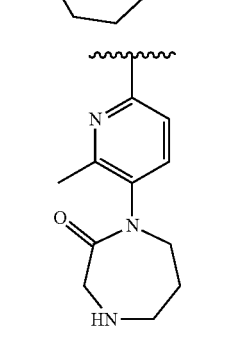 | H | 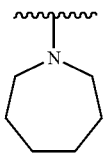 |
TABLE 63
| Compound No. | R1 | R2 | R3 | 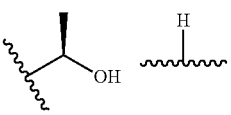 |
|---|---|---|---|---|
| 307 |  | 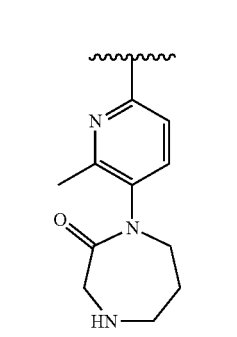 [SMILES: *c1ccc(N2CCCNCC2=O)c(C)n1] | H | 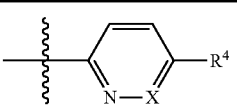 |

TABLE 63-continued

| Compound No. | R1 | R2 | R3 | ![](R4 header: pyridazine with N–X and R⁴) |
|---|---|---|---|---|
| 308 | piperidin-1-yl | -CH(OH)- | H | pyridine-5-carbonyl-piperazine-N-CH₂CH₂OH |
| 309 | piperidin-1-yl | -CH(OH)- | H | pyridine-5-carbonyl-(4-methylpiperazine) |
| 310 | piperidin-1-yl | -CH(OH)- | H | pyridine-5-carbonyl-morpholine |
| 311 | piperidin-1-yl | -CH(OH)- | H | pyridine-5-carbonyl-(4-hydroxypiperidine) |
| 312 | piperidin-1-yl | -CH(OH)- | H | pyridine-5-carbonyl-(3-(dimethylamino)pyrrolidine) |

TABLE 64

![structure header: pyridazine with R4 and X]

| Compound No. | R1 | R2 | R3 | (pyridazine substituent) |
|---|---|---|---|---|
| 313 | piperidin-1-yl | CH(OH)- (wedge) | H | 6-{[(3S)-3-(dimethylamino)pyrrolidin-1-yl]carbonyl}pyridin-3-yl |
| 314 | piperidin-1-yl | CH(OH)- | H | 6-[(1,1-dioxidothiomorpholin-4-yl)carbonyl]pyridin-3-yl |
| 315 | piperidin-1-yl | CH(OH)- | H | 6-{[4-(dimethylamino)piperidin-1-yl]carbonyl}pyridin-3-yl |
| 316 | piperidin-1-yl | CH(OH)- | H | 6-{[2-(dimethylamino)ethyl](methyl)carbamoyl}pyridin-3-yl |
| 317 | piperidin-1-yl | CH(OH)- | H | 6-[(4-ethylpiperazin-1-yl)carbonyl]pyridin-3-yl |

TABLE 64-continued
| Compound No. | R1 | R2 | R3 | |
|---|---|---|---|---|
| 318 | 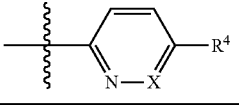 | 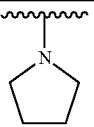 | 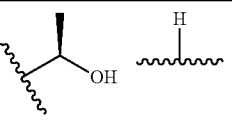 |  |
TABLE 65
| Compound No. | R1 | R2 | R3 | |
|---|---|---|---|---|
| 319 | 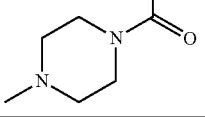 | 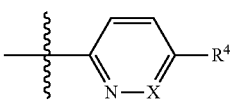 | 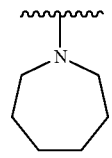 [SMILES: *N1CCCCCC1] | 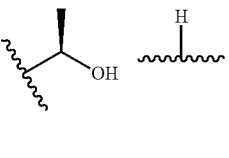 |
| 320 |  | 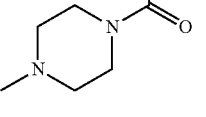 | 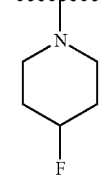 | 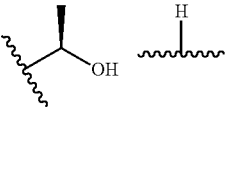 |
| 321 |  | 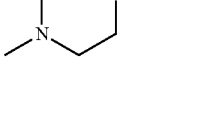 | 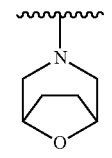 | 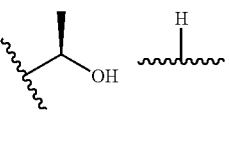 |

TABLE 65-continued
| Compound No. | R1 | R2 | R3 | ![structure](pyridazine with R4) |
|---|---|---|---|---|
| 322 | 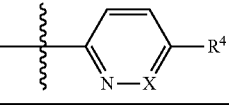 | 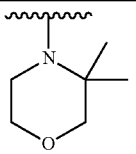 | H | 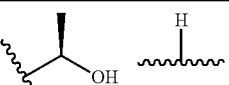 |
| 323 |  | 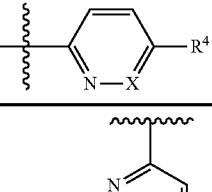 | H | 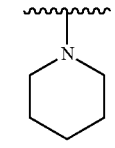 |
| 324 |  |  | H | 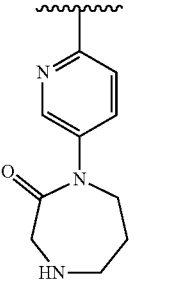 [SMILES: *c1ccc(N2CCCNCC2=O)cn1] |
TABLE 66
| Compound No. | R1 | R2 | R3 | ![structure](pyridazine with R4) |
|---|---|---|---|---|
| 325 | 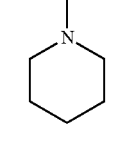 | 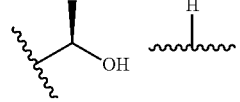 | H |  |

TABLE 66-continued
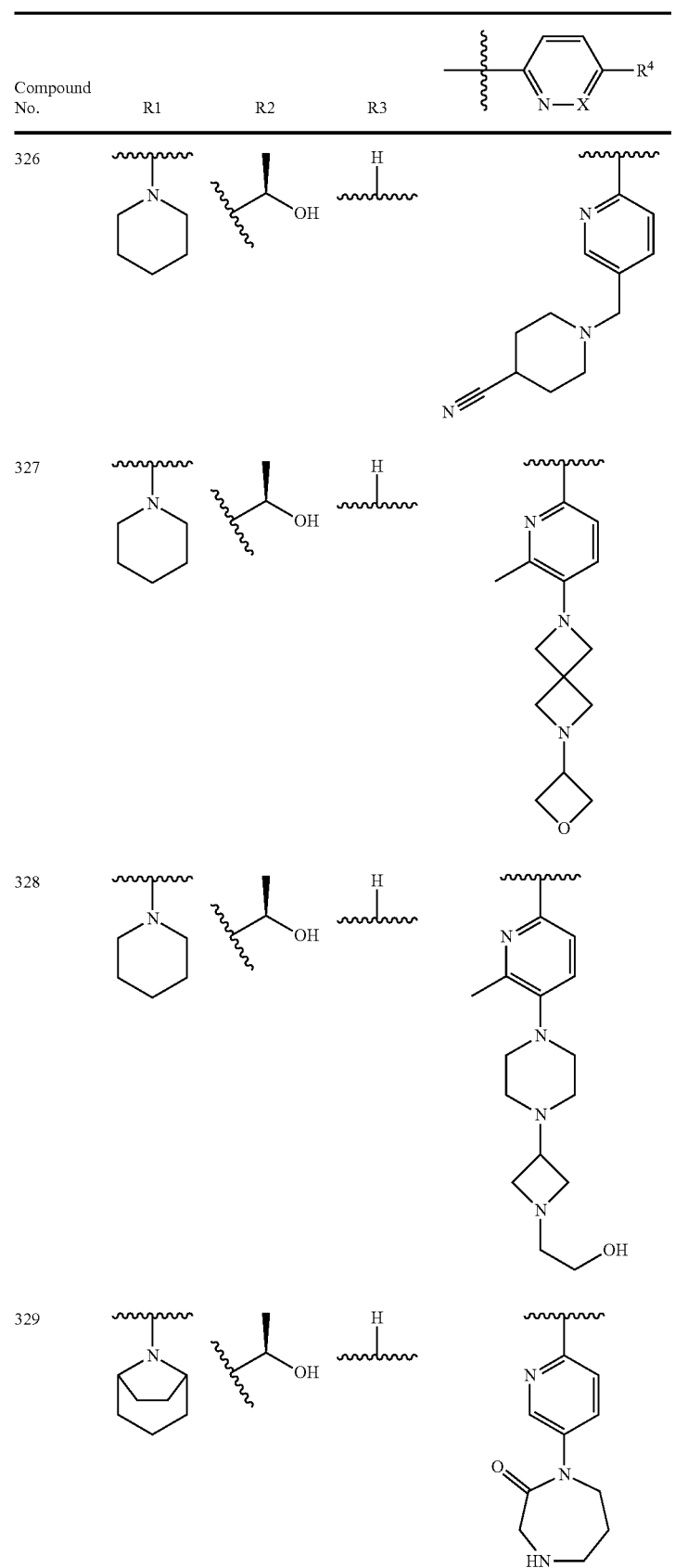

TABLE 66-continued

| Compound No. | R1 | R2 | R3 | ![structure](pyridazine with R4) |
|---|---|---|---|---|
| 330 | piperidinyl | CH(OH)— | H | 2-(5,6,7,8-tetrahydro-1,6-naphthyridin-2-yl), N-acylated with 2-(pyridin-3-yl)acetyl |

TABLE 67

| Compound No. | R1 | R2 | R3 | ![structure](pyridazine with R4) |
|---|---|---|---|---|
| 331 | piperidinyl | CH(OH)— | H | 2-(5,6,7,8-tetrahydro-1,6-naphthyridin-2-yl), N-acylated with 2-(1H-pyrazol-1-yl)acetyl |
| 332 | piperidinyl | CH(OH)— | H | 2-(5,6,7,8-tetrahydro-1,6-naphthyridin-2-yl), N-acylated with 2-(1H-1,2,4-triazol-1-yl)acetyl |
| 333 | piperidinyl | CH(OH)— | H | 2-(5,6,7,8-tetrahydro-1,6-naphthyridin-2-yl), N-acylated with 2-(4H-1,2,4-triazol-4-yl)acetyl |

US 11,084,814 B2
TABLE 67-continued
| Compound No. | R1 | R2 | R3 | ![pyridazine](pyridazine with R4) |
|---|---|---|---|---|
| 334 | 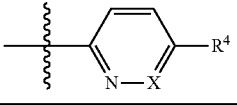 | 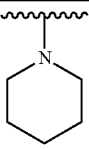 | H | 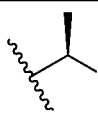 |
| 335 | 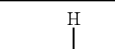 | 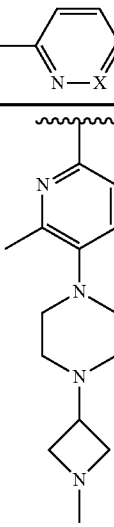 | H | 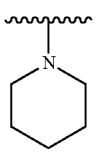 |
| 336 | 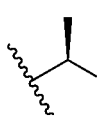 | 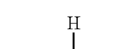 | H | 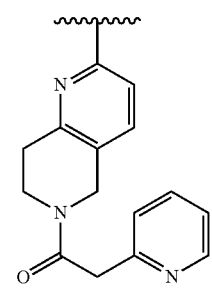 [SMILES: *c1ccc2c(n1)CCN(C(=O)Cc1ccccn1)C2] |
TABLE 68
| Compound No. | R1 | R2 | R3 | ![pyridazine](pyridazine with R4) |
|---|---|---|---|---|
| 337 | 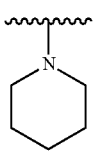 | 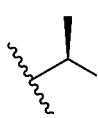 | H |  |

TABLE 69

| Compound No. | NMR data | (M + H)+ | Exact Mass |
|---|---|---|---|
| 1 | | 437.25 | 436.23 |
| 2 | 1H-NMR (CD3OD) δ: 7.64 (1.0H, d, J = 2.9 Hz), 7.32 (1.0H, dd, J = 9.3, 2.9 Hz), 6.98 (1.0H, s), 6.58 (1.0H, d, J = 9.3 Hz), 5.54 (1.0H, s), 4.45 (2.0H, s), 3.08-3.00 (8.0H, m), 2.68-2.64 (4.0H, m), 2.38 (3.0H, s), 1.80-1.74 (4.0H, m), 1.66-1.59 (2.0H, m). | 435.25 | 434.25 |
| 3 | 1H-NMR (CD3OD) δ: 9.29 (1.0H, s), 8.28 (1.0H, d, J = 8.8 Hz), 7.94 (1.0H, d, J = 2.9 Hz), 7.78 (1.0H, s), 7.41 (1.0H, dd, J = 8.8, 2.9 Hz), 4.69 (2.0H, br s), 3.90-3.40 (2.0H, m), 3.20-3.15 (4.0H, m), 2,67-2.50 6.0H, m , 2.35 (3.0H, s), 2.03-1.95 (4.0H, m). | 449.25 | 448.23 |
| 4 | 1H-NMR (CDCl3) δ: 9.13 (1.0H, s), 8.27 (1.0H, d, J = 9.0 Hz), 8.20 (1.0H, br s), 8.07 (1.0H, d, J = 2.9 Hz), 7.38-7.32 (2.0H, m), 6.57 (1.0H, t, J = 56.0 Hz), 3.99-3.87 (8.0H, br m), 3.29-3.10 (4.0H, m), 2.70-2.60 (4.0H, m), 2.41 (3.0H, s). | 457.20 | 456.22 |
| 6 | | 428.37 | 427.21 |
| 7 | | 423.15 | 422.22 |
| 8 | | 443.15 | 442.20 |
| 9 | | 421.31 | 420.24 |
| 10 | | 414.23 | 413.20 |
| 11 | | 441.32 | 440.22 |
| 12 | | 434.15 | 433.18 |
| 13 | | 455.19 | 454.24 |
| 14 | | 428.35 | 427.21 |
| 15 | | 428.32 | 427.21 |
| 16 | | 420.32 | 419.15 |
| 17 | | 404.23 | 403.18 |
| 18 | | 442.0 | 441.23 |
| 19 | | 442.0 | 441.23 |
| 20 | | 434.24 | 433.17 |
| 21 | | 418.27 | 417.19 |
| 22 | | 432.28 | 431.24 |
| 23 | | 435.3 | 434.22 |
| 24 | | 435.33 | 434.25 |
| 25 | | 449.31 | 448.23 |
| 26 | | 433.3 | 432.24 |
| 27 | | 462.41 | 461.27 |
| 28 | | 434.37 | 433.23 |
| 29 | | 448.4 | 447.25 |

TABLE 70

| Compound No. | NMR data | (M + H)+ | Exact Mass |
|---|---|---|---|
| 30 | | 448.37 | 447.20 |
| 31 | | 474.35 | 423.16 |
| 32 | | 437.43 | 436.23 |
| 33 | | 437.40 | 436.23 |
| 34 | | 451.33 | 450.25 |
| 35 | | 491.39 | 490.21 |
| 36 | | 457.39 | 456.22 |
| 37 | | 451.43 | 450.25 |
| 38 | | 437.3 | 436.23 |
| 39 | | 466.3 | 465.22 |
| 40 | | 480.3 | 479.24 |
| 41 | | 480.3 | 479.24 |
| 42 | | 479.3 | 478.24 |
| 43 | | 463.4 | 462.29 |
| 44 | | 504.30 | 503.31 |
| 45 | | 493.25 | 492.30 |
| 46 | | 507.30 | 506.31 |
| 47 | | 465.3 | 464.26 |
| 48 | 1H-NMR (CDCl3) δ: 9.03 (1H, s), 8.63 1H, s), 8.28-8.18 (2H, m), 7.66 (1H, dd, J = 8.7, 2.3 Hz), 6.66 (1H, s), 4.78 (1H, q, J = 6.4 Hz), 4.02 (4H, br s), 3.60 (2H, t, J = 5.5 Hz), 3.48 (2H, s), 2.62-2.44 (10H, m), 2.03-1.95 (4H, m), 1.51 (3H, d, J = 6.9 Hz). | 479.4 | 478.28 |
| 49 | 1H-NMR (CDCl3) δ: 9.17 (2H, d, J = 3.7 Hz), 8.54 (1H, d, J = 8.7 Hz), 8.33 (1H, d, J = 1.8 Hz), 7.72 (1H, dd., J = 8.5, 2.1 Hz), 6.94 (1H, s), 4.84 (1H, q, J = 6.4 Hz), 3.85 (4H, t, J = 5.3 Hz), 3.60 (2H, t, J = 5.3 Hz), 3.51 (2H, s), 2.54 (10H, t, J = 5.5 Hz), 1.83 (4H, t, J = 5.3 Hz), 1.75 (2H, d, J = 5.0 Hz), 1.52 (3H, d, J = 6.4 Hz). | 493.4 | 492.30 |
| 50 | | 421.3 | 420.20 |
| 51 | 1H-NMR (CDCl3) δ: 9.01 (1H, s), 8.34-8.25 (3H, m), 7.69 (1H, dd, J = 8.9, 2.5 Hz), 6.67 (1H, s), 4.79 (1H, q, J = 6.4 Hz), 4.03 (4H, br s), 3.71 (4H, d, J = 7.8 Hz), 3.25 (2H, t, J = 5.3 Hz), 2.04-1.96 (4H, m), 1.51 (3H, d, J = 6.4 Hz). | 435.3 | 434.22 |

TABLE 71

| Compound No. | NMR data | (M + H)+ | Exact mass |
|---|---|---|---|
| 52 | 1H-NMR (CDCl3) δ: 9.67 (1H, s), 9.19 (1H, s), 8.61 (1H, d, J = 9.1 Hz), 8.42 (1H, d, J = 2.7 Hz), 7.70 (1H, dd, J = 8.9, 2.5 Hz), 6.94 (1H, s), 4.83 (1H, q, J = 6.6 Hz), 3.80 (4H, t, J = 5.0 Hz), 3.73 (4H, t, J = 5.3 Hz), 3.25 (2H, t, J = 5.3 Hz), 1.81 (4H, br s), 1.75-1.68 (2H, m), 1.52 (3H, d, J = 6.4 Hz). | 449.3 | 448.23 |
| 53 | | 449.3 | 448.27 |
| 54 | | 463.4 | 462.29 |
| 55 | 1H-NMR (CDCl3) δ: 9.03 (1H, s), 8.60 (1H, s), 8.26 (1H, d, J = 1.8 Hz), 8.19 (1H, d, J = 8.7 Hz), 7.67 (1H, dd, J = 8.7, 2.3 Hz), 6.66 (1H, s), 4.78 (1H, q, J = 6.4 Hz), 4.02 (4H, br s), 3.48 (2H, s), 2.47 (8H, br s), 2.28 (3H, s), 2.01-1.97 (4H, m), 1.51 (3H, d, J = 6.9 Hz). | 449.3 | 448.27 |
| 56 | 1H-NMR (CDCl3) δ: 9.48 (1H, s), 9.19 (1H, s), 8.53 (1H, d, J = 8.2 Hz), 8.36 (1H, d, J = 1.8 Hz), 7.71 (1H, dd, J = 8.5, 2.1 Hz), 6.94 (1H, s), 4.83 (1H, q, J = 6.6 Hz), 3.84 (4H, t, J = 5.3 Hz), 3.49 (2H, s), 2.46 (8H, br s), 2.27 (3H, s), 1.87-1.80 (4H, m), 1.77-1.70 (2H, m), 1.52 (3H, d, J = 6.4 Hz). | 463.4 | 462.29 |
| 57 | 1H-NMR (CDCl3) δ: 9.01 (1H, s), 8.29 (1H, d, J = 9.1 Hz), 8.24 (1H, d, J = 1.8 Hz), 8.20 (1H, s), 7.70 (1H, dd, J = 8.7, 2.3 Hz), 6.69 (1H, s), 4.78 (1H, q, J = 6.4 Hz), 4.47 (4H, br s), 3.60 (2H, t, J = 5.5 Hz), 3.51 (2H, s), 2.59-2.46 (10H, m), 2.25 (4H, t, J = 7.5 Hz), 1.93-1.85 (2H, m), 1.50 (3H, d, J = 6.4 Hz). | 505.4 | 504.30 |
| 58 | 1H-NMR (CDCl3) δ: 9.14 (1H, d, J = 3.7 Hz), 8.57 (1H, s), 8.40 (1H, d, J = 8.7 Hz), 8.28 (1H, d, J = 1.8 Hz), 7.72 (1H, dd, J = 8.2, 2.3 Hz), 7.03 (1H, d, J = 0.9 Hz), 4.87 (1H, q, J = 6.4 Hz), 3.99 (4H, t, J = 4.6 Hz), 3.93 (4H, t, J = 4.6 Hz), 3.61 (2H, t, J = 5.3 Hz), 3.51 (2H, s), 2.60-2.46 (10H, m), 1.54 (3H, d, J = 6.4 Hz). | 495.3 | 494.28 |
| 59 | 1H-NMR (CDCl3) δ: 9.01 (1H, s), 8.22 (1H, d, J = 2.3 Hz), 8.16 (1H, d, J = 8.7 Hz), 8.05 (1H, s), 7.67 (1H, dd, J = 8.7, 2.3 Hz), 6.70 (1H, s), 4.78 (1H, q, J = 6.4 | 507.4 | 506.31 |

TABLE 71-continued

| Compound No. | NMR data | (M + H)⁺ | Exact mass |
|---|---|---|---|
| | Hz), 4.18 (4H, t, J = 5.9 Hz), 3.60 (2H, t, J = 5.5 Hz), 3.49 (2H, s), 2.59-2.45 (10H, m), 1.87 (4H, s), 1.61-1.55 (4H, m), 1.50 (3H, d, J = 6.4 Hz). | | |

TABLE 72

| Compound No. | NMR data | (M + H)⁺ | Exact Mass |
|---|---|---|---|
| 60 | 1H-NMR (DMSO-D6) δ: 9.97 (1H, s), 9.29 (1H, s), 8.20 (1H, d, J = 8,7 Hz), 7.49 (1H, d, J = 8.7 Hz), 7.24 (1H, s), 5.26 (1H, d, J = 4.6 Hz), 4.70-4.61 (1H, m), 3.84-3.66 (4H, m), 3.57 (2H, s), 2.86-2.73 (4H, m), 2.61-2.53 (2H, m), 2.46-2.38 (2H, m), 2.16 (6H, s), 1.78-1.60 (6H, m), 1.38 (3H, d, J = 6.4 Hz). | 477.4 | 476.30 |
| 61 | 1H-NMR (DMSO-D6) δ: 10.03 (1H, s), 9.31 (1H, s), 8.12 (1H, d, J = 8.2 Hz), 7.49 (1H, d, J = 8.7 Hz), 7.28 (1H, s), 5.28 (1H, d, J = 4.6 Hz), 5.03-4.82 (1H, m), 4.71-4.62 (1H, m), 4.10-3.94 (2H, m), 3.82-3.65 (2H, m), 3.57 (2H, s), 2.86-2.73 (4H, m), 2.62-2.53 (2H, m), 2.46-2.38 (2H, m), 2.22-1.98 (8H, m), 1.95-1.79 (2H, m), 1.39 (3H, d, J = 6.4 Hz). | 495.3 | 494.29 |
| 62 | 1H-NMR (DMSO-D6) δ: 9.93 (1H, s), 9.29 (1H, s), 8.19 (1H, d, J = 8.2 Hz), 7.45 (1H, d, J = 8.2 Hz), 7.24 (1H, s), 5.26 (1H, d, J = 4.6 Hz), 4.70-4.61 (1H, m), 3.86-3.66 (6H, m), 3.05-2.97 (2H, m), 2.75-2.67 (2H, m), 1.79-1,60 (6H, m), 1.38 (3H, d, J = 6.4 Hz). | 406.3 | 405.23 |
| 63 | 1H-NMR (DMSO-D6) δ: 10.00 (1H, s), 9.31 (1H, s), 8.11 (1H, d, J = 8.2 Hz), 7.46 (1H, d, J = 8.2 Hz), 7.27 (1H, s), 5.29 (1H, d, J = 4.6 Hz), 5.03-4.82 (1H, m), 4.71-4.62 (1H, m), 4.09-3.93 (2H, m), 3.86-3.66 (4H, m), 3.06-2.97 (2H, m), 2.75-2.66 (2H, m), 2.16-1.98 (2H, m), 1.95-1.79 (2H, m), 1.39 (3H, d, J = 6.4 Hz). | 424.2 | 423.22 |
| 64 | 1H-NMR (DMSO-D6) δ: 10.36 (1H, s), 9.38 (1H, s), 8.31 (1H, d, J = 2.7 Hz), 8.26 (1H, d, J = 8.7 Hz), 7.82 (1H, dd, J = 8.9, 2.5 Hz), 7.34 (1H, s), 5.32 (1H, d, J = 4.6 Hz), 4.73-4.63 (1H, m), 4.08-3.90 (4H, m), 3.64 (2H, t, J = 5.5 Hz), 3.40 (2H, s), 3.03 (2H, t, J = 5.5 Hz), 2.79 (1H, s), 2.23-2.08 (4H, m), 1.40 (3H, d, J = 6.4 Hz). | 485.48 | 484.21 |
| 65 | 1H-NMR (DMSO-D6) δ: 10.14 (1H, s), 9.32 (1H, s), 8.34 (1H, d, J = 8.7 Hz), 8.20 (1H, d, J = 2.3 Hz), 7.70 (1H, dd, J = 8.7, 2.3 Hz), 7.25 (1H, s), 5.27 (1H, d, J = 4.6 Hz), 4.69-4.62 (1H, m), 4.54 (1H d, J = 3.2 Hz), 3.80-3.68 (4H, m), 3.47-3.40 (3H, m), 2.66 (2H, d, J = 11.0 Hz), 2.02 (2H, t, J = 9.8 Hz), 1.74-1.63 (8H, m), 1.41-1.32 (5H, m). | 464.25 | 463.27 |
| 66 | 1H-NMR (DMSO-D6) δ: 9.93 (1H, s), 9.21 (1H, s), 8.17 (1H, s), 7.96 (1H, d, J = 8.7 Hz), 7.68 (1H, d, J = 7.8 Hz), 6.99 (1H, s), 5.17 (1H, d, J = 4.6 Hz), 4.62-4.52 (2H, m), 3.89 (4H, br s), 3.47-3.37 (3H, m), 2.66 (2H, br s), 2.03 (2H, brs), 1.93-1.86 (4H, m), 1.73-1.67 (2H, m), 1.42-1.33 (5H, m). | 450.2 | 449.25 |

TABLE 73

| Compound No. | NMR data | (M + H)⁺ | Exact Mass |
|---|---|---|---|
| 67 | 1H-NMR (DMSO-D6) δ: 10.25 (1H, s), 9.35 (1H, s), 8.23-8.15 (2H, m), 7.76-7.72 (1H, m), 7.31 (1H, s), 5.30 (1H, d, J = 4.6 Hz), 4.71-4.64 (1H, m), 4.57 (1H, br s), 3.86-3.74 (8H, m), 3.48-3.41 (3H, m), 2.68 (2H, br s), 2.06 (1H, br s), 1.73-1.67 (2H, m), 1.44-1.34 (5H, m). | 466.2 | 465.25 |
| 68 | 1H-NMR (DMSO-D6) δ: 10.13 (1H, s), 9.32 (1H, s), 8.34 (1H, d, J = 8.7 Hz), 8.20 (1H, d, J = 2.3 Hz), 7.70 (1H, dd, J = 8.7, 2.3 Hz), 7.26 (1H, s), 5.28 (1H, br s), 4.69-4.62 (1H, m), 4.40 (1H, br s), 3.82-3.70 (4H, m), 3.42 (2H, s), 3.22 (2H, d, J = 5.9 Hz), 2.90 (1H, t, J = 5.5 Hz), 2.80 (2H, d, J = 11.4 Hz), 1.88 (2H, t, J = 10.5 Hz), 1.75-1.55 (9H, m), 1.41-1.30 (5H, m), 1.16-1.06 (2H, m). | 478.25 | 477.29 |
| 69 | 1H-NMR (DMSO-D6) δ: 9.93 (1H, s), 9.22 (1H, s), 8.19 (1H, s), 7.97 (1H, d, J = 8.2 Hz), 7.69 (1H, d, J = 8.2 Hz), 6.99 (1H, s), 5.16 (1H, d, J = 4.6 Hz), 4.63-4.56 (1H, m), 4.42 (1H, br s), 3.89 (4H, br s), 3.47 (2H, br s), 3.22 (2H, br s), 2.85 (2H, br s), 1.95-1.87 (6H, m), 1.63 (2H, d, J = 8.0 Hz), 1.40-1.31 (4H, m), 1.17-1.08 (2H, m). | 464.25 | 463.27 |
| 70 | 1H-NMR (DMSO-D6) δ: 10.35 (1H, s), 9.37 (1H, s), 8.30-8.21 (2H, m), 7.81 (1H, br s), 7.32 (1H, s), 5.31 (1H, d, J = 4.6 Hz), 4.71-4.64 (1H, m), 4.50 (1H, br 5), 3.87-3.75 (14H, m), 3.24 (2H, br s), 1.69 (2H, br s), 1.46-1.08 (6H, m). | 480.2 | 479.26 |
| 71 | 1H-NMR (DMSO-D6) δ: 10.15 (1H, s), 9.33 (1H, s), 8.35 (1H, d, J = 8.7 Hz), 8.20 (1H, d, J = 1.8 Hz), 7.69 (1H, dd, J = 8.7, 2.3 Hz), 7.26 (1H, s), 5.27 (1H, s), 4.75-4.63 (2H, m), 4.45-4.33 (3H, m), 3.75-3.67 (1H, m), 3.26-3.18 (5H, m), 2.80 (2H, d, J = 11.0 Hz), 2.70 (1H, s), 1.94-1.85 (4H, m), 1.65-1.57 (4H, m), 1.46-1.28 (5H, m), 1.15-1.04 (2H, m). | 495.25 | 493.28 |
| 72 | 1H-NMR (DMSO-D6) δ: 10.31 (1H, s), 9.34 (1H, s), 8.44 (1H, d, J = 8.7 Hz), 8.30 (1H, d, J = 2.7 Hz), 7.81 (1H, dd, J = 9.1, 2.7 Hz), 7.72 (1H, s), 5.28 (1H, d, J = 4.6 Hz), 4.69-4.64 (1H, m), 3.83-3.69 (6H, m), 3.19 (2H, br s), 2.80 (2H, br s), 2.33 (3H, s), 1.76-1.64 (6H, m), 1.39 (3H, d, J = 6.9 Hz). | 463.25 | 462.25 |
| 73 | 1H-NMR (DMSO-D6) δ: 10.09 (1H, s), 9.23 (1H, s), 8.27 (1H, d, J = 2.7 Hz), 8.05 (1H, d, J = 9.1 Hz), 7.77 (1H, dd, J = 8.9, 2.5 Hz), 7.00 (1H, s), 5.18 (1H, d, J = 4.6 Hz), 4.63-4.57 (1H, m), 3.90 (4H, br s) 3.69 (2H, t, J = 5.5 Hz), 3.16 (2H, s), 2.77 (2H, br s), 2.31 (3H, s), 1.94-1.88 (4H, m), 1.38 (3H, d, J = 6.4 Hz). | 449.2 | 448.23 |

TABLE 74

| Compound No. | NMR data | (M + H)+ | Exact Mass |
|---|---|---|---|
| 74 | 1H-NMR (DMSO-D6) δ: 10.38 (1H, s), 9.37 (1H, s), 8.31 (1H, s), 8.25 (1H, d, J = 8.7 Hz), 7.84 (1H, d, J = 9.1 Hz), 7.32 (1H, s), 5.31 (1H, d, J = 4.6 Hz), 4.71-4.64 (1H, m), 3.86-3.71 (10H, m), 3.19 (2H, s), 2.80 (2H, s), 2.32 (3H, s), 1.39 (3H, d, J = 6.4 Hz). | 465.2 | 464.23 |
| 75 | 1H-NMR (DMSO-D6) δ: 9.90 (1H, s), 9.19 (1H, s), 8.17 (1H, s), 7.91 (1H, d, J = 8.4 Hz), 7.69 (1H, d, J = 8.4 Hz.), 6.99 (1H, s), 5.23 (1H, d, J = 4.4 Hz), 4.62-4.64 (1H, m), 4.41 (1H, br s), 4.28-4.30 (2H, m), 3.47-3.49 (2H, m), 3.34(1H, s), 2.40 (10H, m), 1.83-1.87 (4H, m), 1.60 (6H, s), 1.31-1.41 (3H, d, J = 6.4 Hz). | 507.35 | 506.31 |
| 76 | 1H-NMR (DMSO-D6) δ: 10.19 (1H, s), 9.34 (1H, s), 8.31 (1H, d, J = 8.4 Hz), 8.21 (1H, s), 7.68 (1H, dd, J1 = 2 Hz, J = 8.4 Hz.), 7.28 (1H, s), 5.28 (1H, br s), 4.56-4.69 (3H, m), 3.45-3.48 (5H, m), 3.03-3.08 (10H, m), 1.95-1.98 (2H, br m), 1.74-1.84 (2H, br m), 1.40 (3H, d, J = 6.4 Hz). | 537.35 | 536.29 |
| 77 | 1H-NMR (DMSO-D6) δ: 10.21 (1H, s), 9.35 (1H, s), 8.21-8.25 (2H, m), 7.69-7.71 (1H, d, J = 8.8 Hz), 7.29 (1H, s), 5.31 (1H, d, J = 4.8 Hz), 4.66-4.70 (1H, m), 4.35-4.38 (1H, m), 3.79-3.84 (14H, m), 3.46-3.49 (4H, m), 2.54 (6H, s), 2.35-2.37 (8H, m), 2.29 (3H, s) 1.40 (3H, d, J = 6.4 Hz). | 508.35 | 507.31 |
| 78 | 1H-NMR (DMSO-D6) δ: 10.21 (1H, s), 9.36 (1H, s), 8.29 (1H, d, J = 8.4 Hz), 8.21 (1H, s), 7.74 (1H, d, J = 7.2 Hz.), 7.03 (1H, s), 5.32 (1H, d, J = 4.8 Hz), 4.87-5.03 (1H, br d), 4.66-4.69 (1H, m), 3.37 (1H, br s), 4.03 (2H, br s), 3.74-3.71 (2H, br m), 3.44-3.49 (4H, s), 2.35-2.38 (10H, m), 2.06-2.09 (2H, br m), 1.89-1.90 (2H, br m), 1.40 (3H, d, J = 6.4 Hz). | 511.35 | 510.29 |
| 79 | 1H-NMR (DMSO-D6) δ: 10.26 (1H, s), 9.38 (1H, s), 8.19-8.22 (2H, m), 7.75 (1H, d, J = 8.4 Hz,), 7.34 (1H, s), 5.34 (1H, d, J = 4.4 Hz), 4.67-4.70 (1H, m), 4.46-4.50 (1H, br s), 3.98-3.99 (4H, br m), 3.46 (4H, s), 2.33-2.41 (10H, br m), 2.12-2.19 (4H, br m), 1.41 (3H, d, J = 6.4 Hz). | 529.3 | 528.28 |
| 80 | 1H-NMR (DMSO-D6) δ: 10.05 (1H, s), 9.33 (1H, s), 8.04 (1H, d, J = 8.2 Hz), 7.47 (1H, d, J = 8.7 Hz), 7.31 (1H, s), 5.31 (1H, d, J = 4.1 Hz), 4.72-4.62 (1H, m), 4.06-3.90 (4H, m), 3.82 (2H, s), 3.02 (2H, t, J = 5.7 Hz), 2.70 (2H, t, J = 5.3 Hz), 2.22-2.05 (4H, m), 1.39 (3H, d, J = 6.4 Hz). | 442.3 | 441.21 |

TABLE 75

| Compound No. | NMR data | (M + H)+ | Exact Mass |
|---|---|---|---|
| 81 | 1H-NMR (DMSO-D6) δ: 10.08 (1H, s), 9.34 (1H, s), 8.05 (1H, d, J = 87 Hz), 7.51 (1H, d, J = 8.7 Hz), 7.31 (1H, s), 5.30 (1H, d, J = 4.6 Hz), 4.72-4.63 (1H, m), 4.49 (1H, t, J = 5.3 Hz), 4.06-3.90 (4H, m), 3.63-3.55 (4H, m), 2.86-2.74 (4H, m), 2.58 (2H, t, J = 6.2 Hz), 2.22-2.05 (4H, m), 1.39 (3H, d, J = 6.4 Hz). | 486.48 | 485.24 |
| 82 | 1H-NMR (DMSO-D6) δ: 10.08 (1H, s), 9.34 (1H, s), 8.04 (1H, d, J = 8.7 Hz), 7.50 (1H, d, J = 8.2 Hz), 7.31 (1H, s), 5.31 (1H, d, J = 4.1 Hz), 4.73-4.62 (1H, m), 4.06-3.89 (4H, m), 3.57 (2H, s), 2.86-2.73 (4H, m), 2.62-2.54 (2H, m), 2.47-2.39 (2H, m), 2.24-2.05 (10H, m), 1.39 (3H, d, J = 6.4 Hz). | 513.4 | 512.28 |
| 83 | 1H-NMR (DMSO-D6) δ: 9.95 (1H, s), 9.23 (1H, s), 8.19 (1H, d, J = 2 Hz), 7.96 (1H, d, J = 8.4 Hz), 7.70 (1H, dd, J1 = 2 Hz, J2 = 2.4 Hz), 7.03 (1H, s), 5.21 (1H, d, J = 4.0 Hz), 4.84-4.83 (1H,br m), 4.61-4.64 (1H, m), 4.34-4.36 (1H, m), 4.16-4.19 (1H, m), 3.88-3.91 (1H, m), 3.46-3.49 (2H, m), 3.43-3.45 (2H, m), 2.34-2.50 (10H, br m), 2.08-2.11 (1H, m), 1.97-2.06 (1H, m), 1.80-1.83 (1H, m), 1.63-1.67 (1H, m), 1.39 (3H, d, J = 4.0 Hz), 1.17 (3H, d, J = 4.0 Hz). | 493.35 | 492.30 |
| 84 | 1H-NMR (DMSO-D6) δ: 10.22 (1H, s), 9.36 (1H, s), 8.21-8.26 (2H, m), 7.66 (1H, d, J = 8.0 Hz), 7.31 (1H, s), 5.31 (1H, d, J = 8.0 Hz), 4.77-4.87 (2H, m), 4.67-4.70 (1H, m), 4.34-4.37 (1H, m), 3.33-3.49 (4H, m), 2.90-2.98 (1H, m), 2.60-2.67 (1H, m), 2.34-2.37 (10H, m), 1.92-1.95 (2H, m), 1.71-1.74 (2H, m), 1.41 (3H, d, J = 8.0 Hz) | 561.30 | 560.28 |
| 85 | 1H-NMR (DMSO-D6) δ: 10.27 (1H, s), 9.40 (1H, s), 8.22 (1H, d, J = 2 Hz), 8.08 (1H, d, J = 8.4 Hz), 7.76-7.79 (1H, m), 7.38 (1H, s), 5.35 (1H, d, J = 4.8 Hz), 4.69-4.73 (1H, m) 4.42 (4H br s) 4.34-4.37 (1H, m), 3.45-3.49 (4H, m), 3.28-2.29 (4H, br m), 2.34-2.38 (10H, br m), 1.41 (3H, d, J = 6.8 Hz). | 543.30 | 542.24 |
| 86 | 1H-NMR (CDCl3) δ: 8.97 (1H, s), 8.02-7.95 (2H, m), 7.36 (1H, d. J = 8.7 Hz), 6.62 (1H, s), 4.77 (1H, q, J = 6.4 Hz), 4.01 (4H, br s), 3.46 (1H, s), 3.03 (4H, t, J = 4.6 Hz), 2.85 (4H, t, J = 4.6 Hz), 2.47 (3H, s), 1.98 (4H, t, J = 6.6 Hz), 1.50 (3H, d, J = 6.4 Hz). | 435.3 | 434.25 |
| 87 | 1H-NMR (CDCl3) δ: 9.03 (1H, s), 8.30-8.24 (2H, m), 7.39 (1H, d, J = 8.7 Hz), 6.90 (1H, s), 5.26 (2H, s), 4.81 (1H, q, J = 6.4 Hz), 3.81 (4H, t, J = 5.3 Hz), 3.01 (4H, t, J = 4.8 Hz), 2.85 (4H, t, J = 4.6 Hz), 7.45 (3H, s), 1.83-1.77 (4H, m), 1.75-1.69 (2H, m), 1.49 (3H, d, J = 6.9 Hz). | 449.3 | 448.27 |

TABLE 76

| Compound No. | NMR data | (M + H)+ | Exact Mass |
|---|---|---|---|
| 88 | 1H-NMR (CDCl3) δ: 9.05 (1H, s), 8.29 (1H, d, J = 8.7 Hz), 8.14 (1H, s), 7.42 (1H, d, J = 9.1 Hz), 6.90 (1H, s), 4.83 (1H, q, J = 6.4 Hz), 3.85 (4H, t, J = 5.3 Hz), 3.67 (2H, t, J = 5.3 Hz), 2.95 (4H, t, J = 4.8 Hz), 2.72 (4H, br s), 2.65 (2H, t, J = 5.3 Hz), 2.48 (3H, s), 1.88-1.80 (4H, m), 1.78-1.72 (2H, m), 1.51 (3H, t, J = 5.9 Hz). | 493.3 | 492.30 |
| 89 | 1H-NMR (CDCl3) δ: 9.09 (1H, d, J = 2.3 Hz), 8.59 (1H, d, J = 9.1 Hz), 8.43 (1H, s), 8.21 (1H, d, J = 2.7 Hz), 7.63 (1H, dd, J = 9.1, 2.7 Hz), 6.93 (1H, s), 4.84 (1H, q, J = 6.4 Hz), 3.88-3.82 (6H, m), 3.17-3.11 (4H, m), 2.89-2.84 | 463.3 | 462.25 |

TABLE 76-continued

| Compound No. | NMR data | (M + H)+ | Exact Mass |
|---|---|---|---|
| | (2H, m), 1.88-1.81 (4H, m), 1.77-1.72 (2H, m), 1.52 (3H, d, J = 6.4 Hz). | | |
| 90 | 1H-NMR (DMSO-D6) δ: 10.75 (1H, s), 9.96 (1H, s), 9.16 (1H, d, J = 7.0 Hz), 9.12 (1H, d, J = 1.8 Hz), 8.71 (1H, dd, J = 7.1, 2.0 Hz), 8.32 (1H, s), 6.72 (1H, d, J = 3.7 Hz), 6.42 (1H, d, J = 39.2 Hz), 6.24-6.18 (1H, m), 5.72-5.63 (2H, m), 5.53-5.44 (2H, m), 5.40 (2H, t, J = 4.0 Hz), 5.22 (2H, s), 4.92 (2H, s), 4.20-4.10 (2H, m), 3.99 (2H, br s), 3.59 (3H, d, J = 5.1 Hz). | 467.3 | 466.22 |
| 91 | 1H-NMR (CDCl3) δ: 9.06 (1H, s), 8.59 (1H, d, J = 10.1 Hz), 8.32 (1H, s), 7.05 (1H, d, J = 9.6 Hz), 6.92 (1H, s), 4.84 (1H, q, J = 6.4 Hz), 3.83 (4H, t, J = 5.3 Hz), 3.57 (4H, t, J = 5.0 Hz), 3.04 (4H, t, J = 5.3 Hz), 1.84-1.70 (6H, m), 1.52 (4H, d, J = 6.9 Hz). | 436.3 | 435.25 |
| 92 | 1H-NMR (CDCl3) δ: 9.06 (1H, s), 8.53 (1H, d, J = 8.2 Hz), 8.36 (1H, s), 8.27 (1H, d, J = 2.3 Hz), 7.75 (1H, dd, J = 8.2, 2.3 Hz), 6.86 (1H, s), 4.03 (2H, t, J = 5.3 Hz), 3.85-3.75 (4H, m), 3.50 (2H, s), 2.98 (2H, t, J = 5.3 Hz), 2.94-2.86 (4H, m), 2.53-2.36 (4H, br m), 1.93-1.83 (4H, m), 1.80-1.71 (2H, m). | 449.4 | 448.27 |
| 93 | 1H-NMR (CDCl3) δ: 9.09 (1H, s), 8.65 (1H, d, J = 9.1 Hz), 8.57 (1H, s), 8.35 (1H, d, J = 2.3 Hz), 7.76 (1H, dd, J = 8.7, 2.7 Hz), 6.87 (1H, s), 4.03 (2H, t, J = 5.3 Hz), 3.84-3.71 (8H, m), 3.27 (2H, t, J = 5.3 Hz), 2.98 (2H, t, J = 5.3 Hz), 1.92-1.82 (4H, m), 1.79-1.68 (2H, m). | 449.3 | 448.23 |
| 94 | 1H-NMR (CDCl3) δ: 9.05 (1H, s), 8.61 (1H, d, J = 10.1 Hz), 8.35 (1H, s), 7.07 (1H, d, J = 9.6 Hz), 6.86 (1H, s), 4.03 (2H, t, J = 5.3 Hz), 3.80-3.72 (4H, m), 3.61-3.55 (4H, m), 3.08-3.02 (4H, m), 2.97 (2H, t, J = 5.3 Hz), 1.88-1.78 (4H, m), 1.78-1.68 (2H, m). | 436.3 | 435.25 |

TABLE 77

| Compound No. | NMR data | (M + H)+ | Exact Mass |
|---|---|---|---|
| 95 | 1H-NMR (DMSO-D6) δ: 9.93 (1H, s), 9.21 (1H, s), 8.19 (1H, d, J = 8.2 Hz), 7.45 (1H, d, J = 8.7 Hz), 7.01 (1H, s), 4.60 (1H, t, J = 5.3 Hz), 3.84-3.69 (8H, m), 3.01 (2H, t, J = 5.9 Hz), 2.81 (2H, t, J = 6.9 Hz), 2.70 (2H, t, J = 5.7 Hz), 1.77-1.60 (6H, m). | 406.3 | 405.23 |
| 96 | 1H-NMR (DMSO-D6) δ: 10.15 (1H, s), 9.32 (1H, s), 8.34 (1H, d, J = 8.7 Hz), 8.20 (1H, d, J = 1.8 Hz), 7.70 (1H, dd, J = 8.7, 2.3 Hz), 7.22 (1H, s), 5.36 (1H, s), 4.50 (2H, d, J = 3.7 Hz), 4.35 (1H, s), 3.73 (4H, br s), 3.47-3.41 (4H, m), 2.44-2.32 (10H, m), 1.75-1.63 (6H, m). | 479.3 | 478.28 |
| 97 | 1H-NMR (DMSO-D6) δ: 10.35 (1H, br s), 9.32 (1H, s), 8.42 (1H, d, J = 8.2 Hz), 8.31 (1H, s), 7.77 (1H, d, J = 8.0 Hz), 7.21 (1H, s), 5.36 (1H, s), 4.49 (2H, s), 3.76-3.63 (6H, m), 3.50 (2H, s), 3.12 (2H, t, J = 5.3 Hz), 1.75-1.61 (6H, m). | 435.2 | 434.22 |
| 98 | 1H-NMR (DMSO-D6) δ: 9.98 (1H, s), 9.23 (1H, s), 8.19 (1H,d, J = 4.0 Hz), 7.94 (1H, d, J = 12 Hz), 7.70 (1H, d, J = 2.0 Hz), 7.00 (1H, s), 5.17 (1H, d, J = 8.0 Hz), 4.89-4.90 (1H, br m), 4.59- | 493.30 | 492.30 |

TABLE 77-continued

| Compound No. | NMR data | (M + H)+ | Exact Mass |
|---|---|---|---|
| | 4.61 (1H, m), 4.35-4.38 (1H, m), 4.15-4.18 (1H, m), 3.86-3.90 (1H, m), 3.34-3.49 (4H, m), 2.34-2.49 (10H, m), 2.97-1.10 (2H, m), 1.81-1.84 (1H, m), 1.63-1.68 (1H, m), 1.41 (3H, d, J = 4.0 Hz), 1.16 (3H, d, J = 8.0 Hz). | | |
| 99 | 1H-NMR (DMSO-D6) δ: 9.94 (1H, s), 9.22 (1H, s), 8.18 (1H, d, J = 1.6 Hz), 7.95 (1H, d, J = 8.4 Hz), 7.65-7.68 (1H, m), 6.99 (1H, s), 5.17 (1H, d, J = 4.4 Hz), 4.58-4.63 (1H, m), 4.34-4.37 (1H, m), 4.17-4.21 (1H, br m), 3.92-3.98 (1H, br m), 3.77-3.87 (1H, br m), 3.43-3.49 (5H, m), 2.34-2.37 (11H, br m), 2.05 (1H, br s), 1.45-1.58 (1H, m), 1.38 (3H, d, J = 6.4 Hz), 1.09 (3H, d, J = 6.8 Hz). | 493.40 | 492.30 |
| 100 | 1H-NMR (DMSO-D6) δ: 9.95 (1H, s), 9.22 (1H, s), 8.18 (1H,d, J = 1.6 Hz), 7.97 (1H, d, J = 8.8 Hz), 7.68 (1H, dd, J1 = 2.4 Hz, J2 = 2.0 Hz), 6.99 (1H, s), 5.18 (1H, d, J = 4.0 Hz), 4.58-4.61 (1H, m), 4.34-4.37 (11H, m), 4.10-4.20 (1H, m), 3.91-3.99 (1H, m), 3.79-3.87 (1H, m), 3.43-3.45 (5H, m), 2.27-2.37 (11H, br m), 2.01-2.10 (1H, br m), 1.47-1.52 (1H, m), 1.40 (3H, d, 1 = 6.4 Hz), 1.10 (3H, d, J = 64 Hz) | 493.35 | 492.30 |

TABLE 78

| Compound No. | NMR data | (M + H)+ | Exact Mass |
|---|---|---|---|
| 101 | 1H-NMR (DMSO-D6) δ: 9.80 (1H, s), 9.21 (1H, s), 8.18 (1H, d, J = 1.6 Hz), 7.73 (2H, dd, J1 = 2.0 Hz, J2 = 2.0 Hz), 6.98 (1H, s), 5.18 (1H, d, J = 4.0 Hz), 4.98-4.99 (H-1, m), 4.88-4.89 (1H, m), 4.59-4.61 (1H, m), 4.35-4.38 (1H, m), 3.50-3.43 (4H, m), 2.34-2.38 (10H, br m), 2.01-2.05 (2H, m), 1.73-1.74 (2H, m), 1.40 (3H, d, J = 4.0 Hz), 1.24-1.25 (6H, m). | 507.35 | 506.31 |
| 102 | 1H-NMR (DMSO-D6) δ: 9.97 (1H, s), 9.22 (1H, s), 8.18 (1H, d, J = 2.0 Hz), 7.93 (1H, d, J = 8.0 Hz), 7.67 (1H, dd, J1 = 2.0 Hz, J2 = 2.0 Hz ), 6.99 (1H, s), 5.19 (1H, d, J = 4.0 Hz), 4.59-4.62 (1H, m), 4.35-4.38 (1H, m), 3.90-3.94 (2H, m), 3.77 (2H, s), 3.43-3.48 (4H, m), 2.34-2.37 (10H, br m), 1.69-1.73 (2H, m), 1.38-1.39 (3H, m), 1.08-1.09 (6H, s). | 507.35 | 506.31 |
| 103 | 1H-NMR (DMSO-D6) δ: 10.19 (1H, s), 9.32 (1H, s), 8.37 (1H, d, J = 8.0 Hz), 8.22 (1H, d, J = 1.6 Hz), 7.72 (1H, dd, J1 = 1.6 Hz, J2 = 1.6 Hz), 7.24 (1H, s), 5.27 (1H, d, J = 4.0 Hz), 5.20 (2H, s), 4.64-4.67 (1H, m), 4.35-4.37 (1H, br m), 3.45-3.48 (4H, br m), 2.31-2.39 (8H, br s), 1.78-1.80 (4H, br m), 1.49 (4H, d, J = 6.4 Hz), 1.40 (3H, d, J = 6.4 Hz), 1.23 (2H, s). | 505.35 | 504.30 |
| 104 | 1H-NMR (DMSO-D6) δ: 10.01 (1H, s), 9.24 (1H, s), 8.19 (1H, d, J = 1.5 Hz), 7.95 (1H, d, J = 9.0 Hz), 7.71 (1H, d, J = 12 Hz), 7.04 (1H, s), 5.20 (1H, d, J = 3.0 Hz), 4.62-4.58 (1H, m), 4.42-4.49 (2H, m), 4.34-4.38 (1H, m), 3.68-3.72 (2H, m), 3.44-3.50 (4H, m), 2.34-2.38 (10H, br m), 1.64-1.67 (2H, br m), 1.38 (3H, d, J = 6.0 Hz), 0.69-0.71 (1H, m), 0.18-0.22 (1H, m). | 491.30 | 490.28 |
| 105 | 1H-NMR (DMSO-D6) δ: 10.08 (1H, s), 9.27 (1H, s), 8.19 (1H,d, J = 2.0 Hz), 8.06 (1H, d, J = 8.0 Hz), 7.68 (1H, dd, J1 = 2.4 Hz, J2 = 2.4 Hz), 7.10 (1H, s), 5.42 (2H, d, | 519.40 | 518.31 |

TABLE 78-continued

| Compound No. | NMR data | (M + H)⁺ | Exact Mass |
|---|---|---|---|
|  | J = 24 Hz), 5.22 (1H, d, J = 4.0 Hz), 4.61-4.64 (1H, m), 4.34-4.37 (1H, m), 3.41-3.44 (4H, m), 2.36-2.37 (10H, br m), 1.96-1.98 (2H, m), 1.84-1.85 (3H, m), 1.78-1.80 (2H, m), 1.41-1.51 (3H, m), 1.39-1.40 (3H, m). |  |  |
| 106 | 1H-NMR (DMSO-D6) δ: 10.17 (1H, s), 9.34 (1H, s), 8.38 (1H, d, J = 9.0 Hz), 8.22 (1H, d, J = 3.0 Hz), 7.72 (1H, dd, J1 = 2.1 Hz, J2 = 2.1 Hz), 7.27 (1H, s), 5.29 (1H, d, J = 6.0 Hz), 4.76 (1H, d, 3.0 Hz), 4.63-4.71 (1H, m), 4.34-4.45 (3H, m), 3.71-3.77 (1H, m), 3.45-3.49 (4H, m), 3.18-3.27 (2H, m), 2.27-2.38 (10H, br m), 1.91-1.95 (2H, br m), 1.64-1.67 (2H, br m), 1.39 (3H, d, J = 3.0 Hz). | 509.35 | 508.29 |

TABLE 79

| Compound No. | NMR data | (M + H)⁺ | Exact Mass |
|---|---|---|---|
| 107 | 1H-NMR (DMSO-D6) δ: 10.27 (1H, s), 9.28 (1H, s), 8.23 (1H, d, J = 10.1 Hz), 7.37 (1H, d, J = 10.1 Hz), 7.18 (1H, s), 5.33 (1H, brs), 4.48 (2H, d, J = 3.7 Hz), 3.70 (4H, br s), 3.43 (4H, t, J = 5.0 Hz), 2.82 (4H, t, J = 5.0 Hz), 1.64 (6H, br s). | 422.2 | 421.23 |
| 108 | 1H-NMR (DMSO-D6) δ: 10.13 (1H, s), 9.32 (1H, s), 8.33 (1H, d, J = 8.2 Hz), 8.20 (1H, d, J = 1.8 Hz), 7.70 (1H, dd, J = 8.7, 2.3 Hz), 7.22 (1H, s), 5.35 (1H, br s), 4.50 (2H, d, J = 4.6 Hz), 3.74 (4H, br s), 3.41 (2H, s), 2.66 (4H, t, J = 4.6 Hz), 2.28 (4H, brs), 1.75-1.63 (6H, m). | 435.25 | 434.25 |
| 109 | 1H-NMR (DMSO-D6) δ: 9.97 (1H, s), 9.22 (1H, s), 8.20 (1H, d, J = 8.2 Hz), 7.49 (1H, d, J = 8.7 Hz), 7.01 (1H, s), 4.60 (1H, t, J = 5.5 Hz), 4.49 (1H, t, J = 5.5 Hz), 3.81-3.70 (6H, m), 3.62-3.54 (4H, m), 2.86-2.74 (6H, m), 2.57 (2H, t, J = 6.2 Hz), 1.77-1.60 (6H, m). | 450.3 | 449.25 |
| 110 |  | 477.3 | 476.30 |
| 111 | 1H-NMR (DMSO-D6) δ: 9.96 (1H, s), 9.29 (1H, s), 8.20 (1H, d, J = 8.7 Hz), 7.49 (1H, d, J = 8.7 Hz), 7.24 (1H, d, J = 0.9 Hz), 5.25 (1H, d, J = 4.6 Hz), 4.71-4.60 (1H, m), 4.48 (1H, t, J = 5.3 Hz), 3.84-3.66 (4H, m), 3.64-3.54 (4H, m), 2.86-2.74 (4H, m), 2.58 (2H, t, J = 6.2 Hz), 1.79-1.59 (6H, m), 1.38 (3H, d, J = 6.4 Hz). | 450.3 | 449.25 |
| 112 |  | 468.3 | 467.24 |
| 113 | 1H-NMR (DMSO-D6) δ: 9.94 (1H, s), 9.21 (1H, s), 8.18 (1H, s), 7.95 (1H, d, J = 9.0 Hz), 7.64-7.68 (1H, m), 6.98 (1H, s), 5.16 (1H, d, J = 6.0 Hz), 4.56-4.59 (1H, m), 4.33-4.37 (1H, m), 3.96-3.99 (1H, m), 3.66-3.67 (2H, m), 3.43-3.50 (5H, m), 2.27-2.38 (12H, br m), 1.39 (3H, d, J = 6.0 Hz), 0.96 (6H, d, J = 6.0 Hz | 507.40 | 506.31 |
| 114 | 1H-NMR (CDCl3) δ: 9.08 (1H, s), 8.61 (1H, d, J = 9.6 Hz), 8.42 (1H, s), 7.06 (1H, d, J = 9.6 Hz), 6.93 (1H, s), 4.84 (1H, q, J = 6.4 Hz), 3.98 (1H, brs), 3.82 (4H, t, J = 5.3 Hz), 3.61 (4H, t, J = 5.0 Hz), 3.20 (2H, t, J = 6.4 Hz), 3.05 (3H, s), 2.95 (2H, t, J = 6.4 Hz), 2.68 (4.14, t, J = 4.8 Hz), 1.83-1.71 (6H, m), 1.52 (3H, d, J = 6.4 Hz). | 542.3 | 541.26 |
| 115 | 1H-NMR (CDCl3) δ: 9.12 (1H, s), 8.51 (1H, s), 8.45 (1H, d, J = 8.2 Hz), 8.28 (1H, d, J = 1.8 Hz), 7.73 (1H, dd, J = 8.7, 2.3 Hz), 7.00 (1H, s), 5.05-4.80 (2H, m), 4.12-4.03 (2H, m), 3.96-3.90 (2H, m), 3.51 (2H, s), 2.55 (8H, s), 2.34 (3H, s), 2.23-2.03 (4H, m), 1.53 (3H, d, J = 6.4 Hz). | 481.3 | 480.28 |

TABLE 80

| Compound No. | NMR data | (M + H)⁺ | Exact Mass |
|---|---|---|---|
| 116 | 1H-NMR (CDCl3) δ: 9.03 (1H, d, J = 4.1 Hz), 8.22 (1H, d, J = 1.8 Hz), 8.17 (1H, d, J = 8.2 Hz), 8.09 (1H, s), 7.68 (1H, dd, J = 8.7, 2.3 Hz), 6.76 (1H, s), 5.39 (1H, d, J = 53.1 Hz), 4.81 (1H, q, J = 6.4 Hz), 4.46-4.12 (5H, m), 3.50 (2H, s), 2.62-2.38 (10H, m), 2.34 (3H, s), 1.53 (3H, d, J = 6.4 Hz). | 467.3 | 466.26 |
| 117 |  | 467.3 | 466.26 |
| 118 | 1H-NMR (CDCl3) δ: 9.18-9.05 (2H, m), 8.61 (1H, d, J = 9.6 Hz), 7.08-7.01 (2H, m), 4.34 (1H, q, J = 6.3 Hz), 3.75 (4H, br s), 3.58 (4H, br s), 3.37 (3H, s), 3.06 (4H, br s), 1.79-1.65 (6H, m), 1.46 (3H, d, J = 6.4 Hz). | 450.3 | 449.27 |
| 119 |  | 463.3 | 462.29 |
| 120 | 1H-NMR (CDCl3) δ: 9.01 (1H, s), 8.31-8.26 (2H, m), 8.19 (1H, d, J = 2.7 Hz), 7.58 (1H, dd, J = 8.9, 2.5 Hz), 6.67 (1H, s), 4.79 (1H, q, J = 6.4 Hz), 4.40 (1H, br s), 4.03 (1H, br s), 3.88-3.84 (2H, m), 2.90-2.86 (2H, m), 2.76-2.70 (4H, m), 2.41 (3H, s), 2.03-1.98 (4H, m), 1.51 (3H, d, J = 6.4 Hz). | 463.3 | 462.25 |
| 121 | 1H-NMR (CDCl3) δ: 9.15 (1H, s), 8.96 (1H, s), 8.60 (1H, d, J = 8.7 Hz), 8.27 (1H, d, J = 2.3 Hz), 7.63 (1H, dd, J = 9.1, 2.7 Hz), 6.94 (1H, s), 4.84 (1H, q, J = 6.4 Hz), 4.07 (1H, br s), 3.90-3.82 (6H, m), 2.91-2.87 (2H, m), 2.75 (4H, t, J = 8.9 Hz), 2.42 (3H, s), 1.87-1.80 (4H, m), 1.76-1.71 (2H, m), 1.52 (3H, d, J = 6.4 Hz). | 477.3 | 476.26 |
| 122 |  | 477.3 | 476.30 |
| 123 | 1H-NMR (CDCl3) δ: 9.10 (1H, s), 8.58 (1H, d, J = 9.6 Hz), 8.51 (1H, s), 7.05 (1H, d, J = 10.1 Hz), 6.93 (1H, s), 4.83 (1H, q, J = 6.4 Hz), 4.02 (1H, s), 3.82 (4H, t, J = 5.3 Hz), 3.63 (1H, t, J = 5.0 Hz), 2.58 (4H, t, J = 5.3 Hz), 2.36 (3H, s), 1.85-1.77 (6H, m), 1.52 (3H, d, J = 6.4 Hz). | 450.3 | 449.27 |
| 124 | 1H-NMR (CDCl3) δ: 9.15 (1H, s), 8.73 (1H, s), 8.50 (1H, d, J = 9.6 Hz), 7.05 (1H, d, J = 9.6 Hz), 7.00 (1H, s), 4.99-4.80 (2H, m), 4.10-4.01 (2H, m), 3.90-3.77 (3H, m), 3.63 (4H, t, J = 5.0 Hz), 2.57 (4H, t, J = 5.0 Hz), 2.36 (3H, s), 2.19-1.95 (4H, m), 1.52 (3H, d, J = 6.4 Hz). | 468.3 | 467.26 |
| 125 | 1H-NMR (CDCl3) δ: 9.18 (1H, s), 8.78 (1H, s), 8.54 (1H, d, J = 10.1 Hz), 7.12 (1H, s), 7.06 (1H, d, J = 10.1 Hz), 4.97-4.80 (2H, m), 4.35 (1H, q, J = 6.6 Hz), 4.13-4.02 (2H, m), 3.83-3.74 (3H, m), 3.63 (4H, t, J = 5.0 Hz), 3.38 (3H, s), 2.57 (4H, t, J = 5.0 Hz), 2.35 (3H, s), 2.18-1.97 (4H, m), 1.47 (3H, d, J = 6.4 Hz). | 482.3 | 481.27 |

TABLE 81

| Compound No. | NMR data | (M + H)+ | Exact Mass |
|---|---|---|---|
| 126 | 1H-NMR (CDCl3) δ: 9.17 (1H, s), 8.82 (1H, s), 8.53 (1H, d, J = 9.6 Hz), 7.12 (1H, s), 7.05 (1H, 1H, J = 9.6 Hz), 4.96-4.80 (1H, m), 4.35 (1H, q, J = 6.4 Hz), 4.12-4.02 (2H, m), 3.84-3.75 (2H, m), 3.57 (4H, br s), 3.38 (3H, s), 3.04 (4H, br s), 2.06 (4H, d, J = 48.5 Hz), 1.47 (3H, d, J = 6.9 Hz). | 468.3 | 467.26 |
| 127 | 1H-NMR (CDCl3) δ: 9.14 (1H, s), 8.93 (1H, s), 8.60 (1H, d, J = 9.1 Hz), 8.29 (1H, d, J = 2.3 Hz), 7.65 (1H, dd, J = 8.7, 2.7 Hz), 6.94 (1H, s), 4.84 (1H, q, J = 6.3 Hz), 3.86 (7H, td, J = 9.7, 5.0 Hz), 3.76 (2H, s), 3.18 (2H, t, J = 5.5 Hz), 1.96-1.91 (2H, m), 1.83-1.73 (6H, m), 1.52 (3H, d, J = 6.4 Hz). | 463.3 | 462.25 |
| 128 |  | 499.3 | 498.27 |
| 129 | 1H-NMR (CDCl3) δ: 9.15 (1H, s), 8.46-8.43 (2H, m), 8.27 (1H, d, J = 1.8 Hz), 7.75 (1H, dd, J = 8.7, 2.3 Hz), 7.32 (1H, s), 6.56 (1H, t, J = 56.0 Hz), 4.58-4.51 (2H, m), 4.04-3.97 (1H, m), 3.61 (2H, q, J = 5.2 Hz), 3.51 (2H, s), 3.46-3.38 (2H, m), 2.57-2.50 (10H, m), 2,15-2.08 (2H, m), 1.86-1.77 (2H, m). | 515.3 | 514.26 |
| 130 | 1H-NMR (DMSO-D6) δ: 9.96 (1H, s), 9.29 (1H, s), 8.20 (1H, d, J = 8.2 Hz), 7.50 (1H, d, J = 8.2 Hz), 7.24 (1H, s), 5.25 (1H, d, J = 4.6 Hz), 4.71-4.61 (1H, m), 4.51-4.40 (1H, m), 3.84-3.66 (4H, m), 3.57-3.43 (4H, m), 2.86-2.78 (1H, m), 2,77-2.69 (2H, m), 2.56-2.48 (2H, m), 1.79-1.59 (8H, m), 1.38 (3H, d, J = 6.4 Hz). | 464.55 | 463.27 |
| 131 | 1H-NMR (DMSO-D6) δ: 10.00 (1H, s), 9.29 (1H, s), 8.27 (1H, d, J = 9.1 Hz), 8.11 (1H, d, J = 2.7 Hz), 7.55 (1H, dd, J = 9.1, 3.2 Hz), 7.23 (1H, d, J = 0.9 Hz), 5.24 (1H, d, J = 4.6 Hz), 4.73-4.52 (2H, m), 4.49-4.38 (2H, m), 3.83-3.67 (4H, m), 3.54-3.46 (2H, m), 3.22-3.11 (1H, m), 2.82-2.73 (1H, m), 2.54-2.41 (2H, m), 2.34-2.17 (2H, m), 2.13-2.03 (1H, m), 1.77-1.48 (7H, m), 1.38 (3H, d, J = 6.4 Hz). | 512.53 | 511.27 |
| 132 | 1H-NMR (DMSO-D6) δ: 10.00 (1H, s), 9.29 (1H, s), 8.28 (1H, d, J = 9.1 Hz), 8.10 (1H, d, J = 3.2 Hz), 7.55 (1H, dd, J = 8.9, 3.0 Hz), 7.23 (1H, d, J = 0.9 Hz), 5.24 (1H, d, J = 4.6 Hz), 4.93-4.75 (1H, m), 4.70-4.52 (2H, m), 4.41 (1H, t, J = 5.3 Hz), 3.84-3.66 (4H, m), 3.50 (2H, q, J = 5.8 Hz), 3.02-2.88 (1H, m), 2.76-2.40 (4H, m), 2.40-2.28 (1H, m), 1.97-1.60 (8H, m), 1.38 (3H, d, J = 6.4 Hz). | 512.57 | 511.27 |
| 133 |  | 471.3 | 470.24 |

TABLE 82

| Compound No. | NMR data | (M + H)+ | Exact mass |
|---|---|---|---|
| 134 | 1H-NMR (CDCl3) δ: 9.10 (1H, s), 8.51-8.45 (2H, m), 8.27 (1H, s), 7.74 (1H, t, J = 4.3 Hz), 6.97 (1H, s), 4.85 (1H, q, J = 6.4 Hz), 4.53-4.47 (2H, m), 4.04-3.97 (1H, m), 3.50-3.39 (4H, m), 2.49 (8H, br s), 2.29 (3H, s), 2.15-1.82 (4H, m), 1.53 (3H, d, J = 6.4 Hz). | 479.3 | 478.28 |
| 135 | 1H-NMR (DMSO-D6) δ: 9.99 (1H, s), 9.29 (1H, s), 8.21 (1H, d, J = 8.2 Hz), 7.52 (1H, d, J = 8.7 Hz), 7.20 (1H, s), 5.33 (1H, t, J = 5.7 Hz), 4.69-4.44 (3H, m), 3.80-3.58 (8H, m), 2.86 (4H, br s), 2.70-2.63 (2H, m), 1.75-1.62 (6H, m). | 436.25 | 435.24 |
| 136 | 1H-NMR (DMSO-D6) δ: 9.91 (1H, s), 9.23 (1H, s), 8.19 (1H, d, J = 2.1 Hz), 7.96 (1H, d, J = 9.7 Hz), 7.05 (1H, dd, J = 2.1 Hz, J2 = 8.4 Hz), 7.00 (1H, s), 5.16 (1H, d, 4.5 Hz), 4.87-4.93 (1H, m), 4.58-4.62 (1H, m), 4.14-4.18 (1H, m), 3.86-3.88 (1H, m), 3.46 (2H, s), 2.49 (8H, m), 2.23 (3H, s), , 2.11-1.94 (2H, m), 1.80-1.86 (1H, m), 1.62-1.67 (1H, m), 1.42 (3H, d, J = 6.3 Hz), 1.17 (3H, d, J = 6.0 Hz). | 463.30 | 462.29 |
| 137 | 1H-NMR (DMSO-D6) δ: 9.98 (1H, s), 9.23 (1H, s), 8.19 (1H, d, J = 9.0 Hz), 7.95 (1H, d, J = 9.0 Hz), 7.69 (1H, d, J = 12.0 Hz), 7.00 (1H, s), 5.15 (1H, d, J = 6.0 Hz), 4.88-4.93 (1H, m), 4.58-4.62 (1H, m), 4.15-4.18 (1H, m), 3.86-3.93 (1H, m), 3.46 (2H, s), 2.42 (6H, br s), 2.23 (3H, s), 1.81-2.11 (3H, m), 1.63-1.68 (1H, m), 1.41 (3H, d, J = 6.0 Hz), 1.16 (3H, d, J = 6.0 Hz) | 463.30 | 462.29 |
| 138 | 1H-NMR (300 MHz DMSO-d6) δ: 9.93 (1H, s), 9.22(1H, s), 8.18 (1H, s), 7.96 (1H, d, J = 9.0 Hz), 7.67 (1H, d, J = 6.0 Hz), 6.99 (1H, s), 5.16 (1H, d, J = 6.0 Hz), 4.57-4.61 (1H, m), 4.14-4.20 (1H, m), 3.83-3.96 (2H, m), 3.43-3.52 (4H, m), 2.32-2.36 (8H, br m), 2.14(3H, s), 2.04-2.06 (1H, m), 1.45-1.55 (1H, m), 1.40 (3H, d, J = 9.0 Hz), 1.10 (3H, d, J = 9.0 Hz). | 463.30 | 462.29 |
| 139 | 1H-NMR (DMSO-D6) δ: 9.94 (1H, s), 9.21 (1H, s), 8.18 (1H, s), 7.96 (1H, d, J = 9.0 Hz), 7.67 (1H, d, J = 6.0 Hz), 6.99 (1H, s), 5.17 (1H, s ), 4.61 (1H, br s), 4.15-4.22 (1H, m), 3.97 (1H, s), 3.83 (1H, br s), 3.44 (4H, s), 2.36 (9H, br s) 2.21 (3H, s), 2.06-2.16 (1H, m), 1.48-1.58 (1H m), 1.38 (3H, d, J = 6.0 Hz), 1.10 (3H, d, J = 9.0 Hz). | 463.35 | 462.29 |

TABLE 83

| Compound No. | NMR data | (M + H)+ | Exact Mass |
|---|---|---|---|
| 140 | 1H-NMR (DMSO-D6) δ: 9.78 (1H, s), 9.21 (1H, s), 8.19 (1H, d, J = 2 Hz), 7.64-7.74 (2H, m), 6.98 (1H, s), 5.17 (1H, d, J = 4.5 Hz), 4.98-5.00 (1H, br m), 4.88-4.91 (1H, br m), 3.43 (2H, s), 2.36 (8H, br s), 2.14 (3H, s), 2.03-2.06 (2H, br m), 1.72-1.77 (2H, m), 1.40 (3H, d, J = 6.3 Hz), 1.25-1.21 (6H, m). | 477.35 | 476.30 |
| 141 | 1H-NMR (DMSO-D6) δ: 9.94 (1H, s), 9.21 (1H,s) 8.19 (1H, s), 7.95 (1H, d, J = 9.0 Hz), 7.66 (1H, d, J = 12.0 Hz), 6.98 (1H, s), 5.17 (1H, d, J = 3.0 Hz ), 4.58-4.62 (1H, m), 4.00-4.04 (2H, br m), 3.64-3.67 (2H, br m), 3.44 (2H, s), 2.27-2.37 (10H, br m), 2.13 (3H, s) 0.96 (6H, d, J= 6.0 Hz). | 477.35 | 476.30 |
| 142 | 1H-NMR (300 MHz DMSO-d6) δ: 9.95 (1H, s), 9.22 (1H, s), 8.18 (1H, s), 7.93 (1H, d, J = 6.0 Hz), 7.65-7.68 (1H, m), 6.99 (1H, s), 5.17 (1H, d, J = 3.0 Hz), 4.58-4.62 (1H, m), 3.90-3.95 (1H, m), 3.77 (2H, s), 3.39-3.48 (2H, m), 2.27-2.37 (6H, br m), 2.16 (3H , s), 1.69-1.74 (2H, m), 1.39 (3H, d, J = 6.0 Hz), 1.10 (6H, s). | 477.35 | 476.30 |

TABLE 83-continued

| Compound No. | NMR data | (M + H)⁺ | Exact Mass |
|---|---|---|---|
| 143 | 1H-NMR (DMSO-D6) δ: 10.17 (1H, s), 9.32 (1H, s), 8.37 (1H, d, J = 9.0 Hz), 8.22 (1H, s), 7.68-7.72 (1H, m), 7.24 (1H, s), 5.27 (1H, d, J = 3.0 Hz), 5.20 (2H, s), 4.63-4.68 (1H, m), 3.45 (2H, s), 2.27-2.43 (8H, br m), 2.15 (3H, s), 1.77 (4H, s), 1.48 (4H, d, J = 9.0 Hz), 1.40 (3H, d, J = 9.0 Hz ). | 475.35 | 474.29 |
| 144 | 1H-NMR (300 MHz DMSO-d6) δ: 10.20 (1H, s), 9.36 (1H, s), 8.22-8.26 (2H, m), 7.66 (1H, d, J = 9.0 Hz), 7.31 (1H, s), 5.30 (1H, d, J = 6.0 Hz), 4.77-4.87 (2H, m), 4.67-4.70 (1H, m), 3.46 (2H, s), 2.89-2.97 (2H, m), 2.55-2.60 (1H, m), 2.32-2.37 (8H, br m), 2.14 (3H, s), 1.94 (2H, d, J = 12 Hz), 1.68-1.76 (2H, br m), 1.0 (3H, d, J = 6.0 Hz). | 531.30 | 530.27 |
| 145 | 1H-NMR (DMSO-D6) δ: 10.20 (1H, s), 9.36 (1H, s), 8.19 (2H, d, J = 12 Hz), 7.74 (1H, d, J = 9 Hz), 7.32 (1H, s), 5.29 (1H, d, J = 6 Hz), 4.69 (1H, s), 3.77-3.84 (8H, m), 3.45 (2H, s), 2.33-2.38 (8H, br m), 2.15 (3H, s), 1.40 (3H, d, J = 6 Hz) | 465.30 | 464.26 |
| 146 | 1H-NMR (DMSO-D6) δ: 10.15 (1H, s), 9.34 (1H, s), 8.40 (1H, d, J = 9 Hz), 8.25 (1H, s), 7.74 (1H, d, J = 9 Hz), 7.26 (1H, s), 5.21 (1H, d, J = 3 Hz), 4.44-4.50 (1H, m), 3.69-3.83 (4H, m), 3.53 (2H, s), 2.73-2.90 (11H, br m), 1.56-1.92 (8H, br m), 0.85-0.90 (3H, m) | 477.35 | 476.30 |

TABLE 84

| Compound No. | NMR data | (M + H)⁺ | Exact Mass |
|---|---|---|---|
| 147 | 1H-NMR (DMSO-D6) δ: 10.09 (1H, d, J = 12.6 Hz), 9.32 (1H, s), 8.22-8.35 (1H, m), 7.66 (1H, d, J = 8.4 Hz), 7.26 (1H, s), 5.27 (1H, d, J = 4.5 Hz), 4.61-4.74 (3H, m), 3.76-3.85 (6H, br m), 3.05 (2H, d, J = 12.9 Hz), 2.09 (2H, br s), 2.68-2.78 (3H, br m), 1.55-1.80 (10H, br m), 1.39 (3H, d, J = 6.6 Hz). | 517.40 | 516.30 |
| 148 | 1H-NMR (DMSO-D6) δ: 10.08 (1H, d, J = 10.2 Hz), 9.32 (1H, s), 8.26-8.33 (1H, m), 7.66 (1H, d, J = 8.7 Hz), 7.26 (1H, s), 5.27 (1H, d, J = 4.5 Hz), 4.61-4.73 (3H, m), 4.44 (1H, br m), 3.76-3.83 (6H, br m), 3.52 (2H, br s), 2.90 (3H, br s), 2.72-2.78 (2H, br m), 2.40 (2H, br s), 2.13 (2H, br s), 1.55-1.80 (10H, br m), 1.39 (3H, d, J = 6.3 Hz). | 561.35 | 560.32 |
| 149 | 1H-NMR (DMSO-D6) δ: 10.08 (1H, d, J = 8.4 Hz), 9.32 (1H, s), 8.26-8.33 (1H, m), 7.64-7.68 (1H, m), 7.26 (1H, d, s), 5.27 (1H, d, J = 4.5 Hz), 4.61-4.73 (3H, m), 3.72-3.78 (6H, br m), 2.66-2.90 (5H, br m), 2.17 (3H, s), 1.95 (2H, br s), 1.55-1.78 (10H, br m), 1.39 (3H, d, J = 6.3 Hz). | 531.40 | 530.31 |
| 150 | | 499.3 | 498.27 |
| 151 | 1H-NMR (CDCl3) δ: 9.10 (1H, s), 8.60 (1H, d, J = 8.7 Hz), 8.52 (1H, s), 8.22 (1H, d, J = 2.7 Hz), 7.63 (1H, dd, J = 8.7, 2.7 Hz), 6.93 (1H, s), 4.84 (1H, q, J = 6.6 Hz), 3.89-3.85 (6H, m), 3.67 (2H, t, J = 5.3 Hz), 2.88 (6H, dd, J = 14.2, 8.2 Hz), 2.71 (2H, t, J = 5.5 Hz), 1.86-1.81 (4H, m), 1.76-1.72 (2H, m), 1.52 (3H, d, J = 6.4 Hz). | 507.3 | 506.28 |
| 152 | 1H-NMR (CDCl3) δ: 9.16 (2H, br s), 8.51 (1H, d, J = 8.7 Hz), 8.34 (1H, d, J = 1.8 Hz), 7.69 (1H, dd, J = 8.7, 2.3 Hz), 6.93 (1H, s), 4.84 (1H, q, J = 6.4 Hz), 4.04 (1H, d, J = 13.3 Hz), 3.88-3.83 (4H, m), 3.16 (1H, d, J = 13.3 Hz), 2.72-2.61 (3H, m), 2.53-2.46 (1H, m), 2.24-2.18 (4H, m), 2.15-2.08 (1H, m), 2.01-1.94 (1H, m), 1.88-1.80 (4H, m), 1.77-1.72 (2H, m), 1.52 (3H, d, J = 6.4 Hz), 1.18 (3H, d, J = 6.4 Hz). | 477.3 | 476.30 |
| 153 | | | 449.25 |
| 154 | | | 405.19 |
| 155 | | 449.3 | 448.27 |
| 156 | | 490.3 | 489.29 |

TABLE 85

| Compound No. | NMR data | (M + H)⁺ | Exact Mass |
|---|---|---|---|
| 157 | 1H-NMR (DMSO-D6) δ: 9.99 (1H, s), 9.24 (1H, s), 8.20 (1H, d, J = 1.8 Hz), 7.93 (1H, d, J = 8.4 Hz), 7.67-7.71 (1H, m), 7.04 (1H, s), 5.17 (1H, d, J = 4.8 Hz), 4.582-4.62 (1H, m), 3.70 (2H, d, J = 12 Hz), 3.45 (2H, s), 2.22-2.45 (8H, br m), 2.14 (3H, s), 1.64-1.66 (2H, br m), 1.38 (3H, d, J = 6.3 Hz), 0.68-0.73 (1H, m), 0.20-0.22 (1H, m). | 461.30 | 460.27 |
| 158 | 1H-NMR (DMSO-D6) δ: 9.93 (1H, s), 9.23 (1H, s), 8.19 (1H, s), 7.84 (1H, d, J = 8.7 Hz), 7.65-7.68 (1H, m), 7.03 (1H, s), 5.18 (1H, d, J = 4.5 Hz), 4.58-4.62 (1H, m), 4.09-4.19 (4H, m), 3.43 (2H, s), 2.36 (8H, br s), 2.15 (3H, s), 1.74 (4H, br s), 1.47 (4H, br s), 1.38 (3H, d, J = 6.36 Hz). | 477.40 | 476.30 |
| 159 | 1H-NMR (DMSO-D6) δ: 10.12 (1H, s), 9.33 (1H, s), 8.36 (1H, d, J = 8.7 Hz), 8.21 (1H, d, J = 1.8 Hz), 7.70-7.73 (1H, m), 7.25 (1H, s), 5.21 (1H, d, J = 4.8 Hz), 4.44-4.49 (1H, m), 4.36 (1H, br s), 3.70-3.82 (4H, m), 3.45-3.56 (4H, m), 2.31-2.39 (10H, br m), 1.84-1.92 (1H, m), 1.63-1.72 (7H, m), 0.841-0.91 (3H, m). | 507.40 | 506.31 |
| 160 | 1H-NMR (DMSO-D6) δ: 10.12 (1H, s), 9.33 (1H, s), 8.36 (1H, d, J = 8.1 Hz), 8.21 (1H, d, J = 1.5 Hz), 7.70-7.73 (1H, m), 7.25 (1H, s), 5.19 (1H, d, J = 4.8 Hz), 4.44-4.49 (1H, m), 4.38 (1H, br s), 3.70-3.82 (4H, m), 3.46-3.56 (4H, m), 2.40 (10H, br s), 1.84-1.92 (1H, m), 1.58-1.72 (7H, m), 0.85-0.90 (3H, m). | 507.40 | 506.31 |
| 161 | 1H-NMR (DMSO-D6) δ: 10.01 (1H, s), 9.31 (1H, s), 8.23 (1H, d, J = 8.4 Hz), 7.52 (1H, d, J = 8.4 Hz) 7.26 (1H, s), 5.26 (1H, d, J = 4.5 Hz), 4.61-4.69 (3H, m), 4.526-4.56 (2H, m), 3.71-3.82 (4H, m), 3.62-3.66 (1H, m), 3.46 (2H, s), 2.84-2.88 (2H, m), 2.62-2.65 (2H, m), 1.67-1.73 (6H, br m), 1.39 (3H, d, J = 6.3 Hz). | 462.30 | 461.25 |
| 162 | 1H-NMR (DMSO-D6) δ: 9.99 (1H, s), 9.29 (1H, s), 8.20 (1H, d, J = 87 Hz), 7.49 (1H, d, J = 8.7 Hz), 7.24 (1H, s), 5.26 (1H, br s), 4.65 (1H, q, J = 6.3 Hz), 3.83-3.66 (4H, m), 3.64-3.50 (6H, m), 2.85-2.74 (4H, m), 2.67-2.57 (2H, m), 2.54-2.35 | 519.4 | 518.31 |

TABLE 85-continued

| Compound No. | NMR data | (M + H)⁺ | Exact Mass |
|---|---|---|---|
| | (6H, m), 1.77-1.60 (6H, m), 1.38 (3H, d, J = 6.4 Hz). | | |
| 163 | 1H-NMR (DMSO-D6) δ: 10.12 (1H, s), 9.31 (1H, s), 8.27 (1H, d, J = 8.2 Hz), 7.63 (1H, d, J = 8.7 Hz), 7.25 (1H, s), 5.27 (1H, d, J = 4.1 Hz), 4.70-4.60 (1H, m), 4.46 (2H, s), 3.84-3.68 (4H, m), 3.64 (2H, t, J = 5.9 Hz), 2.99 (2H, d, J = 11.9 Hz), 2.87 (2H, t, J = 5.5 Hz), 2.50-2.39 (2H m), 1.91-1.81 (2H, m), 1.77-1.60 (6H, m), 1.56-1.42 (2H, m), 1.38 (3H, d, J = 6.9 Hz). | 553.3 | 552.26 |

TABLE 86

| Compound No. | NMR data | (M + H)⁺ | Exact Mass |
|---|---|---|---|
| 164 | 1H-NMR (DMSO-D6) δ: 9.97 (1H, s), 9.28 (1H, s), 8.25 (1H, d, J = 8.7 Hz) 8.05 (1H, d, J = 3.2 Hz), 7.48 (1H, dd, J = 9.1, 2.7 Hz), 7.23 (1H, s), 5.25 (1H, d, J = 4.6 Hz), 4.69-4.60 (1H, m), 4.45-4.36 (1H, m), 3.83-3.66 (4H, m), 2.99-2.88 (2H, m), 2.60-2.50 (2H, m), 1,95-1.85 (2H, m), 1.76-1.60 (6H, m), 1.50-1.35 (5H, m). | 450.3 | 449.25 |
| 165 | 1H-NMR (DMSO-D6) δ: 9.97 (1H, s), 9.28 (1H, s), 8.26 (1H, d, J = 9.1 Hz), 8.05 (1H, d, J = 2.7 Hz), 7.49 (1H, dd, J = 9.1, 3.2 Hz), 7.23 (1H, s), 5.25 (1H, d, J = 4.6 Hz), 4.69-4.60 (1H, m), 4.43-4.34 (2H, m), 3.83-3.66 (4H, m), 3.52-3.45 (2H, m), 2.78-2.66 (2H, m), 2.39 (2H, t, J = 6.2 Hz), 2.30-2.19 (2H, m), 1.97-1.87 (2H, m), 1.77-1.55 (8H, m), 1.38 (3H, d, J = 6.9 Hz). | 494.3 | 493.28 |
| 166 | 1H-NMR (DMSO-D6) δ: 9.92 (1H, s), 9.23 (1H, s), 8.20 (1H, d, J = 8.7 Hz), 7.45 (1H, d, J = 8.2 Hz), 7.00 (1H, s), 4.57 (1H, t, J = 5.5 Hz), 3.84-3.64 (7H, m), 3.54-3.45 (1H, m), 3.01 (2H, t, J = 5.9 Hz), 2.93-2.82 (4H, m), 2.70 (2H, t, J = 5.7 Hz), 1.77-1.59 (6H, m), 1.21 (3H, d, J = 6.9 Hz). | 420.3 | 419.24 |
| 167 | 1H-NMR (DMSO-D6) δ: 10.13 (1H, s), 9.26 (1H, s), 8.36 (1H, d, J = 8.2 Hz), 8.20 (1H, d, J = 2.3 Hz), 7.70 (1H, dd, J = 8.7, 2.3 Hz), 7.02 (1H, s), 4.57 (1H, t, J = 5.5 Hz), 4.35 (1H, t, J = 5.3 Hz), 3.84-3.65 (5H, m), 3.55-3.39 (5H, m), 2.94-2.82 (1H, m), 2.35-2.34 (10H, m), 1.79-1.61 (6H, m), 1.22 (3H, d, J = 6.9 Hz). | 507.4 | 506.31 |
| 168 | 1H-NMR (CDCl3, J = 6.9 Hz).), 8.53 (1H, d, J = 8.2 Hz), 8.33 (1H, s), 8.27 (1H, d, J = 1.8 Hz), 7.73 (1H, dd, J = 8.2, 2.3 Hz), 6.84 (1H, s), 4.27-4.16 (1H, m), 3.88-3.73 (4H, m), 3.65 (2H, t, J = 5.3 Hz), 3.53 (2H, s), 2.92-2.74 (2H, m), 2.74-2.38 (10H, m), 1.96-1.64 (6H, m), 1.30 (3H, d, J = 5.9 Hz). | 507.4 | 506.31 |
| 169 | | 463.3 | 462.25 |
| 170 | 1H-NMR (DMSO-D6) δ: 9.97 (1H, s), 9.22 (1H, s), 8.21 (1H, d, J = 8.7 Hz), 7.49 (1H, d, J = 8.7 Hz), 6.99 (1H, s), 4.68 (1H, d, J = 4.6 Hz), 4.50 (1H, br s), 4.13-4.00 (1H, m), 3.81-3.68 (4H, m), 3.64-3.54 (4H, m), 2.87-2.72 (5H, m), 2.70-2.54 (3H, m), 1.80-1.59 (6H, m), 1.09 (3H, d, J = 5.9 Hz). | 464.3 | 463.27 |
| 171 | | 464.3 | 463.27 |

TABLE 87

| Compound No. | NMR data | (M + H)⁺ | Exact Mass |
|---|---|---|---|
| 172 | 1H-NMR (DMSO-D6) δ: 9.96 (1H, s), 9.25 1H, s), 8.18 (1H, d, J = 1.5 Hz), 8.07 (1H, d, J = 8.4 Hz), 7.74 (1H, d, J = 8.4 Hz), 7.05 (1H, s), 5.20 (1H, d, J = 4.5 Hz), 4.59 (2H, t, J = 5.7 Hz), 4.38 (4H, br m), 3.43 (1H, s), 2.38-2.27 (9H, br m), 2.15 (1H, s), 1.39 (3H, d, J = 6.3 Hz). | 435.30 | 434.25 |
| 173 | 1H-NMR (DMSO-D6) δ: 9.87 (1H, s), 9.19 (1H, s), 8.18 (1H, d, J = 1.8 Hz), 7.91 (2H, d, J = 10.2 Hz), 7.68 (1H, dd, J1 = 8.7 Hz, J2 = 2.1 Hz), 7.0 (1H, s), 5.20 (1H, d, J = 4.5 Hz), 4.62-4.65 (1H, br m), 4.29 (2H, t, J = 6.3 Hz), 3.46 (2H, br s), 2.50 (5H, br m), 2.270 (4H, br s), 1.81-1.90 (4H, br m), 1.61 (6H, s), 1.40 (3HH, d, J = 6.3 Hz). | 477.35 | 476.30 |
| 174 | 1H-NMR (DMSO-D6) δ: 10.08 (1H, s), 9.27 (1H, s), 8.20 (1H, s), 8.05 (1H, d, J = 8.4 Hz), 7.67 (1H, d, J = 7.8 Hz), 7.10 (1H, s), 5.42 (2H, d, J = 16.5 Hz), 5.21 (1H, s), 4.625 (1H, br s), 3.43 (2H, s), 2.36-2.74 (8H, br m), 2.14 (3H, s), 1.63-1.97 (7H, br m), 1.24-1.48 (6H, br m). | 489.40 | 488.30 |
| 175 | 1H-NMR (DMSO-D6) δ: 9.98 (1H, s), 9.31 (1H, s), 8.22 (1H, d, J = 8.7 Hz), 7.52 (2H, d, J = 8.7 Hz), 7.25 (1H, s), 5.27 (1H, d, J = 4.2 Hz), 4.65-4.68 (1H, br m), 3.76-3.82 (5H, br m), 3.42-3.53 (6H, br m), 2.83 (1H, s), 2.66 (2H, br s), 1.72 (6H, br m), 1.39 (3H, d, J = 6.3 Hz). | 461.35 | 460.27 |

TABLE 88

| Compound No. | NMR data | (M + H)⁺ | Exact Mass |
|---|---|---|---|
| 176 | 1H-NMR (DMSO-D6) δ: 9.95 (1H, s), 9.27 (1H, s), 8.18 (1H, d, J = 8.4 Hz), 7.52 (1H, d, J = 8.4 Hz), 7.22 (1H, s), 5.24 (1H, d, J = 4.8 Hz), 4.63 (1H, br s), 4.33-4.36 (2H, m), 3.71 (4H, br s), 3.42-3.49 (8H, br m), 3.03 (1H, br s), 2.79-2.87 (4H, br m), 2.54-2.58 (2H, m), 1.69 (6H, br s), 1.36 (4H, d, J = 6.6 Hz), 1.20 (1H, s). | 505.35 | 504.30 |
| 177 | 1H-NMR (DMSO-D6) δ: 10.04 (1H, s), 9.27 (1H, s), 8.19 (1H, d, J = 1.8 Hz), 7.85 (1H, d, J = 8.4 Hz), 7.69 (1H, dd, J1 = 2.1 Hz, J2 = 8.7 Hz), 7.10 (1H, s), 5.22 (1H, d, J = 4.8 Hz), 4.59-4.63 (1H, m), 4.30-4.39 (2H, m), 4.15-4.19 (2H, m), 3.71-3.75 (2H, m), 3.61-3.63 (2H, m), 3.59 (1H, s), 2.37-2.49 (10H, br m), 2.14 (3H, s), 1.88-1.95 (2H, m), 1.39 (3H, d, J = 6.6 Hz). | 479.35 | 478.28 |
| 178 | 1H-NMR (DMSO-D6) δ: 10.04 (1H, s), 9.27 (1H, s), 8.19 (1H, d, J = 2.1 Hz), 7.85 (1H, d, J = 8.4 Hz), 7.69 (1H, dd, J1 = 2.1 Hz, J2 = 8.4 Hz), 7.10 (1H, s), 5.22 (1H, d, J = 4.8 Hz), 4.59-4.63 (1H, m), 4.30-4.39 (3H, m), 4.15-4.19 (2H, m), 3.71-3.75 (2H, m), 3.61-3.63 (2H, m), 3.48-3.59 (4H, m), 2.34-2.50 (10H, br m), 1.90-1.95 (2H, m), 1.39 (3H, d, J = 6.6 Hz). | 509.40 | 508.29 |
| 179 | 1H-NMR (DMSO-D6) δ: 10.17 (1H, s), 9.35 (1H, s), 8.30 (1H, d, J = 8.4 Hz), 8.22 (1H, s), 7.72 (1H, d, J = 9 Hz), 7.30 (1H, s), 5.30 (1H, d, J = 4.5 Hz), 4.90 (1H, d, J = 48 Hz), 4.68-4.73 (1H, m), 4.07-4.14 (1H, br m), 3.96-4.02 (1H, br m), 3.86-3.92 (1H, br m), 3.73-3.77 (1H, br m), 3.45 (2H, s), 2.33-2.37 (8H, br m), 2.14 (3H, s), 1.85-2.04 (2H, br m), 1.68 (2H, br s), 1.39 (3H, d, J = 6.6 Hz). | 481.35 | 480.28 |
| 180 | 1H-NMR (DMSO-D6) δ: 10.17 (1H, s), 9.35 (1H, s), 8.32 (1H, d, J = 8.4 Hz), 8.22 (1H, s), 7.23 (1H, d, J = 8.4 Hz), 7.29 (1H, s), 5.31 (1H, d, J = 4.8 Hz), 4.82-4.98 (1H, br d), 4.67-4.71 (1H, m), 4.37 (1H, br s), | 511.40 | 510.29 |

TABLE 88-continued

| Compound No. | NMR data | (M + H)+ | Exact Mass |
|---|---|---|---|
|  | 3.77-4.10 (4H, m), 3.45-3.48 (4H, m), 2.39 (10H, br s), 1.97-2.03 (2H, m), 1.85 (1H, br s), 1.68 (1H, br s), 1.40 (3H, d, J = 6.3 Hz). |  |  |
| 181 | 1H-NMR (DMSO-D6) δ: 10.01 (1H, s), 9.27 (1H, s), 8.19 (1H, s), 7.97 (1H, d, J = 8.4 Hz), 7.71 (1H, d, J = 8.7 Hz), 7.07 (1H, s), 5.34-5.52 (1H, br d), 5.21 (1H, d, J = 4.5 Hz), 4.62-4.64 (1H, m), 4.92-3.36 (5H, m), 3.39-3.49 (4H, m), 2.05-2.50 (12H, m), 1.42 (3H, d, J = 6.3 Hz). | 497.40 | 496.27 |
| 182 | 1H-NMR (DMSO-D6) δ: 10.02 (1H, s), 9.27 (1H, s), 8.19 (1H, s), 7.95 (1H, d, J = 9 Hz), 7.70 (1H, d, J = 9 Hz), 7.07 (1H, s), 5.45 (1H, d, J = 60 Hz), 5.21 (1H, d, J = 6.0 Hz), 4.60-4.68 (1H, m), 3.88-4.37 (5H, m), 3.44-3.50 (4H, m), 2.09-2.54 (12H, br m), 1.40 (3H, d, J = 6.0 Hz) | 497.35 | 496.27 |
| 183 |  | 507.4 | 506.31 |
| 184 | 1H-NMR (CDCl3) δ: 9.10 (1H, d, J = 5.5 Hz), 8.54-8.49 (2H, m), 8.26 (1H, d, J = 2.3 Hz), 7.72 (1H, dd, J = 8.7, 2.3 Hz), 6.93 (1H, s), 4.84 (1H, q, J = 6.4 Hz), 3.87-3.80 (6H, m), 3.50 (2H, s), 2.70 (2H, br s), 2.54-2.40 (6H, m), 2.34-2.22 (3H, m), 1.88-1.72 (6H, m), 1.52 (3H, d, J = 6.4 Hz), 1.11 (3H, d, J = 5.9 Hz). | 507.4 | 506.31 |
| 185 |  | 475.3 | 474.29 |
| 186 |  | 477.4 | 476.30 |

TABLE 89

| Compound No. | NMR data | (M + H)+ | Exact Mass |
|---|---|---|---|
| 187 |  | 489.3 | 488.30 |
| 188 |  | 477.4 | 476.30 |
| 189 |  | 489.3 | 488.30 |
| 190 |  | 486.3 | 485.25 |
| 191 |  | 442.2 | 441.19 |
| 192 |  | 463.3 | 462.25 |
| 193 |  | 464.3 | 463.27 |
| 194 |  | 463.3 | 462.25 |
| 195 |  | 507.4 | 506.31 |
| 196 | 1H-NMR (DMSO-D6) δ: 10.03 (1H, s), 9.31 (1H, s), 8.23 (1H, d, J = 8.4 Hz), 7.57 (1H, d, J = 8.4 Hz), 7.26 (1H, s), 5.27 (1H, d, J = 4.5 Hz), 4.65-4.69 (1H, m), 3.95 (2H, s), 3.72-3.83 (4H, br m), 3.68 (1H, s), 2.88 (4H, br s), 1.73 (6H, br s), 1.40 (3H, d, J = 6.6 Hz). | 445.25 | 444.24 |
| 197 | 1H-NMR (DMSO-D6) δ: 9.97 (1H, s), 9.30 (1H, s), 8.22 (1H, d, J = 9.0 Hz), 7.50 (1H, d, J = 9.0 Hz), 7.25 (1H, s), 5.26 (1H, d, J = 6.0 Hz), 4.65-4.71 (1H, m), 4.30-4.34 (2H, m), 3.71-3.82 (4H, m), 3.51 (2H, s), 2.82 (4H, d, J = 6.0 Hz ), 2.74 (2H, d, J = 6.0 Hz), 1.72-1.73 (6H, br m), 1.39 (3H, d, J = 6.0 Hz). | 476.30 | 475.27 |
| 198 | 1H-NMR (DMSO-D6) δ: 10.18 (1H, s), 9.35 (1H, s), 8.22-8.32 (2H, m), 7.70-7.73 (1H, m), 7.30(1H, s), 5.31 (1H, d, J = 3.0 Hz), 4.89 (1H, d, J = 45.0 Hz), 4.65-4.71 (1H, m), 4.01-4.13 (2H, m), 3.82 (2H, s), 3.43 (2H, d, J = 12.0 Hz), 2.37 (8H, br s), 2.15 (3H, m), 1.98-2.08 (2H, m), 1.75-1.84 (1H, m), 1.69 (1H, br m), 1.42 (3H, d). | 481.30 | 480.28 |
| 199 | 1H-NMR (DMSO-D6) δ: 10.18 (1H, s), 9.36 (1H, s), 8.23-8.32 (2H, m), 7.72-7.73 (1H, br m), 7.31 (1H, s), 5.30 (1H, d, J = 3.0 Hz), 4.89 (1H, d, J = 48.0 Hz), 4.58 (2H, s), 4.02-4.11 (2H, m), 3.82 (2H, s), 3.49 (4H, s), 1.99-2.50 | 511.35 | 510.29 |

TABLE 89-continued

| Compound No. | NMR data | (M + H)+ | Exact Mass |
|---|---|---|---|
|  | (10H, br m), 1.69-1.84 (4H, br m), 1.42 (3H, d, J = 8.0 Hz). |  |  |
| 200 | 1H-NMR (DMSO-D6) δ: 9.98 (1H, s), 9.30 (1H, s), 8.22 (1H, d, J = 8.7 Hz), 7.52 (1H d, J = 8.4 Hz), 7.25 (1H, s), 5.26 (1H, d, J = 6.0 Hz), 4.65-4.69 (1H, m), 3.71-3.82 (4H, m), 3.34-3.48 (4H, m), 3.01-3.06 (1H, m), 2.80-2.86 (4H, m), 2.57-2.61 (2H, m), 2.24 (3H, s), 1.72 (6H, br, s), 1.39 (3H, d, J = 6.3 Hz) | 475.30 | 474.29 |

TABLE 90

| Compound No. | NMR data | (M + H)+ | Exact Mass |
|---|---|---|---|
| 201 | 1H-NMR (DMSO-D6) δ: 10.09 (1H, s), 9.32 (1H, s), 8.26 (1H, d, J = 8.4 Hz), 7.68 (1H, d, J = 8.4 Hz), 7.25 (1H, s), 5.26 (1H, d, J = 4.5 Hz), 4.65-4.69 (1H, m), 4.54 (1H, t, 5.4 Hz), 3.87 (2H, s), 3.83 (2H, s), 3.74-3.78 (4H, m), 3.55-3.61 (2H, m), 2.78-2.82 (2H, m), 1.69-1.73 (6H, br, m), 1.41 (3H, d, J = 6.3 Hz). | 436.25 | 435.24 |
| 202 | 1H-NMR (CDCl3) δ: 9.08 (1H, s), 8.58-8.47 (2H, m), 8.29 (1H, d, J = 2.0 Hz), 7.74 (1H, dd, J = 8.5, 2.2 Hz), 6.84 (1H, s), 5.93 (1H, br s), 4.28-4.16 (1H, m), 3.89-3.72 (4H, m), 3.61 (2H, t, J = 5.4 Hz), 3.52 (2H, s), 2.94-2.29 (12H, m), 1.96-1.62 (6H, m), 1.30 (3H, d, J = 5.9 Hz). | 507.4 | 506.31 |
| 203 | 1H-NMR (CDCl3) δ: 9.10 (1H, s), 8.72-8.61 (2H, m), 8.36 (1H, d, J = 2.4 Hz), 7.76 (1H, dd, J = 9.0, 2.7 Hz), 6.85 (1H, s), 5.90 (1H, br s), 4.28-4.16 (1H, m), 3.88-3.71 (8H, m), 3.27 (2H, t, J = 5.4 Hz), 2.94-2.73 (2H, m), 1.98-1.59 (6H, m), 1.30 (3H, d, J = 6.3 Hz). | 463.3 | 462.25 |
| 204 | 1H-NMR (CDCl3) δ: 9.05 (1H, s), 8.36 (1H, d, J = 8.3 Hz), 8.21 (1H, d, J = 8.3 Hz), 6.82 (1H, s), 5.94 (1H, br s), 4.26-4.16 (1H, m), 3.87-3.66 (8H, m), 3.03-2.72 (8H, m), 1.93-1.62 (6H, m), 1.29 (3H, d, J = 5.9 Hz). | 464.3 | 463.27 |
| 205 | 1H-NMR (CDCl3) δ: 9.06 (1H, s), 8.60 (1H, d, J = 8.7 Hz), 8.49 (1H, br s), 8.29 (1H, d, J = 1.4 Hz), 7.72 (1H, dd, J = 8.7, 1.8 Hz), 6.87 (1H, s), 5.22 (2H, br s), 4.20 (1H, t, J = 8.0 Hz), 4.12-4.04 (1H, m), 4.03-3.95 (1H, m), 3.90 (1H, t, J = 8.0 Hz), 3.57-3.45 (3H, m), 2.99-2.83 (4H, m), 2.56-2.35 (4H, m), 2.28 (2H, q, J = 7.3 Hz), 2.02-1.86 (4H, m), 1.61-1.47 (4H, m). | 487.3 | 486.29 |
| 206 | 1H-NMR (CDCl3) δ: 9.07 (1H, s), 8.62-8.45 (2H, m), 8.29 (1H, s), 7.73 (1H, d, J = 8.2 Hz), 6.88 (1H, s), 4.20 (1H, t, J = 8.0 Hz), 4.12-4.04 (1H, m), 4.03-3.76 (6H, m), 3.59-3.44 (3H, m), 2.98-2.84 (4H, m), 2.54-2.37 (4H, m), 2.29 (2H, q, J = 7.3 Hz), 1.93-1.65 (6H, m). | 475.3 | 474.29 |
| 207 | 1H-NMR (CDCl3) δ: 9.04 (1H, s), 8.65 (1H, d, J = 9.6 Hz), 8.36 (1H, s), 7.04 (1H, d, J = 10.1 Hz), 6.87 (1H, s), 5.15 (2H, br s), 4.19 (1H, t, J = 8.0 Hz), 4.12-4.04 (1H, m), 4.03-3.95 (1H, m), 3.89 (1H, t, J = 7.8 Hz), 3.62-3.46 (5H, m), 3.08-3.01 (4H, m), 2.28 (2H, q, J = 7.3 Hz), 1.99-1.82 (4H, m), 1.59-1.45 (4H, m). | 474.3 | 473.27 |

TABLE 91

| Compound No. | NMR data | (M + H)+ | Exact Mass |
|---|---|---|---|
| 208 | 1H-NMR (CDCl3) δ: 9.05 (1H, s), 8.62 (1H, d, J = 10.1 Hz), 8.40 (1H, s), 7.07 (1H, d, J = 9.6 Hz), 6.89 (1H, s), 4.19 (1H, t, J = 7.8 Hz), 4.12-4.04 (1H, m), 4.03-3.88 (2H, m), 3.86-3.74 (4H, m), 3.63-3.48 (5H, m), 3.10-3.01 (4H, m), 2.34-2.24 (2H, m), 1.88-1.62 (6H, m). | 462.3 | 461.27 |
| 209 | 1H-NMR (CDCl3) δ: 9.13-9.07 (1H, m), 8.49-8.40 (1H, m), 8.32-8.17 (1H, m), 7.57-7.47 (1H, m), 6.97-6.92 (1H, m), 4.91-4.57 (3H, m), 4.06-3.76 (7H, m), 3.28-3.15 (1H, m), 3.07-2.80 (3H, m), 2.26-2.06 (1H, m), 1.95-1.61 (9H, m), 1.54 (3H, d, J = 6.4 Hz). | 503.4 | 502.28 |
| 210 | 1H-NMR (CDCl3) δ: 9.14-9.06 (1H, m), 8.49-8.40 (1H, m), 8.30-8.14 (1H, m), 7.58-7.47 (1H, m), 6.99-6.90 (1H, m), 4.91-4.81 (1H, m), 4.80-4.65 (2H, m), 4.03-3.79 (6H, m), 3.34-2.79 (7H, m), 2.15-1.66 (8H, m), 1.54 (3H, d, J = 6.3 Hz). | 503.3 | 502.28 |
| 211 | 1H-NMR (DMSO-D6) δ: 10.17-10.05 (1H, m), 9.31 (1H, s), 8.36-8.22 (1H, m), 7.65 (1H, d, J = 8.8 Hz), 7.25 (1H, s), 5.28 (1H, d, J = 4.4 Hz), 4.89-4.52 (3H, m), 3.93-3.59 (7H, m), 3.04-2.71 (3H, m), 2.60-2.44 (1H, m), 1.87-1.13 (15H, m). | 517.4 | 516.30 |
| 212 | 1H-NMR (DMSO-D6) δ: 10.16-10.07 (1H, m), 9.31 (1H, s), 8.36-8.23 (1H, m), 7.66 (1H, d, J = 8.3 Hz), 7.28-7.22 (1H, m), 5.28 (1H, d, J = 4.4 Hz), 4.83-4.54 (4H, m), 4.25-4.04 (2H, m), 3.92-3.64 (6H, m), 3.09-2.73 (3H, m), 2.59-2.49 (1H, m), 1.92-1.59 (8H, m), 1.38 (3H, d, J = 6.8 Hz). | 519.3 | 518.28 |
| 213 | 1H-NMR (CDCl3) δ: 9.13-9.07 (1H, m), 8.51-8.41 (1H, m), 8.34-8,18 (1H, m), 7.58-7.46 (1H, m), 6.99-6.90 (1H, m), 4.92-4.63 (1H, m), 4.39-4.29 (1H, m), 4.25-4.15 (1H, m), 4.06-3.79 (6H, m), 3.27-3.15 (1H, m), 3.11-2.87 (3H, m), 2.31-2.17 (1H, m), 2.08-1.66 (7H, m), 1.54 (3H, d, J = 6.8 Hz). | 519.3 | 518.28 |
| 214 | 1H-NMR (CDCl3) δ: 9.13-9.07 (1H, m), 8.49-8.39 (1H, m), 8.32-8.15 (1H, m), 7.57-7.47 (1H, m), 6.97-6.92 (1H, m), 4.86 (1H, q, J = 6.4 Hz), 4.81-4.64 (2H, m), 4.01-3.76 (6H, m), 3.16-2.62 (7H, m), 1.98-1.46 (13H, m). | 517.4 | 516.30 |
| 215 | 1H-NMR (CDCl3) δ: 9.13-9.07 (1.0H, m), 8.45 (1.0H, d, J = 8.7 Hz), 8.32-8.17 (1.0H, m), 7.59-7.43 (1.0H, m), 6.97-6.92 (1.0H, m), 4.91-4.73 (2.3H, m), 4.51-4.31 (1.7H, m), 4.09-3.42 (8.0H, m), 3.05-2.84 (3.0H, m), 2.38-2.17 (1.0H, m), 1.94-1.70 (6.0H, m), 1.54 (3.0H, d, J = 6.4 Hz). | 489.3 | 488.26 |

TABLE 92

| Compound No. | NMR data | (M + H)+ | Exact Mass |
|---|---|---|---|
| 216 | 1H-NMR (CDCl3) δ: 9.13-9.06 (1H, m), 8.49-8.38 (1H, m), 8.29-8.14 (1H, m), 7.58-7.46 (1H, m), 6.99-6.90 (1H, m), 4.93-4.78 (2H, m), 4.74-4.59 (1H, m), 4.37-4.26 (1H, m), 4.12-3.76 (7H, m), 3.76-3.63 (1H, m), 3.25-3.23 (6H, m), 1.94-1.68 (6H, m), 1.54 (3H, d, J = 6.3 Hz). | 519.3 | 518.28 |
| 217 | 1H-NMR (DMSO-D6) δ: 9.99 (1H, s), 9.31 (1H, s), 8.26 (1H, d, J = 8.4 Hz), 7.52 (1H, d, J = 8.7 Hz), 7.26 (1H, s), 6.00 (1H, br s), 5.26 (1H, br s), 4.66-4.67 (1H, br m), 3.60-3.66 (4H, m), 3.82 (2H, s),2.72-2.93 (5H, m), 2.56-2.60 (2H, m), 1.72-1.73 (6H, br m), 1.69-1.73 (6H, br, m), 1.39 (3H, d, J = 6.3 Hz). | 449.1 | 448.27 |
| 218 | 1H-NMR (DMSO-D6): δ: 10.04 (1H, s), 9.28 (1H, s), 8.29 (1H, d, J = 9.0 Hz), 8.08 (1H, d, J = 2.9 Hz), 7.51 (1H, d, J = 12 Hz), 7.21 (1H, s), 5.23 (3H, d, J = 18 Hz), 4.63-4.67 (1H, m), 4.43 (2H, s), 4.02-4.67 (1H, m), 2.79-2.82 (2H, s), 2.26-2.28 (4H, m), 1.96(2H, br s), 1.76 (6H, s), 1.46 (4H, d, J = 9 Hz), 1.39 (3H, d, J = 6 Hz) | 506.30 | 505.28 |
| 219 | 1H-NMR (DMSO-D6) δ: 9.85 (1H, s), 9.23 (1H, s), 8.05 (1H, s), 7.86 (1H, d, J = 9 Hz), 7.04 (1H, s), 5.34-5.52 (1H, br s), 5.19 (1H, d, J = 3 Hz), 4.61-4.64 (1H, m), 3.89-4.38 (6H, m), 3.49 (2H, d, J = 9 Hz), 2.73 (2H, s), 2.19 (4H, d, J = 6 Hz) 2.04 (2H, s), 1.64 (2H, d, J = 9 Hz), 1.39 (3H, d, J = 6 Hz) | 498.30 | 497.26 |
| 220 | 1H-NMR (DMSO-D6) δ: 9.99 (1H, s), 9.27 (1H, s), 8.27 (1H, d, J = 9 Hz), 8.05-8.06 (1H, s), 7.49 (1H, d, J = 12 Hz), 5.19-5.25 (3H, m), 4.61-4.68 (1H, m), 4.40-4.45 (1H, m), 2.96 (2H, d, J = 12 Hz), 2.62 (2H, d, J = 3 Hz), 1.93 (2H, d, J = 9 Hz), 1.94 (4H, s), 1.37-1.52 (9H, m) | 462.25 | 461.25 |
| 221 | 1H-NMR (DMSO-D6) δ: 9.81 (1H, s), 9.22 (1H, s), 8.03 (1H, s), 7.85 (1H, d, J = 9 Hz), 7.49 (1H, d, J = 9 Hz), 7.04 (1H, s), 5.34-5.52 (1H, br s), 5.18 (1H, d, J = 6 Hz), 4.61-4.64 (1H, m), 4.42 (1H, s), 4.36-4.41 (4H, m), 2.95 (2H, d, J = 18 Hz), 2.60 (2H, d, J = 3 Hz), 2.24-2.25 (3H, m), 2.10 (2H, d, J = 15 Hz), 1.38-1.50 (5H, m) | 454.25 | 453.23 |
| 222 | 1H-NMR (DMSO-d6) δ: 9.30 (1H, s), 8.21(1H, d, J = 9.0 Hz), 8.06 (1H, d, J = 3.0 Hz), 7.48-7.52 (1H, m), 7.27 (1H, s), 4.72-4.96 (1H, m), 4.65-4.69 (1H, m), 4.39-4.40 (1H, m), 4.01-4.07 (2H, m), 3.87-3.93 (1H, m), 3.65-3.73 (1H, br m), 3.49-3.53 (2H, m), 2.75 (2H, br s), 2.32-2.45 (2H, m), 2.29-2.32 (2H, m), 1.84-2.07 (5H, br m), 1.64-1.67 (3H, m), 1.39 (3H, d, J = 3.0 Hz) | 512.25 | 511.27 |

TABLE 93

| Compound No. | NMR data | (M + H)+ | Exact Mass |
|---|---|---|---|
| 223 | 1H-NMR (CDCl3) δ: 9.12-9.05 (1H, m), 8.52-8.42 (1H, m), 8.29-8.12 (1H, m), 7.55-7.44 (1H, m), 6.96-6.88 (1H, m), 5.41-5.14 (2H, br m), 4.90-4.68 (3H, m), 4.11-3.83 (3H, m), 3.29-3.13 (2H, m), 3.04-2.91 (2H, m), 2.45-2.11 (5H, m), 2.07-1.45 (13H, m). | 529.3 | 528.30 |
| 224 | 1H-NMR (CDCl3) δ: 9.12-9.05 (1H, m), 8.51-8.42 (1H, m), 8.28-8.12 (1H, m), 7.54-7.43 (1H, m), 6.95-6.88 (1H, m), 5.36-5.18 (2H, br m), 4.89-4.69 (3H, m), 4.11-3.83 (3H, m), 3.27-3.12 (2H, m), 3.03-2.91 (2H, m), 2.45-2.10 (5H, m), 2.06-1.45 (13H, m). | 529.4 | 528.30 |
| 225 | 1H-NMR (DMSO-D6) δ: 10.22-10.14 (1H, m), 9.29 (1H, s), 8.30-8.18 (1H, m), 7.64 (1H, d, J = 8.7 Hz), 7.22 (1H, s), 5.32-5.13 (3H, m), 4.71-4.57 (3H, m), 3.87-3.74 (2H, m), 3.37 (2H, t, J = 13.5 Hz), 2.92-2.73 (3H, m), 2.66-2.29 (2H, m), 2.26-2.19 (3H, m), 2.08-1.86 (2H, m), 1.86-1.67 (4H ,m), 1.55-1.34 (7H, m). | 529.3 | 528.30 |
| 226 | 1H-NMR (CDCl3) δ: 9.10-9.04 (1H, m), 8.51-8.43 (1H, m), 8.22-8.08 (1H, m), 7.54-7.43 (1H, m), 6.95-6.89 (1H, m), 5.37-5.16 (2H, br m), 4.89-4.62 (3H, m), 4.05-3.79 (3H, m), 3.41-3.28 (1H, m), 3.03-2.90 (3H, m), 2.86-2.76 (1H, m), 2.72-2.59 (1H, m), 2.53-2.43 (1H, m), 2.42-2.36 (3H, m), 2.23-2.07 (2H, m), 2.02-1.85 (4H, m), 1.61-1.48 (7H, m). | 529.4 | 528.30 |
| 227 | | 545.3 | 544.29 |
| 228 | 1H-NMR (CDCl3) δ: 9.10-9.05 (1H, m), 8.50-8.41 (1H, m), 8.23-8.08 (1H, m), 7.53-7.44 (1H, m), 6.94-6.89 (1H, m), 5.37-5.17 (2H, br m), 4.88-4.70 (3H, m), 4.03-3.88 (3H, m), 3.47-3.40 (2H, m), 3.02-2.91 (2H, m), 2.66-2.54 (4H, m), 2.00-1.88 (4H, m), 1.85-1.60 (5H, m), 1.60-1.49 (6H, m). | 529.3 | 528.30 |
| 229 | 1H-NMR (DMSO-D6) δ: 10.24-10.10 (1H, m), 9.31-9.25 (1H, m), 8.30-8.15 (1H, m), 7.71-7.36 (2H, m), 7.25-7.16 (1H, m), 5.63-5.02 (4H, m), 4.71-4.48 (3H, m), 4.33-4.18 (1H, m), 3.88-3.57 (5H, m), 3.22-2.70 (3H, m), 1.87-1.66 (4H, m), 1.56-1.25 (8H, m). | 531.3 | 530.28 |
| 230 | | 515.3 | 514.28 |
| 231 | 1H-NMR (CDCl3) δ: 9.11-9.05 (1H, m), 8.51-8.42 (1H, m), 8.23-8.11 (1H, m), 7.53-7.45 (1H, m), 6.95- | 547.4 | 546.29 |

TABLE 93-continued

| Compound No. | NMR data | (M + H)+ | Exact Mass |
|---|---|---|---|
| | 6.89 (1H, m), 5.38-5.06 (3H, m), 4.89-4.68 (3H, m), 4.06-3.83 (3H, m), 3.57-3.42 (2H, m), 3.06-2.83 (5H, m), 2.67-2.56 (1H, m), 2.29-1.84 (6H, m), 1.79-1.47 (7H, m). | | |

TABLE 94

| Compound No. | NMR data | (M + H)+ | Exact Mass |
|---|---|---|---|
| 232 | 1H-NMR (CDCl3) δ: 9.10-9.05 (1H, m), 8.52-8.43 (1H, m), 8.23-8.11 (1H, m), 7.53-7.45 (1H, m), 6.95-6.90 (1H, m), 5.37-5.16 (2H, br m), 4.88-4.66 (3H, m), 4.39-4.28 (1H, m), 4.05-3.81 (3H, m), 3.62-3.51 (2H, m), 3.10-2.85 (4H, m), 2.84-2.76 (1H, m), 2.66-2.56 (1H, m), 2.20-1.45 (13H, m). | 545.3 | 544.29 |
| 233 | 1H-NMR (CDCl3) δ: 9.10-9.05 (1H, m), 8.52-8.43 (1H, m), 8.23-8.10 (1H, m), 7.54-7.45 (1H, m), 6.95-6.90 (1H, m), 5.37-5.16 (2H, br m), 4.88-4.66 (3H, m), 4.39-4.78 (1H, m), 4.05-3.81 (3H, m), 3.62-3.51 (2H, m), 3.09-2.86 (4H, m), 2.84-2.76 (1H, m), 2.66-2.56 (1H, m), 2.21-1.47 (13H, m). | 545.4 | 544.29 |
| 234 | 1H-NMR (CDCl3) δ: 9.10-9.05 (1H, m), 8.53-8.45 (1H, m), 8.24-8.10 (1H, m), 7.54-7.45 (1H, m), 6.95-6.89 (1H, m), 5.36-5.16 (2H, br m), 4.88-4.73 (4H, m), 4.59-4.51 (3H, m), 4.10-3.93 (2H, m), 3.74 (1H, t, J = 5.9 Hz), 3.58-3.52 (2H, m), 3.04-2.91 (2H, m). 2.03-1.84 (4H, m), 1.61-1.48 (7H, m). | 531.3 | 530.28 |
| 235 | 1H-NMR (CDCl3) δ: 9.10-9.05 (1H, m), 8.52-8.43 (1H, m), 8.20-8.06 (1H, m), 7.52-7.44 (1H, m), 6.95-6.89 (1H, m), 5.36-5.05 (3H, m), 4.88-4.79 (1H, m), 4.75-4.61 (2H, m), 4.03-3.75 (5H, m), 3.53-3.46 (2H, m), 3.38-3.24 (2H, m), 3.03-2.89 (2H, m), 2.02-1.85 (4H, m), 1.60-1.49 (7H, m). | 533.3 | 532.27 |
| 236 | 1H-NMR (CDCl3) δ: 9.10-9.05 (1H, m), 8.51-8.43 (1H, m), 8.20-8.06 (1H, m), 7.52-7.43 (1H, m), 6.95-6.89 (1H, m), 5.36-5.16 (2H, br m), 4.88-4.58 (7H, m), 4.06-3.72 (3H, m), 3.56-3.50 (4H, m), 3.40-3.34 (2H, m), 3.02-2.88 (2H, m), 2.01-1.87 (4H, m), 1.60-1.49 (7H, m). | 533.3 | 532.27 |
| 237 | 1H-NMR (CDCl3) δ: 9.11-9.05 (1H, m), 8.52-8.42 (1H, m), 8.27-8.12 (1H, m), 7.50 (1H, d, J = 8.7 Hz), 6.95-6.89 (1H, m), 5.38-4.67 (5H, m), 4.34-3.82 (3H, m), 3.12-2.90 (4H, m), 2.31-1.49 (20H, m), 1.42-1.22 (1H, m). | 543.4 | 542.31 |
| 238 | 1H-NMR (CDCl3) δ: 9.11-9.05 (1H, m), 8.52-8.42 (1H, m), 8.25-8.10 (1H, m), 7.50 (1H, d, J = 8.7 Hz), 6.95-6.89 (1H, m), 5.42-4.68 (5H, m), 4.34-3.85 (3H, m), 3.07-2.89 (4H, m), 2.28-1.49 (20H, m), 1.39-1.21 (1H, m). | 543.4 | 542.31 |
| | 1H-NMR (CDCl3) δ: 9.10-9.05 (1H, m), 8.52-8.43 (1H, m), 8.23-8.08 (1H, m), 7.54-7.42 (1H, m), 6.95-6.90 (1H, m), 5.36-5.16 (2H, br m), 4.89-4.43 (3H, m), 4.14-3.79 (2H, m), 3.73-3.48 (4H, m), 3.38-3.27 (2H, m), 2.93 (2H, t, J = 5.7 Hz), 2.37-2.31 (3H, m), 2.04-1.48 (11H, m). | 515.4 | 514.28 |

TABLE 95

| Compound No. | NMR data | (M + H)+ | Exact Mass |
|---|---|---|---|
| 240 | 1H-NMR (CDCl3) δ: 9.12 (1H, br s), 8.58-7.92 (2H, m), 7.42-7.28 (1H, br m), 6.92 (1H, s), 5.38-5.12 (2H, br m), 4.84 (1H, q, J = 6.4 Hz), 3.67 (2H, t, J = 6.4 Hz), 3.54-3.39 (2H, m). 3.23-3.12 (1H, m), 3.09-2.91 (4H, m), 2.81-2.59 (2H, m), 2.41 (3H, s), 2.02-1.72 (4H, m), 1.61-1.46 (7H, m). | 487.3 | 486.29 |

TABLE 95-continued

| Compound No. | NMR data | (M + H)+ | Exact Mass |
|---|---|---|---|
| 241 | 1H-NMR (DMSO-D6) δ: 9.95 (1H, s), 9.29 (1H, s), 8.27 (1H, d, J = 9 Hz), 8.26 (1H, d, J = 3 Hz), 7.48-7.52 (1H, m), 7.24 (1H, s), 5.25 (1H, d, J = 4.2 Hz), 4.64-4.68 (1H, m), 4.28-4.32 (4H, m), 3.08-3.12 (1H, br m), 2.73-2.80 (1H, m), 2.54-2.61 (2H, m), 2.00 (1H, br s), 1.69-1.71 (7H, br m) 1.43-1.60 (2H, m), 1.39 (3H, d, J = 6.6 Hz). | 450.20 | 449.25 |
| 242 | 1H-NMR (DMSO-D6) δ: 10.01 (1H, s), 9.28 (1H, s), 8.28 (1H, d, J = 9 Hz), 8.06 (1H, d, = 3 Hz), 7.48-7.52 (1H, m), 7.21 (1H, s), 5.24 (1H, d, J = 4.5 Hz), 5.19 (1H, br s), 4.63-4.66 (1H, m), 4.25-4.30 (1H, m), 3.09 (1H, d, J = 12.3 Hz), 2.73-2.80 (1H m), 2.54 (2H, br s), 2.02-2.05 (1H, br m), 1.59-1.76 (5H, m), 1.40-1.55 (9H, m). | 462.20 | 461.25 |
| 243 | 1H-NMR (DMSO-D6) δ: 9.98 (1H, s), 9.31 (1H, s), 8.19 (1H, d, J = 9 Hz), 8.06 (1H, d, J = 2.7 Hz), 7.46-7.50 (1H, m), 7.27 (1H, s), 5.27 (1H, d, J = 4.5 Hz), 4.73-4.92 (1H, br m), 4.66-4.70 (1H, m), 4.38-4.42 (1H, m), 3.78-4.11 (4H, m), 2.92-2.99 (2H, br m), 2.56-2.60 (2H, m), 1.83-2.20 (6H, m), 1.66 (1H, br s), 1.38-1.51 (5H, m). | 468.25 | 467.24 |
| 244 | | 449.15 | 448.23 |
| 245 | 1H-NMR (DMSO-D6) δ: 10.01 (1H, s), 9.24 (1H, s), 8.28 (1H, d, J = 2.4 Hz), 8.01 (1H, d, J = 8.7 Hz), 7.76 (1H, dd, J1 = 12.0 Hz, J2 = 2.7 Hz), 6.98 (1H, s), 5.05 (1H, d, J = 5.1 Hz), 4.87-4.89 (1H, m), 4.38-4.40 (1H, m), 4.16-4.18 (1H, m), 3.88-3.92 (1H, m), 3.61-3.65 (2H, m), 3.41 (2H, s), 3.01-3.05 (2H, m), 2.85 (1H, br s), 1.83-2.09 (4H, m), 1.62-1.69 (2H, m), 1.674 (3H, d, J = 6.3 Hz), 0.86-0.91 (3H, m) | 463.20 | 462.25 |
| 246 | 1H-NMR (DMSO-D6) δ: 10.01 (1H, s), 9.24 (1H, s), 8.28 (1H, d, J = 2.4 Hz), 8.01 (1H, d, J = 8.7 Hz), 7.76 (1H, dd, J1 = 12.0 Hz, J2 = 2.7 Hz), 6.98 (1H, s), 5.05 (1H, d, J = 5.1 Hz), 4.87-4.89 (1H, m), 4.38-4.40 (1H, m), 4.16-4.18 (1H, m), 3.88-3.92 (1H, m), 3.61-3.65 (2H, m), 3.41 (2H, s), 3.01-3.05 (2H, m), 2.85 (1H, br s), 1.83-2.09 (4H, m), 1.62-1.69 (2H, m), 1.674 (3H, d, J = 6.3 Hz), 0.86-0.91 (3H, m) | 463.20 | 462.25 |

TABLE 96

| Compound No. | NMR data | (M + H)+ | Exact Mass |
|---|---|---|---|
| 247 | 1H-NMR (DMSO-D6) δ: 9.92 (1H, s), 9.23 (1H, s), 8.19 (1H, s), 7.95 (1H, d, J = 9.0 Hz), 7.70 (1H, d, J = 9.0 Hz), 6.98 (1H, s), 5.06 (1H, d, J = 6 Hz), 4.89 (1H, m), 4.4 (2H, m), 4.18-4.14 (1H, m), 3.91-3.88 (1H, m), 3.44 (4H, br s), 2.51 (10H, br s), 2.11-1.83 (4H, m), 1.69-1.62 (2H, m), 1.16 (3H, d, J = 6 Hz), 0.91-0.86 (3H, m). | 507.30 | 506.31 |
| 248 | 1H-NMR (DMSO-D6) δ: 9.92 (1H, s), 9.23 (1H, s), 8.20 (1H, s), 7.98 (1H, d, J = 9.0 Hz), 7.70 (1H, d, J = 6.0 Hz), 7.02 (1H, s), 5.12 (1H, d, J = 6 Hz), 4.85-4.83 (1H, m), 4.45-4.43 (1H, m), 4.20-4.16 (1H, m), 3.91-3.87 (1H, m), 3.48 (4H, br s), 2.50 (10H, br s), 2.12-1.83 (4H, m), 1.67-1.60 (2H, m), 1.16 (3H, d, J = 6 Hz), 0.89-0.84 (3H, m). | 507.30 | 506.31 |
| 249 | 1H-NMR (DMSO-D6) δ: 10.19 (1H, s), 9.34 (1H, s), 8.40 (1H, d, J = 9 Hz), 8.25 (1H, s), 7.74-7.78 (1H, m), 7.27 (1H, s), 5.27 (1H, d, J = 3 Hz) 4.64-4.72 (2H, m), | 507.25 | 506.28 |

TABLE 96-continued

| Compound No. | NMR data | (M + H)⁺ | Exact Mass |
|---|---|---|---|
| 250 | 3.70-3.88 (4H, m), 3.47-3.49 (4H, m), 3.32-3.38 (2H, m), 3.01 (2H, s), 2.72-2.73 (2H, s), 1.68-1.74 (6H, m), 1.40 (3H, d, J = 6 Hz). 1H-NMR (DMSO-D6) δ: 9.85 (1H, s), 9.28 (1H, s), 8.04 (1H, d, J = 3 Hz), 7.85 (1H, d, J = 9.3 Hz), 7.47-7.51 (1H, m), 7.04 (1H, s), 5.34-5.52 (1H, br m), 5.19 (1H, d, J = 4.8 Hz), 4.61-4.64 (1H, m), 3.89-4.32 (5H, m), 3.05-3.15 (1H, br m), 2.75-2.79 (2H, m), 2.54 (2H, br s), 2.03-2.24 (3H, br m), 1.68-1.71 (1H, m), 1.45-1.53 (2H, m), 1.39 (3H, d, J = 6.6 Hz). | 454.15 | 453.23 |
| 251 | 1H-NMR (DMSO-d6) δ: 10.00 (1H, s), 9.31 (1H, s), 8.20(1H, d, J = 9.3 Hz), 8.06 (1H, d, J = 3.0 Hz), 7.46-7.50 (1H, m), 7.27 (1H, s), 5.27 (1H, d, J = 4.5 Hz), 4.75-5.01 (1H, m), 4.66-4.70 (1H, m), 4.23-4.26 (1H, m), 3.78-4.19 (4H, m), 3.07-3.12 (1H, m), 2.72-2.78 (1H, m), 2.50-2.55 (2H, m), 1.97-2.03 (4H, m), 1.64-1.83 (2H, m), 1.49-1.59 (2H, m), 1.38-1.47 (3H, m). | 468.20 | 467.24 |
| 252 | 1H-NMR (DMSO-d6) δ: 9.97 (1H, s), 9.29 (1H, s), 8.27(1H, d, J = 9.0 Hz), 8.06 (1H, d, J = 2.7 Hz), 7.49-7.53 (1H, m), 7.24 (1H, s), 5.25 (1H, d, J = 4.8 Hz), 4.64-4.68 (1H, m), 4.35-4.39 (2H, m), 3.71-3.77 (4H, m), 3.46-3.52 (2H, m), 3.01 (1H, d, J = 11.4 Hz), 2.65-2.69 (1H, m), 2.40-2.45 (2H, m), 2.12-2.18 (2H, m), 1.97-2.08 (1H, m), 1.62-1.78 (7H, br s), 1.48-1.60 (1H, m), 1.30-1.45 (4H, m). | 494.20 | 493.28 |

TABLE 97

| Compound No. | NMR data | (M + H)⁺ | Exact Mass |
|---|---|---|---|
| 253 | 1H-NMR (DMSO-d6) δ: 10.02 (1H, s), 9.28 (1H, s), 8.28 (1H, d, J = 9.0 Hz), 8.07 (1H, d, J = 2.4 Hz), 7.49-7.53 (1H, m), 7.22 (1H, s), 5.19-5.26 (3H, m), 4.61-4.69 (1H, m), 4.39 (2H, br s), 3.49 (2H, d, J = 3.9 Hz), 3.01 (2H, d, J = 8.7 Hz), 2.67-2.73 (1H, m), 2.35-2.45 (2H, s), 1.98-2.27 (3H, m), 1.77 (5H, br m), 1.38-1.56 (9H, m). | 506.30 | 505.28 |
| 254 | 1H-NMR (DMSO-d6) δ: 9.83 (1H, s), 9.19 (1H, s), 8.00 (1H, d, J = 3.0 Hz), 7.82 (1H, d, J = 9.0 Hz), 7.45-7.49 (1H, m), 7.01 (1H, s), 5.31-5.49 (1H, m), 5.15 (1H, d, J = 4.8 Hz), 4.57-4.61 (1H, m), 3.87-4.36 (6H, m), 3.42-3.48 (2H, m), 2.97 (1H, d, J = 7.2 Hz), 2.62-2.67 (1H, m), 2.37-2.47 (2H, m), 1.99-2.23 (5H, m), 1.47-1.59 (1H, m), 1.34-1.36 (3H, m). | 498.20 | 497.26 |
| 255 | 1H-NMR (DMSO-D6) δ: 10.03 (1H, s), 9.31 (1H, s), 8.20 (1H, d, J = 9 Hz), 8.06 (1H, d, J = 2.7 Hz), 7.48-7.52 (1H, m), 7.27 (1H, s), 5.28 (1H, d, J = 4.5 Hz), 4.80-4.96 (1H, br m), 4.66-4.70 (1H, m), 4.37 (2H, br s), 3.78-4.10 (4H, m), 3.49 (2H, d, J = 6.4 Hz), 3.02-3.00 (1H, m), 2.66-2.73 (1H, m), 2.49 (2H, br m), 1.97-2.27 (5H, m), 1.53-1.97 (4H, m), 1.38-1.42 (4H, m). | 512.25 | 511.27 |
| 256 |  | 461.3 | 460.23 |
| 257 |  | 449.3 | 448.23 |
| 258 |  | 463.3 | 462.25 |
| 259 |  | 569.3 | 568.26 |
| 260 |  | 463.3 | 462.25 |
| 261 |  | 463.21 | 462.25 |
| 262 | 1H-NMR (CDCl3) δ: 9.09 (1H, s), 8.51-8.43 (1H, m), 8.27-8.18 (1H, m), 7.53-7.44 (1H, m), 6.95-6.90 (1H, m), 5.36-5.18 (2H, br m), 4.89-4.71 (3H, m), 4.01-3.89 (3H, m), 3.79-3.64 (1H, m), 3.33-3.76 (2H, m), 3.07-2.91 (2H, m), 2.86-2.73 (2H, m), 2.34-2.22 (2H, m), 2.02-1.81 (6H, m), 1.74-1.41 (9H, m). | 559.4 | 558.31 |
| 263 | 1H-NMR (CDCl3) δ: 9.10-9.05 (1H, m), 8.52-8.42 (1H, m), 8.23-8.07 (1H, m), 7.53-7.44 (1H, m), 6.95-6.90 (1H, m), 5.37-5.17 (2H, br m), 4.88-4.70 (3H, m), 4.02-3.86 (3H, m), 3.65-3.55 (2H, m), 3.34-3.28 (2H, m), 3.06-2.90 (2H, m), 2.82-2.32 (10H, m), 2.02-1.86 (4H, m), 1.62-1.49 (7H, m). | 588.4 | 587.33 |

TABLE 98

| Compound No. | NMR data | (M + H)⁺ | Exact Mass |
|---|---|---|---|
| 264 | 1H-NMR (CDCl3) δ: 9.10-9.05 (1H, m), 8.52-8.42 (1H, m), 8.20-8.05 (1H, m), 7.53-7.44 (1H, m), 6.95-6.89 (1H, m), 5.36-5.18 (2H, br m), 4.88-4.71 (3H, m), 4.02-3.88 (3H, m), 3.34-3.27 (2H, m), 3.08-2.89 (2H, m), 2.78-2.20 (11H, m), 2.02-1.87 (4H, m), 1.61-1.50 (7H, m). | 558.4 | 557.32 |
| 265 | 1H-NMR (CDCl3) δ: 9.10-9.05 (1H, m), 8.51-8.42 (1H, m), 8.22-8.09 (1H, m), 7.52-7.43 (1H, m), 6.95-6.89 (1H, m), 5.37-5.17 (2H, br m), 4.84 (1H, q, J = 6.4 Hz), 4.73-4.61 (2H, m), 3.95-3.74 (2H, m), 3.45-3.26 (10H, m), 3.02-2.89 (2H, m), 2.31-2.24 (3H, m), 2.01-1.86 (4H, m), 1.60-1.50 (7H, m). | 570.4 | 569.32 |
| 266 | 1H-NMR (CDCl3) δ: 9.10-9.05 (1H, m), 8.48-8.39 (1H, m), 8.17-8.03 (1H, m), 7.55-7.45 (1H, m), 6.97-6.91 (1H, m), 4.91-4.81 (1H, m), 4.80-4.58 (6H, m), 4.03 (1H, br s), 3.95-3.73 (6H, m), 3.56-3.50 (4H, m), 3.40-3.34 (2H, m), 3.01-2.88 (2H, m), 1.92-1.70 (6H, m), 1.53 (3H, d, J = 6.4 Hz). | 545.3 | 544.29 |
| 267 | 1H-NMR (CDCl3) δ: 9.10-9.05 (1H, m), 8.51-8.42 (1H, m), 8.23-8.10 (1H, m), 7.52-7.44 (1H, m), 6.95-6.89 (1H, m), 5.34-5.19 (2H, br m), 4.84 (1H, q, J = 6.4 Hz), 4.73-4.62 (2H, m), 4.24-4.12 (1H, m), 4.04-3.76 (3H, m), 3.41-3.28 (6H, m), 3.03-2.87 (2H, m), 2.59-2.46 (2H, m), 2.09-1.86 (6H, m), 1.67-1.52 (7H, m). | 571.4 | 570.31 |
| 268 | 1H-NMR (CDCl3) δ: 9.11-9.05 (1H, m), 8.48-8.38 (1H, m), 8.21-8.08 (1H, m), 7.54-7.46 (1H, m), 6.97-6.90 (1H, m), 4.86 (1H, q, J = 6.4 Hz), 4.74-4.62 (2H, m), 4.23-3.98 (2H, m), 3.94-3.76 (6H, m), 3.41-3.28 (6H, m), 3.03-2.86 (2H, m), 2.58-2.46 (2H, m), 2.09-1.97 (2H, m), 1.92-1.58 (6H, m), 1.54 (3H, d, J = 6.4 Hz). | 559.4 | 558.31 |
| 269 | 1H-NMR (CDCl3) δ: 9.12-9.06 (1H, m), 8.49-8.39 (1H, m), 8.24-8.08 (1H, m), 7.55-7.46 (1H, m), 6.97-6.91 (1H, m), 5.29-5.05 (1H, m), 4.91-4.80 (1H, m), 4.76-4.60 (2H, m), 4.05 (1H, br s), 3.96-3.75 (8H, m), 3.53-3.46 (2H, m), 3.38-3.23 (2H, m), 3.03-2.89 (2H, m), 1.91-1.71 (6H, m), 1.54 (3H, d, J = 6.4 Hz). | 521.3 | 520.27 |
| 270 | 1H-NMR (CDCl3) δ: 9.11-9.05 (1H, m), 8.48-8.38 (1H, m), 8.24-8.09 (1H, m), 7.54-7.47 (1H, m), 6.96-6.91 (1H, m), 4.86 (1H, q, J = 6.3 Hz), 4.74-4.66 (2H, m), 4.06 (1H, br s), 3.96-3.78 (6H, m), 3.41-3.29 (6H, m), 3.03-2.88 (2H, m), 2.17-2.06 (2H, m), 1.91-1.71 (6H, m), 1.54 (3H, d, J = 6.4 Hz). | 503.4 | 502.28 |

TABLE 99

| Compound No. | NMR data | (M + H)⁺ | Exact Mass |
|---|---|---|---|
| 271 | 1H-NMR (CDCl3) δ: 9.16 (1H, s), 8.57 (1H, s), 8.43 (1H, d, J = 8.7 Hz), 8.31 (1H, d, J = 2.3 Hz), 7.75 (1H, dd, J = 8.7, 2.3 Hz), 7.07 (1H, s), 4.88 (1H, q, J = 6.4 Hz), 4.31-4.19 (2H, m), 3.83-3.70 (2H, m), | 518.3 | 517.29 |

TABLE 99-continued

| Compound No. | NMR data | (M + H)+ | Exact Mass |
|---|---|---|---|
| | 3.61 (2H, t, J = 5.5 Hz), 3.53 (2H, s), 3.02-2.92 (1H, m), 2.78-2.32 (10H, m), 2.27-2.07 (4H, m), 1.55 (3H, d, J = 6.4 Hz). | | |
| 272 | 1H-NMR (DMSO-D6) δ: 10.36 (1H, s), 9.37 (1H, s), 8.35-8.29 (2H, m), 7.80 (1H, dd, J = 8.7, 2.7 Hz), 7.32 (1H, d, J = 0.9 Hz), 5.32 (1H, d, J = 4.6 Hz), 4.73-4.63 (1H, m), 4.14-3.97 (2H, m), 3.73-3.55 (4H, m), 3.40 (2H, s), 3.21-3.11 (1H, m), 3.03 (2H, t, J = 5.3 Hz), 2.83 (1H, br s), 2.15-2.01 (2H, m), 1.99-1.85 (2H, m), 1.39 (3H, d, J = 6.4 Hz). | 474.3 | 473.23 |
| 273 | 1H-NMR (CDCl3) δ: 9.16 (1H, s), 8.53 (1H, s), 8.47 (1H, d, J = 10.1 Hz), 7.11-7.04 (2H, m), 4.87 (1H, q, J = 6.4 Hz), 4.29-4.16 (2H, m), 3.80-3.67 (2H, m), 3.64-3.55 (4H, m), 3.11-3.02 (4H, m), 2.99-2.89 (1H, m), 2.23-2.01 (4H, m), 1.55 (3H, d, J = 6.4 Hz). | 461.3 | 460.24 |
| 274 | 1H-NMR (DMSO-D6) δ: 10.04 (1H, s), 9.33 (1H, s), 8.10 (1H, d, J = 8.2 Hz), 7.47 (1H, d, J = 8.2 Hz), 7.30 (1H, s), 5.31 (1H, d, J = 4.6 Hz), 4.73-4.62 (1H, m), 4.17-3.99 (2H, m), 3.83 (2H, s), 3.71-3.52 (2H, m), 3.22-3.12 (1H, m), 3.02 (2H, t, J = 5.9 Hz), 2.71 (2H, t, J = 5.7 Hz), 2.14-2.01 (2H, m), 1.99-1.84 (2H, m), 1.40 (3H, d, J = 6.4 Hz). | 431.3 | 430.22 |
| 275 | 1H-NMR (CDCl3) δ: 9.06 (1H, s), 8.55 (1H, d, J = 8.7 Hz), 8.39 (1H, s), 8.27 (1H, d, J = 2.3 Hz), 7.74 (1H, dd, J = 8.2, 2.3 Hz), 6.87 (1H, s), 5.11-4.96 (4H, m), 4.43-4.32 (1H, m), 3.98-3.87 (4H, m), 3.61 (2H, t, J = 5.3 Hz), 3.52 (2H, s), 3.02-2.23 (10H, m), 1.95-1.70 (6H, m). | 505.4 | 504.30 |
| 276 | 1H-NMR (CDCl3) δ: 9.09 (1H, s), 8.67-8.57 (2H, m), 8.25 (1H, d, J = 2.3 Hz), 7.65 (1H, dd, J = 8.9, 2.5 Hz), 6.87 (1H, s), 5.10-5.04 (2H, m), 5.03-4.97 (2H, m), 4.42-4.33 (1H, m), 3.96-3.83 (6H, m), 3.21-3.11 (4H, m), 2.93-2.85 (2H, m), 1.92-1.70 (6H, m). | 475.3 | 474.25 |
| 277 | 1H-NMR (CDCl3) δ: 9.05 (1H, s), 8.62 (1H, d, J = 10.1 Hz), 8.39 (1H, br s), 7.08 (1H, d, J = 10.1 Hz), 6.86 (1H, s), 5.10-4.95 (4H, m), 4.42-4.31 (1H, m), 3.95-3.83 (4H, m), 3.65-3.55 (4H, m), 3.12-3.02 (4H, m), 2.02-1.70 (6H, m). | 448.3 | 447.25 |

TABLE 100

| Compound No. | NMR data | (M + H)+ | Exact Mass |
|---|---|---|---|
| 278 | 1H-NMR (DMSO-D6) δ: 10.06 (1H, s), 9.33 (1H, s), 8.11 (1H, d, J = 8.2 Hz), 7.51 (1H, d, J = 8.7 Hz), 7.30 (1H, d, J = 0.9 Hz), 5.30 (1H, d, J = 4.6 Hz), 4.73-4.63 (1H, m), 4.49 (1H, t, J = 5.3 Hz), 4.18-4.01 (2H, m), 3.71-3.52 (6H, m), 3.22-3.11 (1H, m), 2.89-2.74 (4H, m), 2.59 (2H, t, J = 6.2 Hz), 2.15-2.01 (2H, m), 1.99-1.84 (2H, m), 1.40 (3H, d, J = 6.4 Hz). | 475.3 | 474.25 |
| 279 | 1H-NMR (DMSO-D6) δ: 10.08 (1H, s), 9.33 (1H, s), 8.11 (1H, d, J = 8.2 Hz), 7.52 (1H, d, J = 8.2 Hz), 7.30 (1H, d, J = 0.9 Hz), 5.30 (1H, d, J = 4.6 Hz), 4.73-4.62 (1H, m), 4.18-4.00 (2H, m), 3.68-3.52 (2H, m), 3.51-3.38 (4H, m), 3.21-3.11 (1H, m), 3.08-2.99 (1H, m), 2.89-2.77 (4H, m), 2.64-2.55 (2H, m), 2.24 (3H, s), 2.14-2.01 (2H, m), 1.99-1.84 (2H, m), 1.40 (3H, d, J = 6.4 Hz). | 500.3 | 499.28 |

TABLE 100-continued

| Compound No. | NMR data | (M + H)+ | Exact Mass |
|---|---|---|---|
| 280 | 1H-NMR (DMSO-D6) δ: 9.95 (1H, s), 9.30 (1H, s), 8.18 (1H, d, J = 6 Hz), 7.46 (1H, d, J = 9 Hz), 7.25 (1H, s), 5.26 (1H, d, J = 6 Hz), 4.65-4.69 (1H, m), 4.37-4.41 (1H, m), 4.00 (1H, d, J = 3 Hz), 3.70-3.82 (4H, br s), 3.48-3.58 (3H, m), 3.08-3.10 (1H, m), 2.51-2.58 (1H, m), 2.40-2.46 (2H, m), 2.08-2.13 (2H, br s), 1.63-1.73 (8H, m), 1.39 (3H, d, J = 6 Hz) | 476.20 | 475.27 |
| 281 | 1H-NMR (DMSO-d6) δ: 10.21 (1H, s), 9.29 (1H, s), 8.14 (1H, d, J = 9.0 Hz), 7.75 (1H, dd, J1 = 3.0 Hz, J2 = 3.0 Hz), 7.11 (1H, s), 5.40-5.45 (2H, m), 5.21 (1H, d, J = 3.0 Hz), 4.61-4.65 (1H, m), 3.62-3.65 (2H, m), 3.32 (2H, s), 3.03 (2H, s), 2.73-2.76 (1H, m), 1.79-1.98 (7H, m), 1.45-1.47 (3H, m), 1.39-1.41 (3H, m) | 475.15 | 474.25 |
| 282 | 1H-NMR (DMSO-D6) δ: 9.95 (1H, s), 9.30 (1H, s), 8.22 (1H, d, J = 9.0 Hz), 7.52 (1H, d, J = 9.0 Hz), 7.25 (1H, s), 5.27-5.25 (1H, d, J = 6.0 Hz), 4.68-4.65 (1H, m), 3.94-3.91 (2H, m), 3.82-3.69 (6H, m), 3.36-3.32 (2H, m), 2.85-2.81 (4H, m), 2.66-2.62 (1H, m), 1.82-1.72 (8H, m), 1.59-1.47 (2H, m), 1.39 (3H, d, J = 6.0 Hz). | 490.15 | 489.29 |
| 283 | 1H-NMR (DMSO-d6) δ: 9.94 (1H, s), 9.30 (1H, s), 8.19 (1H, d, J = 9.0 Hz), 7.49 (1H, d, J = 9.0 Hz), 7.25 (1H, s), 5.25 (1H, d, J = 3.0 Hz), 4.65-4.68 (1H, m), 4.51 (1H, d, J = 3.0 Hz), 3.76-3.82 (4H, m), 3.67-3.71 (2H, m), 3.36-3,41 (1H, m), 2.72-2.81 (4H, m), 2.40-2.43 (1H, m), 1.80-1.89 (4H, m), 1.71-1.73 (6H, m), 1.38-1.40 (3H, m), 1.08-1.33 (4H, m) | 504.25 | 503.30 |

TABLE 101

| Compound No. | NMR data | (M + H)+ | Exact Mass |
|---|---|---|---|
| 284 | 1H-NMR (DMSO-d6) δ: 9.95 (1H, s), 9.30 (1H, s), 8.20 (1H, d, J = 9.0 Hz), 7.52 (1H, d, J = 9.0 Hz), 7.25 (1H, s), 5.26 (1H, d, J = 3.0 Hz), 4.65-4.68 (1H, m), 4.30 (1H, d, J = 3.0 Hz), 3.76-3.78 (4H, m), 3.68-3.74 (2H, s), 2.72-2.81 (4H, m), 2.40-2.43 (1H, m), 1.72-1.80 (10H, m), 1.38-1.47 (7H, m) | 504.25 | 503.30 |
| 285 | 1H-NMR (DMSO-D6) δ: 10.10 (1H, d, J = 15.0 Hz), 9.32 (1H, s), 8.51-8.46 (2H, m), 8.32-8.26 (1H, m), 7.69-7.60 (1H, m), 7.30-7.26 (3H, m), 5.27 (1H, d, J = 3.0 Hz), 4.75-4.65 (3H, m), 3.91-3.76 (8H, m), 2.84-2.80 (2H, m), 1.73 (6H, br s), 1.40 (3H, d, J = 6.0 Hz). | 525.15 | 524.26 |
| 286 | 1H-NMR (DMSO-D6) δ: 10.13 (1H, d, J = 12.0 Hz), 9.32 (1H, s), 8.36-8.27 (1H, m), 7.70-7.66 (1H, m), 7.55 (1H, s), 7.26 (1H, s), 7.08 (1H, s), 6.87 (1H, s), 5.27 (1H, d, J = 6.0 Hz), 5.14 (2H, d, J = 9.0 Hz), 4.73-4.65 (3H, m), 3.84-3.77 (6H, m), 2.99-2.83 (2H, m), 1.74 (6H, m), 1.40 (3H, d, J = 6.0 Hz). | 514.20 | 513.26 |
| 287 | 1H-NMR (DMSO-D6) δ: 9.97 (1H, s), 9.30 (1H, s), 8.21 (1H, d, J = 8.4 Hz), 7.49 (1H, d, J = 8.4 Hz), 7.25 (1H, s), 5.26 (1H, d, J = 4.5 Hz), 4.65-4.69 (1H, m), 3.76-3.78 (4H, m), 3.49 (2H, s), | 470.15 | 419.24 |

TABLE 101-continued

| Compound No. | NMR data | (M + H)⁺ | Exact Mass |
|---|---|---|---|
| | 2.82-2.86 (2H, m), 2.67-2.69 (2H, m), 2.37 (3H, s), 1.73 (6H, br), 1.39 (3H, d, J = 6.3 Hz) | | |
| 288 | | 451.3 | 450.25 |
| 289 | | 451.3 | 450.25 |
| 290 | | 479.3 | 478.28 |
| 291 | 1H-NMR (CDCl3) δ: 9.17 (1H, s), 9.03 (1H, s), 8.35 (1H, d, J = 8.7 Hz), 8.33 (1H, d, J = 2.3 Hz), 7.71 (1H, dd, J = 8.7, 2.3 Hz), 7.00 (1H, s), 5.19-5.13 (1H, m), 4.86 (1H, q, J = 6.4 Hz), 4.25 (1H, d, J = 13.3 Hz), 4.07-4.01 (2H, m), 3.89 (1H, td, J = 11.4, 2.7 Hz), 3.78 (1H, d, J = 11.0 Hz), 3.68-3.59 (1H, m), 3.50 (2H, s), 2.49 (8H, br s), 2.29 (3H, s), 1.53 (3H, d, J = 6.9 Hz), 1.30 (3H, d, J = 6.9 Hz). | 479.4 | 478.28 |
| 292 | 1H-NMR (CDCl3) δ: 9.21 (1H, s), 9.16 (1H, s), 8.35-8.32 (2H, m), 7.69 (1H, dd, J = 8.7, 2.3 Hz), 6.94 (1H, s), 5.26 (2H, s), 4.82 (1H, q, J = 6.4 Hz), 4.03 (2H, dd, J = 10.5, 2.3 Hz), 3.69 (2H, dd, J = 10.5, 1.4 Hz), 3.50 (2H, s), 2.48 (8H, br s), 2.28 (3H, s), 2.14-2.00 (5H, m), 1.52 (3H, d, J = 6.4 Hz). | 491.4 | 490.28 |
| 293 | | 509.4 | 508.29 |
| 294 | | 509.4 | 508.29 |
| 295 | | 521.3 | 520.29 |

TABLE 102

| Compound No. | NMR data | (M + H)⁺ | Exact mass |
|---|---|---|---|
| 296 | | 465.3 | 464.26 |
| 297 | | 465.3 | 464.26 |
| 298 | | 477.3 | 476.26 |
| 299 | | 465.3 | 464.23 |
| 300 | | 465.3 | 464.23 |
| 301 | | 477.3 | 476.26 |
| 302 | | 449.3 | 448.23 |
| 303 | | 463.3 | 462.25 |
| 304. | | 491.4 | 490.28 |
| 305 | | 477.3 | 476.26 |
| 306 | | 491.4 | 490.28 |
| 307 | | 477.3 | 476.26 |
| 308 | | 507.4 | 506.28 |
| 309 | | 477.3 | 476.26 |
| 310 | | 464.3 | 463.23 |
| 311 | | 478.3 | 477.25 |
| 312 | | 491.4 | 490.28 |
| 313 | | 491.4 | 490.28 |
| 314 | | 512.3 | 511.20 |
| 315 | | 505.4 | 504.30 |
| 316 | | 479.3 | 478.28 |
| 317 | | 491.3 | 490.28 |
| 318 | | 463.3 | 462.25 |
| 319 | | 491.4 | 490.28 |
| 320 | | 495.4 | 494.26 |
| 321 | | 491.4 | 490.28 |
| 322 | | 493.4 | 492.30 |
| 323 | 1H-NMR (CDCl3) δ: 9.09 (1H, s), 8.64 (1H, d, J = 9.1 Hz), 8.57 (1H, s), 8.27 (1H, d, J = 2.7 Hz), 7.67 (1H, dd, J = 8.7, 2.7 Hz), 6.87 (1H, s), 5.10-5.04 (2H, m), 5.03-4.97 (2H, m), 4.43-4.32 (1H, m), 3.96-3.85 (6H, m), 3.78 (2H, s), 3.25-3.14 (2H, m), 1.99-1.62 (8H, m). | 475.3 | 474.25 |
| 324 | 1H-NMR (CDCl3) δ: 9.10 (1H, s), 8.59 (1H, d, J = 9.6 Hz), 8.45 (1H, s), 6.94 (1H, s), 6.71 (1H, d, J = 9.6 Hz), 4.85 (1H, q, J = 6.4 Hz), 4.71 (2H, t, J = 6.6 Hz), 4.55-4.48 (2H, m), 4.24 (4H, s), 4.04 (1H, br s), 3.87-3.80 (4H, m), 3.80-3.72 (1H, m), 3.51 (4H, s), 1.88-1.58 (6H, m), 1.53 (3H, d, J = 6.4 Hz). | 504.3 | 503.8 |

TABLE 103

| Compound No. | NMR data | (M + H)⁺ | Exact Mass |
|---|---|---|---|
| 325 | 1H-NMR (CDCl3) δ: 9.10 (1H, s), 8.53 (1H, d, J = 8.2 Hz), 8.35 (1H, s), 8.24 (1H, d, J = 1.8 Hz), 7.72 (1H, dd. J = 8.7, 2.3 Hz), 6.95 (1H, d, J = 0.9 Hz), 4.86 (1H, q, J = 6.4 Hz), 4.41 (4H, s), 4.04 (1H, br s), 3.93-3.82 (4H, m), 3.46 (2H, s), 2.52-2.20 (4H, br m), 1.99-1.67 (10H, m), 1.54 (3H, d, J = 6.4 Hz). | 490.4 | 489.29 |
| 326 | 1H-NMR (CDCl3) δ: 9.12 (1H, s), 8.55 (1H, d, J = 8.7 Hz), 8.49 (1H, s), 8.27 (1H, d, J = 1.8 Hz), 7.72 (1H, d, J = 7.8 Hz), 6.95 (1H, s), 4.86 (1H q, J = 6.1 Hz), 4.05 (1H, s), 3.94-3.82 (4H, m), 3.51 (2H, s), 2.82-2.58 (3H, br m), 2.51-2.24 (2H, br m), 2.04-1.72 (10H, m), 1.54 (3H, d, J = 6.4 Hz). | 473.3 | 472.27 |
| 327 | 1H-NMR (CDCl3) δ: 9.03 (1H, s), 8.22 (1H, d, J = 8.7 Hz), 7.96 (1H, s), 6.92-6.85 (2H, m), 4.89-4.79 (1H, m), 4.75-4.67 (2H, m), 4.55-4.48 (2H, m), 4.12 (1H, d, J = 5.0 Hz), 4.00 (4H, s), 3.92-3.81 (4H, m), 3.80-3.71 (1H, m), 3.48 (4H, s), 2.40 (3H, s), 1.90-1.70 (6H, m), 1.53 (3H, d, J = 6.4 Hz). | 517.4 | 516.30 |
| 328 | 1H-NMR (CDCl3) δ: 9.05 (1H, s), 8.30 (1H, d, J = 8.7 Hz), 8.07 (1H, s), 7.46 (1H, d, J = 9.1 Hz), 6.92 (1H, s), 4.85 (1H, q, J = 6.4 Hz), 3.92-3.79 (4H, m), 3.64-3.51 (4H, m), 3.16-2.90 (7H, m), 2.71-2.65 (2H, m), 2.62-2.39 (7H, m), 1.91-1.70 (6H, m), 1.53 (3H, d, J = 6.4 Hz). | 548.4 | 547.34 |
| 329 | 1H-NMR (DMSO-d6) δ: 10.17 (1H, s), 9.28 (1H, s), 8.12-8.19 (2H, m), 7.63 (1H, dd, J1 = 3.0 Hz, J2 = 3.0 Hz), 7.11 (1H, s), 5.40-5.46 (2H, m), 5.21 (1H, d, J = 3.0 Hz), 4.59-4.67 (1H, m), 3.79-3.82 (2H, m), 3.53 (2H, s), 2.96 (2H, m), 2.66-2.82 (1H, m), 2.09 (1H, m), 1.77-1.86 (7H, m), 1.47-1.53 (3H, m), 1.41-1.44 (3H, m) | 489.25 | 488.26 |
| 330 | 1H-NMR (DMSO-d6) δ: 10.11 (1H, s), 9.32 (1H, s), 8.41-8.47 (2H, m), 8.26-8.30 (1H, m), 7.63-7.68 (2H, m), 7.26-7.36 (2H, m), 5.26 (1H, d, J = 3.0 Hz), 4.79 (1H, s), 4.65-4.69 (2H, m), 3.83-3.90 (3H, m), 3.70-3.78 (5H, m). 2,82-2.87 (2H, m), 1.74-1.81 (6H, m), 1.39 (3H, d, J = 3.0 Hz) | 525.20 | 524.26 |
| 331 | 1H-NMR (DMSO-D6) δ: 10.11 (1H, d, J = 12.0 Hz), 9.32 (1H, s), 8.29-8.27 (1H, m), 7.69-7.68 (2H, m), 7.43 (1H, s), 7.26 (1H, s), 6.27 (1H, d, J = 3.0 Hz), 5.27-5.25 (3H, m), 4.76-4.64 (3H, m), 3.88-3.77 (6H, m), 2.93-2.89 (2H, m), 1.74 (6H, m), 1.40 (3H, d, J = 6.0 Hz). | 514.25 | 513.26 |

TABLE 104

| Compound No. | NMR data | (M + H)+ | Exact Mass |
|---|---|---|---|
| 332 | 1H-NMR (DMSO-d6) δ: 10.14 (1H, s), 9.32 (1H, s), 8.46 (1H, s), 8.27-8.37 (1H, m), 7.97 (1H, s), 7.64-7.70 (1H, m), 7.26 (1H, d, J = 3.0 Hz), 5.38-5.42 (2H, m), 5.26 (1H, d, J = 3.0 Hz), 4.65-4.76 (6H, m), 2.83-3.00 (2H, m), 1.74-1.89 (6H, m), 1.39 (3H, d, J = 3.0 Hz) | 515.25 | 514.26 |
| 333 | 1H-NMR (DMSO-D6) δ: 10.16 (1H, d, J = 12.6 Hz), 8.33 (1H, d, J = 1.5 Hz), 8.24-8.40 (2H, m), 7.70 (1H, d, J = 8.4 H), 7.27 (1H, d, J = 2.4 H), 5.24-5.32 (3H, m), 4.66-4.73 (3H, m), 3.76-3.85 (6H, m), 2.99-3.02 (1H, m), 2,84-2.86 (1H, m), 1.74 (6H, br s), 1.39 (3H, d, J = 8.4 H). | 515.25 | 514.26 |
| 334 | 1H-NMR (CDCl3) δ: 9.05 (1H, s), 8.30 (1H, d, J = 8.7 Hz), 8.04 (1H, s), 7.45 (1H, d, J = 8.7 Hz), 6.92 (1H, s), 4.85 (1H, q, J = 6.4 Hz), 4.12 (1H, br s), 3.93-3.80 (4H, m), 3.62-3.53 (2H, m), 3.11-3.01 (1H, m), 3.00-2.90 (6H, m), 2.64-2.42 (7H, m), 2.39 (3H, s), 1.91-1.70 (6H, m), 1.53 (3H, d, J = 6.4 Hz). | 518.4 | 517.33 |
| 335 | 1H-NMR (DMSO-d6) δ: 9.79 (1H, s), 9.28 (1H, s), 8.43 (2H, d, J = 15 Hz), 8.18-8.27 (1H, m), 7.58-7.67 (2H, m), 7.23-7.34 (2H, m), 5.08 (1H, d, J = 4.5 Hz), 4.65-4.81 (3H, m), 3.80-3.88 (8H, m), 2.76-2.93 (2H, m), 1.72 (6H, s), 1.40 (3H, d, J = 6.3 Hz). | 525.20 | 524.26 |
| 336 | 1H-NMR (DMSO-d6) δ: 10.14 (1H, s), 9.33 (1H, s), 8.27-8.34 (1H, m), 8.04 (1H, s), 7.67-7.74 (2H, m), 7.27 (1H, d, J = 3.0 Hz), 5.60-5.64 (2H, m), 4.79 (1H, s), 4,66-4.70 (2H, m), 3.64-3.91 (7H, m), 2.99-3.03 (1H, m), 2.84-2.99 (1H, m), 1.74-1.89 (6H, m), 1.39 (3H, d, J = 3.0 Hz) | 515.25 | 514.26 |
| 337 | 1H-NMR (DMSO-d6) δ: 10.14 (1H, s), 9.33 (1H, s), 8.27-8.34 (1H, m), 8.04 (1H, s), 7.67-7.74 (2H, m), 7.27 (1H, d, J = 3.0 Hz), 5.60-5.64 (2H, m), 5.26 (1H, d, J = 3.0 Hz), 4.66-4.79 (3H, m), 3.77-3.91 (6H, m), 2.86-3.02 (2H, m), 1.74-1.89 (6H, m), 1.39 (3H, d, J = 3.0 Hz) | 515.25 | 514.26 |

Example 20

Human CDK4/Cyclin D3 Inhibitory Activity

Each compound was analyzed for CDK4/cyclin D3 inhibitory activity with an assay kit (QS S Assist CDK4/Cyclin D3_FP Kit, available from Carna Biosciences, Inc.). This assay kit determines kinase activity on the basis of the IMAP technology by Molecular Devices. Specifically, the kinase activity is determined through quantification of a variation in fluorescent polarization caused by binding of a kinase-phosphorylated fluorescent substance to an IMAP-binding reagent.

Each solution was prepared with the 10× assay buffer attached to the kit or a separately prepared assay buffer having the same composition as the assay buffer attached to the kit. An assay buffer was prepared by 10-fold dilution of the 10× assay buffer with distilled water. The assay buffer contains 20 mM HEPES (pH 7.4), 0.01% Tween20, and 2 mM dithiothreitol. A test compound solution was prepared by dilution of the test compound with dimethyl sulfoxide (DMSO) to a concentration 100 times higher than the final concentration and then 25-fold dilution with the assay buffer to a concentration four times higher than the final concentration. An ATP/substrate/Metal solution was prepared by five-fold dilution of the 5×ATP/substrate/Metal solution attached to the kit with the assay buffer. An enzyme solution was prepared by dilution of the CDK4/cyclin D3 attached to the kit with the assay buffer to a concentration twice higher than the final concentration (final concentration of CDK4/cyclin D3: 12.5 to 25 ng/well). A detection reagent was prepared by five-fold dilution of each of 5×IMAP-binding buffer A and 5×IMAP-binding buffer B with distilled water, mixing of IMAP-binding buffer A with IMAP-binding buffer B at a ratio of 85:15, and 400-fold dilution of the IMAP-binding reagent with the mixed buffer.

The test compound solution (5 μL/well) and the ATP/substrate/Metal solution (5 μL/well) were added to a 384-well plate, and the enzyme solution or the assay buffer (10 μL/well) was added to the plate (total amount of the reaction mixture: 20 μL/well) for initiation of enzymatic reaction. The reaction mixture had a composition of 20 mM HEPES (pH 7.4), 0.01% Tween 20, 2 mM dithiothreitol, 100 nM FITC-labeled peptide substrate (the sequence of the substrate peptide is not disclosed by Carna Biosciences, Inc.), 100 μM ATP, 1 mM magnesium chloride, 1% DMSO, and 12.5 to 25 ng/well CDK4/cyclin D3. The reaction was performed at room temperature for 45 minutes, and the detection reagent (60 μL/well) was then added to the plate, followed by further reaction for 30 minutes at room temperature under light shielding conditions. Subsequently, fluorescent polarization was determined with a microplate reader at an excitation wavelength of 485 nm and an emission wavelength of 535 nm.

The percent inhibition of enzyme activity was calculated for each test compound (note: enzyme activity=100% in the case of addition of the enzyme solution and addition of DMSO instead of the test compound solution, whereas enzyme activity 50% in the case of addition of the assay buffer instead of the enzyme solution, and addition of DMSO instead of the test compound solution). The percent inhibition of enzyme activity was fitted to a dose-response curve, to determine a 50% inhibitory concentration against CDK4/cyclin D3.

The inhibitory activity of each compound against CDK4/cyclin D3 was shown in tables described below.

In each table, "+++" corresponds to $IC_{50}$<10 nM. "++" 10 nM 5 $IC_{50}$<100 nM, and "+" 100 nM≤$IC_{50}$.

Example 21

Human CDK2/Cyclin A2 Inhibitory Activity

Each compound was analyzed for CDK2/cyclin A2 inhibitory activity with an assay kit (QS S Assist CDK2/Cyclin A2_FP Kit, available from Carna Biosciences, Inc.). This assay kit determines kinase activity on the basis of the IMAP technology by Molecular Devices. Specifically, the kinase activity is determined through quantification of a variation in fluorescent polarization caused by binding of a kinase-phosphorylated fluorescent substance to an IMAP-binding reagent.

An assay buffer was prepared by 10-fold dilution of the 10× assay buffer attached to the kit with distilled water, and each solution was prepared with the assay buffer. The assay buffer contained 20 mM HEPES (pH 7.4), 0.01% Tween 20, and 2 mM dithiothreitol. A test compound solution was prepared by dilution of the test compound with dimethyl sulfoxide (DMSO) to a concentration 100 times higher than the final concentration and then 25-fold dilution with the assay buffer to a concentration four times higher than the final concentration. An ATP/substrate/Metal solution was prepared by five-fold dilution of the 5×ATP/substrate/Metal solution attached to the kit with the assay buffer. An enzyme solution was prepared by dilution of the CDK2/cyclin A2 attached to the kit with the assay buffer to a concentration twice higher than the final concentration (final concentration of CDK2/cyclin A2: 2.5 ng/well). A detection reagent was prepared by five-fold dilution of 5×IMAP-binding buffer A with distilled water and 400-fold dilution of the IMAP-binding reagent with the diluted buffer.

The test compound solution (5 μL/well) and the ATP/substrate/Metal solution (5 μL/well) were added to a 384-well plate, and the enzyme solution or the assay buffer (10 μL/well) was added to the plate (total amount of the reaction mixture: 20 μL/well) for initiation of enzymatic reaction. The reaction mixture had a composition of 20 mM HEPES (pH 7.4), 0.01% Tween 20, 2 mM dithiothreitol, 100 nM FITC-labeled peptide substrate (the sequence of the substrate peptide is not disclosed by Carna Biosciences, Inc.), 30 μM ATP, 5 mM magnesium chloride, 1% DMSO, and 2.5 ng/well CDK2/cyclin A2. The reaction was performed at room temperature for 60 minutes, and the detection reagent (60 μL/well) was then added to the plate, followed by further reaction for 30 minutes at room temperature under light shielding conditions. Subsequently, fluorescent polarization was determined with a microplate reader at an excitation wavelength of 485 nm and an emission wavelength of 535 nm.

The percent inhibition of enzyme activity was calculated for each test compound (note: enzyme activity=100% in the case of addition of the enzyme solution and addition of DMSO instead of the test compound solution, whereas enzyme activity 50% in the case of addition of the assay buffer instead of the enzyme solution and addition of DMSO instead of the test compound solution). The percent inhibition of enzyme activity was fitted to a dose-response curve, to determine a 50% inhibitory concentration against CDK2/cyclin A2.

The inhibitory activity of each compound against CDK2/cyclin A2 was shown in tables described below.

In each table, "+++" corresponds to $IC_{50} < 10$ nM, "++" $10$ nM $\leq IC_{50} < 100$ nM, and "+" $100$ nM $\leq IC_{50}$.

TABLE 105

| Compound No. | CDK4 Activity symbol | CDK2 Activity symbol |
| --- | --- | --- |
| 1 | +++ | + |
| 2 | +++ | + |
| 3 | + | + |
| 4 | ++ | + |
| 5 | +++ | + |
| 6 | +++ | + |
| 7 | +++ | + |
| 8 | ++ | + |
| 9 | +++ | |
| 10 | ++ | |
| 11 | +++ | |
| 12 | +++ | |
| 13 | +++ | |
| 14 | +++ | |
| 15 | ++ | |
| 16 | +++ | |
| 17 | ++ | |
| 18 | +++ | |
| 19 | +++ | |
| 20 | +++ | |
| 21 | ++ | |
| 22 | +++ | |
| 23 | + | |

TABLE 105-continued

| Compound No. | CDK4 Activity symbol | CDK2 Activity symbol |
| --- | --- | --- |
| 24 | +++ | + |
| 25 | ++ | + |
| 26 | ++ | + |
| 27 | ++ | + |
| 28 | ++ | + |
| 29 | ++ | + |
| 30 | +++ | + |
| 31 | ++ | |
| 32 | ++ | + |
| 33 | +++ | + |
| 34 | ++ | + |
| 35 | ++ | + |
| 36 | + | + |
| 37 | ++ | + |
| 38 | + | + |
| 39 | +++ | + |
| 40 | +++ | + |
| 41 | +++ | + |
| 42 | + | + |
| 43 | +++ | |
| 44 | +++ | |
| 45 | +++ | |
| 46 | +++ | |
| 47 | ++ | + |
| 48 | +++ | + |
| 49 | +++ | + |
| 50 | ++ | + |
| 51 | +++ | + |
| 52 | +++ | + |

TABLE 106

| Compound No. | CDK4 Activity symbol | CDK2 Activity symbol |
| --- | --- | --- |
| 53 | +++ | + |
| 54 | +++ | + |
| 55 | +++ | + |
| 56 | +++ | + |
| 57 | +++ | + |
| 58 | ++ | + |
| 59 | +++ | + |
| 60 | +++ | + |
| 61 | +++ | + |
| 62 | +++ | + |
| 63 | +++ | + |
| 64 | +++ | + |
| 65 | +++ | + |
| 66 | ++ | + |
| 67 | ++ | + |
| 68 | +++ | + |
| 69 | +++ | + |
| 70 | ++ | + |
| 71 | ++ | + |
| 72 | +++ | + |
| 73 | ++ | + |
| 74 | ++ | + |
| 75 | +++ | ++ |
| 76 | +++ | + |
| 77 | ++ | + |
| 78 | +++ | + |
| 79 | +++ | + |
| 80 | +++ | + |
| 81 | +++ | + |
| 82 | +++ | + |
| 83 | +++ | ++ |
| 84 | +++ | + |
| 85 | ++ | + |
| 86 | +++ | + |
| 87 | +++ | + |
| 88 | +++ | + |
| 89 | +++ | + |

TABLE 106-continued

| Compound No. | CDK4 Activity symbol | CDK2 Activity symbol |
|---|---|---|
| 90 | +++ | + |
| 91 | +++ | + |
| 92 | +++ | + |
| 93 | +++ | + |
| 94 | +++ | + |
| 95 | ++ | + |
| 96 | +++ | + |
| 97 | +++ | + |
| 98 | ++ | + |
| 99 | +++ | + |
| 100 | +++ | + |
| 101 | +++ | + |
| 102 | +++ | + |
| 103 | +++ | + |
| 104 | +++ | + |

TABLE 107

| Compound No. | CDK4 Activity symbol | CDK2 Activity symbol |
|---|---|---|
| 105 | +++ | + |
| 106 | +++ | + |
| 107 | +++ | + |
| 108 | +++ | + |
| 109 | +++ | + |
| 110 | +++ | + |
| 111 | +++ | + |
| 112 | +++ | + |
| 113 | +++ | + |
| 114 | +++ | + |
| 115 | +++ | + |
| 116 | +++ | + |
| 117 | +++ | + |
| 118 | +++ | + |
| 119 | +++ | + |
| 120 | +++ | + |
| 121 | +++ | + |
| 122 | +++ | + |
| 123 | +++ | + |
| 124 | +++ | + |
| 125 | ++ | + |
| 126 | +++ | + |
| 127 | +++ | + |
| 128 | +++ | + |
| 129 | +++ | + |
| 130 | +++ | + |
| 131 | ++ | + |
| 132 | +++ | + |
| 133 | ++ | + |
| 134 | +++ | + |
| 135 | +++ | + |
| 136 | +++ | + |
| 137 | ++ | + |
| 138 | +++ | + |
| 139 | +++ | + |
| 140 | +++ | + |
| 141 | +++ | + |
| 142 | +++ | + |
| 143 | +++ | + |
| 144 | +++ | + |
| 145 | ++ | + |
| 146 | +++ | + |
| 147 | +++ | + |
| 148 | +++ | + |
| 149 | +++ | + |
| 150 | +++ | + |
| 151 | +++ | + |
| 152 | +++ | + |
| 153 | ++ | + |
| 154 | +++ | + |

TABLE 107-continued

| Compound No. | CDK4 Activity symbol | CDK2 Activity symbol |
|---|---|---|
| 155 | +++ | + |
| 156 | +++ | + |

TABLE 108

| Compound No. | CDK4 Activity symbol | CDK2 Activity symbol |
|---|---|---|
| 157 | +++ | + |
| 158 | +++ | + |
| 159 | ++ | + |
| 160 | +++ | + |
| 161 | +++ | + |
| 162 | +++ | + |
| 163 | +++ | + |
| 164 | +++ | + |
| 165 | +++ | + |
| 166 | ++ | + |
| 167 | +++ | + |
| 168 | ++ | + |
| 169 | ++ | + |
| 170 | ++ | + |
| 171 | ++ | + |
| 172 | ++ | + |
| 173 | +++ | ++ |
| 174 | +++ | + |
| 175 | +++ | + |
| 176 | +++ | + |
| 177 | +++ | + |
| 178 | +++ | + |
| 179 | +++ | + |
| 180 | +++ | + |
| 181 | ++ | + |
| 182 | +++ | + |
| 183 | +++ | + |
| 184 | +++ | + |
| 185 | +++ | + |
| 186 | +++ | + |
| 187 | +++ | + |
| 188 | +++ | + |
| 189 | +++ | + |
| 190 | ++ | + |
| 191 | ++ | + |
| 192 | ++ | + |
| 193 | ++ | + |
| 194 | +++ | + |
| 195 | ++ | + |
| 196 | ++ | + |
| 197 | ++ | + |
| 198 | +++ | + |
| 199 | +++ | + |
| 200 | +++ | + |
| 201 | +++ | + |
| 202 | ++ | + |
| 203 | +++ | + |
| 204 | ++ | + |
| 205 | +++ | + |
| 206 | +++ | + |
| 207 | +++ | + |
| 208 | +++ | + |

TABLE 109

| Compound No. | CDK4 Activity symbol | CDK2 Activity symbol |
|---|---|---|
| 209 | +++ | + |
| 210 | +++ | + |
| 211 | +++ | + |

TABLE 109-continued

| Compound No. | CDK4 Activity symbol | CDK2 Activity symbol |
| --- | --- | --- |
| 212 | +++ | + |
| 213 | +++ | + |
| 214 | +++ | + |
| 215 | +++ | + |
| 216 | +++ | + |
| 218 | +++ | + |
| 219 | +++ | + |
| 220 | +++ | + |
| 221 | +++ | + |
| 222 | +++ | + |
| 223 | +++ | + |
| 224 | +++ | + |
| 225 | +++ | + |
| 226 | +++ | + |
| 227 | +++ | + |
| 228 | +++ | + |
| 229 | +++ | + |
| 230 | +++ | + |
| 231 | +++ | + |
| 232 | +++ | + |
| 233 | +++ | + |
| 234 | ++ | + |
| 235 | +++ | + |
| 236 | +++ | + |
| 237 | +++ | + |
| 238 | +++ | + |
| 239 | +++ | + |
| 240 | +++ | + |
| 241 | +++ | + |
| 242 | +++ | + |
| 243 | +++ | + |
| 244 | +++ | + |
| 245 | +++ | + |
| 246 | +++ | + |
| 247 | +++ | + |
| 248 | +++ | + |
| 249 | ++ | + |
| 250 | +++ | + |
| 251 | +++ | + |
| 252 | +++ | + |
| 253 | +++ | + |
| 254 | +++ | + |
| 255 | +++ | + |
| 256 | +++ | + |
| 257 | +++ | + |
| 258 | +++ | + |
| 259 | +++ | + |
| 260 | +++ | + |
| 261 | +++ | + |

TABLE 110

| Compound No. | CDK4 Activity symbol | CDK2 Activity symbol |
| --- | --- | --- |
| 262 | +++ | + |
| 263 | +++ | + |
| 264 | +++ | + |
| 265 | +++ | + |
| 266 | +++ | + |
| 267 | +++ | + |
| 268 | +++ | + |
| 269 | +++ | + |
| 270 | +++ | + |
| 271 | +++ | + |
| 272 | +++ | + |
| 273 | +++ | + |
| 274 | +++ | + |
| 275 | +++ | + |
| 276 | +++ | + |
| 277 | ++ | + |
| 278 | +++ | + |

TABLE 110-continued

| Compound No. | CDK4 Activity symbol | CDK2 Activity symbol |
| --- | --- | --- |
| 279 | +++ | + |
| 280 | ++ | + |
| 281 | +++ | + |
| 282 | +++ | + |
| 283 | ++ | + |
| 284 | ++ | + |
| 285 | ++ | + |
| 286 | +++ | + |
| 287 | +++ | + |
| 288 | +++ | + |
| 289 | +++ | + |
| 290 | +++ | + |
| 291 | +++ | |
| 292 | +++ | + |
| 293 | ++ | + |
| 294 | +++ | + |
| 295 | +++ | + |
| 296 | +++ | + |
| 297 | +++ | + |
| 298 | +++ | + |
| 299 | ++ | + |
| 300 | ++ | + |
| 301 | ++ | + |
| 302 | +++ | ++ |
| 303 | +++ | + |
| 304 | +++ | ++ |
| 305 | +++ | ++ |
| 306 | +++ | ++ |
| 307 | +++ | ++ |
| 308 | +++ | + |
| 309 | +++ | + |
| 310 | +++ | + |
| 311 | +++ | + |
| 312 | +++ | + |
| 313 | +++ | + |

TABLE 111

| Compound No. | CDK4 Activity symbol | CDK2 Activity symbol |
| --- | --- | --- |
| 314 | +++ | + |
| 315 | +++ | + |
| 316 | +++ | + |
| 317 | +++ | + |
| 318 | +++ | + |
| 319 | +++ | ++ |
| 320 | +++ | + |
| 321 | +++ | + |
| 322 | +++ | + |
| 323 | +++ | + |
| 324 | +++ | + |
| 325 | +++ | + |
| 326 | +++ | + |
| 327 | +++ | + |
| 328 | +++ | + |
| 329 | +++ | ++ |
| 330 | ++ | + |
| 331 | ++ | + |
| 332 | ++ | + |
| 333 | +++ | + |
| 334 | +++ | + |
| 335 | ++ | + |
| 336 | ++ | + |
| 337 | ++ | + |

Example 22

Human CDK6/Cyclin D3 Inhibitory Activity

CDK6/cyclin D3 inhibitory activity was determined by the off-chip mobility shift assay (MSA). The MSA separates proteins from one another on the basis of a difference in electrophoretic mobility depending on the molecular weight or electric charge of the proteins. The kinase activity is determined by quantifying the degree of phosphorylation through electrophoretic analysis of a positive to negative change in electric charge of the substrate phosphorylated by the kinase.

Each solution was prepared with an assay buffer containing 20 mM HEPES (pH 7.5), 0.01% Triton X-100, and 2 mM dithiothreitol. A test compound solution was prepared by dilution of the test compound with dimethyl sulfoxide (DMSO) to a concentration 100 times higher than the final concentration and then 25-fold dilution with the assay buffer to a concentration four times higher than the final concentration. An ATP/substrate/metal solution was prepared to have a concentration four times higher than the final concentration. An enzyme solution was prepared to have a concentration twice higher than the final concentration. The final enzyme concentration was adjusted to an appropriate level on the basis of the enzyme activity signal and the inhibitory activity of a positive control compound.

The test compound solution (5 μL/well) and the ATP/substrate/metal solution (5 μL/well) were added to a 384-well plate, and the enzyme solution or the assay buffer (10 μL/well) was added to the plate (total amount of the reaction mixture: 20 μL/well) for initiation of enzymatic reaction. The reaction mixture had a composition of 20 mM HEPES (pH 7.5), 0.01% Triton X-100, 2 mM dithiothreitol, 1000 nM peptide substrate (DYRKtide-F), 300 μM ATP, 5 mM magnesium chloride, 1% DMSO, and a predetermined concentration of CDK6/cyclin D3. The reaction was performed at room temperature for five hours, and a termination buffer (QuickScout Screening Assist MSA, manufactured by Carna Biosciences, Inc.) (60 μL/well) was then added to the plate for termination of the reaction. Subsequently, the substrate peptide and the phosphorylated peptide in the reaction mixture were separated from each other and quantified with LabChip 3000 (manufactured by Caliper Lifesciences). The kinase reaction was evaluated by the product ratio (P/(P+S)) calculated from the peak height (S) of the substrate peptide and the peak height (P) of the phosphorylated peptide.

The percent inhibition of enzyme activity was calculated for each test compound (note: enzyme activity=100% in the case of addition of the enzyme solution and addition of DMSO instead of the test compound solution, whereas enzyme activity 50% in the case of addition of the assay buffer instead of the enzyme solution and addition of DMSO instead of the test compound solution). The percent inhibition of enzyme activity was fitted to a dose-response curve, to determine a 50% inhibitory concentration against CDK6/cyclin D3.

The inhibitory activity of each compound against CDK6/cyclin D3 was shown in tables described below. In each table, "+++" corresponds to $IC_{50}$<10 nM, "++" 10 nM≤$IC_{50}$<100 nM, and "+" 100 nM≤$IC_{50}$.

Example 23

Evaluation of Pathological State after Administration of Compound According to the Present Invention A monoclonal antibody cocktail against type II collagen (Arthritogenic MoAb Cocktail (Chondrex #53100), 4.8 mg/mL) was intraperitoneally administered (250 μL/head) to a group of mice with collagen antibody-induced arthritis (CAIA) (vehicle/+, group of drug administration) (day 1). LPS (LPS Solution (*E. coli* 0111:B4) (Chondrex #9028), 0.5 mg/mL) was intraperitoneally administered (100 μL/head) on day 4, to induce the disease. The drug was evaluated on the basis of pathological scoring until day 9. The drug was orally administered consecutively from day 4 to day 8 once a day.

In mice of a non-disease-induced group (vehicle/−group), PBS (pH 7.2, Gibco #20012-027) was intraperitoneally administered (250 μL/head) on day 1, and LPS was intraperitoneally administered on day 4.

The drug was evaluated on the basis of the pathological scoring (score 0 to score 4 for each of the extremities, evaluated by the total score). Scoring criteria are as follows:

score 0: no change;

score 1: swelling of only one limb:

score 2: swelling of wrist and ankle or swelling of two or more limbs;

score 3: swelling of wrist and ankle and swelling of one or more limbs; and score 4: swelling of wrist and ankle and swelling of all the limbs.

Example 24

Cell Proliferation Assay Using Cell Lines

The effect of the test compounds to glioblastoma was evaluated according to cell proliferation assay using cell lines. An ATP amount in the cultured cells after 120 hours with a test compound was measured to evaluate an influence of the test compound over the cell proliferation.

The cell lines used were T98G cells and U-87MG cells derived from glioblastoma, both of which were obtained from American Type Culture Collection (ATCC). A cell suspension (45 μL) containing a culture solution containing 10% of fetal bovine serum (FBS) was distributed into a 384-well plate, and was cultured at 37° C. with 5% CO2. After 24 hours of the culture, 5 μL of 20 mM HEPES (pH 7.4) containing the test compound was added (DMSO final concentration: 0.4%), and the cell suspension was again cultured on the same conditions. After 120 hours, 25 μL of ATPlite 1-step reagent (PerkinElmer) was distributed into each of the wells, and the plate was shaken for two minutes. The plate was allowed to stand in a dark place for five minutes, and the luminescence was recorded on the Envision multimode reader (PerkinElmer). The test compound was evaluated in the range of 10-5 M to 10-9 M.

The background value before the addition of the test compound was determined as follows: 5 μL of 20 mM HEPES (pH 7.4) containing 4% DMSO was distributed into wells after 24 hours of culturing, 25 μL of ATPlite 1-step reagent was added, and the luminescence as the background value was recorded. The maximum luminescence (100%) was recorded from a cell suspension cultured for 120 hours on the same conditions as above. The contents of the test compounds and their luminescence (%) were plotted, and the 50% inhibitory concentration to the maximum value of cell proliferation was calculated.

The invention claimed is:
1. A compound represented by formula (I):

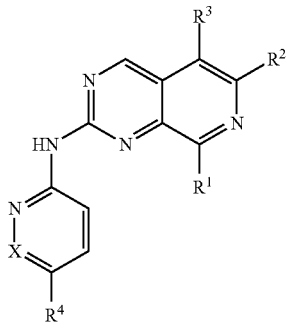

wherein in the formula,
R$^1$ represents C$_{3\text{-}12}$ cycloalkyl, C$_{4\text{-}12}$ cycloalkenyl, 4- to 12-membered heterocyclyl, C$_{6\text{-}10}$ aryl, or 5- to 10-membered heteroaryl, wherein each heteroatom-containing group represented by R$^1$ contains one to four heteroatoms independently selected from oxygen, sulfur, and nitrogen atoms,
R$^1$ is optionally substituted with one to six substituents selected from the group consisting of a halogen atom, =O, —OH, —CN, —COOH, —COOR$^6$, —R$^7$, C$_{3\text{-}6}$ cycloalkyl substituted with [zero to two —OH groups, zero to two C$_{1\text{-}8}$ alkoxy groups, and zero to six fluorine atoms], 3- to 10-membered heterocyclyl substituted with [zero to two —OH groups, zero to two C$_{1\text{-}8}$ alkoxy groups, and zero to six fluorine atoms], C$_{1\text{-}8}$ acyl substituted with [zero to two —OH groups, zero to two C$_{1\text{-}8}$ alkoxy groups, and zero to six fluorine atoms], and C$_{1\text{-}8}$ alkoxy substituted with [zero to two —OH groups, zero to two C$_{1\text{-}8}$ alkoxy groups, and zero to six fluorine atoms];
R$^6$ and R$^7$ each independently represent C$_{1\text{-}6}$ alkyl substituted with [zero to two —OH groups, zero to two C$_{1\text{-}8}$ alkoxy groups, and zero to six fluorine atoms];
R$^2$ represents C$_{1\text{-}8}$ alkyl, C$_{3\text{-}8}$ cycloalkyl, 4- to 6-membered heterocyclyl, C$_{1\text{-}8}$ acyl, —COOR$^8$, or —CONR$^9$R$^{10}$, wherein each of C$_{1\text{-}8}$ alkyl represented by R$^2$ is substituted independently with zero to one —OH group, zero to two C$_{1\text{-}8}$ alkoxy groups substituted with [zero to one —OH group, zero to one C$_{1\text{-}4}$ alkoxy group, and zero to three fluorine atoms], and zero to five fluorine atoms; each of C$_{3\text{-}8}$ cycloalkyl represented by R$^2$ is independently substituted with zero to one —OH group, zero to two C$_{1\text{-}8}$ alkoxy groups substituted with [zero to one —OH group, zero to one C$_{1\text{-}4}$ alkoxy group, and zero to three fluorine atoms], zero to one hydroxymethyl group, and zero to five fluorine atoms; provided that R$^2$ is neither an unsubstituted C$_{1\text{-}8}$alkyl, nor an unsubstituted C$_{3\text{-}8}$ cycloalkyl, nor trifluoromethyl group;
each of R$^8$, R$^9$, and R$^{10}$ independently represents a hydrogen atom or C$_{1\text{-}8}$ alkyl;
each 4- to 6-membered heterocyclyl represented by R$^2$ is optionally substituted with one to four substituents selected from the group consisting of a fluorine atom, —OH group, C$_{1\text{-}4}$ alkyl groups, and C$_{1\text{-}4}$ alkoxy groups;
each of C$_{1\text{-}8}$ acyl group, —COOR$^8$, and —CONR$^9$R$^{10}$ represented by R$^2$ is optionally substituted independently with one to four substituents selected from the group consisting of a fluorine atom, —OH group, and C$_{1\text{-}4}$ alkoxy groups;
R$^9$ and R$^{10}$ of —CONR$^9$R$^{10}$ represented by R$^2$ are optionally bonded via a single bond or —O— to form a ring including the nitrogen atom bonded to R$^9$ and R$^{10}$;
each heterocyclyl group represented by R$^2$ contains one oxygen atom as a heteroatom in the case of a 4- or 5-membered ring, and one to two oxygen atoms as heteroatoms in the case of a 6-membered ring;
R$^3$ represents a hydrogen atom, C$_{1\text{-}8}$ alkyl, or a halogen atom;
X represents CR$^{11}$ or a nitrogen atom;
R$^{11}$ represents a hydrogen atom, C$_{1\text{-}6}$ alkyl, or C$_{3\text{-}6}$ cycloalkyl;
R$^4$ is represented by -A$^1$-A$^2$-A$^3$;
A$^1$ represents a single bond or C$_{1\text{-}8}$ alkylene;
one to two sp$^3$ carbon atoms at any positions of A$^1$ are optionally replaced independently with one to two structures selected from the group consisting of [—O—, —NR$^{14}$—, —C(=O)—, —C(=O)—O—, —O—C(=O)—, —O—C(=O)—O—, —C(=O)—NR$^{15}$—, —O—C(=O)—NR$^{16}$—, —NR$^{17}$—C(=O)—, —NR$^{18}$—C(=O)—O—, —NR$^{19}$—C(=O)—NR$^{20}$—, —S(=O)$_p$—, —S(=O)$_2$—NR$^{21}$—, —NR$^{22}$—S(=O)$_2$—, and —NR$^{23}$—S(=O)$_2$—NR$^{24}$—], provided that no structure selected from —O—O—, —O—NR$^{14}$—, —NR$^{14}$—O—, —O—CH$_2$—O—, —O—CH$_2$—NR$^{14}$—, and —NR$^{14}$—CH$_2$—O— is formed in the case of replacement of two sp$^3$ carbon atoms;
A$^2$ represents a single bond, C$_{1\text{-}7}$ alkylene, C$_{3\text{-}12}$ cycloalkylene, C$_{3\text{-}12}$ cycloalkylidene, 4- to 12-membered heterocyclylene, 4- to 12-membered heterocyclylidene, C$_{6\text{-}10}$ arylene, or 5- to 10-membered heteroarylene;
A$^3$ represents a halogen, —CN, —NO$_2$, —R$^{25}$, —OR$^{26}$, —NR$^{27}$R$^{28}$, —C(=O)R$^{29}$, —C(=O)—OR$^{30}$, —O—C(=O)R$^{31}$, —O—C(=O)—NR$^{32}$R$^{33}$, —C(=O)—NR$^{34}$R$^{35}$, —NR$^{36}$—C(=O)R$^{37}$, —NR$^{38}$—C(=O)—OR$^{39}$, —S(=O)$_2$—R$^{40}$, —S(=O)$_2$—NR$^{41}$R$^{42}$, or —NR$^{43}$—S(=O)$_2$R$^{44}$; provided that A$^3$ represents —R$^{25}$ if the terminal of A$^1$ on the side of A$^2$ is a structure selected from the group consisting of [—O—, —NR$^{14}$—, —C(=O)—, —C(=O)—O—, —O—C(=O)—, —O—C(=O)—O—, —C(=O)—NR$^{15}$—, —O—C(=O)—NR$^{16}$—, —NR$^{17}$—C(=O)—, —NR$^{18}$—C(=O)—O—, —NR$^{19}$—C(=O)—NR$^{20}$—, —S(=O)$_p$—, —S(=O)$_2$—NR$^{21}$—, —NR$^{22}$—S(=O)$_2$—, and —NR$^{23}$—S(=O)$_2$—NR$^{24}$—] and A$^2$ is a single bond;
each of R$^{14}$, R$^{32}$, R$^{34}$, R$^{36}$, R$^{38}$, R$^{41}$, and R$^{43}$ independently represents a hydrogen atom, C$_{1\text{-}8}$ alkyl, C$_{1\text{-}8}$ acyl, C$_{1\text{-}8}$ alkylsulfonyl, 4- to 12-membered heterocyclyl, C$_{3\text{-}12}$ cycloalkyl, C$_{6\text{-}10}$ aryl, 5- to 10-membered heteroaryl, (4- to 12-membered heterocyclyl)C$_{1\text{-}3}$ alkyl, (C$_{3\text{-}12}$ cycloalkyl)C$_{1\text{-}3}$ alkyl, (C$_{6\text{-}10}$ aryl)C$_{1\text{-}3}$ alkyl, or (5- to 10-membered heteroaryl)C$_{1\text{-}3}$ alkyl;
each of R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, R$^{30}$, R$^{31}$, R$^{33}$, R$^{35}$, R$^{37}$, R$^{39}$, R$^{40}$, R$^{42}$, and R$^{44}$ independently represents a hydrogen atom, C$_{1\text{-}8}$ alkyl, 12-membered heterocyclyl, C$_{3\text{-}12}$ cycloalkyl, C$_{6\text{-}10}$ aryl, 5- to 10-membered heteroaryl, (4- to 12-membered heterocyclyl)C$_{1\text{-}3}$ alkyl, (C$_{3\text{-}12}$ cycloalkyl)C$_{1\text{-}3}$ alkyl, (C$_{6\text{-}10}$ aryl)C$_{1\text{-}3}$ alkyl, or (5- to 10-membered heteroaryl)C$_{1\text{-}3}$ alkyl;
each of A$^1$, A$^2$, A$^3$, and each of R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, and $R^{44}$ contained in $A^1$ and $A^3$ are optionally substituted independently with one to four substituents selected from the group consisting of —OH, =O, —COOH, —SO$_3$H, —PO$_3$H$_2$, —CN, —NO$_2$, a halogen, $C_{1-8}$ alkyl substituted with [zero to two —OH groups, zero to two —OR$^{45}$ groups, and zero to six fluorine atoms], $C_{3-12}$ cycloalkyl substituted with [zero to two —OH groups, zero to two —OR$^{46}$ groups, and zero to six fluorine atoms], $C_{1-8}$ alkoxy substituted with [zero to two —OH groups, zero to two —OR$^{47}$ groups, and zero to six fluorine atoms], and 4- to 12-membered heterocyclyl substituted with [zero to two —OH groups, zero to two —OR$^{49}$ groups, and zero to six fluorine atoms];

each of $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, and $R^{44}$ are optionally bonded in $A^1$, in $A^3$, [between $A^1$ and $A^2$], [between $A^1$ and $A^3$], or [between $A^2$ and $A^3$] via [a single bond, —O—, —NR$^{50}$—, or —S(=O)$_p$—] to form a ring;

$R^{11}$ is optionally bonded with [$A^1$, $A^2$, or $A^3$] via [a single bond, —O—, —NR$^{51}$—, or —S(=O)$_p$—] to form a ring;

$R^{45}$, $R^{46}$, $R^{47}$, $R^{49}$, $R^{50}$, and $R^{51}$ each independently represents a hydrogen atom, or $C_{1-4}$ alkyl substituted with [zero to one —OH group and zero to six fluorine atoms];

p represents an integer of zero to two; and each of the heterocyclyl, heteroaryl, (heterocyclyl)alkyl, and (heteroaryl)alkyl represented by $A^1$ and $A^3$ and the heterocyclylene, heterocyclylidene, and heteroarylene represented by $A^2$ contains one to four heteroatoms independently selected from oxygen, sulfur, and nitrogen atoms, or a pharmaceutically acceptable salt thereof.

2. A compound represented by formula (I):

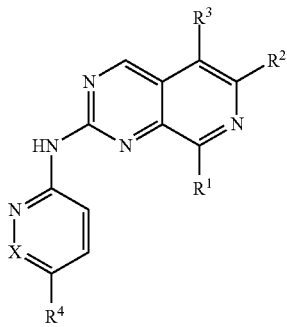

(I)

wherein in the formula,
$R^1$ represents $C_{3-8}$ cycloalkyl, $C_{4-7}$ cycloalkenyl, 4- to 8-membered heterocyclyl, phenyl, or 5- to 10-membered heteroaryl;

each heteroatom-containing group represented by $R^1$ contains one to four heteroatoms independently selected from oxygen, sulfur, and nitrogen atoms;

$R^1$ is optionally substituted with one to six substituents selected from the group consisting of a fluorine atoms, =O, —OH, —COOH, and $C_{1-6}$ alkyl substituted with [zero to two —OH groups, zero to two $C_{1-8}$ alkoxy groups, and zero to six fluorine atoms];

$R^2$ represents $C_{1-8}$ alkyl, 4- to 6-membered heterocyclyl, $C_{1-8}$ acyl, —COOR$^8$, or —CONR$^9$R$^{10}$, $C_{1-8}$ alkyl represented by $R^2$ is substituted with zero to one —OH, zero to two $C_{1-8}$ alkoxy groups substituted with [zero to one —OH group, zero to one $C_{1-4}$ alkoxy group, and zero to three fluorine atoms], and zero to five fluorine atoms;

provided that $R^2$ is neither an unsubstituted $C_{1-8}$ alkyl nor trifluoromethyl;

each of $R^8$, $R^9$, and $R^{10}$ independently represents a hydrogen atom or $C_{1-8}$ alkyl;

$R^3$ represents a hydrogen atom or $C_{1-8}$ alkyl;

X represents CR$^{11}$ or a nitrogen atom;

$R^{11}$ represents a hydrogen atom or $C_{1-6}$ alkyl;

$R^4$ is represented by -$A^1$-$A^2$-$A^3$; where $A^1$ represents a single bond or $C_{1-4}$ alkylene;

one sp$^3$ carbon atom at any position of $A^1$ is optionally replaced with one structure selected from the group consisting of [—O—, —NR$^{14}$—, —NR$^7$—C(=O)—, and —NR$^{22}$—S(=O)$_2$—], $A^2$ represents a single bond, 4- to 12-membered heterocyclylene, $C_{6-10}$ arylene, or 5- to 10-membered heteroarylene;

$A^3$ represents a halogen, —CN, —R$^{25}$, —OR$^{26}$, —NR$^{27}$R$^{28}$, —C(=O)R$^{29}$, —C(=O)—OR$^{30}$, —O—C(=O)R$^{31}$, —O—C(=O)—NR$^{32}$R$^{33}$, —C(=O)—NR$^{34}$R$^{35}$, —NR$^{36}$—C(=O)R$^{37}$, —NR$^{38}$—C(=O)—OR$^{39}$, —S(=O)$_2$—R$^{40}$, —S(=O)$_2$—NR$^{41}$R$^{42}$, or —NR$^{43}$—S(=O)$_2$R$^{44}$; provided that $A^3$ represents —R$^{25}$ if the terminal of $A^1$ on the side of $A^2$ is [—O—, —NR$^{14}$—, —NR$^{17}$—C(=O)—, or —NR$^{22}$—S(=O)$_2$—] and $A^2$ is a single bond;

each of $R^{14}$, $R^{32}$, $R^{34}$, $R^{36}$, $R^{38}$, $R^{41}$, and $R^{43}$ independently represents a hydrogen atom, $C_{1-8}$ alkyl, $C_{1-8}$ acyl, $C_{1-8}$ alkylsulfonyl, 4- to 12-membered heterocyclyl, $C_{3-12}$ cycloalkyl, $C_{6-10}$ aryl, 5- to 10-membered heteroaryl, (4- to 12-membered heterocyclyl)$C_{1-3}$ alkyl, ($C_{3-12}$ cycloalkyl)$C_{1-3}$ alkyl, ($C_{6-10}$ aryl)$C_{1-3}$ alkyl, or (5- to 10-membered heteroaryl)$C_{1-3}$ alkyl;

each of $R^{17}$, $R^{22}$, $R^{25}$, $R^{26}$, $R^{27}$, $R^{28}$, $R^{29}$, $R^{30}$, $R^{31}$, $R^{33}$, $R^{35}$, $R^{37}$, $R^{39}$, $R^{40}$, $R^{42}$, and $R^{44}$ independently represents a hydrogen atom, $C_{1-8}$ alkyl, 4- to 12-membered heterocyclyl, $C_{3-12}$ cycloalkyl, $C_{6-10}$ aryl, 5- to 10-membered heteroaryl, (4- to 12-membered heterocyclyl)$C_{1-3}$ alkyl, ($C_{3-12}$ cycloalkyl)$C_{1-3}$ alkyl, ($C_{6-10}$ aryl)$C_{1-3}$ alkyl, or (5- to 10-membered heteroaryl)$C_{1-3}$ alkyl;

each of $A^1$, $A^2$, $A^3$, and each of $R^{14}$, $R^{17}$, $R^{22}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, and $R^{44}$ in $A^1$ and $A^3$ are optionally substituted independently with one to four substituents selected from the group consisting of —OH, =O, halogen, $C_{1-6}$ alkylsulfonyl, and $C_{1-8}$ alkyl substituted with [zero to one —OH group, and zero to six fluorine atoms];

$R^{11}$ and $A^1$ are optionally bonded via a single bond to form a ring, or a pharmaceutically acceptable salt thereof.

3. The compound or pharmaceutically acceptable salt thereof according to claim 1, wherein $R^1$ represents $C_{3-12}$ cycloalkyl.

4. The compound or pharmaceutically acceptable salt thereof according to claim 1, wherein $R^1$ represents 4- to 12-membered heterocyclyl.

5. The compound or pharmaceutically acceptable salt thereof according to claim 1, wherein $R^1$ represents $C_{6-10}$ aryl or 5- to 10-membered heteroaryl.

6. The compound or pharmaceutically acceptable salt thereof according to claim 1, wherein $R^2$ is $C_{1-8}$ alkyl substituted with one to four fluorine atoms.

7. The compound or pharmaceutically acceptable salt thereof according to claim 1, wherein $R^2$ is $C_{1-8}$ alkyl substituted with zero to one —OH, and zero to two $C_{1-8}$ alkoxy groups substituted with [zero to one —OH group, zero to one $C_{1-4}$ alkoxy group, and zero to three fluorine atoms].

8. The compound or pharmaceutically acceptable salt thereof according to claim 1, wherein $R^2$ is 4- to 6-membered heterocyclyl which is optionally substituted with one to four substituents selected from the group consisting of a fluorine atom, —OH, $C_{1-4}$ alkyl, and $C_{1-4}$ alkoxy.

9. The compound or pharmaceutically acceptable salt thereof according to claim 1, wherein $R^2$ is a $C_{1-8}$ acyl group, —COOR$^8$, or —CONR$^9$R$^{10}$, each group is optionally substituted with one to four substituents selected from the group consisting of a fluorine atom, —OH, and $C_{1-4}$ alkoxy.

10. The compound or pharmaceutically acceptable salt thereof according to claim 1, wherein X represents CR$^{11}$.

11. The compound or pharmaceutically acceptable salt thereof according to claim 1, wherein X represents a nitrogen atom.

12. The compound or pharmaceutically acceptable salt thereof according to claim 11, wherein $A^1$ is a single bond.

13. The compound or pharmaceutically acceptable salt thereof according to claim 1, wherein $A^1$ represents a methylene group whose sp$^3$ carbon atom is not replaced with another structure.

14. The compound or pharmaceutically acceptable salt thereof according to claim 1, wherein $A^1$ is —O—.

15. The compound or pharmaceutically acceptable salt thereof according to claim 1, wherein X represents CR$^{11}$;
R$^{11}$ represents $C_{1-6}$ alkyl;
$A^1$ represents $C_{1-8}$ alkylene;
one sp$^3$ carbon atom at any position of $A^1$ is replaced with one structure selected from the group consisting of [—NR$^{14}$—, —NR$^{17}$—C(=O)—, and —NR$^{22}$—S(=O)$_2$—]; and
R$^{11}$ and $A^1$ are bonded via a single bond to form a ring.

16. The compound or pharmaceutically acceptable salt thereof according to claim 1, wherein $A^2$ represents 5- to 9-membered heterocyclylene;
wherein $A^2$ is optionally substituted with one to four substituents selected from the group consisting of —OH, =O, —COOH, —SO$_3$H, —PO$_3$H$_2$, —CN, —NO$_2$, halogen, $C_{1-8}$alkyl substituted with [zero to two —OH groups, zero to two —OR$^{45}$ groups, and zero to six fluorine atoms], $C_{3-12}$ cycloalkyl substituted with [zero to two —OH groups, zero to two —OR$^{46}$ groups, and zero to six fluorine atoms], $C_{1-8}$ alkoxy substituted with [zero to two —OH groups, zero to two —OR$^{47}$ groups, and zero to six fluorine atoms], and 4- to 12-membered heterocyclyl substituted with [zero to two —OH groups, zero to two —OR$^{49}$ groups, and zero to six fluorine atoms].

17. The compound or pharmaceutically acceptable salt thereof according to claim 1, wherein $A^3$ is a hydrogen atom.

18. The compound or pharmaceutically acceptable salt thereof according to claim 1, wherein $A^3$ is a halogen, —CN, —R$^{25}$, —OR$^{26}$, —NR$^{27}$R$^{28}$, —C(=O)R$^{29}$, or —C(=O)—OR$^{30}$, and each of R$^{25}$, R$^{26}$, R$^{27}$, R$^{28}$, R$^{29}$, and R$^{30}$ independently represents a hydrogen atom, optionally substituted $C_{1-8}$ alkyl, optionally substituted 4- to 12-membered heterocyclyl, optionally substituted $C_{3-12}$ cycloalkyl, optionally substituted (4- to 12-membered heterocyclyl)$C_{1-3}$ alkyl, or optionally substituted ($C_{3-12}$ cycloalkyl)$C_{1-3}$ alkyl.

19. The compound or pharmaceutically acceptable salt thereof according to claim 1, wherein $R^3$ is a hydrogen atom.

20. The compound or pharmaceutically acceptable salt thereof according to claim 1, wherein $R^3$ represents $C_{1-4}$ alkyl, a fluorine atom, or a chlorine atom.

21. A compound or pharmaceutically acceptable salt thereof selected from:
[2-[[5-(4-methylpiperazin-1-yl)pyridin-2-yl]amino]-8-morpholin-4-ylpyrido[3,4-d]pyrimidin-6-yl]methanol
[2-[[5-(4-methylpiperazin-1-yl)pyridin-2-yl]amino]-8-piperidin-1-ylpyrido[3,4-d]pyrimidin-6-yl]methanol
1-[6-(hydroxymethyl)-2-[[5-(4-methylpiperazin-1-yl)pyridin-2-yl]amino]pyrido[3,4-d]pyrimidin-8-yl]piperidin-2-one
6-(difluoromethyl)-N-[5-(4-methylpiperazin-1-yl)pyridin-2-yl]-8-morpholin-4-ylpyrido[3,4-d]pyrimidin-2-amine
[8-cyclohexyl-2-[[5-(4-methylpiperazin-1-yl)pyridin-2-yl]amino]pyrido[3,4-d]pyrimidin-6-yl]methanol
[2[[5-(4-methylpiperazin-1-yl)pyridin-2-yl]amino]-8-phenylpyrido[3,4-d]pyrimidin-6-yl]methanol
[8-morpholin-4-yl-2-[(5-piperazin-1-ylpyridin-2-yl)amino]pyrido[3,4-d]pyrimidin-6-yl]methanol
6-(difluoromethyl)-8-morpholin-4-yl-N-(5-piperazin-1-ylpyridin-2-yl)pyrido[3,4-d]pyrimidin-2-amine
[2-[(5-piperazin-1-ylpyridin-2-yl)amino]-8-piperidin-1-ylpyrido[3,4-d]pyrimidin-6-yl]methanol
[8-phenyl-2-[(5-piperazin-1-ylpyridin-2-yl)amino]pyrido[3,4-d]pyrimidin-6-yl]methanol
6-(difluoromethyl)-N-(5-piperazin-1-ylpyridin-2-yl)-8-piperidin-1-ylpyrido[3,4-d]pyrimidin-2-amine
6-(difluoromethyl)-8-phenyl-N-(5-piperazin-1-ylpyridin-2-yl)pyrido[3,4-d]pyrimidin-2-amine
6-(difluoromethyl)-N-[5-(4-methylpiperazin-1-yl)pyridin-2-yl]-8-piperidin-1-ylpyrido[3,4-d]pyrimidin-2-amine
[8-(4-methylphenyl)-2-[(5-piperazin-1-ylpyridin-2-yl)amino]pyrido[3,4-d]pyrimidin-6-yl]methanol
[8-(2-methylphenyl)-2-[(5-piperazin-1-ylpyridin-2-yl)amino]pyrido[3,4-d]pyrimidin-6-yl]methanol
[2-[(5-piperazin-1-ylpyridin-2-yl)amino]-8-thiophen-3-ylpyrido[3,4-d]pyrimidin-6-yl]methanol
[8-(furan-3-yl)-2-[(5-piperazin-1-ylpyridin-2-yl)amino]pyrido[3,4-d]pyrimidin-6-yl]methanol
[8-(4-methylphenyl)-2-[[5-(4-methylpiperazin-1-yl)pyridin-2-yl]amino]pyrido[3,4-d]pyrimidin-6-yl]methanol
[8-(2-methylphenyl)-2-[[5-(4-methylpiperazin-1-yl)pyridin-2-yl]amino]pyrido[3,4-d]pyrimidin-6-yl]methanol
[2[[5-(4-methylpiperazin-1-yl)pyridin-2-yl]amino]-8-thiophen-3-ylpyrido[3,4-d]pyrimidin-6-yl]methanol
[8-(furan-3-yl)-2-[[5-(4-methylpiperazin-1-yl)pyridin-2-yl]amino]pyrido[3,4-d]pyrimidin-6-yl]methanol
[8-(cyclohexen-1-yl)-2-[[5-(4-methylpiperazin-1-yl)pyridin-2-yl]amino]pyrido[3,4-d]pyrimidin-6-yl]methanol
2-[(5-piperazin-1-ylpyridin-2-yl)amino]-8-piperidin-1-ylpyrido[3,4-d]pyrimidine-6-carboxylic acid
1-[2-[(5-piperazin-1-ylpyridin-2-yl)amino]-8-piperidin-1-ylpyrido[3,4-d]pyrimidin-6-yl]ethanol
methyl 2-[(5-piperazin-1-ylpyridin-2-yl)amino]-8-piperidin-1-ylpyrido[3,4-d]pyrimidine-6-carboxylate
1-[2-[(5-piperazin-1-ylpyridin-2-yl)amino]-8-piperidin-1-ylpyrido[3,4-d]pyrimidin-6-yl]ethanone N,N-dimethyl-2-[(5-piperazin-1-ylpyridin-2-yl)amino]-8-piperidin-1-ylpyrido[3,4-d]pyrimidine-6-carboxamide
2-[(5-piperazin-1-ylpyridin-2-yl)amino]-8-piperidin-1-ylpyrido[3,4-d]pyrimidine-6-carboxamide
N-methyl-2-[(5-piperazin-1-ylpyridin-2-yl)amino]-8-piperidin-1-ylpyrido[3,4-d]pyrimidine-6-carboxamide
6-(difluoromethyl)-8-(2-methylphenyl)-N-(5-piperazin-1-ylpyridin-2-yl)pyrido[3,4-d]pyrimidin-2-amine
6-(difluoromethyl)-8-(furan-3-yl)-N-(5-piperazin-1-ylpyridin-2-yl)pyrido[3,4-d]pyrimidin-2-amine
6-(methoxymethyl)-8-morpholin-4-yl-N-(5-piperazin-1-ylpyridin-2-yl)pyrido[3,4-d]pyrimidin-2-amine
[5-methyl-8-morpholin-4-yl-2-[(5-piperazin-1-ylpyridin-2-yl)amino]pyrido[3,4-d]pyrimidin-6-yl]methanol
1-[8-morpholin-4-yl-2-[(5-piperazin-1-ylpyridin-2-yl)amino]pyrido[3,4-d]pyrimidin-6-yl]propan-1-ol
2,2,2-trifluoro-1[8-morpholin-4-yl-2-[(5-piperazin-1-ylpyridin-2-yl)amino]pyrido[3,4-d]pyrimidin-6-yl]ethanol
6-(1,1-difluoroethyl)-8-morpholin-4-yl-N-(5-piperazin-1-ylpyridin-2-yl)pyrido[3,4-d]pyrimidin-2-amine
2[8-morpholin-4-yl-2-[(5-piperazin-1-ylpyridin-2-yl)amino]pyrido[3,4-d]pyrimidin-6-yl]propan-2-ol
2[8-morpholin-4-yl-2-[(5-piperazin-1-ylpyridin-2-yl)amino]pyrido[3,4-d]pyrimidin-6-yl]ethanol
1-[6-[(1R)-1-hydroxyethyl]-2-[(6-piperazin-1-ylpyridazin-3-yl)amino]pyrido[3,4-d]pyrimidin-8-yl]pyrrolidine-2-carboxylic acid
1-[6-[(1R)-1-hydroxyethyl]-2-[(6-piperazin-1-ylpyridazin-3-yl)amino]pyrido[3,4-d]pyrimidin-8-yl]piperidine-3-carboxylic acid
1-[6-[(1R)-1-hydroxyethyl]-2-[(6-piperazin-1-ylpyridazin-3-yl)amino]pyrido[3,4-d]pyrimidin-8-yl]piperidine-2-carboxylic acid
1-[6-[(1R)-1-hydroxyethyl]-2-[[5-(piperazin-1-ylmethyl)pyridin-2-yl]amino]pyrido[3,4-d]pyrimidin-8-yl]pyrrolidine-2-carboxylic acid
6-(1-methoxyethyl)-N-[5-(piperazin-1-ylmethyl)pyridin-2-yl]-8-piperidin-1-ylpyrido[3,4-d]pyrimidin-2-amine
8-(1,2,3,3a,4,5,7,7a-octahydropyrrolo[2,3-c]pyridin-6-yl)-6-(1-methoxyethyl)-N-[5-(piperazin-1-ylmethyl)pyridin-2-yl]pyrido[3,4-d]pyrimidin-2-amine
[1-[6-(1-methoxyethyl)-2-[[5-(piperazin-1-ylmethyl)pyridin-2-yl]amino]pyrido[3,4-d]pyrimidin-8-yl]piperidin-4-yl]methanol
6-(1-methoxyethyl)-8-[4-(methoxymethyl)piperidin-1-yl]-N-[5-(piperazin-1-ylmethyl)pyridin-2-yl]pyrido[3,4-d]pyrimidin-2-amine
(1R)-1-[8-(azetidin-1-yl)-2-[[5-[[4-(2-hydroxyethyl)piperazin-1-yl]methyl]pyridin-2-yl]amino]pyrido[3,4-d]pyrimidin-6-yl]ethanol
(1R)-1-[2-[[5-[[4-(2-hydroxyethyl)piperazin-1-yl]methyl]pyridin-2-yl]amino]-8-pyrrolidin-1-ylpyrido[3,4-d]pyrimidin-6-yl]ethanol
(1R)-1-[2-[[5-[[4-(2-hydroxyethyl)piperazin-1-yl]methyl]pyridin-2-yl]amino]-8-piperidin-1-ylpyrido[3,4-d]pyrimidin-6-yl]ethanol
1-[6-[[8-(azetidin-1-yl)-6-[(1R)-1-hydroxyethyl]pyrido[3,4-d]pyrimidin-2-yl]amino]pyridin-3-yl]piperazin-2-one
1-[6[[6-[(1R)-1-hydroxyethyl]-8-pyrrolidin-1-ylpyrido[3,4-d]pyrimidin-2-yl]amino]pyridin-3-yl]piperazin-2-one
1-[6[[6-[(1R)-1-hydroxyethyl]-8-piperidin-1-ylpyrido[3,4-d]pyrimidin-2-yl]amino]pyridin-3-yl]piperazin-2-one
(1R)-1-[2-[[6-methyl-5-(4-methylpiperazin-1-yl)pyridin-2-yl]amino]-8-pyrrolidin-1-ylpyrido[3,4-d]pyrimidin-6-yl]ethanol
(1R)-1-[2-[[6-methyl-5-(4-methylpiperazin-1-yl)pyridin-2-yl]amino]-8-piperidin-1-ylpyrido[3,4-d]pyrimidin-6-yl]ethanol
(1R)-1[2-[[5-[(4-methylpiperazin-1-yl)methyl]pyridin-2-yl]amino]-8-pyrrolidin-1-ylpyrido[3,4-d]pyrimidin-6-yl]ethanol
(1R)-1[2-[[5-[(4-methylpiperazin-1-yl)methyl]pyridin-2-yl]amino]-8-piperidin-1-ylpyrido[3,4-d]pyrimidin-6-yl]ethanol
(1R)-1-[8-(2-azaspiro[3.3]heptan-2-yl)-2-[[5-[[4-(2-hydroxyethyl)piperazin-1-yl]methyl]pyridin-2-yl]amino]pyrido[3,4-d]pyrimidin-6-yl]ethanol
(1R)-1[2-[[5-[[4-(2-hydroxyethyl)piperazin-1-yl]methyl]pyridin-2-yl]amino]-8-morpholin-4-ylpyrido[3,4-d]pyrimidin-6-yl]ethanol
(1R)-1-[8-(azepan-1-yl)-2-[[5-[[4-(2-hydroxyethyl)piperazin-1-yl]methyl]pyridin-2-yl]amino]pyrido[3,4-d]pyrimidin-6-yl]ethanol
(1R)-1[2-[[6-[2-(dimethylamino)ethyl]-7,8-dihydro-5H-1,6-naphthyridin-2-yl]amino]-8-piperidin-1-ylpyrido[3,4-d]pyrimidin-6-yl]ethanol
(1R)-1[2-[[6-[2-(dimethylamino)ethyl]-7,8-dihydro-5H-1,6-naphthyridin-2-yl]amino]-8-(4-fluoropiperidin-1-yl)pyrido[3,4-d]pyrimidin-6-yl]ethanol
(1R)-1-[8-piperidin-1-yl-2-(5,6,7,8-tetrahydro-1,6-naphthyridin-2-ylamino)pyrido[3,4-d]pyrimidin-6-yl]ethanol
(1R)-1-[8-(4-fluoropiperidin-1-yl)-2-(5,6,7,8-tetrahydro-1,6-naphthyridin-2-ylamino)pyrido[3,4-d]pyrimidin-6-yl]ethanol
1-[6-[[8-(4,4-difluoropiperidin-1-yl)-6-[(1R)-1-hydroxyethyl]pyrido[3,4-d]pyrimidin-2-yl]amino]pyridin-3-yl]piperazin-2-one
1-[[6-[[6-[(1R)-1-hydroxyethyl]-8-piperidin-1-ylpyrido[3,4-d]pyrimidin-2-yl]amino]pyridin-3-yl]methyl]piperidin-4-ol
1-[[6-[[6-[(1R)-1-hydroxyethyl]-8-pyrrolidin-1-ylpyrido[3,4-d]pyrimidin-2-yl]amino]pyridin-3-yl]methyl]piperidin-4-ol
1-[[6-[[6-[(1R)-1-hydroxyethyl]-8-morpholin-4-ylpyrido[3,4-d]pyrimidin-2-yl]amino]pyridin-3-yl]methyl]piperidin-4-ol
(1R)-1-[2-[[5-[[4-(hydroxymethyl)piperidin-1-yl]methyl]pyridin-2-yl]amino]-8-piperidin-1-ylpyrido[3,4-d]pyrimidin-6-yl]ethanol
(1R)-1-[2-[[5-[[4-(hydroxymethyl)piperidin-1-yl]methyl]pyridin-2-yl]amino]-8-pyrrolidin-1-ylpyrido[3,4-d]pyrimidin-6-yl]ethanol
(1R)-1-[2-[[5-[[4-(hydroxymethyl)piperidin-1-yl]methyl]pyridin-2-yl]amino]-8-morpholin-4-ylpyrido[3,4-d]pyrimidin-6-yl]ethanol
1-[6-[(1R)-1-hydroxyethyl]-2-[[5-[[4-(hydroxymethyl)piperidin-1-yl]methyl]pyridin-2-yl]amino]pyrido[3,4-d]pyrimidin-8-yl]piperidin-4-ol
1-[6-[[6-[(1R)-1-hydroxyethyl]-8-piperidin-1-ylpyrido[3,4-d]pyrimidin-2-yl]amino]pyridin-3-yl]-4-methylpiperazin-2-one
1-[6-[[6-[(1R)-1-hydroxyethyl]-8-pyrrolidin-1-ylpyrido[3,4-d]pyrimidin-2-yl]amino]pyridin-3-yl]-4-methylpiperazin-2-one
1-[6-[[6-[(1R)-1-hydroxyethyl]-8-morpholin-4-ylpyrido[3,4-d]pyrimidin-2-yl]amino]pyridin-3-yl]-4-methylpiperazin-2-one (1R)-1-[8-(2,2-dimethylpyrrolidin-1-yl)-2-[[5-[[4-(2-hydroxyethyl)piperazin-1-yl]methyl]pyridin-2-yl]amino]pyrido[3,4-d]pyrimidin-6-yl]ethanol 1-[6-[(1R)-1-hydroxyethyl]-2-[[5-[[4-(2-hydroxyethyl)piperazin-1-yl]methyl]pyridin-2-yl]amino]pyrido[3,4-d]pyrimidin-8-yl]piperidine-4-carboxylic acid (1R)-1-[2-[[5-[[4-(2-hydroxyethyl)piperazin-1-yl]methyl]pyridin-2-yl]amino]-8-(4-methylpiperazin-1-yl)pyrido[3,4-d]pyrimidin-6-yl]ethanol (1R)-1-[8-(4-fluoropiperidin-1-yl)-2-[[5-[[4-(2-hydroxyethyl)piperazin-1-yl]methyl]pyridin-2-yl]amino]pyrido[3,4-d]pyrimidin-6-yl]ethanol (1R)-1-[8-(4,4-difluoropiperidin-1-yl)-2-[[5-[[4-(2-hydroxyethyl)piperazin-1-yl]methyl]pyridin-2-yl]amino]pyrido[3,4-d]pyrimidin-6-yl]ethanol (1R)-1-[8-(4,4-difluoropiperidin-1-yl)-2-(5,6,7,8-tetrahydro-1,6-naphthyridin-2-ylamino)pyrido[3,4-d]pyrimidin-6-yl]ethanol (1R)-1-[8-(4,4-difluoropiperidin-1-yl)-2-[[6-(2-hydroxyethyl)-7,8-dihydro-5H-1,6-naphthyridin-2-yl]amino]pyrido[3,4-d]pyrimidin-6-yl]ethanol (1R)-1-[8-(4,4-difluoropiperidin-1-yl)-2-[[6-[2-(dimethylamino)ethyl]-7,8-dihydro-5H-1,6-naphthyridin-2-yl]amino]pyrido[3,4-d]pyrimidin-6-yl]ethanol (1R)-1-[2-[[5-[[4-(2-hydroxyethyl)piperazin-1-yl]methyl]pyridin-2-yl]amino]-8-[(2R)-2-methylpyrrolidin-1-yl]pyrido[3,4-d]pyrimidin-6-yl]ethanol (1R)-1-[2-[[5-[[4-(2-hydroxyethyl)piperazin-1-yl]methyl]pyridin-2-yl]amino]-8-[4-(trifluoromethyl)piperidin-1-yl]pyrido[3,4-d]pyrimidin-6-yl]ethanol (1R)-1-[8-(1,1-dioxo-1,4-thiazinan-4-yl)-2-[[5-[[4-(2-hydroxyethyl)piperazin-1-yl]methyl]pyridin-2-yl]amino]pyrido[3,4-d]pyrimidin-6-yl]ethanol (1R)-1-[2-[(6-methyl-5-piperazin-1-ylpyridin-2-yl)amino]-8-pyrrolidin-1-ylpyrido[3,4-d]pyrimidin-6-yl]ethanol (1R)-1-[2-[(6-methyl-5-piperazin-1-ylpyridin-2-yl)amino]-8-piperidin-1-ylpyrido[3,4-d]pyrimidin-6-yl]ethanol (1R)-1-[2-[[5-4-(2-hydroxyethyl)piperazin-1-yl]-6-methylpyridin-2-yl]amino]-8-piperidin-1-ylpyrido[3,4-d]pyrimidin-6-yl]ethanol 4-[6-[[6-[(1R)-1-hydroxyethyl]-8-piperidin-1-ylpyrido[3,4-d]pyrimidin-2-yl]amino]pyridin-3-yl]-1,4-diazepan-5-one 1-[6-[[8-(4-fluoropiperidin-1-yl)-6-[(1R)-1-hydroxyethyl]pyrido[3,4-d]pyrimidin-2-yl]amino]pyridin-3-yl]piperazin-2-one (1R)-1-[2-[(6-piperazin-1-ylpyridazin-3-yl)amino]-8-piperidin-1-ylpyrido[3,4-d]pyrimidin-6-yl]ethanol 2-[2-[[5-(piperazin-1-ylmethyl)pyridin-2-yl]amino]-8-piperidin-1-ylpyrido[3,4-d]pyrimidin-6-yl]ethanol 1-[6-[[6-(2-hydroxyethyl)-8-piperidin-1-ylpyrido[3,4-d]pyrimidin-2-yl]amino]pyridin-3-yl]piperazin-2-one 2-[2-[(6-piperazin-1-ylpyridazin-3-yl)amino]-8-piperidin-1-ylpyrido[3,4-d]pyrimidin-6-yl]ethanol 2-[8-piperidin-1-yl-2-(5,6,7,8-tetrahydro-1,6-naphthyridin-2-ylamino)pyrido[3,4-d]pyrimidin-6-yl]ethanol 2-[4-[[6-[[6-(hydroxymethyl)-8-piperidin-1-ylpyrido[3,4-d]pyrimidin-2-yl]amino]pyridin-3-yl]methyl]piperazin-1-yl]ethanol 1-[6-[[6-(hydroxymethyl)-8-piperidin-1-ylpyrido[3,4-d]pyrimidin-2-yl]amino]pyridin-3-yl]piperazin-2-one (1R)-1-[2-[[5-[[4-(2-hydroxyethyl)piperazin-1-yl]methyl]pyridin-2-yl]amino]-8-[(2 S)-2-methylpyrrolidin-1-yl]pyrido[3,4-d]pyrimidin-6-yl]ethanol (1R)-1-[2-[[5-[[4-(2-hydroxyethyl)piperazin-1-yl]methyl]pyridin-2-yl]amino]-8-[(3 S)-3-methylpyrrolidin-1-yl]pyrido[3,4-d]pyrimidin-6-yl]ethanol (1R)-1-[2-[[5-[[4-(2-hydroxyethyl)piperazin-1-yl]methyl]pyridin-2-yl]amino]-8-[(3R)-3-methylpyrrolidin-1-yl]pyrido[3,4-d]pyrimidin-6-yl]ethanol (1R)-1-[8-(2,5-dimethylpyrrolidin-1-yl)-2-[[5-[[4-(2-hydroxyethyl)piperazin-1-yl]methyl]pyridin-2-yl]amino]pyrido[3,4-d]pyrimidin-6-yl]ethanol (1R)-1-[8-(3,3-dimethylpyrrolidin-1-yl)-2-[[5-[[4-(2-hydroxyethyl)piperazin-1-yl]methyl]pyridin-2-yl]amino]pyrido[3,4-d]pyrimidin-6-yl]ethanol (1R)-1-[8-(7-azabicyclo[2.2.1]heptan-7-yl)-2-[[5-[[4-(2-hydroxyethyl)piperazin-1-yl]methyl]pyridin-2-yl]amino]pyrido[3,4-d]pyrimidin-6-yl]ethanol (1R)-1-[8-(3-azabicyclo[3.1.0]hexan-3-yl)-2-[[5-[[4-(2-hydroxyethyl)piperazin-1-yl]methyl]pyridin-2-yl]amino]pyrido[3,4-d]pyrimidin-6-yl]ethanol (1R)-1-[8-(8-azabicyclo[3.2.1]octan-8-yl)-2-[[5-[[4-(2-hydroxyethyl)piperazin-1-yl]methyl]pyridin-2-yl]amino]pyrido[3,4-d]pyrimidin-6-yl]ethanol 1-[6-[(1R)-1-hydroxyethyl]-2-[[5-[[4-(2-hydroxyethyl)piperazin-1-yl]methyl]pyridin-2-yl]amino]pyrido[3,4-d]pyrimidin-8-yl]piperidin-4-ol

[2-[(6-piperazin-1-ylpyridazin-3-yl)amino]-8-piperidin-1-ylpyrido[3,4-d]pyrimidin-6-yl]methanol

[2-[[5-(piperazin-1-ylmethyl)pyridin-2-yl]amino]-8-piperidin-1-ylpyrido[3,4-d]pyrimidin-6-yl]methanol 2-[2-[[6-(2-hydroxyethyl)-7,8-dihydro-5H-1,6-naphthyridin-2-yl]amino]-8-piperidin-1-ylpyrido[3,4-d]pyrimidin-6-yl]ethanol 2-[2-[[6-[2-(dimethylamino)ethyl]-7,8-dihydro-5H-1,6-naphthyridin-2-yl]amino]-8-piperidin-1-ylpyrido[3,4-d]pyrimidin-6-yl]ethanol (1R)-1-[2-[[6-(2-hydroxyethyl)-7,8-dihydro-5H-1,6-naphthyridin-2-yl]amino]-8-piperidin-1-ylpyrido[3,4-d]pyrimidin-6-yl]ethanol (1R)-1-[8-(4-fluoropiperidin-1-yl)-2-[[6-(2-hydroxyethyl)-7,8-dihydro-5H-1,6-naphthyridin-2-yl]amino]pyrido[3,4-d]pyrimidin-6-yl]ethanol (1R)-1-[8-(3,4-dimethylpyrrolidin-1-yl)-2-[[5-[[4-(2-hydroxyethyl)piperazin-1-yl]methyl]pyridin-2-yl]amino]pyrido[3,4-d]pyrimidin-6-yl]ethanol (1R)-1-[2-[[6-[4-(2-methylsulfonylethyl)piperazin-1-yl]pyridazin-3-yl]amino]-8-piperidin-1-ylpyrido[3,4-d]pyrimidin-6-yl]ethanol (1R)-1-[8-(4-fluoropiperidin-1-yl)-2-[[5-[(4-methylpiperazin-1-yl)methyl]pyridin-2-yl]amino]pyrido[3,4-d]pyrimidin-6-yl]ethanol (1R)-1-[8-[(3R)-3-fluoropyrrolidin-1-yl]-2-[[5-[(4-methylpiperazin-1-yl)methyl]pyridin-2-yl]amino]pyrido[3,4-d]pyrimidin-6-yl]ethanol (1R)-1-[8-[(3 S)-3-fluoropyrrolidin-1-yl]-2-[[5-[(4-methylpiperazin-1-yl)methyl]pyridin-2-yl]amino]pyrido[3,4-d]pyrimidin-6-yl]ethanol 6-[(1R)-1-methoxyethyl]-N-(6-piperazin-1-ylpyridazin-3-yl)-8-piperidin-1-ylpyrido[3,4-d]pyrimidin-2-amine 6-[(1R)-1-methoxyethyl]-N-[5-(piperazin-1-ylmethyl)pyridin-2-yl]-8-piperidin-1-ylpyrido[3,4-d]pyrimidin-2-amine 4-[6-[[6-[(1R)-1-hydroxyethyl]-8-pyrrolidin-1-ylpyrido[3,4-d]pyrimidin-2-yl]amino]pyridin-3-yl]-1-methyl-1,4-diazepan-5-one 4-[6-[[6-[(1R)-1-hydroxyethyl]-8-piperidin-1-ylpyrido[3,4-d]pyrimidin-2-yl]amino]pyridin-3-yl]-1-methyl-1,4-diazepan-5-one (1R)-1[2-[[5-[(4-ethylpiperazin-1-yl)methyl]pyridin-2-yl]amino]-8-piperidin-1-ylpyrido[3,4-d]pyrimidin-6-yl]ethanol (1R)-1-[2-[[6-(4-methylpiperazin-1-yl)pyridazin-3-yl]amino]-8-piperidin-1-ylpyrido[3,4-d]pyrimidin-6-yl]ethanol (1R)-1-[8-(4-fluoropiperidin-1-yl)-2-[[6-(4-methylpiperazin-1-yl)pyridazin-3-yl]amino]pyrido[3,4-d]pyrimidin-6-yl]ethanol 8-(4-fluoropiperidin-1-yl)-6-[(1R)-1-methoxyethyl]-N-[6-(4-methylpiperazin-1-yl)pyridazin-3-yl]pyrido[3,4-d]pyrimidin-2-amine 8-(4-fluoropiperidin-1-yl)-6-[(1R)-1-methoxyethyl]-N-(6-piperazin-1-ylpyridazin-3-yl)pyrido[3,4-d]pyrimidin-2-amine 1-[6-[[6-[(1R)-1-hydroxyethyl]-8-piperidin-1-ylpyrido[3,4-d]pyrimidin-2-yl]amino]pyridin-3-yl]-1,4-diazepan-2-one 2-[4-[[6-[[6-(difluoromethyl)-8-piperidin-1-ylpyrido[3,4-d]pyrimidin-2-yl]amino]pyridin-3-yl]methyl]piperazin-1-yl]ethanol 1-[6-(difluoromethyl)-2-[[5-[[4-(2-hydroxyethyl)piperazin-1-yl]methyl]pyridin-2-yl]amino]pyrido[3,4-d]pyrimidin-8-yl]piperidin-4-ol 3-[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]propan-1-ol (1R)-1-[2-[[5-[(3 S,4S)-3-fluoro-1-(2-hydroxyethyl)piperidin-4-yl] oxypyridin-2-yl]amino]-8-piperidin-1-ylpyrido[3,4-d]pyrimidin-6-yl]ethanol (1R)-1-[2-[[5-[(3 S,4R)-3-fluoro-1-(2-hydroxyethyl)piperidin-4-yl]oxypyridin-2-yl]amino]-8-piperidin-1-ylpyrido[3,4-d]pyrimidin-6-yl]ethanol (1R)-1-[8-(3,3-difluoroazetidin-1-yl)-2-[[5-[(4-methylpiperazin-1-yl)methyl]pyridin-2-yl]amino]pyrido[3,4-d]pyrimidin-6-yl]ethanol 1-[6-[(1R)-1-hydroxyethyl]-2-[[5-[(4-methylpiperazin-1-yl)methyl]pyridin-2-yl]amino]pyrido[3,4-d]pyrimidin-8-yl]piperidin-4-ol 2-[2-[[6-(hydroxymethyl)-8-piperidin-1-ylpyrido[3,4-d]pyrimidin-2-yl]amino]-7,8-dihydro-5H-1,6-naphthyridin-6-yl]ethanol (1R)-1[2-[[5-[(4-methylpiperazin-1-yl)methyl]pyridin-2-yl]amino]-8-[(2R)-2-methylpyrrolidin-1-yl]pyrido[3,4-d]pyrimidin-6-yl]ethanol (1R)-1[2-[[5-[(4-methylpiperazin-1-yl)methyl]pyridin-2-yl]amino]-8-[(2 S)-2-methylpyrrolidin-1-yl]pyrido[3,4-d]pyrimidin-6-yl]ethanol (1R)-1[2-[[5-[(4-methylpiperazin-1-yl)methyl]pyridin-2-yl]amino]-8-[(3R)-3-methylpyrrolidin-1-yl]pyrido[3,4-d]pyrimidin-6-yl]ethanol (1R)-1[2-[[5-[(4-methylpiperazin-1-yl)methyl]pyridin-2-yl]amino]-8-[(3 S)-3-methylpyrrolidin-1-yl]pyrido[3,4-d]pyrimidin-6-yl]ethanol (1R)-1-[8-(2,5-dimethylpyrrolidin-1-yl)-2-[[5-[(4-methylpiperazin-1-yl)methyl]pyridin-2-yl]amino]pyrido[3,4-d]pyrimidin-6-yl]ethanol (1R)-1-[8-(3,4-dimethylpyrrolidin-1-yl)-2-[[5-[(4-methylpiperazin-1-yl)methyl]pyridin-2-yl]amino]pyrido[3,4-d]pyrimidin-6-yl]ethanol (1R)-1-[8-(3,3-dimethylpyrrolidin-1-yl)-2-[[5-[(4-methylpiperazin-1-yl)methyl]pyridin-2-yl]amino]pyrido[3,4-d]pyrimidin-6-yl]ethanol (1R)-1-[8-(7-azabicyclo[2.2.1]heptan-7-yl)-2-[[5-[(4-methylpiperazin-1-yl)methyl]pyridin-2-yl]amino]pyrido[3,4-d]pyrimidin-6-yl]ethanol (1R)-1-[2-[[5-[(4-methylpiperazin-1-yl)methyl]pyridin-2-yl]amino]-8-[4-(trifluoromethyl)piperidin-1-yl]pyrido[3,4-d]pyrimidin-6-yl]ethanol (1R)-1-[2-[[5-[(4-methylpiperazin-1-yl)methyl]pyridin-2-yl]amino]-8-morpholin-4-ylpyrido[3,4-d]pyrimidin-6-yl]ethanol 1-[2-[[5-[(4-methylpiperazin-1-yl)methyl]pyridin-2-yl]amino]-8-piperidin-1-ylpyrido[3,4-d]pyrimidin-6-yl]propan-1-ol

[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]-piperidin-4-ylmethanone

[1-(2-hydroxyethyl)piperidin-4-yl]-[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]methanone

[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]-(1-methylpiperidin-4-yl)methanone (1R)-1-[8-(4,4-difluoropiperidin-1-yl)-2-[[5-[(4-methylpiperazin-1-yl)methyl]pyridin-2-yl]amino]pyrido[3,4-d]pyrimidin-6-yl]ethanol 1-(2-hydroxyethyl)-4-[6-[[6-[(1R)-1-hydroxyethyl]-8-piperidin-1-ylpyrido[3,4-d]pyrimidin-2-yl]amino]pyridin-3-yl]-1,4-diazepan-5-one (1R)-1-[2-[[5-[[(2R)-2,4-dimethylpiperazin-1-yl]methyl]pyridin-2-yl]amino]-8-piperidin-1-ylpyrido[3,4-d]pyrimidin-6-yl]ethanol (1R)-1-[8-cyclopropyl-2-[[5-[[4-(2-hydroxyethyl)piperazin-1-yl]methyl]pyridin-2-yl]amino]pyrido[3,4-d]pyrimidin-6-yl]ethanol 1-[6-[[8-cyclopropyl-6-[(1R)-1-hydroxyethyl]pyrido[3,4-d]pyrimidin-2-yl]amino]pyridin-3-yl]piperazin-2-one (1R)-1[2-[[5-(piperazin-1-ylmethyl)pyridin-2-yl]amino]-8-piperidin-1-ylpyrido[3,4-d]pyrimidin-6-yl]ethanol (1R)-1-[8-(cyclohexen-1-yl)-2-[[5-[[4-(2-hydroxyethyl)piperazin-1-yl]methyl]pyridin-2-yl]amino]pyrido[3,4-d]pyrimidin-6-yl]ethanol (1R)-1-[8-(3-azabicyclo[3.1.0]hexan-3-yl)-2-[[5-[(4-methylpiperazin-1-yl)methyl]pyridin-2-yl]amino]pyrido[3,4-d]pyrimidin-6-yl]ethanol (1R)-1-[8-(azepan-1-yl)-2-[[5-[(4-methylpiperazin-1-yl)methyl]pyridin-2-yl]amino]pyrido[3,4-d]pyrimidin-6-yl]ethanol (1R)-1-[2-[[5-[[4-(2-hydroxyethyl)piperazin-1-yl]methyl]pyridin-2-yl]amino]-8-piperidin-1-ylpyrido[3,4-d]pyrimidin-6-yl]propan-1-ol (1 s)-1-[2-[[5-[[4-(2-hydroxyethyl)piperazin-1-yl]methyl]pyridin-2-yl]amino]-8-piperidin-1-ylpyrido[3,4-d]pyrimidin-6-yl]propan-1-ol (1R)-1-[2-[[6-(oxetan-3-yl)-7,8-dihydro-5H-1,6-naphthyridin-2-yl]amino]-8-piperidin-1-ylpyrido[3,4-d]pyrimidin-6-yl]ethanol (1R)-1-[2-[[6-(2-morpholin-4-ylethyl)-7,8-dihydro-5H-1,6-naphthyridin-2-yl]amino]-8-piperidin-1-ylpyrido[3,4-d]pyrimidin-6-yl]ethanol (1R)-1-[8-piperidin-1-yl-2-[(6-piperidin-4-ylsulfonyl-7,8-dihydro-5H-1,6-naphthyridin-2-yl)amino]pyrido[3,4-d]pyrimidin-6-yl]ethanol (1R)-1-[8-piperidin-1-yl-2-[(5-piperidin-4-yloxypyridin-2-yl)amino]pyrido[3,4-d]pyrimidin-6-yl]ethanol (1R)-1[2-[[5-[1-(2-hydroxyethyl)piperidin-4-yl] oxypyridin-2-yl]amino]-8-piperidin-1-ylpyrido[3,4-d]pyrimidin-6-yl]ethanol (2S)-2-[8-piperidin-1-yl-2-(5,6,7,8-tetrahydro-1,6-naphthyridin-2-ylamino)pyrido[3,4-d]pyrimidin-6-yl]propan-1-ol (2R)-2-[2-[[5-[[4-(2-hydroxyethyl)piperazin-1-yl]methyl]pyridin-2-yl]amino]-8-piperidin-1-ylpyrido[3,4-d]pyrimidin-6-yl]propan-1-ol (2R)-1-[2-[[5-[[4-(2-hydroxyethyl)piperazin-1-yl]methyl]pyridin-2-yl]amino]-8-piperidin-1-ylpyrido[3,4-d]pyrimidin-6-yl]propan-2-ol 1-[6-[[6-[(2R)-2-hydroxypropyl]-8-piperidin-1-ylpyrido[3,4-d]pyrimidin-2-yl]amino]pyridin-3-yl]piperazin-2-one (2R)-1-[2-[[6-(2-hydroxyethyl)-7,8-dihydro-5H-1,6-naphthyridin-2-yl]amino]-8-piperidin-1-ylpyrido[3,4-d]pyrimidin-6-yl]propan-2-ol (2R)-2-[2-[[6-(2-hydroxyethyl)-7,8-dihydro-5H-1,6-naphthyridin-2-yl]amino]-8-piperidin-1-ylpyrido[3,4-d]pyrimidin-6-yl]propan-1-ol (1R)-1-[8-(azetidin-1-yl)-2-[[5-[(4-methylpiperazin-1-yl)methyl]pyridin-2-yl]amino]pyrido[3,4-d]pyrimidin-6-yl]ethanol (1R)-1-[8-(2,2-dimethylpyrrolidin-1-yl)-2-[[5-[(4-methylpiperazin-1-yl)methyl]pyridin-2-yl]amino]pyrido[3,4-d]pyrimidin-6-yl]ethanol (1R)-1-[8-(8-azabicyclo[3.2.1]octan-8-yl)-2-[[5-[(4-methylpiperazin-1-yl)methyl]pyridin-2-yl]amino]pyrido[3,4-d]pyrimidin-6-yl]ethanol (1R)-1-[2-[[6-(azetidin-3-yl)-7,8-dihydro-5H-1,6-naphthyridin-2-yl]amino]-8-piperidin-1-ylpyrido[3,4-d]pyrimidin-6-yl]ethanol (1R)-1-[2-[[6-[1-(2-hydroxyethyl)azetidin-3-yl]-7,8-dihydro-5H-1,6-naphthyridin-2-yl]amino]-8-piperidin-1-ylpyrido[3,4-d]pyrimidin-6-yl]ethanol (1R)-1[2-[[5-[(4-methylpiperazin-1-yl)methyl]pyridin-2-yl]amino]-8-(1,4-oxazepan-4-yl)pyrido[3,4-d]pyrimidin-6-yl]ethanol (1R)-1[2-[[5-[[4-(2-hydroxyethyl)piperazin-1-yl]methyl]pyridin-2-yl]amino]-8-(1,4-oxazepan-4-yl)pyrido[3,4-d]pyrimidin-6-yl]ethanol (1R)-1-[8-[(3 S)-3-fluoropiperidin-1-yl]-2-[[5-[(4-methylpiperazin-1-yl)methyl]pyridin-2-yl]amino]pyrido[3,4-d]pyrimidin-6-yl]ethanol (1R)-1-[8-[(3 S)-3-fluoropiperidin-1-yl]-2-[[5-[[4-(2-hydroxyethyl)piperazin-1-yl]methyl]pyridin-2-yl]amino]pyrido[3,4-d]pyrimidin-6-yl]ethanol (1R)-1-[8-[(3 S)-3-fluoropyrrolidin-1-yl]-2-[[5-[[4-(2-hydroxyethyl)piperazin-1-yl]methyl]pyridin-2-yl]amino]pyrido[3,4-d]pyrimidin-6-yl]ethanol (1R)-1-[8-[(3R)-3-fluoropyrrolidin-1-yl]-2-[[5-[[4-(2-hydroxyethyl)piperazin-1-yl]methyl]pyridin-2-yl]amino]pyrido[3,4-d]pyrimidin-6-yl]ethanol (2S)-1-[4-[[6-[[6-[(1R)-1-hydroxyethyl]-8-piperidin-1-ylpyrido[3,4-d]pyrimidin-2-yl]amino]pyridin-3-yl]methyl]piperazin-1-yl]propan-2-ol (2R)-1-[4[[6-[[6-[(1R)-1-hydroxyethyl]-8-piperidin-1-ylpyrido[3,4-d]pyrimidin-2-yl]amino]pyridin-3-yl]methyl]piperazin-1-yl]propan-2-ol (1R)-1-[8-(7-azabicyclo[2.2.1]heptan-7-yl)-2-[[6-methyl-5-(4-methylpiperazin-1-yl)pyridin-2-yl]amino]pyrido[3,4-d]pyrimidin-6-yl]ethanol (1R)-1[2-[[5-[[(2S)-2,4-dimethylpiperazin-1-yl]methyl]pyridin-2-yl]amino]-8-piperidin-1-ylpyrido[3,4-d]pyrimidin-6-yl]ethanol (1R)-1-[8-(7-azabicyclo[2.2.1]heptan-7-yl)-2-[[5-[[(2 S)-2,4-dimethylpiperazin-1-yl]methyl]pyridin-2-yl]amino]pyrido[3,4-d]pyrimidin-6-yl]ethanol (1R)-1-[2-[[5-[[(3S)-3,4-dimethylpiperazin-1-yl]methyl]pyridin-2-yl]amino]-8-piperidin-1-ylpyrido[3,4-d]pyrimidin-6-yl]ethanol (1R)-1-[8-(7-azabicyclo[2.2.1]heptan-7-yl)-2-[[5-[[(3S)-3,4-dimethylpiperazin-1-yl]methyl]pyridin-2-yl]amino]pyrido[3,4-d]pyrimidin-6-yl]ethanol (1R)-1-[2-[[5-[[4-(2-hydroxyethyl)piperazin-1-yl]methyl]pyridin-2-yl]amino]-8-phenylpyrido[3,4-d]pyrimidin-6-yl]ethanol 1-[6-[[6-[(1R)-1-hydroxyethyl]-8-phenylpyrido[3,4-d]pyrimidin-2-yl]amino]pyridin-3-yl]piperazin-2-one 1-[6-[[6-[(2 S)-1-hydroxypropan-2-yl]-8-piperidin-1-ylpyrido[3,4-d]pyrimidin-2-yl]amino]pyridin-3-yl]piperazin-2-one (2S)-2-[2-[[6-(2-hydroxyethyl)-7,8-dihydro-5H-1,6-naphthyridin-2-yl]amino]-8-piperidin-1-ylpyrido[3,4-d]pyrimidin-6-yl]propan-1-ol 1-[6-[[6-[(2R)-1-hydroxypropan-2-yl]-8-piperidin-1-ylpyrido[3,4-d]pyrimidin-2-yl]amino]pyridin-3-yl]piperazin-2-one (2S)-2-[2-[[5-[[4-(2-hydroxyethyl)piperazin-1-yl]methyl]pyridin-2-yl]amino]-8-piperidin-1-ylpyrido[3,4-d]pyrimidin-6-yl]propan-1-ol 2-[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]acetonitrile (1R)-1-[2-[[6-(oxetan-3-ylmethyl)-7,8-dihydro-5H-1,6-naphthyridin-2-yl]amino]-8-piperidin-1-ylpyrido[3,4-d]pyrimidin-6-yl]ethanol (1R)-1-[8-[(3R)-3-fluoropiperidin-1-yl]-2-[[5-[(4-methylpiperazin-1-yl)methyl]pyridin-2-yl]amino]pyrido[3,4-d]pyrimidin-6-yl]ethanol (1R)-1-[8-[(3R)-3-fluoropiperidin-1-yl]-2-[[5-[[4-(2-hydroxyethyl)piperazin-1-yl]methyl]pyridin-2-yl]amino]pyrido[3,4-d]pyrimidin-6-yl]ethanol (1R)-1-[2-[[6-(1-methylazetidin-3-yl)-7,8-dihydro-5H-1,6-naphthyridin-2-yl]amino]-8-piperidin-1-ylpyrido[3,4-d]pyrimidin-6-yl]ethanol (1R)-1-[2-[[6-(2-hydroxyethyl)-5,7-dihydropyrrolo[3,4-b]pyridin-2-yl]amino]-8-piperidin-1-ylpyrido[3,4-d]pyrimidin-6-yl]ethanol (2S)-1-[2-[[5-[[4-(2-hydroxyethyl)piperazin-1-yl]methyl]pyridin-2-yl]amino]-8-piperidin-1-ylpyrido[3,4-d]pyrimidin-6-yl]propan-2-ol 1-[6-[[6-[(2S)-2-hydroxypropyl]-8-piperidin-1-ylpyrido[3,4-d]pyrimidin-2-yl]amino]pyridin-3-yl]piperazin-2-one (2S)-1-[2-[[6-(2-hydroxyethyl)-7,8-dihydro-5H-1,6-naphthyridin-2-yl]amino]-8-piperidin-1-ylpyrido[3,4-d]pyrimidin-6-yl]propan-2-ol 8-(7-azabicyclo[2.2.1]heptan-7-yl)-6-(oxolan-3-yl)-N-[5-(piperazin-1-ylmethyl)pyridin-2-yl]pyrido[3,4-d]pyrimidin-2-amine 6-(oxolan-3-yl)-N-[5-(piperazin-1-ylmethyl)pyridin-2-yl]-8-piperidin-1-ylpyrido[3,4-d]pyrimidin-2-amine 8-(7-azabicyclo[2.2.1]heptan-7-yl)-6-(oxolan-3-yl)-N-(6-piperazin-1-ylpyridazin-3-yl)pyrido[3,4-d]pyrimidin-2-amine 6-(oxolan-3-yl)-N-(6-piperazin-1-ylpyridazin-3-yl)-8-piperidin-1-ylpyrido[3,4-d]pyrimidin-2-amine

[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]-[(2R)-pyrrolidin-2-yl]methanone

[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]-[(3S)-pyrrolidin-3-yl]methanone

[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]-[(2R)-piperidin-2-yl]methanone

[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]-[(2R,4S)-4-hydroxypyrrolidin-2-yl]methanone
[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]-[(2R,4R)-4-hydroxypyrrolidin-2-yl]methanone
[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]-[(3R)-piperidin-3-yl]methanone
[(2R)-azetidin-2-yl]-[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]methanone
[2-[[6-[(1R)-1-hydroxyethyl]-8-piperidin-1-ylpyrido[3,4-d]pyrimidin-2-yl]amino]-7,8-dihydro-5H-1,6-naphthyridin-6-yl]-morpholin-2-ylmethanone
(1R)-1-[2-[[6-(2-aminoethyl)-7,8-dihydro-5H-1,6-naphthyridin-2-yl]amino]-8-piperidin-1-ylpyrido[3,4-d]pyrimidin-6-yl]ethanol
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R)-1-methylpyrrolidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S)-1-methylpyrrolidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(3S)-1-methylpyrrolidin-3-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(3R)-1-methylpyrrolidin-3-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R)-1-methylpiperidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S)-1-methylpiperidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R,4S)-4-hydroxy-1-methylpyrrolidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S,4R)-4-hydroxy-1-methylpyrrolidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R,4R)-4-hydroxy-1-methylpyrrolidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S,4S)-4-hydroxy-1-methylpyrrolidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(3R)-1-methylpiperidin-3-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(3S)-1-methylpiperidin-3-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R)-1-methylazetidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S)-1-methylazetidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-(4-methylmorpholin-3-yl)methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-(4-methylmorpholin-2-yl)methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-(1-methylazetidin-3-yl)methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R)-1-(2-hydroxyethyl)pyrrolidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S)-1-(2-hydroxyethyl)pyrrolidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(3S)-1-(2-hydroxyethyl)pyrrolidin-3-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(3R)-1-(2-hydroxyethyl)pyrrolidin-3-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R)-1-(2-hydroxyethyl)piperidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S)-1-(2-hydroxyethyl)piperidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R,4S)-4-hydroxy-1-(2-hydroxyethyl)pyrrolidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S,4R)-4-hydroxy-1-(2-hydroxyethyl)pyrrolidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2R,4R)-4-hydroxy-1-(2-hydroxyethyl)pyrrolidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8-dihydro-5H-1,6-naphthyridin-6-yl]-[(2S,4S)-4-hydroxy-1-(2-hydroxyethyl)pyrrolidin-2-yl]methanone
[2-[[8-(7-azabicyclo[2.2.1]heptan-7-yl)-6-[(1R)-1-hydroxyethyl]pyrido[3,4-d]pyrimidin-2-yl]amino]-7,8- dihydro-5H-1,6-naphthyridin-6-yl]-[(3R)-1-(2-hy-
droxyethyl)piperidin-3-yl]methanone
[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-[(3S)-1-(2-hy-
droxyethyl)piperidin-3-yl]methanone
[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-[(2R)-1-(2-hy-
droxyethyl)azetidin-2-yl]methanone
[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-[(2S)-1-(2-hy-
droxyethyl)azetidin-2-yl]methanone
[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-[4-(2-hydroxy-
ethyl)morpholin-3-yl]methanone
[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-[4-(2-hydroxy-
ethyl)morpholin-2-yl]methanone
[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-[1-(2-hydroxy-
ethyl)azetidin-3-yl]methanone
1-[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-2-pyrrolidin-1-yl
ethanone
1-[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-2-(3-hydroxypyr-
rolidin-1-yl)ethanone
1-[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-2-(3-fluoropyrroli-
din-1-yl)ethanone
1-[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-2-(azetidin-1-yl)
ethanone
1-[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-2-(3-hydroxyazeti-
din-1-yl)ethanone
1-[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-2-(3-fluoroazeti-
din-1-yl)ethanone
1-[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-2-piperidin-1-yle-
thanone
1-[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-2-(4-hydroxypip-
eridin-1-yl)ethanone
1-[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-2-(4-fluoropiperi-
din-1-yl)ethanone
1-[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-2-(3-hydroxypip-
eridin-1-yl)ethanone
1-[2-[[8-(7-azabicyclo[2.2.1]heptan-7-yl)-6-[(1R)-1-hy-
droxyethyl]pyrido[3,4-d]pyrimidin-2-yl]amino]-7,8-
dihydro-5H-1,6-naphthyridin-6-yl]-2-(3-fluoropiperi-
din-1-yl)ethanone
2-[4[[6-[[6-(oxetan-3-yl)-8-piperidin-1-ylpyrido[3,4-d]
pyrimidin-2-yl]amino]pyridin-3-yl]methyl]piperazin-
1-yl]ethanol
2-[4[[6-[[8-(7-azabicyclo[2.2.1]heptan-7-yl)-6-(oxetan-
3-yl)pyrido[3,4-d]pyrimidin-2-yl]amino]pyridin-3-yl]
methyl]piperazin-1-yl]ethanol
[2-[[6-[(1R)-1-hydroxyethyl]-8-piperidin-1-ylpyrido[3,4-
d]pyrimidin-2-yl]amino]-7,8-dihydro-5H-1,6-naphthy-
ridin-6-yl]-morpholin-3-ylmethanone
morpholin-2-yl[2-[[6-(oxetan-3-yl)-8-piperidin-1-
ylpyrido[3,4-d]pyrimidin-2-yl]amino]-7,8-dihydro-
5H-1,6-naphthyridin-6-yl]methanone
morpholin-3-yl-[2-[[6-(oxetan-3-yl)-8-piperidin-1-
ylpyrido[3,4-d]pyrimidin-2-yl]amino]-7,8-dihydro-
5H-1,6-naphthyridin-6-yl]methanone
[2-[[8-(7-azabicyclo[2.2.1]heptan-7-yl)-6-(oxetan-3-yl)
pyrido[3,4-d]pyrimidin-2-yl]amino]-7,8-dihydro-5H-
1,6-naphthyridin-6-yl]-[(2R)-1-methylpyrrolidin-2-yl]
methanone
[2-[[8-(7-azabicyclo[2.2.1]heptan-7-yl)-6-(oxetan-3-yl)
pyrido[3,4-d]pyrimidin-2-yl]amino]-7,8-dihydro-5H-
1,6-naphthyridin-6-yl]-[(2S)-1-methylpyrrolidin-2-yl]
methanone
[2-[[8-(7-azabicyclo[2.2.1]heptan-7-yl)-6-(oxetan-3-yl)
pyrido[3,4-d]pyrimidin-2-yl]amino]-7,8-dihydro-5H-
1,6-naphthyridin-6-yl]-[(3S)-1-methylpyrrolidin-3-yl]
methanone
[2-[[8-(7-azabicyclo[2.2.1]heptan-7-yl)-6-(oxetan-3-yl)
pyrido[3,4-d]pyrimidin-2-yl]amino]-7,8-dihydro-5H-
1,6-naphthyridin-6-yl]-[(3R)-1-methylpyrrolidin-3-yl]
methanone
[2-[[8-(7-azabicyclo[2.2.1]heptan-7-yl)-6-(oxetan-3-yl)
pyrido[3,4-d]pyrimidin-2-yl]amino]-7,8-dihydro-5H-
1,6-naphthyridin-6-yl]-[(2R)-1-methylpiperidin-2-yl]
methanone
[2-[[8-(7-azabicyclo[2.2.1]heptan-7-yl)-6-(oxetan-3-yl)
pyrido[3,4-d]pyrimidin-2-yl]amino]-7,8-dihydro-5H-
1,6-naphthyridin-6-yl]-[(2S)-1-methylpiperidin-2-yl]
methanone
[2-[[8-(7-azabicyclo[2.2.1]heptan-7-yl)-6-(oxetan-3-yl)
pyrido[3,4-d]pyrimidin-2-yl]amino]-7,8-dihydro-5H-
1,6-naphthyridin-6-yl]-[(2R,4S)-4-hydroxy-1-meth-
ylpyrrolidin-2-yl]methanone
[2-[[8-(7-azabicyclo[2.2.1]heptan-7-yl)-6-(oxetan-3-yl)
pyrido[3,4-d]pyrimidin-2-yl]amino]-7,8-dihydro-5H-
1,6-naphthyridin-6-yl]-[(2S,4R)-4-hydroxy-1-meth-
ylpyrrolidin-2-yl]methanone
[2-[[8-(7-azabicyclo[2.2.1]heptan-7-yl)-6-(oxetan-3-yl)
pyrido[3,4-d]pyrimidin-2-yl]amino]-7,8-dihydro-5H-
1,6-naphthyridin-6-yl]-[(2R,4R)-4-hydroxy-1-meth-
ylpyrrolidin-2-yl]methanone
[2-[[8-(7-azabicyclo[2.2.1]heptan-7-yl)-6-(oxetan-3-yl)
pyrido[3,4-d]pyrimidin-2-yl]amino]-7,8-dihydro-5H-
1,6-naphthyridin-6-yl]-[(2S,4S)-4-hydroxy-1-meth-
ylpyrrolidin-2-yl]methanone
[2-[[8-(7-azabicyclo[2.2.1]heptan-7-yl)-6-(oxetan-3-yl)
pyrido[3,4-d]pyrimidin-2-yl]amino]-7,8-dihydro-5H-
1,6-naphthyridin-6-yl]-[(3R)-1-methylpiperidin-3-yl]
methanone
[2-[[8-(7-azabicyclo[2.2.1]heptan-7-yl)-6-(oxetan-3-yl)
pyrido[3,4-d]pyrimidin-2-yl]amino]-7,8-dihydro-5H-
1,6-naphthyridin-6-yl]-[(3S)-1-methylpiperidin-3-yl]
methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2R)-1-methylazetidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2S)-1-methylazetidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-(4-methylmorpholin-3-yl)methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-(4-methylmorpholin-2-yl)methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-(1-methylazetidin-3-yl)methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2R)-1-(2-hydroxyethyl)pyrrolidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2S)-1-(2-hydroxyethyl)pyrrolidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(3S)-1-(2-hydroxyethyl)pyrrolidin-3-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(3R)-1-(2-hydroxyethyl)pyrrolidin-3-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2R)-1-(2-hydroxyethyl)piperidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2S)-1-(2-hydroxyethyl)piperidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2R,4S)-4-hydroxy-1-(2-hydroxyethyl)pyrrolidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2S,4R)-4-hydroxy-1-(2-hydroxyethyl)pyrrolidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2R,4R)-4-hydroxy-1-(2-hydroxyethyl)pyrrolidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2S,4S)-4-hydroxy-1-(2-hydroxyethyl)pyrrolidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(3R)-1-(2-hydroxyethyl)piperidin-3-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(3S)-1-(2-hydroxyethyl)piperidin-3-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2R)-1-(2-hydroxyethyl)azetidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[(2S)-1-(2-hydroxyethyl)azetidin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[4-(2-hydroxyethyl)morpholin-3-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[4-(2-hydroxyethyl)morpholin-2-yl]methanone

[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-[1-(2-hydroxyethyl)azetidin-3-yl]methanone 1-[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-2-pyrrolidin-1-ylethanone 1-[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-2-(3-hydroxypyrrolidin-1-yl)ethanone 1-[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-2-(3-fluoropyrrolidin-1-yl)ethanone 1-[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-2-(azetidin-1-yl)ethanone 1-[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-2-(3-hydroxyazetidin-1-yl)ethanone 1-[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-2-(3-fluoroazetidin-1-yl)ethanone 1-[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-2-piperidin-1-ylethanone 1-[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-2-(4-hydroxypiperidin-1-yl)ethanone 1-[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-2-(4-fluoropiperidin-1-yl)ethanone 1-[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-2-(3-hydroxypiperidin-1-yl)ethanone 1-[2-[[8-(7-azabicyclo[2.2.1]heptan-7-yl)-6-(oxetan-3-yl)pyrido[3,4-d]pyrimidin-2-yl]amino]-7,8-dihydro-5H-1,6-naphthyridin-6-yl]-2-(3-fluoropiperidin-1-yl)ethanone 4-(2-hydroxyethyl)-1-[6-[[6-[(1R)-1-hydroxyethyl]-8-piperidin-1-ylpyrido[3,4-d]pyrimidin-2-yl]amino]pyridin-3-yl]piperazin-2-one (1R)-1-[8-(7-azabicyclo[2.2.1]heptan-7-yl)-2-[[5-[4-(2-hydroxyethyl)piperazin-1-yl]-6-methylpyridin-2-yl]amino]pyrido[3,4-d]pyrimidin-6-yl]ethanol (1R)-1-[2-[[6-[4-(2-hydroxyethyl)piperazin-1-yl]pyridazin-3-yl]amino]-8-piperidin-1-ylpyrido[3,4-d]pyrimidin-6-yl]ethanol (1R)-1-[8-(7-azabicyclo[2.2.1]heptan-7-yl)-2-[[6-[4-(2-hydroxyethyl)piperazin-1-yl]pyridazin-3-yl]amino]pyrido[3,4-d]pyrimidin-6-yl]ethanol 1-[6-[[6-[(1R)-1-hydroxypropyl]-8-piperidin-1-ylpyrido[3,4-d]pyrimidin-2-yl]amino]pyridin-3-yl]-1,4-diazepan-2-one 4-(2-hydroxyethyl)-1-[6-[[6-[(1R)-1-hydroxyethyl]-8-piperidin-1-ylpyrido[3,4-d]pyrimidin-2-yl]amino]pyridin-3-yl]-1,4-diazepan-2-one 1-[6-[[8-(7-azabicyclo[2.2.1]heptan-7-yl)-6-[(1R)-1-hydroxyethyl]pyrido[3,4-d]pyrimidin-2-yl]amino]pyridin-3-yl]-4-methylpiperazin-2-one 1-[6-[[8-(8-azabicyclo[3.2.1]octan-8-yl)-6-[(1R)-1-hydroxyethyl]pyrido[3,4-d]pyrimidin-2-yl]amino]pyridin-3-yl]-4-methylpiperazin-2-one.

22. A pharmaceutical composition comprising a compound or a pharmaceutically acceptable salt thereof according to claim 1 and a pharmaceutically acceptable carrier.

23. A method for inhibiting CDK4 and/or CDK6 in a subject, wherein said method comprises administering an effective amount of the compound or pharmaceutically acceptable salt thereof according to claim 1 to a subject in need thereof.

24. A method for treating rheumatoid arthritis, breast cancer, or glioblastoma, in a subject, wherein said method comprises administering an effective amount of the compound or pharmaceutically acceptable salt thereof according to claim 1 to a subject in need thereof.

25. A pyrido[3,4-d]pyrimidine derivative represented by formula (II):

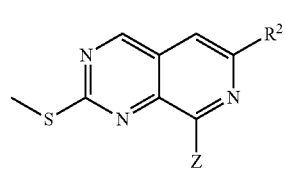

wherein in formula (II), $R^2$ represents $C_{1-8}$ alkyl, $C_{3-8}$ cycloalkyl, 4- to 6-membered heterocyclyl, $C_{1-8}$ acyl, —$COOR^8$, or —$CONR^9R^{10}$;

each $C_{1-8}$ alkyl represented by $R^1$ is substituted independently with zero to one —OH, zero to two $C_{1-8}$ alkoxy groups substituted with [zero to one —OH group, zero to one $C_{1-4}$ alkoxy group, and zero to three fluorine atoms], and zero to five fluorine atoms;

each of $C_{3-8}$ cycloalkyl represented by $R^1$ is substituted independently with zero to one —OH, zero to two $C_{1-8}$ alkoxy groups substituted with [zero to one —OH group, zero to one $C_{1-4}$ alkoxy group, and zero to three fluorine atoms], zero to one hydroxymethyl, and zero to five fluorine atoms;

provided that $R^2$ is neither an unsubstituted $C_{1-8}$ alkyl, nor an unsubstituted $C_{3-8}$ cycloalkyl, nor trifluoromethyl;

each of $R^8$, $R^9$, and 10 independently represents a hydrogen atom or $C_{1-8}$ alkyl;

each 4- to 6-membered heterocyclyl represented by $R^1$ is optionally substituted with one to four substituents selected from the group consisting of a fluorine atom, —OH, $C_{1-4}$ alkyl, and $C_{1-4}$ alkoxy;

each of $C_{1-8}$ acyl group, —$COOR^8$, and —$CONR^9R^{10}$ represented by $R^1$ is optionally substituted with one to four substituents selected from the group consisting of a fluorine atom, —OH, and $C_{1-4}$ alkoxy;

$R^9$ and $R^{10}$ of —$CONR^9R^{10}$ represented by $R^2$ are optionally bonded via a single bond or —O— to form a ring including the nitrogen atom to which $R^9$ and $R^{10}$ are bonded;

each heterocyclyl group represented by $R^2$ contains one oxygen atom as a heteroatom in the case of a 4- or 5-membered ring, and one to two oxygen atoms as heteroatoms in the case of a 6-membered ring, and $R^2$ is optionally protected with a suitable protective group, or a salt thereof.

26. A pyrido[3,4-d]pyrimidine derivative represented by formula (III):

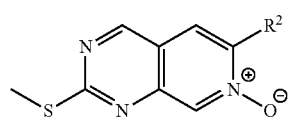

wherein in formula (III), $R^2$ represents $C_{1-8}$ alkyl, $C_{3-8}$ cycloalkyl, 4- to 6-membered heterocyclyl, $C_{1-8}$ acyl, —$COOR^8$, or —$CONR^9R^{10}$;

each $C_{1-8}$ alkyl represented by $R^2$ is independently substituted with zero to one —OH, zero to two $C_{1-8}$ alkoxy groups substituted with [zero to one —OH, zero to one $C_{1-4}$ alkoxy group, and zero to three fluorine atoms], and zero to five fluorine atoms;

each $C_{3-8}$ cycloalkyl represented by $R^2$ is independently substituted with zero to one —OH, zero to two $C_{1-8}$ alkoxy groups substituted with [zero to one —OH, zero to one $C_{1-4}$ alkoxy group, and zero to three fluorine atoms], zero to one hydroxymethyl, and zero to five fluorine atoms;

provided that $R^2$ is neither an unsubstituted $C_{1-8}$ alkyl, nor an unsubstituted $C_{3-8}$ cycloalkyl, nor trifluoromethyl;

each of $R^8$, $R^9$, and 10° independently represents a hydrogen atom or $C_{1-8}$ alkyl;

each 4- to 6-membered heterocyclyl represented by $R^2$ is optionally substituted with one to four substituents selected from the group consisting of a fluorine atom, —OH, $C_{1-4}$ alkyl, and $C_{1-4}$ alkoxy;

each of $C_{1-8}$ acyl group, —$COOR^8$, and —$CONR^9R^{10}$ represented by $R^2$ is optionally substituted with one to four substituents selected from the group consisting of a fluorine atom, —OH, and $C_{1-4}$ alkoxy;

$R^9$ and 10° of —$CONR^9R^{10}$ represented by $R^2$ are optionally bonded via a single bond or —O— to form a ring including the nitrogen atom to which $R^9$ and $R^{10}$ are bonded;

each heterocyclyl group represented by $R^2$ contains one oxygen atom as a heteroatom in the case of a 4- or 5-membered ring, and one to two oxygen atoms as heteroatoms in the case of a 6-membered ring, Z represents a halogen atom, and R² is optionally protected with a suitable protective group, or a salt thereof.

27. A pyrido[3,4-d]pyrimidine derivative represented by formula (IV):

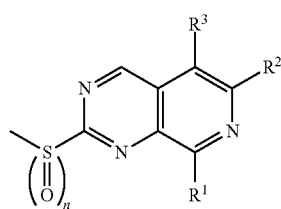

(IV)

wherein in formula (IV),

R¹ represents $C_{3-12}$ cycloalkyl, $C_{4-12}$ cycloalkenyl, 4- to 12-membered heterocyclyl, $C_{6-10}$ aryl, or 5- to 10-membered heteroaryl; each of the heteroatom-containing group represented by R¹ contains one to four heteroatoms independently selected from oxygen, sulfur, and nitrogen atoms;

R¹ is optionally substituted with one to six substituents selected from the group consisting of a halogen, =O, —OH, —CN, —COOH, —COOR⁶, —R⁷, $C_{3-6}$ cycloalkyl substituted with [zero to two —OH groups, zero to two $C_{1-8}$ alkoxy groups, and zero to six fluorine atoms], 3- to 10-membered heterocyclyl substituted with [zero to two —OH groups, zero to two $C_{1-8}$ alkoxy groups, and zero to six fluorine atoms], $C_{1-8}$ acyl substituted with [zero to two —OH groups, zero to two $C_{1-8}$ alkoxy groups, and zero to six fluorine atoms], and $C_{1-8}$ alkoxy substituted with [zero to two —OH groups, zero to two $C_{1-8}$ alkoxy groups, and zero to six fluorine atoms];

each of R⁶ and R⁷ independently represents $C_{1-6}$ alkyl substituted with [zero to two —OH groups, zero to two $C_{1-8}$ alkoxy groups, and zero to six fluorine atoms];

R² represents $C_{1-8}$ alkyl, $C_{3-8}$ cycloalkyl, 4- to 6-membered heterocyclyl, $C_{1-8}$ acyl, —COOR⁸, or —CONR⁹R¹⁰;

each $C_{1-8}$ alkyl represented by R² is independently substituted with zero to one —OH, zero to two $C_{1-8}$ alkoxy groups substituted with [zero to one —OH, zero to one $C_{1-4}$ alkoxy group, and zero to three fluorine atoms], and zero to five fluorine atoms;

each $C_{3-8}$ cycloalkyl represented by R¹ is independently substituted with zero to one —OH, zero to two $C_{1-8}$ alkoxy groups substituted with [zero to one —OH, zero to one $C_{1-4}$ alkoxy group, and zero to three fluorine atoms], zero to one hydroxymethyl, and zero to five fluorine atoms;

provided that R² is neither an unsubstituted $C_{1-8}$ alkyl, nor an unsubstituted $C_{3-8}$ cycloalkyl, nor trifluoromethyl;

each of R⁸, R⁹, and 10° independently represents a hydrogen atom or $C_{1-8}$ alkyl;

each 4- to 6-membered heterocyclyl represented by R¹ is optionally substituted with one to four substituents selected from the group consisting of a fluorine atom, —OH, $C_{1-4}$ alkyl, and $C_{1-4}$ alkoxy;

each of $C_{1-8}$ acyl group, —COOR⁸, and —CONR⁹R¹⁰ represented by R¹ is optionally substituted with one to four substituents selected from the group consisting of a fluorine atom, —OH, and $C_{1-4}$ alkoxy;

R⁹ and R¹⁰ of —CONR⁹R¹⁰ represented by R¹ are optionally bonded via a single bond or —O— to form a ring including the nitrogen atom to which R⁹ and R¹⁰ are bonded;

each heterocyclyl group represented by R¹ contains one oxygen atom as a heteroatom in the case of a 4- or 5-membered ring, and one to two oxygen atoms as heteroatoms in the case of a 6-membered ring;

R³ represents a hydrogen atom, $C_{1-8}$ alkyl, or a halogen atom;

n represents 0, 1, or 2, and each of R¹ and R² is optionally protected with a suitable protective group, or a salt thereof.

\* \* \* \* \*